US008685679B2

(12) United States Patent
Picataggio et al.

(10) Patent No.: US 8,685,679 B2
(45) Date of Patent: Apr. 1, 2014

(54) ACYLTRANSFERASE REGULATION TO INCREASE THE PERCENT OF POLYUNSATURATED FATTY ACIDS IN TOTAL LIPIDS AND OILS OF OLEAGINOUS ORGANISMS

(75) Inventors: Stephen K. Picataggio, Landenberg, PA (US); Narendra S. Yadav, Chadds Ford, PA (US); Hongxiang Zhang, Chadds Ford, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 533 days.

(21) Appl. No.: 11/190,750

(22) Filed: Jul. 27, 2005

(65) Prior Publication Data

US 2006/0094088 A1 May 4, 2006

Related U.S. Application Data

(63) Continuation-in-part of application No. 11/024,544, filed on Dec. 29, 2004, now Pat. No. 7,273,746.

(60) Provisional application No. 60/624,812, filed on Nov. 4, 2004.

(51) Int. Cl.
*C12P 7/64* (2006.01)
*C12Q 1/48* (2006.01)
*C12N 1/00* (2006.01)
*C12N 9/10* (2006.01)
*C07H 21/04* (2006.01)

(52) U.S. Cl.
USPC .......... 435/134; 435/15; 435/193; 435/254.2; 536/23.2

(58) Field of Classification Search
USPC ............... 435/134, 190, 254.2, 483; 536/23.2
See application file for complete search history.

(56) References Cited

U.S. PATENT DOCUMENTS

| 5,244,921 | A | 9/1993 | Kyle et al. | |
|---|---|---|---|---|
| 5,246,841 | A | 9/1993 | Yazawa et al. | |
| 5,246,842 | A | 9/1993 | O'Brien et al. | |
| 5,401,646 | A | 3/1995 | Shinmen et al. | |
| 6,136,574 | A | 10/2000 | Knutzon et al. | |
| 6,140,486 | A | 10/2000 | Facciotti et al. | |
| 6,459,018 | B1 | 10/2002 | Knutzon | |
| 6,635,451 | B2* | 10/2003 | Mukerji et al. | 435/71.1 |
| 2003/0135882 | A1* | 7/2003 | Metzlaff et al. | 800/280 |
| 2003/0172399 | A1 | 9/2003 | Fillatti | |
| 2003/0229920 | A1* | 12/2003 | Baulcombe et al. | 800/280 |
| 2004/0098762 | A1 | 5/2004 | Fillatti | |
| 2004/0111763 | A1 | 6/2004 | Heinz et al. | |
| 2004/0172682 | A1 | 9/2004 | Kinney et al. | |
| 2005/0132441 | A1* | 6/2005 | Damude et al. | 800/281 |
| 2006/0160193 | A1* | 7/2006 | Yadav et al. | 435/134 |

FOREIGN PATENT DOCUMENTS

| WO | WO 2003/093482 A2 | 11/2003 |
|---|---|---|
| WO | WO 2004/057001 A2 | 7/2004 |
| WO | WO 2004/087902 A2 | 10/2004 |
| WO | WO 2004/090123 A2 | 10/2004 |
| WO | WO 2004/101757 A2 | 11/2004 |
| WO | WO-2005/005617 | * 1/2005 |

OTHER PUBLICATIONS

Bruening et al. Plant gene silencing regularized, Proc Natl Acad Sci U S A. Nov. 10, 1998;95(23):13349-51.*
Austin MA., Triacylglycerol and coronary heart disease, Proc Nutr Soc., Jul. 1997;56(2):667-70.*
PCT/US05/40341 International Search Report and Written Opinion Sep. 19, 2008 (date of mailing).
Oelkers, Peter et al., The DGA1 Gene Determines a Second Triglyceride Synthetic Pathway in Yeast, The Journal of Bioloigical Chemistry, Mar. 15, 2002, pp. 8877-8881, vol. 277, No. 11, The American Society for Biochemistry and Molecular Biology, Inc.
International Preliminary Report on Patentability in PCT/US2005/040341.
U.S. Appl. No. 60/624,812, Nov. 2, 2005, Damude et al.
U.S. Appl. No. 11/265,761, Nov. 2, 2005, Damude et al.
J.M. Dyer et. al., Metabolic Engineering of *Saccharomyces cerevisiae* for Production of Novel Lipid Compounds, Appl. Microbiol. Biotechnol., 2000, pp. 224-230, vol. 59.
Amine Abbadi et. al., Biosynthesis of Very Long Chain Polyunsaturated Fatty Acids in Transgenic Oilseeds: Constraints on Their Accumlation, the Plant Cell, 2004, pp. 2734-2748, vol. 16.
Frederic Domergue et. al., Cloning and Functional Characterization of Phaeodactylum Tricornutum Front-End Desaturases Involved in Eicosapentaenoic Acid Biosynthesis, Eur. J. Biochem., 2002, pp. 4105-4113, vol. 269.

* cited by examiner

Primary Examiner — Iqbal H Chowdhury

(57) ABSTRACT

Methods to increase the percent of polyunsaturated fatty acids (PUFAs) within the total lipids and oils of PUFA-producing oleaginous organisms are provided herein, by regulating the activity of specific acyltransferases. Specifically, since oil biosynthesis is expected to compete with polyunsaturation during oleaginy, it is possible to reduce or inactivate the activity of an organism's DAG ATs (e.g., phospholipid:diacylglycerol acyltransferase (PDAT) and/or diacylglycerol acyltransferase 1 (DGAT1) and/or diacylglycerol acyltransferase 2 (DGAT2)) to thereby reduce the overall rate of oil biosynthesis while concomitantly increasing the percent of PUFAs that are incorporated into the lipid and oil fractions. The teachings herein will thereby enable one to engineer a wide variety of oleaginous organisms to produce oils with very specific fatty acid compositions.

8 Claims, 13 Drawing Sheets

Figure 6a

Figure 1:
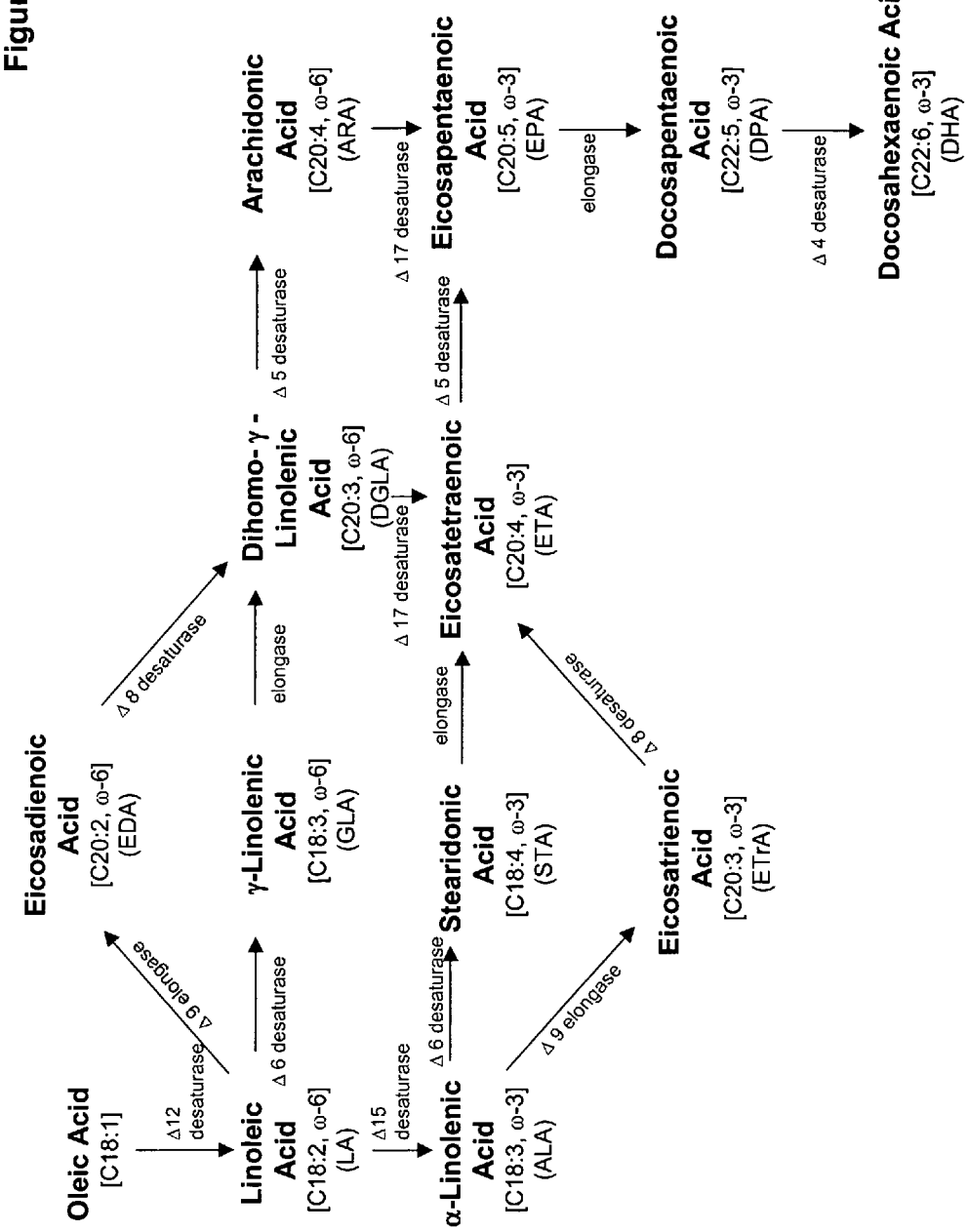

```
                                              . . . . . . . Consensus #1  SEQ
                                                                          ID NO:
1   - - - - - - - - - - - - - - - M S S T - - - - - - Nc DAGAT1           133
1   - - - - - - - - - - - - - - - M N S A T - - - - - - Fm DAGAT1         134
1   - - - - - - - - - - - - - - - M T E S T - - - - - - Ma DGAT1          132
1   M A A A T A T G L D L A A Q E G A Q Q R R S T - - - - - - Mg DAGAT1   135
1   - - - - - - - - - - - - - - - - - - - - - - - - - - An DAGAT1        136
1   - - - - - - - - - - - - - M E V R R R K I D V L K - - - - - - Yl DGAT1   84
1   - - - - - - - - - - - - M G D R G G A C S S - - - - - - Mm DCAT1      137
1   - - - - - - - - - - - M A I S D E P E S V A T - - - - - - Gm DGAT1    138
1   - - - - - - - - - - - M A I L D S A G V T T V T E N G G G E At DGAT1  139
1   - - - - - - - - - - - M V G S D G D G D G G G - - - - - Os DGAT1      140
1   - - - - - - - - - - - M A I L D S P E I L D T T S S S A D N Pfdgat1   141
1   - - - - - - - - - - - M S K G N P D P H L P G S F L - - - - Ta DGAT1  142

. . . . . . . Consensus #1
6   - - - - - - - A T T T G L D P A V H T S N D - - - - - - - Nc DAGAT1
6   - - - - - - - T T S T E T S N G S T S - - - - - - - Fm DAGAT1
6   - - - - - - - T T T C A K E E G I A N - - - - - - - Ma DGAT1
24  - - - - - - - A T N Q S A D D D V T T N A D G - - - - - A Mg DAGAT1
1   - - - - - - - - - - - - - - - - - - - - - - - - - - An DAGAT1
13  - - - - - - - - A Q K N G Y E S G P P S R Q S - - - - - - Yl DGAT1
11  - - - - - - - - - R R R R T G S R - V S V Q G G S - - - - - - Mm DCAT1
13  - A L N H S S L R R R P S - A T S T A G L F N S - - - - - - Gm DGAT1
20  - F V D L D R L R R R K S R G D S S N G L L L G S D N N S At DGAT1
14  - E A H A G G P R R R A G Q L R - - G R L R D E - - - - - - Os DGAT1
20  G A A H H T T L R R R Q S - A R S V P P L D S D S N S L E Pfdgat1
16  - P S H G G P P P K P K T P P R T F R N L P S S - - - - - - Ta DGAT1

. . . . . . . Consensus #1
21  - - - N - - - - - - - - - - - - - - - - - V I R R T H G T Nc DAGAT1
18  - - - - - - - - - - - - - - - - - - - - - - - V S K - - Fm DAGAT1
18  - - - - - - - - - - - - - - - - - - - - - - - - - - Ma DGAT1
41  A A A P - - - - - - - - - - - - - - - - - S L K G T T A D Mg DAGAT1
1   - - - - - - - - - - - - - - - - - - - - - - - - - - An DAGAT1
28  - S Q P - - - - - - - - - - - - - - - S S R A S S R T Yl DGAT1
26  - - - - - - - - - - - - - - - - - - - - G P K V E E D E Mm DCAT1
35  P E T T T D S S - - - - - - - - - - - G D D L A K D S Gm DGAT1
49  P S D D V G A P A D V R - - - - - - D R I D V V N D A A At DGAT1
35  - A A P - - - - - - - - - - - - - - - - - G S P P R P R P Os DGAT1
49  A E S A I N D S E N V R N D A N L I E N L R G G A V E S E N Pfdgat1
39  - S T H - - - - - - - - - - - - - - - - G P A P S V A A Ta DGAT1
```

Figure 6b

|  |  |  | Consensus #1 | SEQ ID NO: |
|---|---|---|---|---|
| 30 | E N G S T P N D K A N A G G E P E T E T R H S K K V - V R | Nc DAGAT1 | | 133 |
| 21 | R X G H D V T R T N G N G T T T T S P P K E A G - - - - - | Fm DAGAT1 | | 134 |
| 18 | - - - S A A L F P I P P K M E J L K S S R T G - - - - - | Ma DGAT1 | | 132 |
| 53 | T N G T S N G N G N G N G N V D E D E Q T K A L R K A - F T | Mg DAGAT1 | | 135 |
| 1 | - - - - - - - - - - - M A T R T A - - - - - - | An DAGAT1 | | 136 |
| 39 | R N K H S S S T L S L S G L T M K V Q K P A G P P N S K | Yl DGAT1 | | 84 |
| 34 | V R D A A V S P D L G A G G D A P A P A P A H T R D K D | Mm DGAT1 | | 137 |
| 51 | G S D D S I N S D - L A V N S Q - - Q Q N E K Q D T D F S | Gm DGAT1 | | 138 |
| 72 | Q G T A N L A G D N N G G G D N N G G G R G G G E G R G N A | At DGAT1 | | 139 |
| 46 | R P R P R G G D S N G R S V L R P G G G G G R G G G D F S | Os DGAT1 | | 140 |
| 79 | E K Q P S Y G K E E - G A K V K L N G E T S N G N G T D V M | Pfdgat1 | | 141 |
| 50 | A T I A T T P E S A S A A P L P P T V H G E A A H G A A A A | Ta DGAT1 | | 142 |

|  |  | . . . . S . . . S . . . . . . . | Consensus #1 |
|---|---|---|---|
| 59 | S - - - - K Y R H V E A V H S Q S R P S C L S H D T T E S - | Nc DAGAT1 |
| 45 | Q - - - - K Y E H V A A V H K K T R P S C L S H D S D A A - | Fm DAGAT1 |
| 39 | S - - - - S Y K E T P V H T E T I P S P L S K E A P P E - | Ma DGAT1 |
| 82 | R - - - - K Y E H V A A L H S Q A R P S T L S H D S E A S - | Mg DAGAT1 |
| 8 | - - - - - I V R H A V A V E S Q V Q H S C L S R D S T K A - | An DAGAT1 |
| 69 | T - - - - P F L H I K P V H T C C S T S M L S R D Y D G S N | Yl DGAT1 |
| 64 | G R T S V G D G Y W D L R C H R L Q D S L P S S D S G F S - | Mm DGAT1 |
| 78 | V L K - F A Y R P S V P A H R K V E S P L S S D T I P R - | Gm DGAT1 |
| 102 | D A T - F T Y R P S V P A H R R A R E S P L S S D A I F K - | At DGAT1 |
| 76 | A - - - F T F R A A P V H R K A K E S P L S S D A I F K - | Os DGAT1 |
| 108 | A V K - F T F R P A A P A H R K N K E S P L S S D A T Y K - | Pfdgat1 |
| 80 | E R R D A L L P G V G A A H R V E S P L S S D A I F R - | Ta DGAT1 |

|  |  | . . . . G . . N . . . . . L . . . . . . . . . . | Consensus #1 |
|---|---|---|---|
| 84 | P S F L G F R N L M V I V L A N N S H - - - - - - - - Q Y C | Nc DAGAT1 |
| 70 | P S F I G F R N L M V I V L G I Y H I - - - - G M S Q F D | Fm DAGAT1 |
| 64 | - S Y R G F V N L G M L L L F G N N I R L I E N Y L K Y G | Ma DGAT1 |
| 107 | P S F V G F R N L M V I V L - - - - - - - - - - - - - | Mg DAGAT1 |
| 32 | T S F I G F R N L M V V L V A M N L R L V I E N F L K Y G | An DAGAT1 |
| 95 | P S F K G F K N T G M I L L I V G N - - - - - - - - - - - | Yl DGAT1 |
| 93 | N - Y R G I L N W C V V M I L S N A R L F L E K L F K Y G | Mm DGAT1 |
| 106 | Q S H A G L F N L C E V V L V A V N S R L I E N L M K Y C | Gm DGAT1 |
| 130 | Q S H A G L F N L C V V L I A V N S R L I I E N L M Y G | At DGAT1 |
| 102 | Q S H A G L F N L C T V V L V A V N S R L I I E N L M K Y G | Os DGAT1 |
| 136 | Q S H A G L F N L C T V V L V A V N S R L T T E N L M K Y G | Pfdgat1 |
| 109 | Q S H A G L L N L C I V V L T A V N S R L I I E N L M H Y G | Ta DGAT1 |

Motif #1

```
                                                              SEQ
                                                              ID NO:
506  Q A K Y G S V S K M T T S Q Q L V Q Q G Q G T C P P L V   Nc DAGAT1  133
485  Q A K Y G S V T D S G F S I S                            Fm DAGAT1  134
519  T K R H X D V L                                          Ma DGAT1   132
483  Q A K Y G S V S K M G Y A T S K A A L T N                Mg DAGAT1  135
447  Q A K Y G S V Q T H P                                    An DAGAT1  136
521  N Y K Q N Q                                              Yl DGAT1    84
490  L N Y D A P V G V                                        Mm DGAT1   137
497  M N R K G K L D                                          Gm DGAT1   138
513  M N R K G S M S                                          At DGAT1   139
493  M N R T E K A R                                          Os DGAT1   140
527  M N R K A S A R                                          Pfdgat1    141
500  M N R Q A Q T N G                                        Ta DGAT1   142
```

Consensus 'Consensus #1': When all match the residue of the Consensus show the residue of the Consensus, otherwise show

SEQUENCE LISTING

```
<160> NUMBER OF SEQ ID NOS: 159

<210> SEQ ID NO 1
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 1
aagcagtggt atcaacgcag agtggccatt acggccggg                         39

<210> SEQ ID NO 2
<211> LENGTH: 59
```

```
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 2
attctagagg ccgaggcggc cgacatgttt tttttttttt tttttttttt tttttttvn        59

<210> SEQ ID NO 3
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 3
aagcagtggt atcaacgcag agt                                              23

<210> SEQ ID NO 4
<211> LENGTH: 21
<212> TYPE: DNA
<213> ORGANISM: Artificial Sequence
<220> FEATURE:
<223> OTHER INFORMATION: Primer MDGAT-FN1
<220> FEATURE:
<221> NAME/KEY: misc_feature
<222> LOCATION: (16)..(16)
<223> OTHER INFORMATION: n is a, c, g, or t

<400> SEQUENCE: 4
gaactacatc ttyggntayc a                                                21

<210> SEQ ID NO 5
<211> LENGTH: 7
<212> TYPE: PRT
<213> ORGANISM: Artificial Sequence
<220> FEATURE:
<223> OTHER INFORMATION: Primer MDGAT-FN1

<400> SEQUENCE: 5

Asn Tyr Ile Phe Gly Tyr His
1               5

<210> SEQ ID NO 6
<211> LENGTH: 20
<212> TYPE: DNA
<213> ORGANISM: Artificial Sequence
<220> FEATURE:
<223> OTHER INFORMATION: Primer MDGAT-RN1
<220> FEATURE:
<221> NAME/KEY: misc_feature
<222> LOCATION: (15)..(15)
<223> OTHER INFORMATION: n is a, c, g, or t

<400> SEQUENCE: 6
tacagctcrt tytcnccraa                                                  20

<210> SEQ ID NO 7
<211> LENGTH: 7
<212> TYPE: PRT
<213> ORGANISM: Artificial Sequence
```

```
<220> FEATURE:
<223> OTHER INFORMATION: Primer MDGAT-RN1

<400> SEQUENCE: 7

Phe Gly Glu Asn Glu Leu Tyr
1               5

<210> SEQ ID NO 8
<211> LENGTH: 20
<212> TYPE: DNA
<213> ORGANISM: Artificial Sequence
<220> FEATURE:
<223> OTHER INFORMATION: Primer MDGAT-RN2
<220> FEATURE:
<221> NAME/KEY: misc_feature
<222> LOCATION: (18)..(18)
<223> OTHER INFORMATION: n is a, c, g, or t

<400> SEQUENCE: 8
ccaaagtcrt arttraanac                                                 20

<210> SEQ ID NO 9
<211> LENGTH: 7
<212> TYPE: PRT
<213> ORGANISM: Artificial Sequence
<220> FEATURE:
<223> OTHER INFORMATION: Primer MDGAT-RN2

<400> SEQUENCE: 9

Val Phe Asn Tyr Asp Phe Gly
1               5

<210> SEQ ID NO 10
<211> LENGTH: 370
<212> TYPE: DNA
<213> ORGANISM: M alpina

<400> SEQUENCE: 10
gaactacatc ttcgggtatc acccacacgg aatcatttcc ttgggtgccc tctgcgcctt     60
tgggaccgag ggccttcatt tctccaaacg cttcccgggt atcaagcctc atctgctcac   120
cattcacgcc aactttcaga tcccactcta tcgcgatatg atcatggccc acggctgtgc   180
ttccgtgtcg agggcctctt gtgaacacat cctgcggtct ggcgaaggat cctcggtcgt   240
gatcgttgtc gggggtgcac aagaaagttt gtcgactcaa cctggcacgt taaatctgac   300
actcaagaaa agactgggat tttgcaagct ggcctttgtc aatggcgcaa gtctggtacc   360
tacgttggcc                                                          370

<210> SEQ ID NO 11
<211> LENGTH: 654
<212> TYPE: DNA
<213> ORGANISM: M alpina
<220> FEATURE:
<221> NAME/KEY: misc_feature
<222> LOCATION: (370)..(370)
<223> OTHER INFORMATION: n is a, c, g, or t

<400> SEQUENCE: 11
gaactacatc tttgggtatc acccacacgg aatcatttcc ttgggtgccc tctgcgcctt     60
tgggaccgag ggccttcatt tctccaaacg cttcccgggt atcaagcctc atctgctcac   120
cattcacgcc aactttcaga tcccactcta tcgcgatatg atcatggccc acggctgtgc   180
ttccgtgtcg agggcctctt gtgaacacat cctgcggtct ggcgaaggat cctcggtcgt   240
gatcgttgtc gggggtgcac aagaaagttt gtcgactcaa cctggcacgt taaatctgac   300
```

```
actcaagaaa agactgggat tttgcaagct ggcccttgtc aatgggtaag gagacggata      360
tctcctgtgn attattttt  tttttttttt tttttttttt tgccggccct tcaaagggc       420 taatgcgtcg ttaaagagga atatcttgcg tctgactctt gctacagata cacgcaaacg      480
aacacggtga actgatactc catggctttc tacgatgctg ttagcgcaag tctggtacct      540
acgttggcct ttggtgagaa cgagctctat gaggtgtacc acaccaagcc cacaagcctg      600
atatacaagc tccagcagtt gactaaacgc acgatcggct tcacaatgcc cgtc            654
```

```
<210> SEQ ID NO 12
<211> LENGTH: 179
<212> TYPE: DNA
<213> ORGANISM: M alpina
<220> FEATURE:
<221> NAME/KEY: misc_feature
<222> LOCATION: (25)..(25)
<223> OTHER INFORMATION: n is a, c, g, or t

<400> SEQUENCE: 12
gtaaggagac ggatatctcc tgtgnattat tttttttttt tttttttttt tttttgccg       60 gcccttcaaa ggggctaatg cgtcgttaaa gaggaatatc ttgcgtctga ctcttgctac      120
agatacacgc aaacgaacac ggtgaactga tactccatgg ctttctacga tgctgttag       179
```

```
<210> SEQ ID NO 13
<211> LENGTH: 2299
<212> TYPE: DNA
<213> ORGANISM: M alpina
<220> FEATURE:
<221> NAME/KEY: misc_feature
<222> LOCATION: (748)..(751)
<223> OTHER INFORMATION: Translation initiation codon 'ATG'
<220> FEATURE:
<221> NAME/KEY: Intron
<222> LOCATION: (1018)..(1201)
<220> FEATURE:
<221> NAME/KEY: Intron
<222> LOCATION: (1570)..(1748)
<220> FEATURE:
<221> NAME/KEY: Intron
<222> LOCATION: (1903)..(2034)
<220> FEATURE:
<221> NAME/KEY: misc_feature
<222> LOCATION: (2117)..(2117)
<223> OTHER INFORMATION: n is a, c, g, or t
<220> FEATURE:
<221> NAME/KEY: misc_feature
<222> LOCATION: (2235)..(2237)
<223> OTHER INFORMATION: Stop codon 'TAG'
<220> FEATURE:
<221> NAME/KEY: misc_feature
<222> LOCATION: (2283)..(2283)
<223> OTHER INFORMATION: n is a, c, g, or t
<220> FEATURE:
<221> NAME/KEY: misc_feature
<222> LOCATION: (2291)..(2291)
<223> OTHER INFORMATION: n is a, c, g, or t

<400> SEQUENCE: 13
actatagggc acgcgtggtc gacggcccgg gctggtctga agacgtggat gtgtactctc      60
ttacgggcaa acatatgcct gatacaatgg taccggagtc gtcggaaaga cctagcatcg      120
agataagaga attatgcaag atatgacagc acagggatga gtgctttgtt gcgtgcgatg      180
tgcatgagtg tgtctgtgta ggcggcccta tgtgtggtgc tgcactcatg tgtatgatgc      240
gcatgtagga ggaaggatgg gcgcaggtcg cttcttttcc ttgtgtccgc caggcacaca      300
caatgcgcac aggcacccaa ttgggttcat gcgaggcata ccgtgcacct ctctgcgctt      360
```

```
ctctctccaa gcgacatgcg tccaaacgca aagctcagct ttgggtttaa tcgtcccgta    420
gtgcatcggc gtgccttcgc gctcacacac tcgcacatct cgcccttttgt tgccctttttt   480
ccttcttctc tcactctgtc ctgtctataa aagccctgca acactgtcct ctctcgcctc    540
tccactctcc acagttttca ctcctcgact cattccttttt tcacacctca ccgctctcca    600
ttgactccat tgacacgtcg cattcgtctc ctggtgcacg actcgtttgc ttttcacacc    660
aagctcgctg tgttgacaaa cagcaactcc actctcctct caacaccatc attgctcccc    720
tgttcctctg ttcctctctc gctcagaatg ccgctctttg cgcctttacg gatgcccgtc    780
aagcgtcgta tgcagacagg agctgtccta tactggattg cggggatgat ttactgcatt    840
ggcatctttg ccttcctctg cacgttcaag atccttcgac ccttgatcat catctatgtc    900
ctgtgggcct acatgctcga ccgagcacca gagcggggtg cacgcacagt ccaatggtat    960
tgtaactgga tcggatggaa acactttgca cagtactttc ctatgaccct tgtcaaggta   1020
ccgaaaccaa catggaggac ggagagtctt ttgagcgcag attttctttt tccttttaat   1080
catgttcgca cgtcccccccc cccagctttc ttctcgtctc taactgtaac caacttttttg  1140
tcgaaatgcc tgttgcatat ttggaaacat actgattttt ttttttttttt cctactcaaa   1200
ggagggagag ctggacccat ccaagaacta catctttggg tatcacccac acggaatcat   1260
tttcttgggt gccctctgcg cctttgggac cgagggcctt catttctcca aacgcttccc   1320
gggtatcaag cctcatctgc tcaccattca cgccaacttt cagatcccac tctatcgcga   1380
tatgatcatg gccacggct gtgcttccgt gtcgagggcc tcttgtgaac acatcctgcg   1440
gtctggcgaa ggatcctcgg tcgtgatcgt tgtcgggggt gcacaagaaa gtttgtcgac   1500
tcaacctggc acgttaaatc tgacactcaa gaaaagactg ggattttgca agctggccct   1560
tgtcaatggg taaggagacg gatatctcct gtgtattatt ttttttttttt tttttttttt   1620
ttttgccgk cccttcaaag gggctaatgc gtcgttaaag aggaatatct tgcgtctgac   1680
tcttgctaca gatacacgca aacgaacacg gtgaactgat actccatggc tttctacgat   1740
gctgttagcg caagtctggt acctacgttg gcctttggtg agaacgagct ctatgaggtg   1800
taccacacca agcccacaag cctgatatac aagctccagc agttgactaa acgcacgatc   1860
ggcttcacaa tgcccgtstt caacggacga ggaatcttca attgtgagtt ctctgacttg   1920
gttcccaaac acactttctg ttgggttttt ttttctcttc aaagtgatca tataatacca   1980
cttactaatc tccctatttc ctttttttttt tttttttttt ggtccccact gtaaatgart   2040
ttggactgct gccaaggagg aagcctgtct atatcgttat aggaaacccc attcatgtag   2100
acaaggtcga gaacccnacg attgaacaga tgcagaaact gcagtcaatt tacattgatg   2160
aggtgctaaa catttgggaa agatacaagg acaagtatgc cgcaggacga actcaggaac   2220
tgtgcatcat cgaataggag ggcttggccg atggcaaccc aaataataaa aaaaaaagaa   2280
agnggtgtag ncttgctcc                                                2299
```

<210> SEQ ID NO 14
<211> LENGTH: 37
<212> TYPE: DNA
<213> ORGANISM: Artificial Sequence
<220> FEATURE:
<223> OTHER INFORMATION: Primer AP

<400> SEQUENCE: 14

```
ggccacgcgt cgactagtac tttttttttt tttttt                              37
```

<210> SEQ ID NO 15

```
<211> LENGTH: 22
<212> TYPE: DNA
<213> ORGANISM: Artificial Sequence
<220> FEATURE:
<223> OTHER INFORMATION: Primer MDGAT-3-1

<400> SEQUENCE: 15
ggcacgttaa atctgacact ca                                            22

<210> SEQ ID NO 16
<211> LENGTH: 49
<212> TYPE: DNA
<213> ORGANISM: Artificial Sequence
<220> FEATURE:
<223> OTHER INFORMATION: Primer UAP
<220> FEATURE:
<221> NAME/KEY: misc_feature
<222> LOCATION: (2)..(2)
<223> OTHER INFORMATION: N = uracil
<220> FEATURE:
<221> NAME/KEY: misc_feature
<222> LOCATION: (5)..(5)
<223> OTHER INFORMATION: N = uracil
<220> FEATURE:
<221> NAME/KEY: misc_feature
<222> LOCATION: (8)..(8)
<223> OTHER INFORMATION: N = uracil
<220> FEATURE:
<221> NAME/KEY: misc_feature
<222> LOCATION: (11)..(11)
<223> OTHER INFORMATION: N = uracil

<400> SEQUENCE: 16
cnacnacnac naggccacgc gtcgactagt acttttttt tttttttt                 49

<210> SEQ ID NO 17
<211> LENGTH: 20
<212> TYPE: DNA
<213> ORGANISM: Artificial Sequence
<220> FEATURE:
<223> OTHER INFORMATION: Primer MDGAT-3-2

<400> SEQUENCE: 17
gactgggatt ttgcaagctg                                               20

<210> SEQ ID NO 18
<211> LENGTH: 19
<212> TYPE: DNA
<213> ORGANISM: Artificial Sequence
<220> FEATURE:
<223> OTHER INFORMATION: Primer MDGAT-3-3

<400> SEQUENCE: 18
gcctttgtca atgcgcaag                                                19

<210> SEQ ID NO 19
<211> LENGTH: 455
<212> TYPE: DNA
<213> ORGANISM: M alpina
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
```

-continued

```
<400> SEQUENCE: 19
ttgtcaatgg cgcaagtctg gtacctacgt tggcctttgg tgagaacgag ctctatgagg      60
tgtaccacac caagcccaca agcctgatat acaagctcca gcagttgact aaacgcacga     120
tcggcttcac aatgcccgtg ttcaacggac gaggaatctt caattatgag tttggactgc     180
tgccaaggag gaagcctgtc tatatcgtta taggaaaccc cattcatgta gacaaggtcg     240
agaacccaac gattgaacag atgcagaaac tgcagtcaat ttacattgat gaggtgctaa     300
acatttggga agatacaag gacaagtatg ccgcaggacg aactcaggaa ctgtgcatca     360
tcgaatagga gggcttggcc gatggcaacc caaataataa aaaaaaaga aagnggtgta     420 gncttgctcc aannaaaaaa aaaaaaaaaa aaaaa                                455

<210> SEQ ID NO 20
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 20
gtaatacgac tatagggcac gcgtggtcga cggcccgggc tggt                       44

<210> SEQ ID NO 21
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
<223> OTHER INFORMATION: 3' end is associated with a -H2N group

<400> SEQUENCE: 21 accagccc                                                                8

<210> SEQ ID NO 22
<211> LENGTH: 22
<212> TYPE: DNA
<213> ORGANISM: Artificial Sequence
<220> FEATURE:
<223> OTHER INFORMATION: Primer AP1

<400> SEQUENCE: 22
gtaatacgac tcactatagg gc                                               22

<210> SEQ ID NO 23
<211> LENGTH: 19
<212> TYPE: DNA
<213> ORGANISM: Artificial Sequence
<220> FEATURE:
<223> OTHER INFORMATION: Primer AP2

<400> SEQUENCE: 23
actatagggc acgcgtggt                                                   19

<210> SEQ ID NO 24
<211> LENGTH: 674
<212> TYPE: DNA
<213> ORGANISM: M alpina
<220> FEATURE:
```

<210> SEQ ID NO 24 (continued)

```
<221> NAME/KEY: misc_feature
<222> LOCATION: (582)..(582)
<223> OTHER INFORMATION: n is a, c, g, or t

<400> SEQUENCE: 24
gactgggatt ttgcaagctg gcccttgtca atgggtaagg agacggatat ctcctgtgta     60
ttattttttt ttttttttt ttttttttt gccgtccctt caaagggct aatgcgtcgt      120 taaagaggaa tatcttgcgt ctgactcttg ctacagatac acgcaaacga acacggtgaa    180
ctgatactcc atggctttct acgatgctgt tagcgcaagt ctggtaccta cgttggcctt    240
tggtgagaac gagctctatg aggtgtacca caccaagccc acaagcctga tatacaagct    300
ccagcagttg actaaacgca cgatcggctt cacaatgccc gtgttcaacg gacgaggaat    360
cttcaattgt gagttctctg acttggttcc caaacacact ttctgttggg tttttttttc    420
tcttcaaagt gatcatataa taccacttac taatctccct atttcctttt ttttttttt     480 tttttggtcc ccactgtaaa tgaatttgga ctgctgccaa ggaggaagcc tgtctatatc    540
gttataggaa accccattca tgtagacaag gtcgagaacc cnacgattga acagatgcag    600
aaactgcagt caatttacat tgatgaggtg ctaaacattt gggaaagata caaggacaag    660
tatgccgcag gacg                                                      674

<210> SEQ ID NO 25
<211> LENGTH: 131
<212> TYPE: DNA
<213> ORGANISM: M alpina

<400> SEQUENCE: 25
gtgagttctc tgacttggtt cccaaacaca ctttctgttg ggttttttt tctcttcaaa      60 gtgatcatat aataccactt actaatctcc ctatttcctt ttttttttt ttttttggt     120 ccccactgta a                                                         131

<210> SEQ ID NO 26
<211> LENGTH: 22
<212> TYPE: DNA
<213> ORGANISM: Artificial Sequence
<220> FEATURE:
<223> OTHER INFORMATION: Primer MDGAT-5-1

<400> SEQUENCE: 26
ggaagcgttt ggagaaatga ag                                              22

<210> SEQ ID NO 27
<211> LENGTH: 22
<212> TYPE: DNA
<213> ORGANISM: Artificial Sequence
<220> FEATURE:
<223> OTHER INFORMATION: Primer MDGAT-5-2

<400> SEQUENCE: 27
aatgattccg tgtgggtgat ac                                              22

<210> SEQ ID NO 28
<211> LENGTH: 1261
<212> TYPE: DNA
<213> ORGANISM: M alpina

<400> SEQUENCE: 28
actatagggc acgcgtggtc gacggcccgg gctggtctga agacgtggat gtgtactctc     60
ttacgggcaa acatatgcct gatacaatgg taccggagtc gtcggaaaga cctagcatcg    120
```

| | |
|---|---|
| agataagaga attatgcaag atatgacagc acagggatga gtgctttgtt gcgtgcgatg | 180 |
| tgcatgagtg tgtctgtgta ggcggcccta tgtgtggtgc tgcactcatg tgtatgatgc | 240 |
| gcatgtagga ggaaggatgg gcgcaggtcg cttcttttcc ttgtgtccgc caggcacaca | 300 |
| caatgcgcac aggcacccaa ttgggttcat gcgaggcata ccgtgcacct ctctgcgctt | 360 |
| ctctctccaa gcgacatgcg tccaaacgca aagctcagct ttgggtttaa tcgtcccgta | 420 |
| gtgcatcggc gtgccttcgc gctcacacac tcgcacatct cgccctttgt tgccctttt | 480 |
| ccttcttctc tcactctgtc ctgtctataa aagccctgca acactgtcct ctctcgcctc | 540 |
| tccactctcc acagttttca ctcctcgact cattcctttt tcacacctca ccgctctcca | 600 |
| ttgactccat tgacacgtcg cattcgtctc ctggtgcacg actcgtttgc ttttcacacc | 660 |
| aagctcgctg tgttgacaaa cagcaactcc actctcctct caacaccatc attgctcccc | 720 |
| tgttcctctg ttcctctctc gctcagaatg ccgctctttg cgcctttacg gatgcccgtc | 780 |
| aagcgtcgta tgcagacagg agctgtccta tactggattg cggggatgat ttactgcatt | 840 |
| ggcatctttg ccttcctctg cacgttcaag atccttcgac ccttgatcat catctatgtc | 900 |
| ctgtgggcct acatgctcga ccgagcacca gagcggggtg cacgcacagt ccaatggtat | 960 |
| tgtaactgga tcggatggaa acactttgca cagtactttc ctatgaccct tgtcaaggta | 1020 |
| ccgaaaccaa catggaggac ggagagtctt tgagcgcag attttctttt tccttttaat | 1080 |
| catgttcgca cgtcccccc cccagctttc ttctcgtctc taactgtaac caacttttg | 1140 |
| tcgaaatgcc tgttgcatat ttggaaacat actgatttt tttttttttt cctactcaaa | 1200 |
| ggagggagag ctggacccat ccaagaacta catctttggg tatcacccac acggaatcat | 1260 |
| t | 1261 |

<210> SEQ ID NO 29
<211> LENGTH: 996
<212> TYPE: DNA
<213> ORGANISM: M alpina

<400> SEQUENCE: 29

| | |
|---|---|
| atgccgctct ttgcgccttt acggatgccc gtcaagcgtc gtatgcagac aggagctgtc | 60 |
| ctatactgga ttgcggggat gatttactgc attggcatct ttgccttcct ctgcacgttc | 120 |
| aagatccttc gacccttgat catcatctat gtcctgtggg cctacatgct cgaccgagca | 180 |
| ccagagcggg gtgcacgcac agtccaatgg tattgtaact ggatcggatg gaaacacttt | 240 |
| gcacagtact ttcctatgac ccttgtcaag gaggagagc tggacccatc caagaactac | 300 |
| atctttgggt atcacccaca cggaatcatt tycttgggtg ccctctgcgc ctttgggacc | 360 |
| gagggccttc atttctccaa cgcttcccg ggtatcaagc ctcatctgct caccattcac | 420 |
| gccaactttc agatcccact ctatcgcgat atgatcatgg cccacggctg tgcttccgtg | 480 |
| tcgagggcct cttgtgaaca catcctgcgg tctggcgaag atcctcggt cgtgatcgtt | 540 |
| gtcggggtg cacaagaaag yttgtcgact caacctggca cgttaaatct gacactcaag | 600 |
| aaaagactgg gattttgcaa gctggccttt gtcaatggcg caagtctggt acctacgttg | 660 |
| gcctttggtg agaacgagct ctatgaggtg taccacacca agcccacaag cctgatatac | 720 |
| aagctccagc agttgactaa acgcacgatc ggcttcacaa tgcccgtgtt caacggacga | 780 |
| ggaatcttca attrtgagtt tggactgctg ccaaggagga agcctgtcta tatcgttata | 840 |
| ggaaacccca ttcatgtaga caaggtcgag aacccaacga ttgaacagat gcagaaactg | 900 |
| cagtcaattt acattgatga ggtgctaaac atttgggaaa gatacaagga caagtatgcc | 960 | gcaggacgaa ctcaggaact gtgcatcatc gaatag        996

<210> SEQ ID NO 30
<211> LENGTH: 331
<212> TYPE: PRT
<213> ORGANISM: M. alpina
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 30

```
Met Pro Leu Phe Ala Pro Leu Arg Met Pro Val Lys Arg Arg Met Gln
1               5                   10                  15

Thr Gly Ala Val Leu Tyr Trp Ile Ala Gly Met Ile Tyr Cys Ile Gly
            20                  25                  30

Ile Phe Ala Phe Leu Cys Thr Phe Lys Ile Leu Arg Pro Leu Ile Ile
        35                  40                  45

Ile Tyr Val Leu Trp Ala Tyr Met Leu Asp Arg Ala Pro Glu Arg Gly
50                  55                  60

Ala Arg Thr Val Gln Trp Tyr Cys Asn Trp Ile Gly Trp Lys His Phe
65                  70                  75                  80

Ala Gln Tyr Phe Pro Met Thr Leu Val Lys Glu Gly Glu Leu Asp Pro
                85                  90                  95

Ser Lys Asn Tyr Ile Phe Gly Tyr His Pro His Gly Ile Ile Xaa Leu
            100                 105                 110

Gly Ala Leu Cys Ala Phe Gly Thr Glu Gly Leu His Phe Ser Lys Arg
        115                 120                 125

Phe Pro Gly Ile Lys Pro His Leu Leu Thr Ile His Ala Asn Phe Gln
130                 135                 140

Ile Pro Leu Tyr Arg Asp Met Ile Met Ala His Gly Cys Ala Ser Val
145                 150                 155                 160

Ser Arg Ala Ser Cys Glu His Ile Leu Arg Ser Gly Glu Gly Ser Ser
                165                 170                 175

Val Val Ile Val Val Gly Gly Ala Gln Glu Ser Leu Ser Thr Gln Pro
            180                 185                 190

Gly Thr Leu Asn Leu Thr Leu Lys Lys Arg Leu Gly Phe Cys Lys Leu
        195                 200                 205

Ala Phe Val Asn Gly Ala Ser Leu Val Pro Thr Leu Ala Phe Gly Glu
210                 215                 220

Asn Glu Leu Tyr Glu Val Tyr His Thr Lys Pro Thr Ser Leu Ile Tyr
225                 230                 235                 240

Lys Leu Gln Gln Leu Thr Lys Arg Thr Ile Gly Phe Thr Met Pro Val
                245                 250                 255

Phe Asn Gly Arg Gly Ile Phe Asn Xaa Glu Phe Gly Leu Leu Pro Arg
            260                 265                 270

Arg Lys Pro Val Tyr Ile Val Ile Gly Asn Pro Ile His Val Asp Lys
        275                 280                 285

Val Glu Asn Pro Thr Ile Glu Gln Met Gln Lys Leu Gln Ser Ile Tyr
290                 295                 300

Ile Asp Glu Val Leu Asn Ile Trp Glu Arg Tyr Lys Asp Lys Tyr Ala
305                 310                 315                 320

Ala Gly Arg Thr Gln Glu Leu Cys Ile Ile Glu
                325                 330
```

<210> SEQ ID NO 31
<211> LENGTH: 184
<212> TYPE: DNA
<213> ORGANISM: M alpina

<400> SEQUENCE: 31

| | |
|---|---|
| gtaccgaaac caacatggag gacggagagt cttttgagcg cagatttct ttttccttt | 60 |
| aatcatgttc gcacgtcccc cccccagct ttcttctcgt ctctaactgt aaccaacttt | 120 |
| ttgtcgaaat gcctgttgca tatttggaaa catactgatt ttttttttt tttcctactc | 180 |
| aaag | 184 |

<210> SEQ ID NO 32
<211> LENGTH: 8196
<212> TYPE: DNA
<213> ORGANISM: Artificial Sequence
<220> FEATURE:
<223> OTHER INFORMATION: Plasmid pY20

<400> SEQUENCE: 32

| | |
|---|---|
| tggagctcca gcttttgttc cctttagtga gggttaattt cgagcttggc gtaatcatgg | 60 |
| tcatagctgt ttcctgtgtg aaattgttat ccgctcacaa ttccacacaa catacgagcc | 120 |
| ggaagcataa agtgtaaagc ctggggtgcc taatgagtga gctaactcac attaattgcg | 180 |
| ttgcgctcac tgcccgcttt ccagtcggga acctgtcgt gccagctgca ttaatgaatc | 240 |
| ggccaacgcg cggggagagg cggtttgcgt attgggcgct cttccgcttc ctcgctcact | 300 |
| gactcgctgc gctcggtcgt tcggctgcgg cgagcggtat cagctcactc aaaggcggta | 360 |
| atacggttat ccacagaatc aggggataac gcaggaaaga acatgtgagc aaaaggccag | 420 |
| caaaaggcca ggaaccgtaa aaaggccgcg ttgctggcgt ttttccatag gctccgcccc | 480 |
| cctgacgagc atcacaaaaa tcgacgctca agtcagaggt ggcgaaaccc gacaggacta | 540 |
| taaagatacc aggcgtttcc ccctggaagc tccctcgtgc gctctcctgt tccgaccctg | 600 |
| ccgcttaccg gatacctgtc cgcctttctc ccttcgggaa gcgtggcgct ttctcatagc | 660 |
| tcacgctgta ggtatctcag ttcggtgtag gtcgttcgct ccaagctggg ctgtgtgcac | 720 |
| gaaccccccg ttcagcccga ccgctgcgcc ttatccggta actatcgtct tgagtccaac | 780 |
| ccggtaagac acgacttatc gccactggca gcagccactg gtaacaggat tagcagagcg | 840 |
| aggtatgtag gcggtgctac agagttcttg aagtggtggc ctaactacgg ctacactaga | 900 |
| aggacagtat ttggtatctg cgctctgctg aagccagtta ccttcggaaa aagagttggt | 960 |
| agctcttgat ccggcaaaca aaccaccgct ggtagcggtg ttttttgt ttgcaagcag | 1020 |
| cagattacgc gcagaaaaaa aggatctcaa gaagatcctt tgatcttttc tacggggtct | 1080 |
| gacgctcagt ggaacgaaaa ctcacgttaa gggattttgg tcatgagatt atcaaaaagg | 1140 |
| atcttcacct agatcctttt aaattaaaaa tgaagtttta atcaatcta agtatatat | 1200 |
| gagtaaactt ggtctgacag ttaccaatgc ttaatcagtg aggcacctat ctcagcgatc | 1260 |
| tgtctatttc gttcatccat agttgcctga ctccccgtcg tgtagataac tacgatacgg | 1320 |
| gagggcttac catctggccc cagtgctgca atgataccgc gagacccacg ctcaccggct | 1380 |
| ccagatttat cagcaataaa ccagccagcc ggaagggccg agcgcagaag tggtcctgca | 1440 |
| actttatccg cctccatcca gtctattaat tgttgccggg aagctagagt aagtagttcg | 1500 |
| ccagttaata gtttgcgcaa cgttgttgcc attgctacag gcatcgtggt gtcacgctcg | 1560 |
| tcgtttggta tggcttcatt cagctccggt tcccaacgat caaggcgagt tacatgatcc | 1620 |

```
cccatgttgt gcaaaaaagc ggttagctcc ttcggtcctc cgatcgttgt cagaagtaag    1680
ttggccgcag tgttatcact catggttatg gcagcactgc ataattctct tactgtcatg    1740
ccatccgtaa gatgcttttc tgtgactggt gagtactcaa ccaagtcatt ctgagaatag    1800
tgtatgcggc gaccgagttg ctcttgcccg gcgtcaatac gggataatac cgcgccacat    1860
agcagaactt taaaagtgct catcattgga aaacgttctt cggggcgaaa actctcaagg    1920
atcttaccgc tgttgagatc cagttcgatg taacccactc gtgcacccaa ctgatcttca    1980
gcatctttta ctttcaccag cgtttctggg tgagcaaaaa caggaaggca aaatgccgca    2040
aaaaagggaa taagggcgac acggaaatgt tgaatactca tactcttcct ttttcaatat    2100
tattgaagca tttatcaggg ttattgtctc atgagcggat acatatttga atgtatttag    2160
aaaaataaac aaataggggt tccgcgcaca tttccccgaa aagtgccacc tgacgcgccc    2220
tgtagcggcg cattaagcgc ggcgggtgtg tggttacgc gcagcgtgac cgctacactt    2280
gccagcgccc tagcgcccgc tcctttcgct ttcttccctt cctttctcgc cacgttcgcc    2340
ggctttcccc gtcaagctct aaatcggggg ctcccttag ggttccgatt tagtgcttta    2400
cggcacctcg accccaaaaa acttgattag ggtgatggtt cacgtagtgg gccatcgccc    2460
tgatagacgg ttttcgccc tttgacgttg gagtccacgt tctttaatag tggactcttg    2520
ttccaaactg gaacaacact caaccctatc tcggtctatt cttttgattt ataagggatt    2580
ttgccgattt cggcctattg gttaaaaaat gagctgattt aacaaaaatt taacgcgaat    2640
tttaacaaaa tattaacgct tacaatttcc attcgccatt caggctgcgc aactgttggg    2700
aagggcgatc ggtgcgggcc tcttcgctat tacgccagct ggcgaaaggg ggatgtgctg    2760
caaggcgatt aagttgggta acgccagggt ttttccagtc acgacgttgt aaaacgacgg    2820
ccagtgaatt gtaatacgac tcactatagg gcgaattggg taccgggccc cccctcgagg    2880
tcgacggtat cgataagctt gatatcgaat tcatgtcaca caaaccgatc ttcgcctcaa    2940
ggaaacctaa ttctacatcc gagagactgc cgagatccag tctacactga ttaattttcg    3000
ggccaataat ttaaaaaat cgtgttatat aatattatat gtattatata tacatcat      3060 gatgatactg acagtcatgt cccattgcta aatagacaga ctccatctgc cgcctccaac    3120
tgatgttctc aatatttaag gggtcatctc gcattgttta ataataaaca gactccatct    3180
accgcctcca aatgatgttc tcaaaatata ttgtatgaac ttatttttat tacttagtat    3240
tattagacaa cttacttgct ttatgaaaaa cacttcctat ttaggaaaca atttataatg    3300
gcagttcgtt catttaacaa tttatgtaga ataaatgtta taaatgcgta tgggaaatct    3360
taaatatgga tagcataaat gatatctgca ttgcctaatt cgaaatcaac agcaacgaaa    3420
aaaatccctt gtacaacata aatagtcatc gagaaatatc aactatcaaa gaacagctat    3480
tcacacgtta ctattgagat tattattgga cgagaatcac acactcaact gtctttctct    3540
cttctagaaa tacaggtaca agtatgtact attctcattg ttcatacttc tagtcatttc    3600
atcccacata ttccttggat ttctctccaa tgaatgacat tctatcttgc aaattcaaca    3660
attataataa gatataccaa agtagcggta tagtggcaat caaaaagctt ctctggtgtg    3720
cttctcgtat ttattttat tctaatgatc cattaaaggt atatatttat ttcttgttat    3780
ataatccttt tgtttattac atgggctgga tacataaagg tatttttgatt taattttttg    3840 cttaaattca atccccctc gttcagtgtc aactgtaatg gtaggaaatt accatacttt    3900
tgaagaagca aaaaaatga agaaaaaaa aaatcgtatt tccaggttag acgttccgca    3960
gaatctagaa tgcggtatgc ggtacattgt tcttcgaacg taaaagttgc gctccctgag    4020
```

```
atattgtaca tttttgcttt tacaagtaca agtacatcgt acaactatgt actactgttg    4080
atgcatccac aacagtttgt tttgttttt tttgttttt tttttctaa tgattcatta       4140 ccgctatgta tacctacttg tacttgtagt aagcccgggtt attggcgttc aattaatcat    4200
agacttatga atctgcacgg tgtgcgctgc gagttacttt tagcttatgc atgctacttg    4260
ggtgtaatat tgggatctgt tcggaaatca acggatgctc aaccgatttc gacagtaata    4320
atttgaatcg aatcggagcc taaaatgaac ccgagtatat ctcataaaat tctcggtgag    4380
aggtctgtga ctgtcagtac aaggtgcctt cattatgccc tcaaccttac catacctcac    4440
tgaatgtagt gtacctctaa aaatgaaata cagtgccaaa agccatggca ctgagctcgt    4500
ctaacggact tgatatacaa ccaattaaaa caaatgaaaa gaaatacagt tctttgtatc    4560
atttgtaaca attaccctgt acaaactaag gtattgaaat cccacaatat tcccaaagtc    4620
cacccctttc caaattgtca tgcctacaac tcatatacca agcactaacc taccaaacac    4680
cactaaaacc ccacaaaata tatcttaccg aatatacagt aacaagctac caccacactc    4740
gttgggtgca gtcgccagct taaagatatc tatccacatc agccacaact cccttccttt    4800
aataaaccga ctacacccctt ggctattgag gttatgagtg aatatactgt agacaagaca    4860
ctttcaagaa gactgtttcc aaaacgtacc actgtcctcc actacaaaca cacccaatct    4920
gcttcttcta gtcaaggttg ctacaccggt aaattataaa tcatcatttc attagcaggg    4980
cagggccctt tttatagagt cttatacact agcggaccct gccggtagac caacccgcag    5040
gcgcgtcagt ttgctccttc catcaatgcg tcgtagaaac gacttactcc ttcttgagca    5100
gctccttgac cttgttggca acaagtctcc gacctcggag gtggaggaag agcctccgat    5160
atcggcggta gtgataccag cctcgacgga ctccttgacg gcagcctcaa cagcgtcacc    5220
ggcgggcttc atgttaagag agaacttgag catcatggcg gcagacagaa tggtggcaat    5280
ggggttgacc ttctgcttgc cgagatcggg ggcagatccg tgacagggct cgtacagacc    5340
gaacgcctcg ttggtgtcgg gcagagaagc cagagaggcg gagggcagca gacccagaga    5400
accggggatg acgaggcct cgtcggagat gatatcgcca aacatgttgg tggtgatgat    5460
gataccattc atcttggagg gctgcttgat gaggatcatg gcggccgagt cgatcagctg    5520
gtggttgagc tcgagctggg ggaattcgtc cttgaggact cgagtgacag tctttcgcca    5580
aagtcgagag gaggccagca cgttggcctt gtcaagagac cacacgggaa gagggggggtt    5640 gtgctgaagg gccaggaagg cggccattcg ggcaattcgc tcaacctcag gaacggagta    5700
ggtctcggtg tcggaagcga cgccagatcc gtcatcctcc tttcgctctc caaagtagat    5760
acctccgacg agctctcgga caatgatgaa gtcggtgccc tcaacgtttc ggatggggga    5820
gagatcggcg agcttgggcg acagcagctg gcagggtcgc aggttggcgt acaggttcag    5880
gtcctttcgc agcttgagga gaccctgctc gggtcgcacg tcggttcgtc cgtcgggagt    5940
ggtccatacg gtgttggcag cgcctccgac agcaccgagc ataatagagt cagcctttcg    6000
gcagatgtcg agagtagcgt cggtgatggg ctcgccctcc ttctcaatgg cagctcctcc    6060
aatgagtcgg tcctcaaaca caaactcggt gccgaggcc tcagcaacag acttgagcac    6120
cttgacggcc tcggcaatca cctcgggcc acagaagtcg ccgccgagaa gaacaatctt    6180
cttggagtca gtcttggtct tcttagtttc gggttccatt gtggatgtgt gtggttgtat    6240
gtgtgatgtg gtgtgtggag tgaaaatctg tggctggcaa acgctcttgt atatatacgc    6300
acttttgccc gtgctatgtg gaagactaaa cctccgaaga ttgtgactca ggtagtgcgg    6360
tatcggctag ggacccaaac cttgtcgatg ccgatagcgc tatcgaacgt accccagccg    6420
```

```
gccgggagta tgtcggaggg gacatacgag atcgtcaagg gtttgtggcc aactggtaaa    6480
taaatgatga ctcaggcgac gacggaattc ctgcagccca tctgcagaat tcaggagaga    6540
ccgggttggc ggcgtatttg tgtcccaaaa aacagcccca attgcccaa ttgaccccaa     6600 attgacccag tagcgggccc aaccccggcg agagccccct tcaccccaca tatcaaacct    6660
cccccggttc ccacacttgc cgttaagggc gtagggtact gcagtctgga atctacgctt    6720
gttcagactt tgtactagtt tctttgtctg gccatccggg taacccatgc cggacgcaaa    6780
atagactact gaaaattttt ttgctttgtg gttgggactt tagccaaggg tataaaagac    6840
caccgtcccc gaattacctt tcctcttctt ttctctctct ccttgtcaac tcacacccga    6900
aatcgttaag catttccttc tgagtataag aatcattcaa aggatccact agttctagag    6960
cggccgctta aaccatgaaa aagcctgaac tcaccgcgac gtctgtcgag aagtttctga    7020
tcgaaaagtt cgacagcgtc tccgacctga tgcagctctc ggagggcgaa gaatctcgtg    7080
ctttcagctt cgatgtagga gggcgtggat atgtcctgcg ggtaaatagc tgcgccgatg    7140
gtttctacaa agatcgttat gtttatcggc actttgcatc ggccgcgctc ccgattccgg    7200
aagtgcttga cattggggaa ttcagcgaga gcctgaccta ttgcatctcc cgccgtgcac    7260
agggtgtcac gttgcaagac ctgcctgaaa ccgaactgcc cgctgttctg cagccggtcg    7320
cggaggccat ggatgcgatc gctgcggccg atcttagcca gacgagcggg ttcggcccat    7380
tcggaccgca aggaatcggt caatacacta catggcgtga tttcatatgc gcgattgctg    7440
atccccatgt gtatcactgg caaactgtga tggacgacac cgtcagtgcg tccgtcgcgc    7500
aggctctcga tgagctgatg ctttgggccg aggactgccc cgaagtccgg cacctcgtgc    7560
acgcggattt cggctccaac aatgtcctga cggacaatgg ccgcataaca gcggtcattg    7620
actggagcga ggcgatgttc ggggattccc aatacgaggt cgccaacatc ttcttctgga    7680
ggccgtggtt ggcttgtatg gagcagcaga cgcgctactt cgagcggagg catccggagc    7740
ttgcaggatc gccgcggctc cgggcgtata tgctccgcat tggtcttgac caactctatc    7800
agagcttggt tgacggcaat ttcgatgatg cagcttgggc gcagggtcga tgcgacgcaa    7860
tcgtccgatc cggagccggg actgtcgggc gtacacaaat cgcccgcaga agcgcggccg    7920
tctggaccga tggctgtgta gaagtactcg ccgatagtgg aaaccgacgc cccagcactc    7980
gtccgagggc aaaggaatag tgaggtacct aaagcggccg ccaccgcggc ccgagattcc    8040
ggcctcttcg gccgccaagc gacccggtg gacgtctaga ggtacctagc aattaacaga    8100
tagtttgccg gtgataattc tcttaacctc ccacactcct ttgacataac gatttatgta    8160
acgaaactga aatttgacca gatattgtgt ccgcgg                              8196
```

<210> SEQ ID NO 33
<211> LENGTH: 1026
<212> TYPE: DNA
<213> ORGANISM: Escherichia coli

<400> SEQUENCE: 33

```
atgaaaaagc ctgaactcac cgcgacgtct gtcgagaagt ttctgatcga aaagttcgac     60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
```

-continued

```
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg agcgaggcg     660 atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 34
<211> LENGTH: 341
<212> TYPE: PRT
<213> ORGANISM: Escherichia coli

<400> SEQUENCE: 34

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255
```

```
Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 35
<211> LENGTH: 1710
<212> TYPE: DNA
<213> ORGANISM: Yarrowia lipolytica

<400> SEQUENCE: 35
gtcgacgagt atctgtctga ctcgtcattg ccgcctttgg agtacgactc caactatgag     60
tgtgcttgga tcactttgac gatacattct tcgttggagg ctgtgggtct gacagctgcg    120
ttttcggcgc ggttggccga caacaatatc agctgcaacg tcattgctgg ctttcatcat    180
gatcacattt ttgtcggcaa aggcgacgcc cagagagcca ttgacgttct ttctaatttg    240
gaccgatagc cgtatagtcc agtctatcta aagttcaac taactcgtaa ctattaccat    300
aacatatact tcactgcccc agataaggtt ccgataaaaa gttctgcaga ctaaatttat    360
ttcagtctcc tcttcaccac caaaatgccc tcctacgaag ctcgagctaa cgtccacaag    420
tccgcctttg ccgctcgagt gctcaagctc gtggcagcca agaaaaccaa cctgtgtgct    480
tctctggatg ttaccaccac caaggagctc attgagcttg ccgataaggt cggacccttat   540 gtgtgcatga tcaagaccca tatcgacatc attgacgact tcacctacgc cggcactgtg    600
ctccccctca aggaacttgc tcttaagcac ggtttcttcc tgttcgagga cagaaagttc    660
gcagatattg caacactgt caagcaccag tacaagaacg gtgtctaccg aatcgccgag    720
tggtccgata tcaccaacgc ccacggtgta cccggaaccg gaatcattgc tggcctgcga    780
gctggtgccg aggaaactgt ctctgaacag aagaaggagg acgtctctga ctacgagaac    840
tcccagtaca aggagttcct ggtccccctct cccaacgaga gctggccag aggtctgctc    900 atgctggccg agctgtcttg caagggctct ctggccactg gcgagtactc caagcagacc    960
attgagcttg cccgatccga ccccgagttt gtggttggct tcattgccca gaaccgacct   1020
aagggcgact ctgaggactg gcttattctg accccccgggg tgggtcttga cgacaaggga   1080
gacgctctcg acagcagta ccgaactgtt gaggatgtca tgtctaccgg aacggatatc    1140
ataattgtcg gccgaggtct gtacggccag aaccgagatc ctattgagga ggccaagcga   1200
taccagaagg ctggctggga ggcttaccag aagattaact gttagaggtt agactatgga   1260
tatgtcattt aactgtgtat atagagagcg tgcaagtatg gagcgcttgt tcagcttgta   1320
tgatggtcag acgacctgtc tgatcgagta tgtatgatac tgcacaacct gtgtatccgc   1380
atgatctgtc caatggggca tgttgttgtg tttctcgata cggagatgct gggtacaagt   1440
agctaatacg attgaactac ttatacttat atgaggcttg aagaaagctg acttgtgtat   1500
gacttattct caactacatc cccagtcaca ataccaccac tgcactacca ctacaccaaa   1560
accatgatca aaccacccat ggacttcctg gaggcagaag aacttgttat ggaaaagctc   1620
```
aagagagaga agccaagata ctatcaagac atgtgtcgca acttcaagga ggaccaagct    1680
ctgtacaccg agaaacaggc ctttgtcgac                                     1710

<210> SEQ ID NO 36
<211> LENGTH: 286
<212> TYPE: PRT
<213> ORGANISM: Yarrowia lipolytica

<400> SEQUENCE: 36

Met Pro Ser Tyr Glu Ala Arg Ala Asn Val His Lys Ser Ala Phe Ala
1               5                   10                  15

Ala Arg Val Leu Lys Leu Val Ala Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125

Ala Gly Leu Arg Ala Gly Ala Glu Glu Thr Val Ser Glu Gln Lys Lys
    130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Val Gly Phe Ile Ala
        195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Val Gly
                245                 250                 255

Arg Gly Leu Tyr Gly Gln Asn Arg Asp Pro Ile Glu Glu Ala Lys Arg
            260                 265                 270

Tyr Gln Lys Ala Gly Trp Glu Ala Tyr Gln Lys Ile Asn Cys
        275                 280                 285

<210> SEQ ID NO 37
<211> LENGTH: 35
<212> TYPE: DNA
<213> ORGANISM: Artificial Sequence
<220> FEATURE:
<223> OTHER INFORMATION: Primer KU5

<400> SEQUENCE: 37
tttgcccggg cgagtatctg tctgactcgt cattg                                 35

```
<210> SEQ ID NO 38
<211> LENGTH: 33
<212> TYPE: DNA
<213> ORGANISM: Artificial Sequence
<220> FEATURE:
<223> OTHER INFORMATION: Primer KU3

<400> SEQUENCE: 38
aaagcccggg caaaggcctg tttctcggtg tac                                   33

<210> SEQ ID NO 39
<211> LENGTH: 29
<212> TYPE: DNA
<213> ORGANISM: Artificial Sequence
<220> FEATURE:
<223> OTHER INFORMATION: Primer P7
<220> FEATURE:
<221> NAME/KEY: misc_feature
<222> LOCATION: (24)..(24)
<223> OTHER INFORMATION: n is a, c, g, or t

<400> SEQUENCE: 39
aactacatct tcggctayca yccncaygg                                        29

<210> SEQ ID NO 40
<211> LENGTH: 10
<212> TYPE: PRT
<213> ORGANISM: Artificial Sequence
<220> FEATURE:
<223> OTHER INFORMATION: DGAT2 Consensus Sequence

<400> SEQUENCE: 40

Asn Tyr Ile Phe Gly Tyr His Pro His Gly
1               5                   10

<210> SEQ ID NO 41
<211> LENGTH: 29
<212> TYPE: DNA
<213> ORGANISM: Artificial Sequence
<220> FEATURE:
<223> OTHER INFORMATION: Primer P8
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 41
agggactcgg aggcgccgcc ncanacdat                                        29

<210> SEQ ID NO 42
<211> LENGTH: 10
<212> TYPE: PRT
<213> ORGANISM: Artificial Sequence
<220> FEATURE:
<223> OTHER INFORMATION: DGAT2 Consensus Sequence

<400> SEQUENCE: 42

Ile Val Val Gly Gly Ala Ser Glu Ser Leu
1               5                   10

<210> SEQ ID NO 43
<211> LENGTH: 2119
<212> TYPE: DNA
<213> ORGANISM: Yarrowia lipolytica
<220> FEATURE:
<221> NAME/KEY: CDS
```

```
<222> LOCATION: (291)..(1835)
<223> OTHER INFORMATION: DGAT2 opening reading frame, comprising 2
      smaller internal opening reading frames
<220> FEATURE:
<221> NAME/KEY: misc_feature
<222> LOCATION: (291)..(293)
<223> OTHER INFORMATION: initiation codon ('ATG')
<220> FEATURE:
<221> NAME/KEY: misc_feature
<222> LOCATION: (456)..(458)
<223> OTHER INFORMATION: initiation codon ('ATG')
<220> FEATURE:
<221> NAME/KEY: misc_feature
<222> LOCATION: (768)..(770)
<223> OTHER INFORMATION: initiation codon ('ATG')

<400> SEQUENCE: 43
aaacgcaccc actgctcgtc ctccttgctc ctcgaaaccg actcctctac acacgtcaaa      60
tccgaggttg aaatcttccc cacatttggc agccaaacca gcacatccca gcaacctcgc     120
acagcgccga atcgacctg tcgacttggc acaaaaaaa agcaccggct ctgcaacagt       180
tctcacgacc aattacgtac aagtacgaaa tcgttcgtgg accgtgactg ataagctccc    240 acttttctt ctaacaacag gcaacagaca agtcacacaa acaaaagct atg act          296
                                                        Met Thr
                                                         1 atc gac tca caa tac tac aag tcg cga gac aaa aac gac acg gca ccc       344
Ile Asp Ser Gln Tyr Tyr Lys Ser Arg Asp Lys Asn Asp Thr Ala Pro
     5               10                  15 aaa atc gcg gga atc cga tat gcc ccg cta tcg aca cca tta ctc aac       392
Lys Ile Ala Gly Ile Arg Tyr Ala Pro Leu Ser Thr Pro Leu Leu Asn
 20                  25                  30 cga tgt gag acc ttc tct ctg gtc tgg cac att ttc agc att ccc act       440
Arg Cys Glu Thr Phe Ser Leu Val Trp His Ile Phe Ser Ile Pro Thr
 35                  40                  45                  50 ttc ctc aca att ttc atg cta tgc tgc gca att cca ctg ctc tgg cca       488
Phe Leu Thr Ile Phe Met Leu Cys Cys Ala Ile Pro Leu Leu Trp Pro
             55                  60                  65 ttt gtg att gcg tat gta gtg tac gct gtt aaa gac gac tcc ccg tcc       536
Phe Val Ile Ala Tyr Val Val Tyr Ala Val Lys Asp Asp Ser Pro Ser
         70                  75                  80 aac gga gga gtg gtc aag cga tac tcg cct att tca aga aac ttc ttc       584
Asn Gly Gly Val Val Lys Arg Tyr Ser Pro Ile Ser Arg Asn Phe Phe
     85                  90                  95 atc tgg aag ctc ttt ggc cgc tac ttc ccc ata act ctg cac aag acg       632
Ile Trp Lys Leu Phe Gly Arg Tyr Phe Pro Ile Thr Leu His Lys Thr
100                 105                 110 gtg gat ctg gag ccc acg cac aca tac tac cct ctg gac gtc cag gag       680
Val Asp Leu Glu Pro Thr His Thr Tyr Tyr Pro Leu Asp Val Gln Glu
115                 120                 125                 130 tat cac ctg att gct gag aga tac tgg ccg cag aac aag tac ctc cga       728
Tyr His Leu Ile Ala Glu Arg Tyr Trp Pro Gln Asn Lys Tyr Leu Arg
            135                 140                 145 gca atc atc tcc acc atc gag tac ttt ctg ccc gcc ttc atg aaa cgg       776
Ala Ile Ile Ser Thr Ile Glu Tyr Phe Leu Pro Ala Phe Met Lys Arg
        150                 155                 160 tct ctt tct atc aac gag cag gag cag cct gcc gag cga gat cct ctc       824
Ser Leu Ser Ile Asn Glu Gln Glu Gln Pro Ala Glu Arg Asp Pro Leu
    165                 170                 175 ctg tct ccc gtt tct ccc agc tct ccg ggt tct caa cct gac aag tgg       872
Leu Ser Pro Val Ser Pro Ser Ser Pro Gly Ser Gln Pro Asp Lys Trp
180                 185                 190 att aac cac gac agc aga tat agc cgt gga gaa tca tct ggc tcc aac       920
Ile Asn His Asp Ser Arg Tyr Ser Arg Gly Glu Ser Ser Gly Ser Asn
```

```
                195                 200                 205                 210
ggc cac gcc tcg ggc tcc gaa ctt aac ggc aac ggc aac aat ggc acc       968
Gly His Ala Ser Gly Ser Glu Leu Asn Gly Asn Gly Asn Asn Gly Thr
                        215                 220                 225 act aac cga cga cct ttg tcg tcc gcc tct gct ggc tcc act gca tct      1016
Thr Asn Arg Arg Pro Leu Ser Ser Ala Ser Ala Gly Ser Thr Ala Ser
                230                 235                 240 gat tcc acg ctt ctt aac ggg tcc ctc aac tcc tac gcc aac cag atc      1064
Asp Ser Thr Leu Leu Asn Gly Ser Leu Asn Ser Tyr Ala Asn Gln Ile
            245                 250                 255 att ggc gaa aac gac cca cag ctg tcg ccc aca aaa ctc aag ccc act      1112
Ile Gly Glu Asn Asp Pro Gln Leu Ser Pro Thr Lys Leu Lys Pro Thr
        260                 265                 270 ggc aga aaa tac atc ttc ggc tac cac ccc cac ggc att atc ggc atg      1160
Gly Arg Lys Tyr Ile Phe Gly Tyr His Pro His Gly Ile Ile Gly Met
275                 280                 285                 290 gga gcc ttt ggt gga att gcc acc gag gga gct gga tgg tcc aag ctc      1208
Gly Ala Phe Gly Gly Ile Ala Thr Glu Gly Ala Gly Trp Ser Lys Leu
                        295                 300                 305 ttt ccg ggc atc cct gtt tct ctt atg act ctc acc aac aac ttc cga      1256
Phe Pro Gly Ile Pro Val Ser Leu Met Thr Leu Thr Asn Asn Phe Arg
                310                 315                 320 gtg cct ctc tac aga gag tac ctc atg agt ctg gga gtc gct tct gtc      1304
Val Pro Leu Tyr Arg Glu Tyr Leu Met Ser Leu Gly Val Ala Ser Val
            325                 330                 335 tcc aag aag tcc tgc aag gcc ctc ctc aag cga aac cag tct atc tgc      1352
Ser Lys Lys Ser Cys Lys Ala Leu Leu Lys Arg Asn Gln Ser Ile Cys
        340                 345                 350 att gtc gtt ggt gga gca cag gaa agt ctt ctg gcc aga ccc ggt gtc      1400
Ile Val Val Gly Gly Ala Gln Glu Ser Leu Leu Ala Arg Pro Gly Val
355                 360                 365                 370 atg gac ctg gtg cta ctc aag cga aag ggt ttt gtt cga ctt ggt atg      1448
Met Asp Leu Val Leu Leu Lys Arg Lys Gly Phe Val Arg Leu Gly Met
                        375                 380                 385 gag gtc gga aat gtc gcc ctt gtt ccc atc atg gcc ttt ggt gag aac      1496
Glu Val Gly Asn Val Ala Leu Val Pro Ile Met Ala Phe Gly Glu Asn
                390                 395                 400 gac ctc tat gac cag gtt agc aac gac aag tcg tcc aag ctg tac cga      1544
Asp Leu Tyr Asp Gln Val Ser Asn Asp Lys Ser Ser Lys Leu Tyr Arg
            405                 410                 415 ttc cag cag ttt gtc aag aac ttc ctt gga ttc acc ctt cct ttg atg      1592
Phe Gln Gln Phe Val Lys Asn Phe Leu Gly Phe Thr Leu Pro Leu Met
        420                 425                 430 cat gcc cga ggc gtc ttc aac tac gat gtc ggt ctt gtc ccc tac agg      1640
His Ala Arg Gly Val Phe Asn Tyr Asp Val Gly Leu Val Pro Tyr Arg
435                 440                 445                 450 cga ccc gtc aac att gtg gtt ggt tcc ccc att gac ttg cct tat ctc      1688
Arg Pro Val Asn Ile Val Val Gly Ser Pro Ile Asp Leu Pro Tyr Leu
                        455                 460                 465 cca cac ccc acc gac gaa gaa gtg tcc gaa tac cac gac cga tac atc      1736
Pro His Pro Thr Asp Glu Glu Val Ser Glu Tyr His Asp Arg Tyr Ile
                470                 475                 480 gcc gag ctg cag cga atc tac aac gag cac aag gat gaa tat ttc atc      1784
Ala Glu Leu Gln Arg Ile Tyr Asn Glu His Lys Asp Glu Tyr Phe Ile
            485                 490                 495 gat tgg acc gag gag ggc aaa gga gcc cca gag ttc cga atg att gag      1832
Asp Trp Thr Glu Glu Gly Lys Gly Ala Pro Glu Phe Arg Met Ile Glu
        500                 505                 510 taa ggaaaactgc ctgggttagg caaatagcta atgagtattt ttttgatggc           1885
```

```
aaccaaatgt agaaagaaaa aaaaaaaaaa agaaaaaaaa aagagaatat tatatctatg    1945
taattctatt aaaagctctg ttgagtgagc ggaataaata ctgttgaaga ggggattgtg    2005
tagagatctg tttactcaat ggcaaactca tctgggggag atccttccac tgtgggaagc    2065
tcctggatag cctttgcatc ggggttcaag aagaccattg tgaacagccc ttga          2119

<210> SEQ ID NO 44
<211> LENGTH: 514
<212> TYPE: PRT
<213> ORGANISM: Yarrowia lipolytica

<400> SEQUENCE: 44

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
```

-continued

```
                    340                 345                 350
Ile Cys Ile Val Val Gly Gly Ala Gln Glu Ser Leu Leu Ala Arg Pro
            355                 360                 365
Gly Val Met Asp Leu Val Leu Leu Lys Arg Lys Gly Phe Val Arg Leu
    370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Ser Lys Leu
                405                 410                 415
Tyr Arg Phe Gln Gln Phe Val Lys Asn Phe Leu Gly Phe Thr Leu Pro
            420                 425                 430
Leu Met His Ala Arg Gly Val Phe Asn Tyr Asp Val Gly Leu Val Pro
    435                 440                 445
Tyr Arg Arg Pro Val Asn Ile Val Val Gly Ser Pro Ile Asp Leu Pro
    450                 455                 460
Tyr Leu Pro His Pro Thr Asp Glu Glu Val Ser Glu Tyr His Asp Arg
465                 470                 475                 480
Tyr Ile Ala Glu Leu Gln Arg Ile Tyr Asn Glu His Lys Asp Glu Tyr
                485                 490                 495
Phe Ile Asp Trp Thr Glu Glu Gly Lys Gly Ala Pro Glu Phe Arg Met
            500                 505                 510
Ile Glu

<210> SEQ ID NO 45
<211> LENGTH: 23
<212> TYPE: DNA
<213> ORGANISM: Artificial Sequence
<220> FEATURE:
<223> OTHER INFORMATION: Primer P80

<400> SEQUENCE: 45
gggcatccct gtttctctta tga                                           23

<210> SEQ ID NO 46
<211> LENGTH: 23
<212> TYPE: DNA
<213> ORGANISM: Artificial Sequence
<220> FEATURE:
<223> OTHER INFORMATION: Primer P81

<400> SEQUENCE: 46
aacttccgag tgcctctcta cag                                           23

<210> SEQ ID NO 47
<211> LENGTH: 24
<212> TYPE: DNA
<213> ORGANISM: Artificial Sequence
<220> FEATURE:
<223> OTHER INFORMATION: LinkAmp Primer 1

<400> SEQUENCE: 47
aggcacagtc gaggacttat ccta                                          24

<210> SEQ ID NO 48
<211> LENGTH: 29
<212> TYPE: DNA
<213> ORGANISM: Artificial Sequence
<220> FEATURE:
<223> OTHER INFORMATION: Primer P95

<400> SEQUENCE: 48
```

```
ggcaagctta ttgtcgttgg tggagcaca                                       29

<210> SEQ ID NO 49
<211> LENGTH: 35
<212> TYPE: DNA
<213> ORGANISM: Artificial Sequence
<220> FEATURE:
<223> OTHER INFORMATION: Primer P96

<400> SEQUENCE: 49
aattccacca gatctgtcgt ggtattcgga cactt                                35

<210> SEQ ID NO 50
<211> LENGTH: 39
<212> TYPE: DNA
<213> ORGANISM: Artificial Sequence
<220> FEATURE:
<223> OTHER INFORMATION: Primer P97

<400> SEQUENCE: 50
ataccacgac agatctggtg gaattgccac cgagggagc                            39

<210> SEQ ID NO 51
<211> LENGTH: 30
<212> TYPE: DNA
<213> ORGANISM: Artificial Sequence
<220> FEATURE:
<223> OTHER INFORMATION: Primer P98

<400> SEQUENCE: 51
gcggaattcg cagatagact ggtttcgctt                                      30

<210> SEQ ID NO 52
<211> LENGTH: 22
<212> TYPE: DNA
<213> ORGANISM: Artificial Sequence
<220> FEATURE:
<223> OTHER INFORMATION: Primer P115

<400> SEQUENCE: 52
aactacatct tcggctatca cc                                              22

<210> SEQ ID NO 53
<211> LENGTH: 22
<212> TYPE: DNA
<213> ORGANISM: Artificial Sequence
<220> FEATURE:
<223> OTHER INFORMATION: Primer P116

<400> SEQUENCE: 53
tgaacaagcg tagattccag ac                                              22

<210> SEQ ID NO 54
<211> LENGTH: 22
<212> TYPE: DNA
<213> ORGANISM: Artificial Sequence
<220> FEATURE:
<223> OTHER INFORMATION: Primer P112

<400> SEQUENCE: 54
cacccttgct cggcgatgta tc                                              22

<210> SEQ ID NO 55
<211> LENGTH: 29
<212> TYPE: DNA
<213> ORGANISM: Artificial Sequence
<220> FEATURE:
```

```
<223> OTHER INFORMATION: Primer P26
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 55
atgctggaca aggagaccgg nctngaycc                                        29

<210> SEQ ID NO 56
<211> LENGTH: 10
<212> TYPE: PRT
<213> ORGANISM: Artificial Sequence
<220> FEATURE:
<223> OTHER INFORMATION: PDAT Consensus Sequence

<400> SEQUENCE: 56

Met Leu Asp Lys Glu Thr Gly Leu Asp Pro
1               5                   10

<210> SEQ ID NO 57
<211> LENGTH: 33
<212> TYPE: DNA
<213> ORGANISM: Artificial Sequence
<220> FEATURE:
<223> OTHER INFORMATION: Primer P27
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 57
ccagatgacg tcgccgccct tgggnarcat nga                                   33

<210> SEQ ID NO 58
<211> LENGTH: 11
<212> TYPE: PRT
<213> ORGANISM: Artificial Sequence
<220> FEATURE:
<223> OTHER INFORMATION: PDAT Consensus Sequence

<400> SEQUENCE: 58

Ser Met Leu Pro Lys Gly Gly Glu Val Ile Trp
1               5                   10

<210> SEQ ID NO 59
<211> LENGTH: 2326
<212> TYPE: DNA
<213> ORGANISM: Yarrowia lipolytica
<220> FEATURE:
<221> NAME/KEY: misc_feature
<222> LOCATION: (2271)..(2271)
<223> OTHER INFORMATION: n is a, c, g, or t

<400> SEQUENCE: 59
tattaatatt atgctcttca tgcaccagca aaataaccga aacgcgcata tgatagtggg       60
attctcgatt tgcccggcag acaaacgccg ctaaaatcgc cacagtatcg aattttaatt     120
gaatacgaac gtcaattccg gcttatcctt ctagcagttg tctcccgcag ctcgctccat    180
gactaatcat tcacgcgaca tgtctcagct accccggtct ggctcatgta aaaaaagtgt    240
```

```
aatcggcttt tttccggttg atcacaacca tcaatgacac aacctgtgaa tcggaaggcg     300
actgtcgagc gggtcgagcc agcagtggag gtggctgact ccgagtccga ggccaagacc     360
gacgtccacg ttcaccacca tcatcaccac cacaagcgaa atccgtcaa gggcaagatt      420
ctcaacttct tcacccgaag tcgacgtatc accttcgtcc tcggcgccgt ggtcggtgtg     480
atagccgcgg gatactacgc tgcgccaccg gagctcagca ttgatatcga tgctcttctc     540
ggcgacttgc cctcgttcga ctttgacgct ctatctctcg acaacttgtc catggacagt     600
gtgtcggact ttgtacaaga catgaaatcg cggtttccga ccaagattct gcaggaggcg     660
gccaagatcg agaagcacca gaaaagcgaa cagaaggctg ccccttttgc tgtgggcaag     720
gctatgaaga gcgagggact caacgccaag tacccggtgg tgctggtgcc cggcgtcatc     780
tccacgggac tggagagctg gtccctggag ggaaccgagg agtgtcccac cgagtcgcac     840
ttcagaaagc gaatgtgggg ctcctggtac atgatccgag tcatgctgct ggacaagtac     900
tgctggctgc agaacctgat gctggacaca gagaccggtc tagaccctcc ccatttcaag     960
ctgcgagccg cccagggatt tgcctccgcc gacttcttta tggcaggcta ctggctgtgg    1020
aacaagctgc tcgagaacct ggctgttatt ggatacgata cggatacaat gtctgctgcg    1080
gcgtacgact ggagactgtc ctaccctgat ttggagcacc gagacggata cttctccaag    1140
ctcaaagctt caatcgaaga gactaagcgt atgacaggtg agaagacagt tctgacgggc    1200
cattccatgg gctcccaggt catcttctac ttcatgaagt gggctgaggc cgagggatat    1260
ggaggaggag gtcccaactg ggtcaatgac catattgaat cctttgtcga catttccggc    1320
tccatgctgg gtactcccaa gaccctggtt gctcttctgt ctggagaaat gaaggatacc    1380
gtgcagctga acgcgatggc tgtgtatgga ctggagcagt tcttctctcg acgagagcga    1440
gccgatctgc tgcgaacatg gggaggaatt gcttccatga ttcccaaggg tggtaaggct    1500
atctggggtg atcattctgg agccctgat gacgagcccg gccagaatgt caccttggc     1560
aacttcatca gttcaagga gtccttgacc gagtactctg ctaagaacct caccatggat    1620
gaaaccgttg acttcctgta ttctcagtct cccgagtggt ttgtgaaccg aaccgagggt    1680
gcttactcct ttggaattgc caagactcga aagcaggttg agcagaatga aagcgacct     1740
tctacctgga gcaaccctct ggaagctgct ctccccaatg ccccgatct caagatctac    1800
tgcttctatg gagtcggtaa ggataccgag cgagcctact actaccagga tgagcccaat    1860
cccgagcaga ccaacttgaa cgtcagtatc gctggaaacg accctgatgg tgtgcttatg    1920
ggtcagggcg atggaaccgt ctcccttgtg acccatacca tgtgtcaccg atggaaggac    1980
gagaattcca agttcaaccc tggtaacgcc caggtcaagg ttgtggagat gttgcaccag    2040
cctgatcgac ttgatattcg aggcggtgct cagactgccg agcatgtgga cattctgggg    2100
cgttctgagt tgaacgagat ggttctgaag gtggctagtg aaagggaaa tgagattgaa     2160
gagagagtca tctccaacat tgatgagtgg gtgtggaaga ttgatctcgg cagcaattag    2220
agagtccgtt ttgtagagta atatgttttg tatatcacac tgatggagaa nggcgttcga    2280
tttctcatga ttccatgtgg ttgtttaatg agcacgtaga acgacg                   2326
```

<210> SEQ ID NO 60
<211> LENGTH: 648
<212> TYPE: PRT
<213> ORGANISM: Yarrowia lipolytica

<400> SEQUENCE: 60

```
Met Thr Gln Pro Val Asn Arg Lys Ala Thr Val Glu Arg Val Glu Pro
1               5                   10                  15
```

```
Ala Val Glu Val Ala Asp Ser Glu Ser Glu Ala Lys Thr Asp Val His
            20              25              30

Val His His His His His His Lys Arg Lys Ser Val Lys Gly Lys
        35              40              45

Ile Leu Asn Phe Phe Thr Arg Ser Arg Arg Ile Thr Phe Val Leu Gly
50              55              60

Ala Val Val Gly Val Ile Ala Ala Gly Tyr Tyr Ala Ala Pro Pro Glu
65              70              75              80

Leu Ser Ile Asp Ile Asp Ala Leu Leu Gly Asp Leu Pro Ser Phe Asp
                85              90              95

Phe Asp Ala Leu Ser Leu Asp Asn Leu Ser Met Asp Ser Val Ser Asp
            100             105             110

Phe Val Gln Asp Met Lys Ser Arg Phe Pro Thr Lys Ile Leu Gln Glu
            115             120             125

Ala Ala Lys Ile Glu Lys His Gln Lys Ser Glu Gln Lys Ala Ala Pro
130             135             140

Phe Ala Val Gly Lys Ala Met Lys Ser Glu Gly Leu Asn Ala Lys Tyr
145             150             155             160

Pro Val Val Leu Val Pro Gly Val Ile Ser Thr Gly Leu Glu Ser Trp
                165             170             175

Ser Leu Glu Gly Thr Glu Glu Cys Pro Thr Glu Ser His Phe Arg Lys
            180             185             190

Arg Met Trp Gly Ser Trp Tyr Met Ile Arg Val Met Leu Leu Asp Lys
            195             200             205

Tyr Cys Trp Leu Gln Asn Leu Met Leu Asp Thr Glu Thr Gly Leu Asp
210             215             220

Pro Pro His Phe Lys Leu Arg Ala Ala Gln Gly Phe Ala Ser Ala Asp
225             230             235             240

Phe Phe Met Ala Gly Tyr Trp Leu Trp Asn Lys Leu Leu Glu Asn Leu
                245             250             255

Ala Val Ile Gly Tyr Asp Thr Asp Thr Met Ser Ala Ala Ala Tyr Asp
            260             265             270

Trp Arg Leu Ser Tyr Pro Asp Leu Glu His Arg Asp Gly Tyr Phe Ser
            275             280             285

Lys Leu Lys Ala Ser Ile Glu Glu Thr Lys Arg Met Thr Gly Glu Lys
290             295             300

Thr Val Leu Thr Gly His Ser Met Gly Ser Gln Val Ile Phe Tyr Phe
305             310             315             320

Met Lys Trp Ala Glu Ala Glu Gly Tyr Gly Gly Gly Pro Asn Trp
                325             330             335

Val Asn Asp His Ile Glu Ser Phe Val Asp Ile Ser Gly Ser Met Leu
            340             345             350

Gly Thr Pro Lys Thr Leu Val Ala Leu Leu Ser Gly Glu Met Lys Asp
            355             360             365

Thr Val Gln Leu Asn Ala Met Ala Val Tyr Gly Leu Glu Gln Phe Phe
            370             375             380

Ser Arg Arg Glu Arg Ala Asp Leu Leu Arg Thr Trp Gly Gly Ile Ala
385             390             395             400

Ser Met Ile Pro Lys Gly Gly Lys Ala Ile Trp Gly Asp His Ser Gly
                405             410             415

Ala Pro Asp Asp Glu Pro Gly Gln Asn Val Thr Phe Gly Asn Phe Ile
            420             425             430

Lys Phe Lys Glu Ser Leu Thr Glu Tyr Ser Ala Lys Asn Leu Thr Met
```

```
                    435                 440                 445

Asp Glu Thr Val Asp Phe Leu Tyr Ser Gln Ser Pro Glu Trp Phe Val
            450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Gln Asp Glu Pro
        515                 520                 525

Asn Pro Glu Gln Thr Asn Leu Asn Val Ser Ile Ala Gly Asn Asp Pro
        530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
            580                 585                 590

Leu Asp Ile Arg Gly Gly Ala Gln Thr Ala Glu His Val Asp Ile Leu
        595                 600                 605

Gly Arg Ser Glu Leu Asn Glu Met Val Leu Lys Val Ala Ser Gly Lys
        610                 615                 620

Gly Asn Glu Ile Glu Glu Arg Val Ile Ser Ile Asp Glu Trp Val
625                 630                 635                 640

Trp Lys Ile Asp Leu Gly Ser Asn
                645

<210> SEQ ID NO 61
<211> LENGTH: 34
<212> TYPE: DNA
<213> ORGANISM: Artificial Sequence
<220> FEATURE:
<223> OTHER INFORMATION: Primer P39

<400> SEQUENCE: 61
ggcggtaccg gatcctcaat cgaagagact aagc                              34

<210> SEQ ID NO 62
<211> LENGTH: 30
<212> TYPE: DNA
<213> ORGANISM: Artificial Sequence
<220> FEATURE:
<223> OTHER INFORMATION: Primer P42

<400> SEQUENCE: 62
ccggaattca gctttgagct tggagaagta                                    30

<210> SEQ ID NO 63
<211> LENGTH: 5105
<212> TYPE: DNA
<213> ORGANISM: Artificial Sequence
<220> FEATURE:
<223> OTHER INFORMATION: Plasmid pLV13
<220> FEATURE:
<221> NAME/KEY: misc_feature
<222> LOCATION: (4446)..(4446)
<223> OTHER INFORMATION: n is a, c, g, or t

<400> SEQUENCE: 63
gtacgagccg gaagcataaa gtgtaaagcc tggggtgcct aatgagtgag ctaactcaca   60
```

```
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg ttttttttgtt    900 tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg aagggccga gcgcagaagt   1320 ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca ataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga cccaaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
```

```
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatta agtcatacac aagtcagctt tcttcgagcc tcatataagt    2640
ataagtagtt caacgtatta gcactgtacc cagcatctcc gtatcgagaa acacaacaac    2700
atgccccatt ggacagatca tgcggataca caggttgtgc agtatcatac atactcgatc    2760
agacaggtcg tctgaccatc atacaagctg aacaagcgct ccatacttgc acgctctcta    2820
tatacacagt taaattacat atccatagtc taacctctaa cagttaatct tctggtaagc    2880
ctcccagcca gccttctggt atcgcttggc ctcctcaata ggatctcggt tctggccgta    2940
cagacctcgg ccgacaatta tgatatccgt tccggtagac atgacatcct caacagttcg    3000
gtactgctgt ccgagagcgt ctcccttgtc gtcaagaccc accccggggg tcagaataag    3060
ccagtcctca gagtcgccct taggtcggtt ctgggcaatg aagccaacca caaactcggg    3120
gtcggatcgg gcaagctcaa tggtctgctt ggagtactcg ccagtggcca gagagcccctt   3180 gcaagacagc tcggccagca tgagcagacc tctggccagc ttctcgttgg gagaggggac    3240
taggaactcc ttgtactggg agttctcgta gtcagagacg tcctccttct tctgttcaga    3300
gacagtttcc tcggcaccag ctcgcaggcc agcaatgatt ccggttccgg gtacaccgtg    3360
ggcgttggtg atatcggacc actcggcgat tcggtgacac cggtactggt gcttgacagt    3420
gttgccaata tctgcgaact ttctgtcctc gaacaggaag aaaccgtgct taagagcaag    3480
ttccttgagg gggagcacag tgccggcgta ggtgaagtcg tcaatgatgt cgatatgggt    3540
tttgatcatg cacacataag gtccgacctt atcggcaagc tcaatgagct ccttggtggt    3600
ggtaacatcc agagaagcac acaggttggt tttcttggct gccacgagct tgagcactcg    3660
agcggcaaag gcggacttgt ggacgttagc tcgagcttcg taggagggca ttttggtggt    3720
gaagaggaga ctgaaataaa tttagtctgc agaactttt atcggaacct tatctggggc    3780
agtgaagtat atgttatggt aatagttacg agttagttga acttatagat agactggact    3840
atacggctat cggtccaaat tagaaagaac gtcaatggct ctctgggcgt cgcctttgcc    3900
gacaaaaatg tgatcatgat gaaagccagc aatgacgttg cagctgatat tgttgtcggc    3960
caaccgcgcc gaaaacgcag ctgtcagacc cacagcctcc aacgaagaat gtatcgtcaa    4020
agtgatccaa gcacactcat agttggagtc gtactccaaa ggcggcaatg acgagtcaga    4080
cagatactcg tcgactcagg cgacgacgga attcagcttt gagcttggag aagtatccgt    4140
ctcggtgctc caaatcaggg taggacagtc tccagtcgta cgccgcagca gacattgtat    4200
ccgtatcgta tccaataaca gccaggttct cgagcagctt gttccacagc cagtagcctg    4260
ccataaagaa gtcggcggag gcaaatccct gggcggctcg cagcttgaaa tggggagggt    4320
ctagaccggt ctctgtgtcc agcatcaggt tctgcagcca gcagtacttg tccagcagca    4380
tgactcggat catgtaccag gagccccaca ttcgctttct gaagtcgcac tcggtgggac    4440
actccnyggt tccctccagg gaccagctct ccagtcccgt ggagatgacg ccgggcacca    4500
gcaccaccgg gtacttggcg ttgagtccct cgctcttcat agccttgccc acagcaaaag    4560
gggcagcctt ctgttcgctt ttctggtgct tctcgatctt gagatctaga atacagaagt    4620
caacggttca tccatggtga ggtcttagca gagtactcgg tcaagactcc ttgaacttga    4680
tgaagttgcc aaaggtgaca ttctggccgg gctcgtcatc aggggctcca gaatgatcac    4740
cccagatagc cttaccaccc ttgggaatca tggaagcaat tcctcccat gttcgcagca    4800 gatcggctcg ctctcgtcga gagaagaact gctccagtcc atacacagcc atcgcgttca    4860
```

```
gctgcacggt atccttcatt tctccagaca gaagagcaac cagggtcttg ggagtaccca    4920
gcatggagcc ggaaatgtcg acaaaggatt caatatggtc attgacccag ttgggacctc    4980
ctcctccata tccctcggcc tcagcccact tcatgaagta gaagatgacc tgggagccca    5040
tggaatggcc cgtcagaact gtcttctcac ctgtcatacg cttagtctct tcgattgagg    5100
atccg                                                                5105
```

<210> SEQ ID NO 64
<211> LENGTH: 41
<212> TYPE: DNA
<213> ORGANISM: Artificial Sequence
<220> FEATURE:
<223> OTHER INFORMATION: Primer P41

<400> SEQUENCE: 64

```
cttctgtatt ctagatctca agatcgagaa gcaccagaaa a                         41
```

<210> SEQ ID NO 65
<211> LENGTH: 48
<212> TYPE: DNA
<213> ORGANISM: Artificial Sequence
<220> FEATURE:
<223> OTHER INFORMATION: Primer P40

<400> SEQUENCE: 65

```
gcttctcgat cttgagatct agaatacaga agtcaacggt tcatccat                  48
```

<210> SEQ ID NO 66
<211> LENGTH: 22
<212> TYPE: DNA
<213> ORGANISM: Artificial Sequence
<220> FEATURE:
<223> OTHER INFORMATION: Primer P51

<400> SEQUENCE: 66

```
tagatagact ggactatacg gc                                              22
```

<210> SEQ ID NO 67
<211> LENGTH: 20
<212> TYPE: DNA
<213> ORGANISM: Artificial Sequence
<220> FEATURE:
<223> OTHER INFORMATION: Primer P52

<400> SEQUENCE: 67

```
gactgtccta ccctgatttg                                                 20
```

<210> SEQ ID NO 68
<211> LENGTH: 33
<212> TYPE: DNA
<213> ORGANISM: Artificial Sequence
<220> FEATURE:
<223> OTHER INFORMATION: Primer P37

<400> SEQUENCE: 68

```
ccaggtacca agatcgagaa gcaccagaaa agc                                  33
```

<210> SEQ ID NO 69
<211> LENGTH: 36
<212> TYPE: DNA
<213> ORGANISM: Artificial Sequence
<220> FEATURE:
<223> OTHER INFORMATION: Primer P38

<400> SEQUENCE: 69

```
ctcgaattca gaatacagaa gtcaacggtt catcca                              36
```

<210> SEQ ID NO 70
<211> LENGTH: 23
<212> TYPE: DNA
<213> ORGANISM: Artificial Sequence
<220> FEATURE:
<223> OTHER INFORMATION: Primer P79

<400> SEQUENCE: 70

```
tctctgtaga gaggcactcg gaa                                            23
```

<210> SEQ ID NO 71
<211> LENGTH: 23
<212> TYPE: DNA
<213> ORGANISM: Artificial Sequence
<220> FEATURE:
<223> OTHER INFORMATION: Primer P84

<400> SEQUENCE: 71

```
tgacgccggg caccagcacc acc                                            23
```

<210> SEQ ID NO 72
<211> LENGTH: 24
<212> TYPE: DNA
<213> ORGANISM: Artificial Sequence
<220> FEATURE:
<223> OTHER INFORMATION: Primer P85

<400> SEQUENCE: 72

```
gtcacctttg gcaacttcat caag                                           24
```

<210> SEQ ID NO 73
<211> LENGTH: 1380
<212> TYPE: DNA
<213> ORGANISM: Yarrowia lipolytica

<400> SEQUENCE: 73

```
atgctatgct gcgcaattcc actgctctgg ccatttgtga ttgcgtatgt agtgtacgct     60
gttaaagacg actccccgtc caacggagga gtggtcaagc gatactcgcc tatttcaaga    120
aacttcttca tctggaagct cttttggccgc tacttcccca taactctgca caagacggtg   180
gatctggagc ccacgcacac atactaccct ctggacgtcc aggagtatca cctgattgct    240
gagagatact ggccgcagaa caagtacctc cgagcaatca tctccaccat cgagtacttt    300
ctgcccgcct tcatgaaacg gtctctttct atcaacgagc aggagcagcc tgccgagcga    360
gatcctctcc tgtctcccgt ttctcccagc tctccgggtt ctcaacctga caagtggatt    420
aaccacgaca gcagatatag ccgtggagaa tcatctggcc caacggcca cgcctcgggc     480
tccgaactta acggcaacgg caacaatggc accactaacc gacgacccttt gtcgtccgcc   540
tctgctggct ccactgcatc tgattccacg cttcttaacg ggtccctcaa ctcctacgcc    600
aaccagatca ttggcgaaaa cgacccacag ctgtcgccca caaaactcaa gcccactggc    660
agaaaataca tcttcggcta ccacccccac ggcattatcg gcatgggagc ctttggtgga    720
attgccaccg agggagctgg atggtccaag ctctttccgg gcatccctgt ttctcttatg    780
actctcacca caacttccg agtgcctctc tacagagagt acctcatgag tctgggagtc    840
gcttctgtct ccaagaagtc ctgcaaggcc ctcctcaagc gaaaccagtc tatctgcatt    900
gtcgttggtg gagcacagga aagtcttctg gccagacccg tgtcatgga cctggtgcta    960
ctcaagcgaa agggtttttgt tcgacttggt atggaggtcg gaaatgtcgc ccttgttccc   1020
```

-continued

```
atcatggcct tggtgagaa cgacctctat gaccaggtta gcaacgacaa gtcgtccaag    1080
ctgtaccgat tccagcagtt tgtcaagaac ttccttggat tcacccttcc tttgatgcat    1140
gcccgaggcg tcttcaacta cgatgtcggt cttgtcccct acaggcgacc cgtcaacatt    1200
gtggttggtt cccccattga cttgccttat ctcccacacc ccaccgacga agaagtgtcc    1260
gaataccacg accgatacat cgccgagctg cagcgaatct acaacgagca caaggatgaa    1320
tatttcatcg attggaccga ggagggcaaa ggagccccag agttccgaat gattgagtaa    1380
```

<210> SEQ ID NO 74
<211> LENGTH: 459
<212> TYPE: PRT
<213> ORGANISM: Yarrowia lipolytica

<400> SEQUENCE: 74

```
Met Leu Cys Cys Ala Ile Pro Leu Leu Trp Pro Phe Val Ile Ala Tyr
1               5                   10                  15

Val Val Tyr Ala Val Lys Asp Asp Pro Ser Asn Gly Gly Val Val
            20                  25                  30

Lys Arg Tyr Ser Pro Ile Ser Arg Asn Phe Phe Ile Trp Lys Leu Phe
        35                  40                  45

Gly Arg Tyr Phe Pro Ile Thr Leu His Lys Thr Val Asp Leu Glu Pro
    50                  55                  60

Thr His Thr Tyr Tyr Pro Leu Asp Val Gln Glu Tyr His Leu Ile Ala
65                  70                  75                  80

Glu Arg Tyr Trp Pro Gln Asn Lys Tyr Leu Arg Ala Ile Ile Ser Thr
                85                  90                  95

Ile Glu Tyr Phe Leu Pro Ala Phe Met Lys Arg Ser Leu Ser Ile Asn
            100                 105                 110

Glu Gln Glu Gln Pro Ala Glu Arg Asp Pro Leu Leu Ser Pro Val Ser
        115                 120                 125

Pro Ser Ser Pro Gly Ser Gln Pro Asp Lys Trp Ile Asn His Asp Ser
    130                 135                 140

Arg Tyr Ser Arg Gly Glu Ser Ser Gly Ser Asn Gly His Ala Ser Gly
145                 150                 155                 160

Ser Glu Leu Asn Gly Asn Gly Asn Asn Gly Thr Thr Asn Arg Arg Pro
                165                 170                 175

Leu Ser Ser Ala Ser Ala Gly Ser Thr Ala Ser Asp Ser Thr Leu Leu
            180                 185                 190

Asn Gly Ser Leu Asn Ser Tyr Ala Asn Gln Ile Ile Gly Glu Asn Asp
        195                 200                 205

Pro Gln Leu Ser Pro Thr Lys Leu Lys Pro Thr Gly Arg Lys Tyr Ile
    210                 215                 220

Phe Gly Tyr His Pro His Gly Ile Ile Gly Met Gly Ala Phe Gly Gly
225                 230                 235                 240

Ile Ala Thr Glu Gly Ala Gly Trp Ser Lys Leu Phe Pro Gly Ile Pro
                245                 250                 255

Val Ser Leu Met Thr Leu Thr Asn Asn Phe Arg Val Pro Leu Tyr Arg
            260                 265                 270

Glu Tyr Leu Met Ser Leu Gly Val Ala Ser Val Ser Lys Lys Ser Cys
        275                 280                 285

Lys Ala Leu Leu Lys Arg Asn Gln Ser Ile Cys Ile Val Val Gly Gly
    290                 295                 300

Ala Gln Glu Ser Leu Leu Ala Arg Pro Gly Val Met Asp Leu Val Leu
305                 310                 315                 320
```

```
Leu Lys Arg Lys Gly Phe Val Arg Leu Gly Met Glu Val Asn Val
                325                 330                 335

Ala Leu Val Pro Ile Met Ala Phe Gly Glu Asn Asp Leu Tyr Asp Gln
            340                 345                 350

Val Ser Asn Asp Lys Ser Ser Lys Leu Tyr Arg Phe Gln Gln Phe Val
        355                 360                 365

Lys Asn Phe Leu Gly Phe Thr Leu Pro Leu Met His Ala Arg Gly Val
370                 375                 380

Phe Asn Tyr Asp Val Gly Leu Val Pro Tyr Arg Pro Val Asn Ile
385                 390                 395                 400

Val Val Gly Ser Pro Ile Asp Leu Pro Tyr Leu Pro His Pro Thr Asp
            405                 410                 415

Glu Glu Val Ser Glu Tyr His Asp Arg Tyr Ile Ala Glu Leu Gln Arg
        420                 425                 430

Ile Tyr Asn Glu His Lys Asp Glu Tyr Phe Ile Asp Trp Thr Glu Glu
            435                 440                 445

Gly Lys Gly Ala Pro Glu Phe Arg Met Ile Glu
450                 455
```

<210> SEQ ID NO 75
<211> LENGTH: 1068
<212> TYPE: DNA
<213> ORGANISM: Yarrowia lipolytica

<400> SEQUENCE: 75

```
atgaaacggt ctctttctat caacgagcag gagcagcctg ccgagcgaga tcctctcctg      60
tctcccgttt ctcccagctc tccgggttct caacctgaca gtggattaac ccacgacagc     120
agatatagcc gtggagaatc atctggctcc aacggccacg cctcgggctc gaacttaac      180
ggcaacggca acaatggcac cactaaccga cgacctttgt cgtccgcctc tgctggctcc     240
actgcatctg attccacgct tcttaacggg tccctcaact cctacgccaa ccagatcatt     300
ggcgaaaacg acccacagct gtcgcccaca aaactcaagc ccactggcag aaaatacatc     360
ttcggctacc accccacgg cattatcggc atggagcct tggtggaat tgccaccgag         420
ggagctggat ggtccaagct cttccgggc atccctgttt ctcttatgac tctcaccaac     480
aacttccgag tgcctctcta cagagagtac ctcatgagtc tgggagtcgc ttctgtctcc     540
aagaagtcct gcaaggcccct cctcaagcga accagtcta tctgcattgt cgttggtgga     600
gcacaggaaa gtcttctggc cagacccggt gtcatggacc tggtgctact caagcgaaag     660
ggttttgttc gacttggtat ggaggtcgga atgtcgccc ttgttcccat catggccttt       720
ggtgagaacg acctctatga ccaggttagc aacgacaagt cgtccaagct gtaccgattc     780
cagcagtttg tcaagaactt ccttggattc acccttcctt tgatgcatgc cgaggcgtc      840
ttcaactacg atgtcggtct tgtccctac aggcgacccg tcaacattgt ggttggttcc     900
cccattgact tgccttatct cccacacccc accgacgaag aagtgtccga ataccacgac     960
cgatacatcg ccgagctgca gcgaatctac aacgagcaca aggatgaata tttcatcgat    1020
tggaccgagg agggcaaagg agccccagag ttccgaatga ttgagtaa                  1068
```

<210> SEQ ID NO 76
<211> LENGTH: 355
<212> TYPE: PRT
<213> ORGANISM: Yarrowia lipolytica

<400> SEQUENCE: 76

Met Lys Arg Ser Leu Ser Ile Asn Glu Gln Glu Gln Pro Ala Glu Arg
1               5                   10                  15

Asp Pro Leu Leu Ser Pro Val Ser Pro Ser Ser Pro Gly Ser Gln Pro
                20                  25                  30

Asp Lys Trp Ile Asn His Asp Ser Arg Tyr Ser Arg Gly Glu Ser Ser
            35                  40                  45

Gly Ser Asn Gly His Ala Ser Gly Ser Glu Leu Asn Gly Asn Gly Asn
        50                  55                  60

Asn Gly Thr Thr Asn Arg Arg Pro Leu Ser Ser Ala Ser Ala Gly Ser
65                  70                  75                  80

Thr Ala Ser Asp Ser Thr Leu Leu Asn Gly Ser Leu Asn Ser Tyr Ala
                85                  90                  95

Asn Gln Ile Ile Gly Glu Asn Asp Pro Gln Leu Ser Pro Thr Lys Leu
            100                 105                 110

Lys Pro Thr Gly Arg Lys Tyr Ile Phe Gly Tyr His Pro His Gly Ile
        115                 120                 125

Ile Gly Met Gly Ala Phe Gly Gly Ile Ala Thr Glu Gly Ala Gly Trp
    130                 135                 140

Ser Lys Leu Phe Pro Gly Ile Pro Val Ser Leu Met Thr Leu Thr Asn
145                 150                 155                 160

Asn Phe Arg Val Pro Leu Tyr Arg Glu Tyr Leu Met Ser Leu Gly Val
                165                 170                 175

Ala Ser Val Ser Lys Lys Ser Cys Lys Ala Leu Leu Lys Arg Asn Gln
            180                 185                 190

Ser Ile Cys Ile Val Val Gly Gly Ala Gln Glu Ser Leu Leu Ala Arg
        195                 200                 205

Pro Gly Val Met Asp Leu Val Leu Leu Lys Arg Lys Gly Phe Val Arg
    210                 215                 220

Leu Gly Met Glu Val Gly Asn Val Ala Leu Val Pro Ile Met Ala Phe
225                 230                 235                 240

Gly Glu Asn Asp Leu Tyr Asp Gln Val Ser Asn Asp Lys Ser Ser Lys
                245                 250                 255

Leu Tyr Arg Phe Gln Gln Phe Val Lys Asn Phe Leu Gly Phe Thr Leu
            260                 265                 270

Pro Leu Met His Ala Arg Gly Val Phe Asn Tyr Asp Val Gly Leu Val
        275                 280                 285

Pro Tyr Arg Arg Pro Val Asn Ile Val Val Gly Ser Pro Ile Asp Leu
    290                 295                 300

Pro Tyr Leu Pro His Pro Thr Asp Glu Glu Val Ser Glu Tyr His Asp
305                 310                 315                 320

Arg Tyr Ile Ala Glu Leu Gln Arg Ile Tyr Asn Glu His Lys Asp Glu
                325                 330                 335

Tyr Phe Ile Asp Trp Thr Glu Glu Gly Lys Gly Ala Pro Glu Phe Arg
            340                 345                 350

Met Ile Glu
        355

<210> SEQ ID NO 77
<211> LENGTH: 1632
<212> TYPE: DNA
<213> ORGANISM: Yarrowia lipolytica (strain CLIB99, chromosome F;
      GenBank Accession No. NC_006072, bases 974607-976238, locus_tag=
      "YALI0F06578g")

<400> SEQUENCE: 77
atggccacac tccaccccga agacgccgca ggacggcccg tgcgacgacg acctcgtccc    60

```
tccagttcgg gcggctccag atcgccgtcc accaaacgac actcgatagt gcgggagcat      120
ctcggagaag agctcaatgt gcccgacggc caggaaatgg acctgggcca ggtcaacaag      180
aacctcaatg ccgcatacgc caaggccgag aaggactcgg acgacgagaa ggaaaagaag      240
gaggagggcg tggtggacga gctgccagag aagtattcct accctcgatt ctcaaagaac      300
aaccgacgct acagattcac cgacatcaag ttcaagccaa caccgtcgat tctcgacaag      360
ttcgcccaca aggactcgga gttctttggc ttctacaccc tgctgtggat ggtgtttgcc      420
ttctgcgtct tccgaaccgg cctgctcaac tacacaaacg aaggcatcct gttccggggc      480
cagattttcg ccattctcag caaagatctc tggaaagtcg cattggtcga tctgggcatg      540
tacctgacca cctatctgtc tgtgtttctg caattggccg tcaagcacgg tctggtcgac      600
tggaactcgt ttggctggat catccagaac gtgcaccaga ccctgttcct cttcttctac      660
ctttgggtcg ccaagtcgag taacctgcct tggatcggta acatcttcat tgtgcttcat      720
gcctttgtca tgctcatgaa acaacactcg tacgccttct acaatggcta cctatggact      780
gtcgaggacg agctctccca cgcaaagcag cgtctcaccg aagacattcc tgtttcagag      840
aaggaggatc tcaagctgga catcgagttc tgcgagacag agctcaaggt ccaatccaga      900
cacacccctt tccccaccaa catcaccttt tctaactact tctggtactc catgttccca      960
acgctcgtct acgaaattga gttccctcga acccccgaa tcaagtggac atacgtgctg     1020
gagaaggtcg ccgcagtctt tggcgtcttc ttccttatga tctgggtcgc agagtcgtac     1080
ctgtatcccc ctgtggtggc tgttattcaa atgcgagacg aacccttctg gaacaaggtc     1140
cgaatctatc ccattttcct gtcggacatt ctgctgccct tgtcattga gtacatgctt     1200 gttttctaca tcatctggga cgccattctc aacggcattg ccgagctcac tcgcttcgcc     1260
gacagagact tttatggccc ctggtggaac tgtaccagct gggagcagtt tagccgagaa     1320
tggaacattc ctgtctacca gttcctcaag cgacacgtct accactcgtc catctctgct     1380
ttcaagttct ccaagggcgc agctaccctc accaccttct gctgtcttc tcttgtccac     1440 gagctggtca tgtttgccat cttttaagaag ttccgaggat acctgctgtt gctgcagatg     1500
acccagctgc ccctggccat gctgcagaaa accaaatgga tccaggacag accgtttttt     1560
ggcaacgctt tcttctggtt ctcgctcatg atcggacctt ctctcatgtg ttccatgtac     1620
ctcctcttct aa                                                          1632
```

<210> SEQ ID NO 78
<211> LENGTH: 543
<212> TYPE: PRT
<213> ORGANISM: Yarrowia lipolytica (strain CLIB99, chromosome F;
      GenBank Accession No. NC_006072, locus_tag="YALI0F06578g")

<400> SEQUENCE: 78

Met Ala Thr Leu His Pro Glu Asp Ala Ala Gly Arg Pro Val Arg Arg
1               5                   10                  15

Arg Pro Arg Pro Ser Ser Ser Gly Gly Ser Arg Ser Pro Ser Thr Lys
            20                  25                  30

Arg His Ser Ile Val Arg Glu His Leu Gly Glu Glu Leu Asn Val Pro
        35                  40                  45

Asp Gly Gln Glu Met Asp Leu Gly Gln Val Asn Lys Asn Leu Asn Ala
    50                  55                  60

Ala Tyr Ala Lys Ala Glu Lys Asp Ser Asp Asp Glu Lys Glu Lys Lys
65                  70                  75                  80

Glu Glu Gly Val Val Asp Glu Leu Pro Glu Lys Tyr Ser Tyr Pro Arg

-continued

```
                    85                  90                  95
Phe Ser Lys Asn Asn Arg Arg Tyr Arg Phe Thr Asp Ile Lys Phe Lys
            100                 105                 110
Pro Thr Pro Ser Ile Leu Asp Lys Phe Ala His Lys Asp Ser Glu Phe
        115                 120                 125
Phe Gly Phe Tyr Thr Leu Leu Trp Met Val Phe Ala Phe Cys Val Phe
    130                 135                 140
Arg Thr Gly Leu Leu Asn Tyr Thr Asn Glu Gly Ile Leu Phe Arg Gly
145                 150                 155                 160
Gln Ile Phe Ala Ile Leu Ser Lys Asp Leu Trp Lys Val Ala Leu Val
                165                 170                 175
Asp Leu Gly Met Tyr Leu Thr Thr Tyr Leu Ser Val Phe Leu Gln Leu
            180                 185                 190
Ala Val Lys His Gly Leu Val Asp Trp Asn Ser Phe Gly Trp Ile Ile
        195                 200                 205
Gln Asn Val His Gln Thr Leu Phe Leu Phe Phe Tyr Leu Trp Val Ala
    210                 215                 220
Lys Ser Ser Asn Leu Pro Trp Ile Gly Asn Ile Phe Ile Val Leu His
225                 230                 235                 240
Ala Phe Val Met Leu Met Lys Gln His Ser Tyr Ala Phe Tyr Asn Gly
                245                 250                 255
Tyr Leu Trp Thr Val Glu Asp Glu Leu Ser His Ala Lys Gln Arg Leu
            260                 265                 270
Thr Glu Asp Ile Pro Val Ser Glu Lys Glu Asp Leu Lys Leu Asp Ile
        275                 280                 285
Glu Phe Cys Glu Thr Glu Leu Lys Val Gln Ser Arg His Thr Pro Phe
    290                 295                 300
Pro Thr Asn Ile Thr Phe Ser Asn Tyr Phe Trp Tyr Ser Met Phe Pro
305                 310                 315                 320
Thr Leu Val Tyr Glu Ile Glu Phe Pro Arg Thr Pro Arg Ile Lys Trp
                325                 330                 335
Thr Tyr Val Leu Glu Lys Val Ala Ala Val Phe Gly Val Phe Phe Leu
            340                 345                 350
Met Ile Trp Val Ala Glu Ser Tyr Leu Tyr Pro Pro Val Val Ala Val
        355                 360                 365
Ile Gln Met Arg Asp Glu Pro Phe Trp Asn Lys Val Arg Ile Tyr Pro
    370                 375                 380
Ile Phe Leu Ser Asp Ile Leu Leu Pro Phe Val Ile Glu Tyr Met Leu
385                 390                 395                 400
Val Phe Tyr Ile Ile Trp Asp Ala Ile Leu Asn Gly Ile Ala Glu Leu
                405                 410                 415
Thr Arg Phe Ala Asp Arg Asp Phe Tyr Gly Pro Trp Trp Asn Cys Thr
            420                 425                 430
Ser Trp Glu Gln Phe Ser Arg Glu Trp Asn Ile Pro Val Tyr Gln Phe
        435                 440                 445
Leu Lys Arg His Val Tyr His Ser Ser Ile Ser Ala Phe Lys Phe Ser
    450                 455                 460
Lys Gly Ala Ala Thr Leu Thr Thr Phe Leu Leu Ser Ser Leu Val His
465                 470                 475                 480
Glu Leu Val Met Phe Ala Ile Phe Lys Lys Phe Arg Gly Tyr Leu Leu
                485                 490                 495
Leu Leu Gln Met Thr Gln Leu Pro Leu Ala Met Leu Gln Lys Thr Lys
            500                 505                 510
```

```
Trp Ile Gln Asp Arg Pro Val Phe Gly Asn Ala Phe Phe Trp Ser
    515                 520                 525

Leu Met Ile Gly Pro Ser Leu Met Cys Ser Met Tyr Leu Leu Phe
    530                 535                 540
```

<210> SEQ ID NO 79
<211> LENGTH: 1581
<212> TYPE: DNA
<213> ORGANISM: Yarrowia lipolytica (strain CLIB99, chromosome D;
      GenBank Accession No. CR382130, bases 1026155-1027735, locus_tag=
      "YALI0D07986g")

<400> SEQUENCE: 79

```
atggaagtcc gacgacgaaa aatcgacgtg ctcaaggccc agaaaaacgg ctacgaatcg      60
ggcccaccat ctcgacaatc gtcgcagccc tcctcaagag catcgtccag aacccgcaac     120
aaacactcct cgtccaccct gtcgctcagc ggactgacca tgaaagtcca agagaaacct     180
gcgggacccc cggcgaactc caaaacgcca ttcctacaca tcaagcccgt gcacacgtgc     240
tgctccacat caatgctttc gcgcgattat gacggctcca accccagctt caagggcttc     300
aaaaacatcg gcatgatcat tctcattgtg ggaaatctac ggctcgcatt cgaaaactac     360
ctcaaatacg gcatttccaa cccgttcttc gaccccaaaa ttactccttc cgagtggcag     420
ctctcaggct tgctcatagt cgtggcctac gcacatatcc tcatggccta cgctattgag     480
agcgctgcca agctgctgtt cctctctagc aaacaccact acatggccgt ggggcttctg     540
cataccatga acactttgtc gtccatctcg ttgctgtcct acgtcgtcta ctactacctg     600
cccaaccccg tggcaggcac aatagtcgag tttgtggccg ttattctgtc tctcaaactc     660
gcctcatacg ccctcactaa ctcggatctc gaaaagccg caattcatgc cagaagctc      720
gacaagacgc aagacgataa cgaaaaggaa tccacctcgt cttcctcttc ttcagatgac     780
gcagagactt tggcagacat tgacgtcatt cctgcatact acgcacagct gccctacccc     840
cagaatgtga cgctgtcgaa cctgctgtac ttctggtttg ctcccacact ggtctaccag     900
cccgtgtacc caagacgga gcgtattcga cccaagcacg tgatccgaaa cctgtttgag      960
ctcgtctctc tgtgcatgct tattcagttt ctcatcttcc agtacgccta ccccatcatg    1020
cagtcgtgtc tggctctgtt cttccagccc aagctcgatt atgccaacat ctccgagcgc    1080
ctcatgaagt tggcctccgt gtctatgatg gtctggctca ttggattcta cgctttcttc    1140
cagaacggtc tcaatcttat tgccgagctc acctgttttg gaaacagaac cttctaccag    1200
cagtggtgga attcccgctc cattggccag tactggactc tatggaacaa gccagtcaac    1260
cagtacttta gacaccacgt ctacgtgcct cttctcgctc ggggcatgtc gcggttcaat    1320
gcgtcggtgg tggttttctt tttctccgcc gtcatccatg aactgcttgt cggcatcccc    1380
actcacaaca tcatcggagc cgccttcttc ggcatgatgt cgcaggtgcc tctgatcatg    1440
gctactgaga accttcagca tattaactcc tctctgggcc ccttccttgg caactgtgca    1500
ttctggttca cctttttcct gggacaaccc acttgtgcat tcctttatta tctggcttac    1560
aactacaagc agaaccagta g                                              1581
```

<210> SEQ ID NO 80
<211> LENGTH: 526
<212> TYPE: PRT
<213> ORGANISM: Yarrowia lipolytica (strain CLIB99, chromosome D;
      GenBank Accession No. CR382130, locus_tag="YALI0D07986g")

<400> SEQUENCE: 80

Met Glu Val Arg Arg Arg Lys Ile Asp Val Leu Lys Ala Gln Lys Asn

-continued

```
1               5                   10                  15
Gly Tyr Glu Ser Gly Pro Pro Ser Arg Gln Ser Ser Gln Pro Ser Ser
                20                  25                  30

Arg Ala Ser Ser Arg Thr Arg Asn Lys His Ser Ser Thr Leu Ser
            35                  40                  45

Leu Ser Gly Leu Thr Met Lys Val Gln Lys Pro Ala Gly Pro Pro
50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
                100                 105                 110

Leu Arg Leu Ala Phe Glu Asn Tyr Leu Lys Tyr Gly Ile Ser Asn Pro
            115                 120                 125

Phe Phe Asp Pro Lys Ile Thr Pro Ser Glu Trp Gln Leu Ser Gly Leu
            130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
            195                 200                 205

Val Glu Phe Val Ala Val Ile Leu Ser Leu Lys Leu Ala Ser Tyr Ala
210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
            275                 280                 285

Leu Tyr Phe Trp Phe Ala Pro Thr Leu Val Tyr Gln Pro Val Tyr Pro
            290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
            355                 360                 365

Met Met Val Trp Leu Ile Gly Phe Tyr Ala Phe Phe Gln Asn Gly Leu
370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430
```

```
Ala Arg Gly Met Ser Arg Phe Asn Ala Ser Val Val Phe Phe Phe
            435                 440                 445

Ser Ala Val Ile His Glu Leu Leu Val Gly Ile Pro Thr His Asn Ile
    450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495

Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
            515                 520                 525

<210> SEQ ID NO 81
<211> LENGTH: 41
<212> TYPE: DNA
<213> ORGANISM: Artificial Sequence
<220> FEATURE:
<223> OTHER INFORMATION: Primer P201

<400> SEQUENCE: 81
ctcgcggccg ccatggaggt ccgacgacga aarathgayg t                  41

<210> SEQ ID NO 82
<211> LENGTH: 46
<212> TYPE: DNA
<213> ORGANISM: Artificial Sequence
<220> FEATURE:
<223> OTHER INFORMATION: Primer P203
<220> FEATURE:
<221> NAME/KEY: misc_feature
<222> LOCATION: (38)..(38)
<223> OTHER INFORMATION: n is a, c, g, or t

<400> SEQUENCE: 82
gaggcggccg ctactggttc tgcttgtagt tgtaggcnar rtarta           46

<210> SEQ ID NO 83
<211> LENGTH: 1578
<212> TYPE: DNA
<213> ORGANISM: Yarrowia lipolytica

<400> SEQUENCE: 83
atggaggtcc gacgacgaaa gatagacgtg ctcaaggccc agaaaaacgg ctacgaatcg    60
ggcccaccat ctcgacaatc gtcgcagccc tcctcaagag catcgtccag aacccgcaac   120
aaacactcct cgtccaccct gtcgctcagc ggactgacca tgaaagtcca gaagaaacct   180
gcgggacccc cggcgaactc caaaacgcca ttcctacaca tcaagcccgt gcacacgtgc   240
tgctccacat caatgctttc gcgcgattat gacggctcca accccagctt caagggcttc   300
aaaaacatcg gcatgatcat tctcattgtg ggaaatctac ggctcgcatt cgaaaactac   360
ctcaaatacg gcatttccaa cccgttcttc gaccccaaaa ttactccttc cgagtggcag   420
ctctcaggct tgctcatagt cgtggcctac gcacatatcc tcatggccta cgctattgag   480
agcgctgcca agctgctgtt cctctctagc aaacaccact acatggccgt ggggcttctg   540
cataccatga acactttgtc gtccatctcg ttgctgtcct acgtcgtcta ctactacctg   600
cccaaccccg tggcaggcac aatagtcgag tttgtggccg ttattctgtc tctcaaactc   660
gcctcatacg ccctcactaa ctcggatctc cgaaaagccg caattcatgc ccagaagctc   720
gacaagacgc aagacgataa cgaaaaggaa tccacctcgt cttcctcttc ttcagatgac   780
```

-continued

```
gcagagactt tggcagacat tgacgtcatt cctgcatact acgcacagct gccctacccc    840
cagaatgtga cgctgtcgaa cctgctgtac ttctggtttg ctcccacact ggtctaccag    900
cccgtgtacc ccaagacgga gcgtattcga cccaagcacg tgatccgaaa cctgtttgag    960
ctcgtctctc tgtgcatgct tattcagttt ctcatcttcc agtacgccta ccccatcatg   1020
cagtcgtgtc tggctctgtt cttccagccc aagctcgatt atgccaacat ctccgagcgc   1080
ctcatgaagt tggcctccgt gtctatgatg gtctggctca ttggattcta cgctttcttc   1140
cagaacggtc tcaatcttat tgccgagctc acctgttttg aaacagaac cttctaccag    1200 cagtggtgga attcccgctc cattggccag tactggactc tatggaacaa gccagtcaac   1260
cagtacttta gacaccacgt ctacgtgcct cttctcgctc ggggcatgtc gcggttcaat   1320
gcgtcggtgg tggttttctt tttctccgcc gtcatccatg aactgcttgt cggcatcccc   1380
actcacaaca tcatcggagc cgccttcttc ggcatgatgt cgcaggtgcc tctgatcatg   1440
gctactgaga accttcagca tattaactcc tctctgggcc ccttccttgg caactgtgca   1500
ttctggttca ccttttttcct gggacaaccc acttgtgcat tcctttacta tttggcctac   1560
aactacaagc agaaccag                                                  1578
```

<210> SEQ ID NO 84
<211> LENGTH: 526
<212> TYPE: PRT
<213> ORGANISM: Yarrowia lipolytica
<220> FEATURE:
<221> NAME/KEY: misc_feature
<222> LOCATION: (518)..(518)
<223> OTHER INFORMATION: Xaa can be any naturally occurring amino acid

<400> SEQUENCE: 84

Met Glu Val Arg Arg Lys Ile Asp Val Leu Lys Ala Gln Lys Asn
1               5                  10                 15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
```

```
                210                 215                 220
Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
                260                 265                 270

Tyr Tyr Ala Gln Leu Pro Tyr Pro Gln Asn Val Thr Leu Ser Asn Leu
                275                 280                 285

Leu Tyr Phe Trp Phe Ala Pro Thr Leu Val Tyr Gln Pro Val Tyr Pro
290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
                340                 345                 350

Asp Tyr Ala Asn Ile Ser Glu Arg Leu Met Lys Leu Ala Ser Val Ser
                355                 360                 365

Met Met Val Trp Leu Ile Gly Phe Tyr Ala Phe Phe Gln Asn Gly Leu
370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
                420                 425                 430

Ala Arg Gly Met Ser Arg Phe Asn Ala Ser Val Val Phe Phe
                435                 440                 445

Ser Ala Val Ile His Glu Leu Leu Val Gly Ile Pro Thr His Asn Ile
                450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495

Gly Asn Cys Ala Phe Trp Phe Thr Phe Leu Gly Gln Pro Thr Cys
                500                 505                 510

Ala Phe Leu Tyr Tyr Xaa Ala Tyr Asn Tyr Lys Gln Asn Gln
                515                 520                 525

<210> SEQ ID NO 85
<211> LENGTH: 44
<212> TYPE: DNA
<213> ORGANISM: Artificial Sequence
<220> FEATURE:
<223> OTHER INFORMATION: Primer P214

<400> SEQUENCE: 85
atctcgacaa tcgtcgcagc cctcctcaag agcatcgtcc agaa                         44

<210> SEQ ID NO 86
<211> LENGTH: 42
<212> TYPE: DNA
<213> ORGANISM: Artificial Sequence
<220> FEATURE:
<223> OTHER INFORMATION: Primer P215

<400> SEQUENCE: 86
```

```
cgaacagatc ccaatattac atgaggcgag tttgagagac ag                        42

<210> SEQ ID NO 87
<211> LENGTH: 44
<212> TYPE: DNA
<213> ORGANISM: Artificial Sequence
<220> FEATURE:
<223> OTHER INFORMATION: Primer P216

<400> SEQUENCE: 87
aactggtatt taaatgatgt ccccaagacg gagcgtattc gacc                      44

<210> SEQ ID NO 88
<211> LENGTH: 40
<212> TYPE: DNA
<213> ORGANISM: Artificial Sequence
<220> FEATURE:
<223> OTHER INFORMATION: Primer P217

<400> SEQUENCE: 88
gtagttgtag gctaggtagt aaaggaatgc acaagtgggt                           40

<210> SEQ ID NO 89
<211> LENGTH: 42
<212> TYPE: DNA
<213> ORGANISM: Artificial Sequence
<220> FEATURE:
<223> OTHER INFORMATION: Primer P218

<400> SEQUENCE: 89
ctgtctctca aactcgcctc atgtaatatt gggatctgtt cg                        42

<210> SEQ ID NO 90
<211> LENGTH: 40
<212> TYPE: DNA
<213> ORGANISM: Artificial Sequence
<220> FEATURE:
<223> OTHER INFORMATION: Primer P219

<400> SEQUENCE: 90
cgaatacgct ccgtcttggg gacatcattt aaataccagt                           40

<210> SEQ ID NO 91
<211> LENGTH: 20
<212> TYPE: DNA
<213> ORGANISM: Artificial Sequence
<220> FEATURE:
<223> OTHER INFORMATION: Primer P226

<400> SEQUENCE: 91
cgacgaaaaa ttgacgtgct                                                 20

<210> SEQ ID NO 92
<211> LENGTH: 20
<212> TYPE: DNA
<213> ORGANISM: Artificial Sequence
<220> FEATURE:
<223> OTHER INFORMATION: Primer P227

<400> SEQUENCE: 92
gatttccgaa cagatcccaa                                                 20

<210> SEQ ID NO 93
<211> LENGTH: 12649
<212> TYPE: DNA
<213> ORGANISM: Artificial Sequence
```

```
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 93
```

| | | | | | |
|---|---|---|---|---|---|
| taaccctcac | taaagggaac | aaaagctgga | gctccaccgc | ggacacaata | tctggtcaaa | 60 |
| tttcagtttc | gttacataaa | tcgttatgtc | aaaggagtgt | gggaggttaa | gagaattatc | 120 |
| accggcaaac | tatctgttaa | ttgctaggta | cctctagacg | tccacccggg | tcgcttggcg | 180 |
| gccgaagagg | ccggaatctc | gggccgcggt | ggcggccgct | tagttggtct | tggacttctt | 240 |
| gggcttcttc | aggtaggact | ggacaaagaa | gttgccgaac | agagcgagca | gggtgatcat | 300 |
| gtacacgccg | agcagctgga | ccagagcctg | agggtagtcg | caggggaaga | ggtagtcgta | 360 |
| cagggactgc | accagcatag | ccatgaactg | ggtcatctgc | agagtggtga | tgtagggctt | 420 |
| gatgggcttg | acgaagccga | agccctgaga | ggaaaagaag | tagtaggcgt | acatgacggt | 480 |
| gtggacgaag | gagttgagga | tgacggagaa | gtaggcgtcg | ccaccaggag | cgtacttggc | 540 |
| aatagcccac | cagatggcga | agatggtggc | atggtggtac | acgtgcagga | aggagacctg | 600 |
| gttgaacttc | ttgcacagga | tcatgatagc | ggtgtccagg | aactcgtagg | ccttggagac | 660 |
| gtagaacacg | tagacgattc | gggacatgcc | ctgagcgtgg | gactcgttgc | ccttctccat | 720 |
| gtcgttgccg | aagaccttgt | agccacccag | gatagcctgt | cggatggtct | cgacgcacat | 780 |
| gtagagggac | agtccgaaga | ggaacaggtt | gtggagcagc | ttgatggtct | tcagctcgaa | 840 |
| gggcttctcc | atctgcttca | tgatgggaat | gccgaagagc | agcatggcca | tgtagccgac | 900 |
| ctcgaaggcg | agcatggtgg | agacgtccat | catgggcaga | ccgtcggtca | gagcgtaggg | 960 |
| cttagctccg | tccatccact | ggtcgacacc | ggtctcgact | cgtccgacca | cgtcgtccca | 1020 |
| gacagaggag | ttggccatgg | tgaatgattc | ttatactcag | aaggaaatgc | ttaacgattt | 1080 |
| cgggtgtgag | ttgacaagga | gagagagaaa | agaagaggaa | aggtaattcg | gggacggtgg | 1140 |
| tcttttatac | ccttggctaa | agtcccaacc | acaaagcaaa | aaaattttca | gtagtctatt | 1200 |
| ttgcgtccgg | catgggttac | ccggatggcc | agacaaagaa | actagtacaa | agtctgaaca | 1260 |
| agcgtagatt | ccagactgca | gtaccctacg | cccttaacgg | caagtgtggg | aaccggggga | 1320 |
| ggtttgatat | gtggggtgaa | gggggctctc | gccggggttg | ggcccgctac | tgggtcaatt | 1380 |
| tggggtcaat | tggggcaatt | ggggctgttt | tttgggacac | aaatacgccg | ccaacccggt | 1440 |
| ctctcctgaa | ttctgcatcg | atcgaggaag | aggacaagcg | gctgcttctt | aagtttgtga | 1500 |
| catcagtatc | caaggcacca | ttgcaaggat | tcaaggcttt | gaacccgtca | tttgccattc | 1560 |
| gtaacgctgg | tagacaggtt | gatcggttcc | ctacggcctc | cacctgtgtc | aatcttctca | 1620 |
| agctgcctga | ctatcaggac | attgatcaac | ttcggaagaa | acttttgtat | gccattcgat | 1680 |
| cacatgctgg | tttcgatttg | tcttagagga | acgcatatac | agtaatcata | gagaataaac | 1740 |
| gatattcatt | tattaaagta | gatagttgag | gtagaagttg | taaagagtga | taaatagcgg | 1800 |
| ccgcgcctac | ttaagcaacg | ggcttgataa | cagcgggggg | ggtgcccacg | ttgttgcggt | 1860 |
| tgcggaagaa | cagaacaccc | ttaccagcac | cctcggcacc | agcgctgggc | tcaacccact | 1920 |
| ggcacatacg | cgcactgcgg | tacatggcgc | ggatgaagcc | acgaggacca | tcctggacat | 1980 |
| cagcccggta | gtgcttgccc | atgatgggct | taatggcctc | ggtggcctcg | tccgcgttgt | 2040 |

```
agaaggggat gctgctgacg tagtggtgga ggacatgagt ctcgatgatg ccgtggagaa    2100
ggtggcggcc gatgaagccc atctcacggt caatggtagc agcggcacca cggacgaagt    2160
tccactcgtc gttggtgtag tggggaaggg tagggtcggt gtgctggagg aaggtgatgg    2220
caacgagcca gtggttaacc cagaggtagg gaacaaagta ccagatggcc atgttgtaga    2280
aaccgaactt ctgaacgagg aagtacagag cagtggccat cagaccgata ccaatatcgc    2340
tgaggacgat gagcttagcg tcactgttct cgtacagagg gctgcgggga tcgaagtggt    2400
taacaccacc gccgaggccg ttatgcttgc ccttgccgcg accctcacgc tggcgctcgt    2460
ggtagttgtg gccggtaaca ttggtgatga ggtagttggg ccagccnacg annnnctcag    2520
taagatgagc gagctcgtgg gtcatctttc cgagacgagt agcctgctgc tcgcgggttc    2580
ggggaacgaa gaccatgtca cgctccatgt tgccagtggc cttgtggtgc tttcggtggg    2640
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgatatca acctcggaca    3060
tggacgagag cgatgtggaa gaggccgagt ggcggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420
gaaaaaagag actggcaacc gattgggaga gccactgttt atatataccc tagacaagcc    3480
ccccgcttgt aagatgttgg tcaatgtaaa ccagtattaa ggttggcaag tgcaggagaa    3540
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctacccccc atcccatccc tttgttggtg    4020 caacccctacc catttattgt tgggtgcagc ccaaccgacg tggagagctt ggcttggcca    4080
tataaaaagg cccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgccccaa    4320
ttgaccccaa attgacccag tagcgggccc aaccccggcg agagccccct tcaccccaca    4380
tatcaaacct ccccccggttc ccacacttgc cgttaagggc gtagggtact gcagtctgga    4440
```

```
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcaccacgt tggcaaggac   4860 ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctgggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccacccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acgtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga ctttctgcca ttgccactag ggggggcct ttttatatgg   6480 ccaagccaag ctctccacgt cggttgggct gcacccaaca ataaatgggt aggttgcac   6540 caacaaaggg atgggatggg gggtagaaga tacgaggata acgggctca atggcacaaa   6600 taagaacgaa tactgccatt aagactcgtg atccagcgac tgcaccatt gcatcatcta   6660 agggcctcaa aactacctcg gaactgctgc gctgatctgg acaccacaga ggttccgagc   6720
actttaggtt gcaccaaatg tcccaccagg tgcaggcaga aaacgctgga acagcgtata   6780
cagtttgtct taacaaaaag tgagggcgct gaggtcgagc agggtggtgt gacttgttat   6840
```

```
agcctttaga gctgcgaaag cgcgtatgga tttggctcat caggccagat tgagggtctg   6900
tggacacatg tcatgttagt gtacttcaat cgcccctgg  atatagcccc gacaataggc   6960
cgtggcctca ttttttgcc  ttccgcacat ttccattgct cggtacccac accttgcttc   7020
tcctgcactt gccaaccta  atactggttt acattgacca acatcttaca agcgggggc    7080
ttgtctaggg tatatataaa cagtggctct cccaatcggt tgccagtctc ttttttcctt   7140
tctttcccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgccctgg ttgcccaggc cgagaagtac attcccacca   7500
ttgtccatca cactcgaggc ttcctggttg ccgtggagtc tcccctggct cgagagctgc   7560
ctctgatgaa cccctcccac gtgctcctga tcgtgctcgc ctacctggtc accgtgtttg   7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttccttcct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc ttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt tgatcatgc  acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaacttttta   8880
tcggaacctt atctggggca gtgaagtata tgttatggta atagttacga gttagttgaa   8940
cttatagata gactggacta tacggctatc ggtccaaatt agaaagaacg tcaatggctc   9000
tctgggcgtc gcctttgccg acaaaaatgt gatcatgatg aaagccagca atgacgttgc   9060
agctgatatt gttgtcggcc aaccgcgccg aaaacgcagc tgtcagaccc acagcctcca   9120
acgaagaatg tatcgtcaaa gtgatccaag cacactcata gttggagtcg tactccaaag   9180
gcggcaatga cgagtcagac agatactcgt cgaccttttc cttgggaacc accaccgtca   9240
```

```
gcccttctga ctcacgtatt gtagccaccg acacaggcaa cagtccgtgg atagcagaat   9300
atgtcttgtc ggtccatttc tcaccaactt taggcgtcaa gtgaatgttg cagaagaagt   9360
atgtgccttc attgagaatc ggtgttgctg atttcaataa agtcttgaga tcagtttggc   9420
gcgccagctg cattaatgaa tcggccaacg cgcggggaga ggcggtttgc gtattgggcg   9480
ctcttccgct tcctcgctca ctgactcgct gcgctcggtc gttcggctgc ggcgagcggt   9540
atcagctcac tcaaaggcgg taatacggtt atccacagaa tcaggggata acgcaggaaa   9600
gaacatgtga gcaaaaggcc agcaaaaggc caggaaccgt aaaaaggccg cgttgctggc   9660
gttttttccat aggctccgcc cccctgacga gcatcacaaa aatcgacgct caagtcagag   9720
gtggcgaaac ccgacaggac tataaagata ccaggcgttt ccccctggaa gctccctcgt   9780
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaaccccc cgttcagccc gaccgctgcg ccttatccgg   9960
taactatcgt cttgagtcca acccggtaag acacgactta tcgccactgg cagcagccac  10020
tggtaacagg attagcagag cgaggtatgt aggcggtgct acagagttct tgaagtggtg  10080
gcctaactac ggctacacta gaagaacagt atttggtatc tgcgctctgc tgaagccagt  10140
taccttcgga aaaagagttg gtagctcttg atccggcaaa caaaccaccg ctggtagcgg  10200
tggtttttttt gtttgcaagc agcagattac gcgcagaaaa aaaggatctc aagaagatcc  10260
tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactccccgt  10500
cgtgtagata actacgatac gggagggctt accatctggc cccagtgctg caatgatacc  10560
gcgagaccca cgctcaccgg ctccagattt atcagcaata aaccagccag ccggaagggc  10620
cgagcgcaga agtggtcctg caactttatc cgcctccatc cagtctatta attgttgccg  10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
tccgatcgtt gtcagaagta agttggccgc agtgttatca ctcatggtta tggcagcact  10920
gcataattct cttactgtca tgccatccgt aagatgcttt tctgtgactg gtgagtactc  10980
aaccaagtca ttctgagaat agtgtatgcg gcgaccgagt tgctcttgcc cggcgtcaat  11040
acgggataat accgcgccac atagcagaac tttaaaagtg ctcatcattg gaaaacgttc  11100
ttcggggcga aaactctcaa ggatcttacc gctgttgaga tccagttcga tgtaacccac  11160
tcgtgcaccc aactgatctt cagcatcttt tactttcacc agcgtttctg ggtgagcaaa  11220
aacaggaagg caaaatgccg caaaaaaggg aataagggcg acacggaaat gttgaatact  11280
catactcttc cttttttcaat attattgaag catttatcag ggttattgtc tcatgagcgg  11340
atacatattt gaatgtattt agaaaaataa acaaataggg gttccgcgca catttccccg  11400
aaaagtgcca cctgatgcgg tgtgaaatac cgcacagatg cgtaaggaga aaataccgca  11460
tcaggaaatt gtaagcgtta atattttgtt aaaattcgcg ttaaattttt gttaaatcag  11520
ctcatttttt aaccaatagg ccgaaatcgg caaaatccct tataaatcaa agaatagac  11580
cgagataggg ttgagtgttg ttccagtttg gaacaagagt ccactattaa agaacgtgga  11640
```

```
ctccaacgtc aaagggcgaa aaaccgtcta tcagggcgat ggcccactac gtgaaccatc   11700
accctaatca agttttttgg ggtcgaggtg ccgtaaagca ctaaatcgga accctaaagg   11760
gagcccccga tttagagctt gacggggaaa gccggcgaac gtggcgagaa aggaagggaa   11820
gaaagcgaaa ggagcgggcg ctagggcgct ggcaagtgta gcggtcacgc tgcgcgtaac   11880
caccacaccc gccgcgctta atgcgccgct acagggcgcg tccattcgcc attcaggctg   11940
cgcaactgtt gggaagggcg atcggtgcgg gcctcttcgc tattacgcca gctggcgaaa   12000 ggggatgtg ctgcaaggcg attaagttgg gtaacgccag ggttttccca gtcacgacgt    12060
tgtaaaacga cggccagtga attgtaatac gactcactat agggcgaatt gggcccgacg   12120
tcgcatgcag tggtggtatt gtgactgggg atgtagttga gaataagtca tacacaagtc   12180 agcttcttc gagcctcata taagtataag tagttcaacg tattagcact gtacccagca    12240
tctccgtatc gagaaacaca acaacatgcc ccattggaca gatcatgcgg atacacaggt   12300
tgtgcagtat catacatact cgatcagaca ggtcgtctga ccatcataca agctgaacaa   12360
gcgctccata cttgcacgct ctctatatac acagttaaat tacatatcca tagtctaacc   12420
tctaacagtt aatcttctgg taagcctccc agccagcctt ctggtatcgc ttggcctcct   12480
caataggatc tcggttctgg ccgtacagac ctcggccgac aattatgata tccgttccgg   12540
tagacatgac atcctcaaca gttcggtact gctgtccgag agcgtctccc ttgtcgtcaa   12600
gacccacccc gggggtcaga ataagccagt cctcagagtc gcccttaat             12649
```

<210> SEQ ID NO 94
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 94

```
aaattgcccc ggagaagacg gccaggccgc ctagatgaca aattcaacaa ctcacagctg     60
actttctgcc attgccacta ggggggggcc tttttatatg gccaagccaa gctctccacg    120
tcggttgggc tgcacccaac aataaatggg tagggttgca ccaacaaagg gatgggatgg    180
ggggtagaag atacgaggat aacggggctc aatggcacaa ataagaacga atactgccat    240
taagactcgt gatccagcga ctgacaccat tgcatcatct aagggcctca aaactacctc    300
ggaactgctg cgctgatctg gacaccacag aggttccgag cactttaggt tgcaccaaat    360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa    480
gcgcgtatgg atttggctca tcaggccaga ttgagggtct gtggacacat gtcatgttag    540
tgtacttcaa tcgcccctg gatatagccc cgacaatagg ccgtggcctc attttttgc     600 cttccgcaca tttccattgc tcggtaccca caccttgctt ctcctgcact tgccaacctt    660
aatactggtt tacattgacc aacatcttac aagcgggggg cttgtctagg gtatatataa    720
acagtggctc tcccaatcgg ttgccagtct cttttttcct ttctttcccc acagattcga    780
aatctaaact acacatcaca caatgcctgt tactgacgtc cttaagcgaa agtccggtgt    840
catcgtcggc gacgatgtcc gagccgtgag tatccacgac aagatcagtg tcgagacgac    900
gcgttttgtg taatgacaca atccgaaagt cgctagcaac acacactctc tacacaaact    960
aacccagctc tcc                                                       973
```

<210> SEQ ID NO 95
<211> LENGTH: 957
<212> TYPE: DNA
<213> ORGANISM: Mortierella alpina
<220> FEATURE:
<221> NAME/KEY: misc_feature
<223> OTHER INFORMATION: synthetic elongase 1 (codon-optimized)

<400> SEQUENCE: 95

```
atggagtcca ttgctcccett cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agaccttctc cctcctgcac aacttctgtc tggtctccat ctccgcctac     360
atgtgcggtg gcatcctgta cgaggcttat caggccaact atggactgtt tgagaacgct     420
gccgatcaca ccttcaaggg tctccctatg gctaagatga tctggctctt ctacttctcc     480
aagatcatgg agtttgtcga caccatgatc atggtcctca gaagaacaa ccgacagatt     540
tcctttctgc acgtgtacca ccactcttcc atcttcacca tctggtggct ggtcaccttc     600
gttgctccca cggtgaagc ctacttctct gctgccctga actccttcat ccacgtcatc     660
atgtacggct actactttct gtctgccctg gcttcaagc aggtgtcgtt catcaagttc     720
tacatcactc gatcccagat gacccagttc tgcatgatgt ctgtccagtc ttcctgggac     780
atgtacgcca tgaaggtcct tggccgacct ggataccct tcttcatcac cgctctgctc     840
tggttctaca tgtggaccat gctcggtctc ttctacaact tttaccgaaa gaacgccaag     900
ctcgccaagc aggccaaggc tgacgctgcc aaggagaagg ccagaaagct ccagtaa       957
```

<210> SEQ ID NO 96
<211> LENGTH: 318
<212> TYPE: PRT
<213> ORGANISM: Mortierella alpina AX464731

<400> SEQUENCE: 96

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
                20                  25                  30

Asp Pro Leu Glu Ala Ala Leu Val Ala Gln Ala Glu Lys Tyr Ile Pro
            35                  40                  45

Thr Ile Val His His Thr Arg Gly Phe Leu Val Ala Val Glu Ser Pro
        50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160
```

```
Lys Ile Met Glu Phe Val Asp Thr Met Ile Met Val Leu Lys Lys Asn
                165                 170                 175
Asn Arg Gln Ile Ser Phe Leu His Val Tyr His Ser Ser Ile Phe
            180                 185                 190
Thr Ile Trp Trp Leu Val Thr Phe Val Ala Pro Asn Gly Glu Ala Tyr
        195                 200                 205
Phe Ser Ala Ala Leu Asn Ser Phe Ile His Val Ile Met Tyr Gly Tyr
    210                 215                 220
Tyr Phe Leu Ser Ala Leu Gly Phe Lys Gln Val Ser Phe Ile Lys Phe
225                 230                 235                 240
Tyr Ile Thr Arg Ser Gln Met Thr Gln Phe Cys Met Met Ser Val Gln
                245                 250                 255
Ser Ser Trp Asp Met Tyr Ala Met Lys Val Leu Gly Arg Pro Gly Tyr
            260                 265                 270
Pro Phe Phe Ile Thr Ala Leu Leu Trp Phe Tyr Met Trp Thr Met Leu
        275                 280                 285
Gly Leu Phe Tyr Asn Phe Tyr Arg Lys Asn Ala Lys Leu Ala Lys Gln
    290                 295                 300
Ala Lys Ala Asp Ala Ala Lys Glu Lys Ala Arg Lys Leu Gln
305                 310                 315
```

<210> SEQ ID NO 97
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 97

```
atggctgccg ctccctctgt gcgaaccttt acccgagccg aggttctgaa cgctgaggct    60
ctgaacgagg gcaagaagga cgctgaggct cccttcctga tgatcatcga caacaaggtg   120
tacgacgtcc gagagttcgt ccctgaccat cctggaggct ccgtgattct cacccacgtt   180
ggcaaggacg cgaccgacgt cttgacacc tttcatcccg aggctgcttg ggagactctc    240
gccaacttct acgttggaga cattgacgag tccgaccgag acatcaagaa cgatgacttt   300
gccgctgagg tccgaaagct gcgaaccctg ttccagtctc tcggctacta cgactcctct   360
aaggcctact acgccttcaa ggtctccttc aacctctgca tctggggact gtccaccgtc   420
attgtggcca gtggggtca gacctccacc ctcgccaacg tgctctctgc tgccctgctc   480
ggcctgttct ggcagcagtg cggatggctg gctcacgact tctgcacca ccaggtcttc   540
caggaccgat ctgggggtga tctcttcgga gccttcctgg aggtgtctg ccagggcttc   600
tcctcttcct ggtggaagga caagcacaac actcaccatg ccgctcccaa cgtgcatggc   660
gaggatcctg acattgacac ccaccctctc ctgacctggt ccgagcacgc tctggagatg   720
ttctccgacg tccccgatga ggagctgacc cgaatgtggt ctcgattcat ggtcctgaac   780
cagacctggt tctacttccc cattctctcc ttcgctcgac tgtcttggtg cctccagtcc   840
attctctttg tgctgcccaa cggtcaggct cacaagccct ccggagctcg agtgcccatc   900
tccctggtcg agcagctgtc cctcgccatg cactggacct ggtacctcgc taccatgttc   960
ctgttcatca aggatcctgt caacatgctc gtgtacttcc tggtgtctca ggctgtgtgc  1020
ggaaacctgc tcgccatcgt gttctcccct aaccacaacg gtatgcctgt gatctccaag  1080
gaggaggctg tcgacatgga tttctttacc aagcagatca tcactggtcg agatgtccat  1140
```

-continued

```
cctggactgt tcgccaactg gttcaccggt ggcctgaact accagatcga gcatcacctg    1200
ttcccttcca tgcctcgaca caacttctcc aagatccagc ctgccgtcga gaccctgtgc    1260
aagaagtaca acgtccgata ccacaccact ggtatgatcg agggaactgc cgaggtcttc    1320
tcccgactga acgaggtctc caaggccacc tccaagatgg gcaaggctca gtaa          1374
```

<210> SEQ ID NO 98
<211> LENGTH: 457
<212> TYPE: PRT
<213> ORGANISM: Mortierella alpina AF465281

<400> SEQUENCE: 98

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
```

```
                340               345               350
Asn Gly Met Pro Val Ile Ser Lys Glu Glu Ala Val Asp Met Asp Phe
                    355               360               365
Phe Thr Lys Gln Ile Ile Thr Gly Arg Asp Val His Pro Gly Leu Phe
370                 375               380
Ala Asn Trp Phe Thr Gly Gly Leu Asn Tyr Gln Ile Glu His His Leu
385                 390               395               400
Phe Pro Ser Met Pro Arg His Asn Phe Ser Lys Ile Gln Pro Ala Val
                405               410               415
Glu Thr Leu Cys Lys Lys Tyr Asn Val Arg Tyr His Thr Thr Gly Met
                420               425               430
Ile Glu Gly Thr Ala Glu Val Phe Ser Arg Leu Asn Glu Val Ser Lys
            435               440               445
Ala Thr Ser Lys Met Gly Lys Ala Gln
            450               455
```

<210> SEQ ID NO 99
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 99

| | | | | | |
|---|---|---|---|---|---|
| taaacagtgt | acgcagtact | atagaggaac | aattgccccg | gagaagacgg | ccaggccgcc | 60 |
| tagatgacaa | attcaacaac | tcacagctga | ctttctgcca | ttgccactag | gggggggcctt | 120 |
| tttatatggc | caagccaagc | tctccacgtc | ggttgggctg | cacccaacaa | taaatgggta | 180 |
| gggttgcacc | aacaaaggga | tgggatgggg | ggtagaagat | acgaggataa | cggggctcaa | 240 |
| tggcacaaat | aagaacgaat | actgccatta | agactcgtga | tccagcgact | gacaccattg | 300 |
| catcatctaa | gggcctcaaa | actacctcgg | aactgctgcg | ctgatctgga | caccacagag | 360 |
| gttccgagca | ctttaggttg | caccaaatgt | cccaccaggt | gcaggcagaa | aacgctggaa | 420 |
| cagcgtgtac | agtttgtctt | aacaaaaagt | gagggcgctg | aggtcgagca | gggtggtgtg | 480 |
| acttgttata | gcctttagag | ctgcgaaagc | gcgtatggat | ttggctcatc | aggccagatt | 540 |
| gagggtctgt | ggacacatgt | catgttagtg | tacttcaatc | gccccctgga | tatagccccg | 600 |
| acaataggcc | gtggcctcat | tttttttgcct | tccgcacatt | tccattgctc | ggtacccaca | 660 |
| ccttgcttct | cctgcacttg | ccaaccttaa | tactggttta | cattgaccaa | catcttacaa | 720 |
| gcggggggct | tgtctagggt | atatataaac | agtggctctc | ccaatcggtt | gccagtctct | 780 |
| ttttttcctttt | ctttccccac | agattcgaaa | tctaaactac | acatcacaca | atgcctgtta | 840 |
| ctgacgtcct | taagcgaaag | tccggtgtca | tcgtcggcga | cgatgtccga | gccgtgagta | 900 |
| tccacgacaa | gatcagtgtc | gagacgacgc | gttttgtgta | atgacacaat | ccgaaagtcg | 960 |
| ctagcaacac | acactctcta | cacaaactaa | cccagctctc | c | | 1001 |

<210> SEQ ID NO 100
<211> LENGTH: 1434
<212> TYPE: DNA
<213> ORGANISM: Fusarium monoliforme
<220> FEATURE:
<221> NAME/KEY: misc_feature
<223> OTHER INFORMATION: delta-12 desaturase

<400> SEQUENCE: 100
atggcgtcca cttcggctct gcccaagcag aaccctgcgc ttagacgcac cgtcacctca    60

```
actactgtga cggattctga gtctgccgcc gtctctcctt cagactctcc ccgccactcg    120
gcctcttcca catcgctctc gtccatgtcc gaggttgata tcgccaagcc caagtccgag    180
tatggtgtca tgctcgacac ctacggcaac cagttcgagg ttcccgactt taccatcaag    240
gacatctaca atgccatccc taagcactgc ttcaagcgct ccgctctcaa gggatacggt    300
tatatcctcc gcgacattgt cctcctgact accactttca gcatctggta caactttgtg    360 accccccgaat atatcccctc caccccccgcc cgcgctggtc tgtgggccgt gtacaccgtt    420
cttcagggtc ttttcggtac tggtctctgg gttattgccc atgagtgcgg tcacggtgct    480
ttctccgatt ctcgcatcat caacgacatt actggctggg ttcttcactc ttccctcctt    540
gtcccctact tcagctggca aatctcccac cgaaagcacc acaaggccac tggcaacatg    600
gagcgtgaca tggtcttcgt tccccgaacc cgcgagcagc aggctactcg tctcggaaag    660
atgacccacg agctcgctca tcttactgag gagaccccccg ctttcactct tctcatgctc    720
gtccttcagc agctcgttgg ctggcccaac tacctcatca ccaatgttac cggccacaac    780
taccacgagc gccagcgtga gggtcgcggc aagggcaagc ataacggcct cggcggtggt    840
gttaaccact tcgatccccg cagccctctg tacgagaaca gtgacgctaa gctcatcgtc    900
ctcagcgata ttggtatcgg tctgatggcc actgctctgt acttcctcgt tcagaagttc    960
ggtttctaca acatggccat ctggtacttt gttccctacc tctgggttaa ccactggctc   1020
gttgccatca ccttcctcca gcacaccgac cctaccttc cccactacac caacgacgag   1080
tggaacttcg tccgtggtgc cgctgctacc attgaccgtg agatgggctt catcggccgc   1140
caccttctcc acggcatcat cgagactcat gtcctccacc actacgtcag cagcatcccc   1200
ttctacaacg cggacgaggc caccgaggcc attaagccca tcatgggcaa gcactaccgg   1260
gctgatgtcc aggatggtcc tcgtggcttc atccgcgcca tgtaccgcag tgcgcgtatg   1320
tgccagtggg ttgagcccag cgctggtgcc gagggtgctg gtaagggtgt tctgttcttc   1380
cgcaaccgca caacgtggg cacccccccc gctgttatca gcccgttgc ttaa          1434
```

<210> SEQ ID NO 101
<211> LENGTH: 477
<212> TYPE: PRT
<213> ORGANISM: Fusarium monoliforme

<400> SEQUENCE: 101

```
Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
```

```
              130                 135                 140
Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
                180                 185                 190

His His Lys Ala Thr Gly Asn Met Glu Arg Asp Met Val Phe Val Pro
                195                 200                 205

Arg Thr Arg Glu Gln Gln Ala Thr Arg Leu Gly Lys Met Thr His Glu
210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
                260                 265                 270

Lys His Asn Gly Leu Gly Gly Val Asn His Phe Asp Pro Arg Ser
                275                 280                 285

Pro Leu Tyr Glu Asn Ser Asp Ala Lys Leu Ile Val Leu Ser Asp Ile
290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
                340                 345                 350

Leu Pro His Tyr Thr Asn Asp Glu Trp Asn Phe Val Arg Gly Ala Ala
                355                 360                 365

Ala Thr Ile Asp Arg Glu Met Gly Phe Ile Gly Arg His Leu Leu His
                370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
                420                 425                 430

Ala Met Tyr Arg Ser Ala Arg Met Cys Gln Trp Val Glu Pro Ser Ala
                435                 440                 445

Gly Ala Glu Gly Ala Gly Lys Gly Val Leu Phe Phe Arg Asn Arg Asn
450                 455                 460

Asn Val Gly Thr Pro Pro Ala Val Ile Lys Pro Val Ala
465                 470                 475

<210> SEQ ID NO 102
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 102
atggccaact cctctgtctg ggacgacgtg gtcggacgag tcgagaccgg tgtcgaccag      60
tggatggacg gagctaagcc ctacgctctg accgacggtc tgcccatgat ggacgtctcc     120
```

-continued

```
accatgctcg ccttcgaggt cggctacatg gccatgctgc tcttcggcat tcccatcatg    180
aagcagatgg agaagcccct cgagctgaag accatcaagc tgctccacaa cctgttcctc    240
ttcggactgt ccctctacat gtgcgtcgag accatccgac aggctatcct gggtggctac    300
aaggtcttcg gcaacgacat ggagaagggc aacgagtccc acgctcaggg catgtcccga    360
atcgtctacg tgttctacgt ctccaaggcc tacgagttcc tggacaccgc tatcatgatc    420
ctgtgcaaga agttcaacca ggtctccttc ctgcacgtgt accaccatgc caccatcttc    480
gccatctggt gggctattgc caagtacgct cctggtggcg acgcctactt ctccgtcatc    540
ctcaactcct tcgtccacac cgtcatgtac gcctactact tcttttcctc tcagggcttc    600
ggcttcgtca agcccatcaa gccctacatc accactctgc agatgaccca gttcatggct    660
atgctggtgc agtccctgta cgactacctc ttcccctgcg actacccctca ggctctggtc    720 cagctgctcg gcgtgtacat gatcacccctg ctcgctctgt tcggcaactt ctttgtccag    780
tcctacctga agaagcccaa gaagtccaag accaactaa                            819
```

<210> SEQ ID NO 103
<211> LENGTH: 272
<212> TYPE: PRT
<213> ORGANISM: Thraustochytrium aureum

<400> SEQUENCE: 103

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255
```

```
Phe Phe Val Gln Ser Tyr Leu Lys Lys Pro Lys Lys Ser Lys Thr Asn
            260                 265                 270
```

<210> SEQ ID NO 104
<211> LENGTH: 10945
<212> TYPE: DNA
<213> ORGANISM: Artificial Sequence
<220> FEATURE:
<223> OTHER INFORMATION: Plasmid pDMW232

<400> SEQUENCE: 104

| | | | | | |
|---|---|---|---|---|---|
| aattcctgca | gcccatcgat | caggagagac | cgggttggcg | gcgtatttgt | gtcccaaaaa | 60 |
| acagccccaa | ttgccccaat | tgaccccaaa | ttgacccagt | agcgggccca | accccggcga | 120 |
| gagccccctt | cacccacat | atcaaacctc | ccccggttcc | cacacttgcc | gttaagggcg | 180 |
| tagggtactg | cagtctggaa | tctacgcttg | ttcagacttt | gtactagttt | ctttgtctgg | 240 |
| ccatccgggt | aacccatgcc | ggacgcaaaa | tagactactg | aaaatttttt | tgctttgtgg | 300 |
| ttgggacttt | agccaagggt | ataaaagacc | accgtccccg | aattaccttt | cctcttcttt | 360 |
| tctctctctc | cttgtcaact | cacacccgaa | atcgttaagc | atttccttct | gagtataaga | 420 |
| atcattcacc | atgggaacgg | accaaggaaa | aaccttcacc | tgggaagagc | tggcggccca | 480 |
| taacaccaag | gacgacctac | tcttggccat | ccgcggcagg | gtgtacgatg | tcacaaagtt | 540 |
| cttgagccgc | catcctggtg | gagtggacac | tctcctgctc | ggagctggcc | gagatgttac | 600 |
| tccggtcttt | gagatgtatc | acgcgtttgg | ggctgcagat | gccattatga | agaagtacta | 660 |
| tgtcggtaca | ctggtctcga | atgagctgcc | catcttcccg | gagccaacgg | tgttccacaa | 720 |
| aaccatcaag | acgagagtcg | agggctactt | tacggatcgg | aacattgatc | ccaagaatag | 780 |
| accagagatc | tggggacgat | acgctcttat | ctttggatcc | ttgatcgctt | cctactacgc | 840 |
| gcagctcttt | gtgcctttcg | ttgtcgaacg | cacatggctt | caggtggtgt | ttgcaatcat | 900 |
| catgggattt | gcgtgcgcac | aagtcggact | caaccctctt | catgatgcgt | ctcactttc | 960 |
| agtgacccac | aaccccactg | tctggaagat | tctgggagcc | acgcacgact | ttttcaacgg | 1020 |
| agcatcgtac | ctggtgtgga | tgtaccaaca | tatgctcggc | catcaccct | acaccaacat | 1080 |
| tgctggagca | gatcccgacg | tgtcgacgtc | tgagcccgat | gttcgtcgta | tcaagcccaa | 1140 |
| ccaaaagtgg | tttgtcaacc | acatcaacca | gcacatgttt | gttcctttcc | tgtacggact | 1200 |
| gctggcgttc | aaggtgcgca | ttcaggacat | caacattttg | tactttgtca | agaccaatga | 1260 |
| cgctattcgt | gtcaatccca | tctcgacatg | gcacactgtg | atgttctggg | gcggcaaggc | 1320 |
| tttctttgtc | tggtatcgcc | tgattgttcc | cctgcagtat | ctgccctgg | gcaaggtgct | 1380 |
| gctcttgttc | acgtcgcgg | acatggtgtc | gtcttactgg | ctggcgctga | ccttccaggc | 1440 |
| gaaccacgtt | gttgaggaag | ttcagtggcc | gttgcctgac | gagaacggga | tcatccaaaa | 1500 |
| ggactgggca | gctatgcagg | tcgagactac | gcaggattac | gcacacgatt | cgcacctctg | 1560 |
| gaccagcatc | actggcagct | tgaactacca | ggctgtgcac | catctgttcc | ccaacgtgtc | 1620 |
| gcagcaccat | tatcccgata | ttctggccat | catcaagaac | acctgcagcg | agtacaaggt | 1680 |
| tccatacctt | gtcaaggata | cgttttggca | agcatttgct | tcacatttgg | agcacttgcg | 1740 |
| tgttcttgga | ctccgtccca | aggaagagta | ggcagctaag | cggccgcatg | agaagataaa | 1800 |
| tatataaata | cattgagata | ttaaatgcgc | tagattagag | agcctcatac | tgctcggaga | 1860 |
| gaagccaaga | cgagtactca | aagggggatta | caccatccat | atccacagac | acaagctggg | 1920 |
| gaaaggttct | atatacactt | tccggaatac | cgtagtttcc | gatgttatca | atgggggcag | 1980 |
| ccaggatttc | aggcacttcg | gtgtctcggg | gtgaaatggc | gttcttggcc | tccatcaagt | 2040 |

```
cgtaccatgt cttcatttgc ctgtcaaagt aaaacagaag cagatgaaga atgaacttga   2100
agtgaaggaa tttaaattgc cccggagaag acggccaggc cgcctagatg acaaattcaa   2160
caactcacag ctgactttct gccattgcca ctagggggg gccttttat atggccaagc     2220
caagctctcc acgtcggttg ggctgcaccc aacaataaat gggtagggtt gcaccaacaa   2280
agggatggga tggggggtag aagatacgag gataacgggg ctcaatggca caaataagaa   2340
cgaatactgc cattaagact cgtgatccag cgactgacac cattgcatca tctaagggcc   2400
tcaaaactac ctcggaactg ctgcgctgat ctggacacca cagaggttcc gagcactta    2460
ggttgcacca aatgtcccac caggtgcagg cagaaaacgc tggaacagcg tgtacagttt   2520
gtcttaacaa aaagtgaggg cgctgaggtc gagcagggtg gtgtgacttg ttatagcctt   2580
tagagctgcg aaagcgcgta tggatttggc tcatcaggcc agattgaggg tctgtggaca   2640
catgtcatgt tagtgtactt caatcgcccc ctggatatag ccccgacaat aggccgtggc   2700
ctcattttt tgccttccgc acatttccat tgctcggtac ccacaccttg cttctcctgc    2760
acttgccaac cttaatactg gtttacattg accaacatct tacaagcggg gggcttgtct   2820
agggtatata taaacagtgg ctctcccaat cggttgccag tctcttttt cctttctttc   2880
cccacagatt cgaaatctaa actacacatc acacaatgcc tgttactgac gtccttaagc   2940
gaaagtccgg tgtcatcgtc ggcgacgatg tccgagccgt gagtatccac gacaagatca   3000
gtgtcgagac gacgcgtttt gtgtaatgac acaatccgaa agtcgctagc aacacacact   3060
ctctacacaa actaacccag ctctccatgg gaacggacca aggaaaaacc ttcacctggg   3120
aagagctggc ggcccataac accaaggacg acctactctt ggccatccgc ggcagggtgt   3180
acgatgtcac aaagttcttg agccgccatc ctggtggagt ggacactctc ctgctcggag   3240
ctggccgaga tgttactccg gtctttgaga tgtatcacgc gtttgggct gcagatgcca    3300
ttatgaagaa gtactatgtc ggtacactgg tctcgaatga gctgcccatc ttcccggagc   3360
caacggtgtt ccacaaaacc atcaagacga gagtcgaggg ctactttacg gatcggaaca   3420
ttgatcccaa gaatagacca gagatctggg gacgatacgc tcttatcttt ggatccttga   3480
tcgcttccta ctacgcgcag ctctttgtgc ctttcgttgt cgaacgcaca tggcttcagg   3540
tggtgtttgc aatcatcatg ggatttgcgt gcgcacaagt cggactcaac cctcttcatg   3600
atgcgtctca cttttcagtg acccacaacc ccactgtctg gaagattctg ggagccacgc   3660
acgactttt caacggagca tcgtacctgg tgtggatgta ccaacatatg ctcggccatc   3720
accccctacac caacattgct ggagcagatc ccgacgtgtc gacgtctgag cccgatgttc   3780
gtcgtatcaa gcccaaccaa aagtggtttg tcaaccacat caaccagcac atgtttgttc   3840
ctttcctgta cggactgctg gcgttcaagg tgcgcattca ggacatcaac attttgtact   3900
ttgtcaagac caatgacgct attcgtgtca atcccatctc gacatggcac actgtgatgt   3960
tctggggcgg caaggctttc tttgtctggt atcgcctgat tgttccctg cagtatctgc    4020
ccctgggcaa ggtgctgctc ttgttcacgg tcgcggacat ggtgtcgtct tactggctgg   4080
cgctgacctt ccaggcgaac cacgttgttg aggaagttca gtggccgttg cctgacgaga   4140
acgggatcat ccaaaaggac tgggcagcta tgcaggtcga gactacgcag gattacgcac   4200
acgattcgca cctctggacc agcatcactg gcagcttgaa ctaccaggct gtgcaccatc   4260
tgttccccaa cgtgtcgcag caccattatc ccgatattct ggccatcatc aagaacacct   4320
gcagcgagta caaggttcca tacccttgtca aggatacgtt ttggcaagca tttgcttcac   4380
atttggagca cttgcgtgtt cttggactcc gtcccaagga agagtaggca gctaagcggc   4440
```

```
cgcaagtgtg gatggggaag tgagtgcccg gttctgtgtg cacaattggc aatccaagat    4500
ggatggattc aacacaggga tatagcgagc tacgtggtgg tgcgaggata tagcaacgga    4560
tatttatgtt tgacacttga gaatgtacga tacaagcact gtccaagtac aatactaaac    4620
atactgtaca tactcatact cgtacccggg caacggtttc acttgagtgc agtggctagt    4680
gctcttactc gtacagtgtg caatactgcg tatcatagtc tttgatgtat atcgtattca    4740
ttcatgttag ttgcgtacgc caccattctg tctgccgcca tgatgctcaa gttctctctt    4800
aacatgaagc ccgccggtga cgctgttgag gctgccgtca aggagtccgt cgaggctggt    4860
atcactaccg ccgatatcgg aggctcttcc tccacctccg aggtcggaga cttgttgcca    4920
acaaggtcaa ggagctgctc aagaaggagt aagtcgtttc tacgacgcat tgatggaagg    4980
agcaaactga cgcgcctgcg ggttggtcta ccggcagggt ccgctagtgt ataagactct    5040
ataaaaaggg ccctgccctg ctaatgaaat gatgatttat aatttaccgg tgtagcaacc    5100
ttgactagaa gaagcagatt gggtgtgttt gtagtggagg acagtggtac gttttggaaa    5160
cagtcttctt gaaagtgtct tgtctacagt atattcactc ataacctcaa tagccaaggg    5220
tgtagtcggt ttattaaagg aagggagttg tggctgatgt ggatagatat ctttaagctg    5280
gcgactgcac ccaacgagtg tggtggtagc ttgttactgt atattcggta agatatattt    5340
tgtgggtttt tagtggtgtt tggtaggtta gtgcttggta tatgagttgt aggcatgaca    5400
atttggaaag gggtggactt tgggaatatt gtgggatttc aataccttag tttgtacagg    5460
gtaattgtta caaatgatac aaagaactgt atttcttttc atttgtttta attggttgta    5520
tatcaagtcc gttagacgag ctcagtgggc gcgccagctg cattaatgaa tcggccaacg    5580
cgcggggaga ggcggtttgc gtattgggcg ctcttccgct tcctcgctca ctgactcgct    5640
gcgctcggtc gttcggctgc ggcgagcggt atcagctcac tcaaaggcgg taatacggtt    5700
atccacagaa tcaggggata acgcaggaaa gaacatgtga gcaaaaggcc agcaaaaggc    5760
caggaaccgt aaaaaggccg cgttgctggc gtttttccat aggctccgcc cccctgacga    5820
gcatcacaaa aatcgacgct caagtcagag gtggcgaaac ccgacaggac tataaagata    5880
ccaggcgttt ccccctggaa gctccctcgt gcgctctcct gttccgaccc tgccgcttac    5940
cggatacctg tccgcctttc tcccttcggg aagcgtggcg ctttctcata gctcacgctg    6000
taggtatctc agttcggtgt aggtcgttcg ctccaagctg ggctgtgtgc acgaaccccc    6060
cgttcagccc gaccgctgcg ccttatccgg taactatcgt cttgagtcca acccggtaag    6120
acacgactta tcgccactgg cagcagccac tggtaacagg attagcagag cgaggtatgt    6180
aggcggtgct acagagttct tgaagtggtg gcctaactac ggctacacta agaacagt     6240 atttggtatc tgcgctctgc tgaagccagt taccttcgga aaaagagttg gtagctcttg    6300
atccggcaaa caaccaccg ctggtagcgg tggtttttt gtttgcaagc agcagattac      6360
gcgcagaaaa aaaggatctc aagaagatcc tttgatcttt tctacggggt ctgacgctca    6420
gtggaacgaa aactcacgtt aagggatttt ggtcatgaga ttatcaaaaa ggatcttcac    6480
ctagatcctt ttaaattaaa aatgaagttt taaatcaatc taaagtatat atgagtaaac    6540
ttggtctgac agttaccaat gcttaatcag tgaggcacct atctcagcga tctgtctatt    6600
tcgttcatcc atagttgcct gactccccgt cgtgtagata actacgatac gggagggctt    6660
accatctggc cccagtgctg caatgatacc gcgagaccca cgctcaccgg ctccagattt    6720
atcagcaata aaccagccag ccggaagggc cgagcgcaga gtggtcctg caacttttatc    6780 cgcctccatc cagtctatta attgttgccg ggaagctaga gtaagtagtt cgccagttaa    6840
```

```
tagtttgcgc aacgttgttg ccattgctac aggcatcgtg gtgtcacgct cgtcgtttgg   6900
tatggcttca ttcagctccg gttcccaacg atcaaggcga gttacatgat cccccatgtt   6960
gtgcaaaaaa gcggttagct ccttcggtcc tccgatcgtt gtcagaagta agttggccgc   7020
agtgttatca ctcatggtta tggcagcact gcataattct cttactgtca tgccatccgt   7080
aagatgcttt tctgtgactg gtgagtactc aaccaagtca ttctgagaat agtgtatgcg   7140
gcgaccgagt tgctcttgcc cggcgtcaat acgggataat accgcgccac atagcagaac   7200
tttaaaagtg ctcatcattg gaaaacgttc ttcggggcga aaactctcaa ggatcttacc   7260
gctgttgaga tccagttcga tgtaacccac tcgtgcaccc aactgatctt cagcatcttt   7320
tactttcacc agcgtttctg ggtgagcaaa aacaggaagg caaaatgccg caaaaaaggg   7380
aataagggcg acacggaaat gttgaatact catactcttc cttttcaat attattgaag   7440
catttatcag ggttattgtc tcatgagcgg atacatattt gaatgtattt agaaaaataa   7500
acaaataggg gttccgcgca catttccccg aaaagtgcca cctgatgcgg tgtgaaatac   7560
cgcacagatg cgtaaggaga aaataccgca tcaggaaatt gtaagcgtta atattttgtt   7620
aaaattcgcg ttaaattttt gttaaatcag ctcattttt aaccaatagg ccgaaatcgg   7680
caaaatccct tataaatcaa agaatagac cgagataggg ttgagtgttg ttccagtttg   7740
gaacaagagt ccactattaa agaacgtgga ctccaacgtc aaagggcgaa aaaccgtcta   7800
tcagggcgat ggcccactac gtgaaccatc accctaatca agttttttgg ggtcgaggtg   7860
ccgtaaagca ctaaatcgga accctaaagg gagcccccga tttagagctt gacggggaaa   7920
gccggcgaac gtggcgagaa aggaagggaa gaaagcgaaa ggagcgggcg ctagggcgct   7980
ggcaagtgta gcggtcacgc tgcgcgtaac caccacaccc gccgcgctta atgcgccgct   8040
acagggcgcg tccattcgcc attcaggctg cgcaactgtt gggaagggcg atcggtgcgg   8100
gcctcttcgc tattacgcca gctggcgaaa ggggatgtg ctgcaaggcg attaagttgg   8160
gtaacgccag ggttttccca gtcacgacgt tgtaaaacga cggccagtga attgtaatac   8220
gactcactat agggcgaatt gggcccgacg tcgcatgcta tcggcatcga caaggtttgg   8280
gtccctagcc gataccgcac tacctgagtc acaatcttcg gaggtttagt cttccacata   8340
gcacgggcaa aagtgcgtat atatacaaga gcgtttgcca gccacagatt ttcactccac   8400
acaccacatc acacatacaa ccacacacat ccacaatgga acccgaaact aagaagacca   8460
agactgactc caagaagatt gttcttctcg gcggcgactt ctgtggcccc gaggtgattg   8520
ccgaggccgt caaggtgctc aagtctgttg ctgaggcctc cggcaccgag tttgtgtttg   8580
aggaccgact cattggagga gctgccattg agaaggaggg cgagcccatc accgacgcta   8640
ctctcgacat ctgccgaaag gctgactcta ttatgctcgg tgctgtcgga ggcgctgcca   8700
acaccgtatg gaccactccc gacggacgaa ccgacgtgcg acccgagcag ggtctcctca   8760
agctgcgaaa ggacctgaac ctgtacgcca acctgcgacc ctgccagctg ctgtcgccca   8820
agctcgccga tctctccccc atccgaaacg ttgagggcac cgacttcatc attgtccgag   8880
agctcgtcgg aggtatctac tttggagagc gaaaggagga tgacggatct ggcgtcgctt   8940
ccgacaccga gacctactcc gttaattaat ttgaatcgaa tcgatgagcc taaaatgaac   9000
ccgagtatat ctcataaaat tctcggtgag aggtctgtga ctgtcagtac aaggtgcctt   9060
cattatgccc tcaaccttac catacctcac tgaatgtagt gtacctctaa aaatgaaata   9120
cagtgccaaa agccaaggca ctgagctcgt ctaacggact tgatatacaa ccaattaaaa   9180
caaatgaaaa gaaatacagt tctttgtatc atttgtaaca attaccctgt acaaactaag   9240
```

```
gtattgaaat cccacaatat tcccaaagtc caccccttc caaattgtca tgcctacaac      9300
tcatatacca agcactaacc taccgtttaa acagtgtacg cagatctggt gtagtggtag      9360
tgcagtggtg gtattgtgac tggggatgta gttgagaata agtcatacac aagtcagctt      9420
tcttcgagcc tcatataagt ataagtagtt caacgtatta gcactgtacc cagcatctcc      9480
gtatcgagaa acacaacaac atgccccatt ggacagatca tgcggataca caggttgtgc      9540
agtatcatac atactcgatc agacaggtcg tctgaccatc atacaagctg aacaagcgct      9600
ccatacttgc acgctctcta tatacacagt taaattacat atccatagtc taacctctaa      9660
cagttaatct tctggtaagc ctcccagcca gccttctggt atcgcttggc ctcctcaata      9720
ggatctcggt tctggccgta cagacctcgg ccgacaatta tgatatccgt tccggtagac      9780
atgacatcct caacagttcg gtactgctgt ccgagagcgt ctcccttgtc gtcaagaccc      9840
accccggggg tcagaataag ccagtcctca gagtcgccct taggtcggtt ctgggcaatg      9900
aagccaacca caaactcggg gtcggatcgg gcaagctcaa tggtctgctt ggagtactcg      9960
ccagtggcca gagagccctt gcaagacagc tcggccagca tgagcagacc tctggccagc     10020
ttctcgttgg gagaggggac taggaactcc ttgtactggg agttctcgta gtcagagacg     10080
tcctccttct tctgttcaga gacagtttcc tcggcaccag ctcgcaggcc agcaatgatt     10140
ccggttccgg gtacaccgtg ggcgttggtg atatcggacc actcggcgat tcggtgacac     10200
cggtactggt gcttgacagt gttgccaata tctgcgaact ttctgtcctc gaacaggaag     10260
aaaccgtgct taagagcaag ttccttgagg gggagcacag tgccggcgta ggtgaagtcg     10320
tcaatgatgt cgatatgggt tttgatcatg cacacataag gtccgacctt atcggcaagc     10380
tcaatgagct ccttggtggt ggtaacatcc agagaagcac acaggttggt tttcttggct     10440
gccacgagct tgagcactcg agcggcaaag gcggacttgt ggacgttagc tcgagcttcg     10500
taggagggca ttttggtggt gaagaggaga ctgaaataaa tttagtctgc agaactttt     10560 atcggaacct tatctggggc agtgaagtat atgttatggt aatagttacg agttagttga     10620
acttatagat agactggact atacggctat cggtccaaat tagaaagaac gtcaatggct     10680
ctctgggcgt cgcctttgcc gacaaaatg tgatcatgat gaaagccagc aatgacgttg     10740
cagctgatat tgttgtcggc caaccgcgcc gaaaacgcag ctgtcagacc cacagcctcc     10800
aacgaagaat gtatcgtcaa agtgatccaa gcacactcat agttggagtc gtactccaaa     10860
ggcggcaatg acgagtcaga cagatactcg tcgacctttt ccttgggaac caccaccgtc     10920
agcccttctg actcacgtat tgtag                                           10945

<210> SEQ ID NO 105
<211> LENGTH: 1341
<212> TYPE: DNA
<213> ORGANISM: Mortierella alpina AF067654
<220> FEATURE:
<221> NAME/KEY: misc_feature
<223> OTHER INFORMATION: delta-5 desaturase

<400> SEQUENCE: 105
atgggaacgg accaaggaaa aaccttcacc tgggaagagc tggcggccca taacaccaag       60
gacgacctac tcttggccat ccgcggcagg gtgtacgatg tcacaaagtt cttgagccgc      120
catcctggtg gagtggacac tctcctgctc ggagctggcc gagatgttac tccggtcttt      180
gagatgtatc acgcgtttgg ggctgcagat gccattatga agaagtacta tgtcggtaca      240
ctggtctcga atgagctgcc catcttcccg gagccaacgg tgttccacaa aaccatcaag      300
```

```
acgagagtcg agggctactt tacggatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcactttc agtgacccac     540
aaccccactg tctggaagat tctgggagcc acgcacgact ttttcaacgg agcatcgtac    600
ctggtgtgga tgtaccaaca tatgctcggc catcacccct acaccaacat tgctggagca    660
gatcccgacg tgtcgacgtc tgagcccgat gttcgtcgta tcaagcccaa ccaaaagtgg    720
tttgtcaacc acatcaacca gcacatgttt gttccttttcc tgtacggact gctggcgttc    780
aaggtgcgca ttcaggacat caacattttg tactttgtca agaccaatga cgctattcgt    840
gtcaatccca tctcgacatg gcacactgtg atgttctggg gcggcaaggc tttctttgtc    900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac catctgttcc caacgtgtc gcagcaccat    1200
tatcccgata ttctggccat catcaagaac acctgcagcg agtacaaggt tccataccTT   1260
gtcaaggata cgttttggca agcatttgct tcacatttgg agcacttgcg tgttcttgga   1320
ctccgtccca aggaagagta g                                            1341
```

<210> SEQ ID NO 106
<211> LENGTH: 446
<212> TYPE: PRT
<213> ORGANISM: Mortierella alpina AF067654

<400> SEQUENCE: 106

```
Met Gly Thr Asp Gln Gly Lys Thr Phe Thr Trp Glu Glu Leu Ala Ala
  1               5                  10                  15

His Asn Thr Lys Asp Asp Leu Leu Ala Ile Arg Gly Arg Val Tyr
             20                  25                  30

Asp Val Thr Lys Phe Leu Ser Arg His Pro Gly Gly Val Asp Thr Leu
         35                  40                  45

Leu Leu Gly Ala Gly Arg Asp Val Thr Pro Val Phe Glu Met Tyr His
     50                  55                  60

Ala Phe Gly Ala Ala Asp Ala Ile Met Lys Lys Tyr Tyr Val Gly Thr
 65                  70                  75                  80

Leu Val Ser Asn Glu Leu Pro Ile Phe Pro Glu Pro Thr Val Phe His
                 85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190
```

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
            245                 250                 255

Leu Leu Ala Phe Lys Val Arg Ile Gln Asp Ile Asn Ile Leu Tyr Phe
                260                 265                 270

Val Lys Thr Asn Asp Ala Ile Arg Val Asn Pro Ile Ser Thr Trp His
            275                 280                 285

Thr Val Met Phe Trp Gly Gly Lys Ala Phe Val Trp Tyr Arg Leu
        290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
            405                 410                 415

Val Pro Tyr Leu Val Lys Asp Thr Phe Trp Gln Ala Phe Ala Ser His
                420                 425                 430

Leu Glu His Leu Arg Val Leu Gly Leu Arg Pro Lys Glu Glu
            435                 440                 445

<210> SEQ ID NO 107
<211> LENGTH: 12690
<212> TYPE: DNA
<213> ORGANISM: Artificial Sequence
<220> FEATURE:
<223> OTHER INFORMATION: Plasmid pZP3L37

<400> SEQUENCE: 107
aaataccagt tggccacaaa cccttgacga tctcgtatgt ccctccgac atactcccgg      60 ccggctgggg tacgttcgat agcgctatcg gcatcgacaa ggtttgggtc cctagccgat    120
accgcactac ctgagtcaca atcttcggag gtttagtctt ccacatagca cgggcaaaag    180
tgcgtatata tacaagagcg tttgccagcc acagattttc actccacaca ccacatcaca    240
catacaacca cacacatcca caatggaacc cgaaactaag aagaccaaga ctgactccaa    300
gaagattgtt cttctcggcg gcgacttctg tggccccgag gtgattgccg aggccgtcaa    360
ggtgctcaag tctgttgctg aggcctccgg caccgagttt gtgtttgagg accgactcat    420
tggaggagct gccattgaga aggagggcga gcccatcacc gacgctactc tcgacatctg    480
ccgaaaggct gactctatta tgctcggtgc tgtcggaggc gctgccaaca ccgtatggac    540
cactcccgac ggacgaaccg acgtgcgacc cgagcagggt ctcctcaagc tgcgaaagga    600
cctgaacctg tacgccaacc tgcgaccctg ccagctgctg tcgcccaagc tcgccgatct    660

-continued

```
ctcccccatc cgaaacgttg agggcaccga cttcatcatt gtccgagagc tcgtcggagg    720
tatctacttt ggagagcgaa aggaggatga cggatctggc gtcgcttccg acaccgagac    780
ctactccgtt cctgaggttg agcgaattgc ccgaatggcc gccttcctgg cccttcagca    840 caaccccct  cttcccgtgt ggtctcttga caaggccaac gtgctggcct cctctcgact    900
ttggcgaaag actgtcactc gagtcctcaa ggacgaattc ccccagctcg agctcaacca    960
ccagctgatc gactcggccg ccatgatcct catcaagcag ccctccaaga tgaatggtat   1020
catcatcacc accaacatgt ttggcgatat catctccgac gaggcctccg tcatccccgg   1080
ttctctgggt ctgctgccct ccgcctctct ggcttctctg cccgacacca acgaggcgtt   1140
cggtctgtac gagccctgtc acggatctgc ccccgatctc ggcaagcaga aggtcaaccc   1200
cattgccacc attctgtctg ccgccatgat gctcaagttc tctcttaaca tgaagcccgc   1260
cggtgacgct gttgaggctg ccgtcaagga gtccgtcgag gctggtatca ctaccgccga   1320
tatcggaggc tcttcctcca cctccgaggt cggagacttg ttgccaacaa ggtcaaggag   1380
ctgctcaaga aggagtaagt cgtttctacg acgcattgat ggaaggagca aactgacgcg   1440
cctgcgggtt ggtctaccgg cagggtccgc tagtgtataa gactctataa aagggccct   1500 gccctgctaa tgaaatgatg atttataatt taccggtgta gcaaccttga ctagaagaag   1560
cagattgggt gtgtttgtag tggaggacag tggtacgttt tggaaacagt cttcttgaaa   1620
gtgtcttgtc tacagtatat tcactcataa cctcaatagc caagggtgta gtcggtttat   1680
taaaggaagg gagttgtggc tgatgtggat agatatcttt aagctggcga ctgcacccaa   1740
cgagtgtggt ggtagcttgt tagatctgta tattcggtaa gatatatttt gtggggtttt   1800
agtggtgttt aaacagtgta cgcagtacta tagaggaaca attgccccgg agaagacggc   1860
caggccgcct agatgacaaa ttcaacaact cacagctgac tttctgccat tgccactagg   1920 gggggggcctt tttatatggc caagccaagc tctccacgtc ggttgggctg cacccaacaa   1980
taaatgggta ggttgcacc  aacaaaggga tgggatgggg ggtagaagat acgaggataa   2040
cggggctcaa tggcacaaat aagaacgaat actgccatta agactcgtga tccagcgact   2100
gacaccattg catcatctaa gggcctcaaa actacctcgg aactgctgcg ctgatctgga   2160
caccacagag gttccgagca ctttaggttg caccaaatgt cccaccaggt gcaggcagaa   2220
aacgctggaa cagcgtgtac agtttgtctt aacaaaaagt gagggcgctg aggtcgagca   2280
gggtggtgtg acttgttata gcctttagag ctgcgaaagc gcgtatggat ttggctcatc   2340
aggccagatt gagggtctgt ggacacatgt catgttagtg tacttcaatc gccccctgga   2400
tatagccccg acaataggcc gtggcctcat ttttttgcct tccgcacatt tccattgctc   2460
ggtacccaca ccttgcttct cctgcacttg ccaaccttaa tactggttta cattgaccaa   2520
catcttacaa gcgggggggct tgtctagggt atatataaac agtggctctc ccaatcggtt   2580
gccagtctct ttttcctttt cttcccccac agattcgaaa tctaaactac acatcacaca   2640
atgcctgtta ctgacgtcct taagcgaaag tccggtgtca tcgtcggcga cgatgtccga   2700
gccgtgagta tccacgacaa gatcagtgtc gagacgacgc gttttgtgta atgacacaat   2760
ccgaaagtcg ctagcaacac acactctcta cacaaactaa cccagctctc catggctgag   2820
gataagacca aggtcgagtt ccctaccctg actgagctga agcactctat ccctaacgct   2880
tgctttgagt ccaacctcgg actctcgctc tactacactg cccgagcgat cttcaacgca   2940
tctgcctctg ctgctctgct ctacgctgcc cgatctactc ccttcattgc cgataacgtt   3000
ctgctccacg ctctggtttg cgccacctac atctacgtgc agggtgtcat cttctgggt   3060
```

```
ttctttaccg tcggtcacga ctgtggtcac tctgccttct cccgatacca ctccgtcaac    3120
ttcatcattg gctgcatcat gcactctgcc attctgactc ccttcgagtc ctggcgagtg    3180
acccaccgac accatcacaa gaacactggc aacattgata aggacgagat cttctaccct    3240
catcggtccg tcaaggacct ccaggacgtg cgacaatggg tctacaccct cggaggtgct    3300
tggtttgtct acctgaaggt cggatatgct cctcgaacca tgtcccactt tgaccctgg    3360 gaccctctcc tgcttcgacg agcctccgct gtcatcgtgt ccctcggagt ctgggctgcc    3420
ttcttcgctg cctacgccta cctcacatac tcgctcggct ttgccgtcat gggcctctac    3480
tactatgctc tctctctttgt cttgcttcg ttcctcgtca ttactacctt cttgcatcac    3540
aacgacgaag ctactccctg gtacggtgac tcggagtgga cctacgtcaa gggcaacctg    3600
agctccgtcg accgatcgta cggagctttc gtggacaacc tgtctcacca cattggcacc    3660
caccaggtcc atcacttgtt ccctatcatt ccccactaca agctcaacga agccaccaag    3720
cactttgctg ccgcttaccc tcacctcgtg agacgtaacg acgagcccat cattactgcc    3780
ttcttcaaga ccgctcacct ctttgtcaac tacggagctg tgcccgagac tgctcagatt    3840
ttcaccctca aagagtctgc cgctgcagcc aaggccaaga gcgactaagc ggccgctatt    3900
tatcactctt tacaacttct acctcaacta tctactttaa taaatgaata tcgtttattc    3960
tctatgatta ctgtatatgc gttcctctaa gacaaatcga aaccagcatg tgatcgaatg    4020
gcatacaaaa gtttcttccg aagttgatca atgtcctgat agtcaggcag cttgagaaga    4080
ttgacacagg tggaggccgt agggaaccga tcaacctgtc taccagcgtt acgaatggca    4140
aatgacgggt tcaaagcctt gaatccttgc aatggtgcct tggatactga tgtcacaaac    4200
ttaagaagca gccgcttgtc ctcttcctcg atcgatcagg agagaccggg ttggcggcgt    4260
atttgtgtcc caaaaaacag ccccaattgc cccaattgac cccaaattga cccagtagcg    4320
ggcccaaccc cggcgagagc ccccttcacc ccacatatca aacctccccc ggttcccaca    4380
cttgccgtta agggcgtagg gtactgcagt ctggaatcta cgcttgttca gacttttgtac    4440 tagtttcttt gtctggccat ccgggtaacc catgccggac gcaaaataga ctactgaaaa    4500 ttttttttgct ttgtggttgg gactttagcc aagggtataa aagaccaccg tccccgaatt    4560
acctttcctc ttcttttctc tctctccttg tcaactcaca cccgaaatcg ttaagcattt    4620
ccttctgagt ataagaatca ttcaccatgg ctgaggataa gaccaaggtc gagttcccta    4680
ccctgactga gctgaagcac tctatcccta acgcttgctt tgagtccaac ctcggactct    4740
cgctctacta cactgcccga gcgatcttca acgcatctgc ctctgctgct ctgctctacg    4800
ctgcccgatc tactcccttc attgccgata acgttctgct ccacgctctg gtttgcgcca    4860
cctacatcta cgtgcagggt gtcatcttct ggggtttctt taccgtcggt cacgactgtg    4920
gtcactctgc cttctcccga taccactccg tcaacttcat cattggctgc atcatgcact    4980
ctgccattct gactcccttc gagtcctggc gagtgaccca ccgacaccat cacaagaaca    5040
ctggcaacat tgataaggac gagatcttct accctcatcg gtccgtcaag gacctccagg    5100
acgtgcgaca atgggtctac accctcggag gtgcttggtt tgtctacctg aaggtcggat    5160
atgctcctcg aaccatgtcc cactttgacc cctgggaccc tctcctgctt cgacgagcct    5220
ccgctgtcat cgtgtccctc ggagtctggg ctgccttctt cgctgcctac gcctacctca    5280
catactcgct cggctttgcc gtcatgggcc tctactacta tgctcctctc tttgtctttg    5340
cttcgttcct cgtcattact accttcttgc atcacaacga cgaagctact ccctggtacg    5400
gtgactcgga gtggacctac gtcaagggca acctgagctc cgtcgaccga tcgtacggag    5460
```

```
ctttcgtgga caacctgtct caccacattg gcacccacca ggtccatcac ttgttcccta      5520
tcattcccca ctacaagctc aacgaagcca ccaagcactt tgctgccgct taccctcacc      5580
tcgtgagacg taacgacgag cccatcatta ctgccttctt caagaccgct cacctctttg      5640
tcaactacgg agctgtgccc gagactgctc agattttcac cctcaaagag tctgccgctg      5700
cagccaaggc caagagcgac taagcggccg caagtgtgga tggggaagtg agtgcccggt      5760
tctgtgtgca caattggcaa tccaagatgg atggattcaa cacagggata tagcgagcta      5820
cgtggtggtg cgaggatata gcaacggata tttatgtttg acacttgaga atgtacgata      5880
caagcactgt ccaagtacaa tactaaacat actgtacata ctcatactcg tacccgggca      5940
acggtttcac ttgagtgcag tggctagtgc tcttactcgt acagtgtgca atactgcgta      6000
tcatagtctt tgatgtatat cgtattcatt catgttagtt gcgtacggtg tgtatcgtag      6060
aggtagtgac gtgttgtcca cagggcgact gtgtccgtgt atatatatat tcctcggccc      6120
gagcttattt gtgtggggtt gaggaaatca aaccaaatcg gtagtcagag aaataaaaca      6180
aaagaaaata aaagaaaata gaggacgcac aacgccatca ccgtcggaga gacaggagaa      6240
gggaaaatgg gcaaaaatgc ccttatcaca cccgcccgct ttgtgctctc attcggctcc      6300
cacaagagcc tcttgtcctg gttccccccc cccacatttt aacaccccac acgacgttgc      6360
tgcacgtgga attttcggcc gaaaacctgt ggggtactta cttttggcac tggagagaag      6420
catctgggat tttgggaacc taggcagaag atgaggaaaa aaataagagg aaccgttgtg      6480
agcttgctta tcagtgtcat atactccccc ctccttgcgt ttttgcgtct ttccccccta      6540
tttttcaaat tttgcgattt ttttttctctt tttttccgct ttttccgct ttttttttgg      6600
ccggctttta tccatttctc caagccgagg atcacatcta tgcagcccag tccgttggag      6660
catatctgcg gtagagtttc ggaacggcgt taagcactgt gtccgggtcg gtctggaacg      6720
agattgagcg ggaaattcgg gggaataaga ccaccgttgg actccccgca atgaggagat      6780
caagatgtgc ttttcagaat tctgattggt ggcgcgccag ctgcattaat gaatcggcca      6840
acgcgcgggg agaggcggtt tgcgtattgg gcgctcttcc gcttcctcgc tcactgactc      6900
gctgcgctcg tcgttcggc tgcggcgagc ggtatcagct cactcaaagg cggtaatacg      6960
gttatccaca gaatcagggg ataacgcagg aaagaacatg tgagcaaaag gccagcaaaa      7020
ggccaggaac cgtaaaaagg ccgcgttgct ggcgttttc cataggctcc gcccccctga      7080
cgagcatcac aaaaatcgac gctcaagtca gaggtggcga aacccgacag gactataaag      7140
ataccaggcg tttccccctg gaagctccct cgtgcgctct cctgttccga ccctgccgct      7200
taccggatac ctgtccgcct ttctcccttc gggaagcgtg gcgctttctc atagctcacg      7260
ctgtaggtat ctcagttcgg tgtaggtcgt tcgctccaag ctgggctgtg tgcacgaacc      7320
ccccgttcag cccgaccgct gcgccttatc cggtaactat cgtcttgagt ccaacccggt      7380
aagacacgac ttatcgccac tggcagcagc cactggtaac aggattagca gagcgaggta      7440
tgtaggcggt gctacagagt tcttgaagtg gtggcctaac tacggctaca ctagaagaac      7500
agtatttggt atctgcgctc tgctgaagcc agttaccttc ggaaaaagag ttggtagctc      7560
ttgatccggc aaacaaacca ccgctggtag cggtggtttt tttgtttgca agcagcagat      7620
tacgcgcaga aaaaaggat ctcaagaaga tcctttgatc ttttctacgg ggtctgacgc      7680
tcagtggaac gaaaactcac gttaagggat tttggtcatg agattatcaa aaaggatctt      7740
cacctagatc cttttaaatt aaaaatgaag ttttaaatca atctaaagta tatatgagta      7800
aacttggtct gacagttacc aatgcttaat cagtgaggca cctatctcag cgatctgtct      7860
```

```
atttcgttca tccatagttg cctgactccc cgtcgtgtag ataactacga tacgggaggg    7920
cttaccatct ggccccagtg ctgcaatgat accgcgagac ccacgctcac cggctccaga    7980
tttatcagca ataaaccagc cagccggaag ggccgagcgc agaagtggtc ctgcaacttt    8040
atccgcctcc atccagtcta ttaattgttg ccgggaagct agagtaagta gttcgccagt    8100
taatagtttg cgcaacgttg ttgccattgc tacaggcatc gtggtgtcac gctcgtcgtt    8160
tggtatggct tcattcagct ccggttccca acgatcaagg cgagttacat gatccccat     8220
gttgtgcaaa aaagcggtta gctccttcgg tcctccgatc gttgtcagaa gtaagttggc    8280
cgcagtgtta tcactcatgg ttatggcagc actgcataat tctcttactg tcatgccatc    8340
cgtaagatgc ttttctgtga ctggtgagta ctcaaccaag tcattctgag aatagtgtat    8400
gcggcgaccg agttgctctt gcccggcgtc aatacgggan aataccgcgc cacatagcag    8460
aactttaaaa gtgctcatca ttggaaaacg ttcttcgggg cgaaaactct caaggatctt    8520
accgctgttg agatccagtt cgatgtaacc cactcgtgca cccaactgat cttcagcatc    8580
tttactttc accagcgttt ctgggtgagc aaaaacagga aggcaaaatg ccgcaaaaaa    8640
gggaataagg cgacacggaa aatgttgaat actcatactc ttcctttttc aatattattg    8700
aagcatttat cagggttatt gtctcatgag cggatacata tttgaatgta tttagaaaaa    8760
taaacaaata ggggttccgc gcacatttcc ccgaaaagtg ccacctgatg cggtgtgaaa    8820
taccgcacag atgcgtaagg agaaaatacc gcatcaggaa attgtaagcg ttaatatttt    8880
gttaaaattc gcgttaaatt tttgttaaat cagctcattt tttaaccaat aggccgaaat    8940
cggcaaaatc ccttataaat caaaagaata gaccgagata gggttgagtg ttgttccagt    9000
ttggaacaag agtccactat taagaacgt ggactccaac gtcaaagggc gaaaaaccgt     9060
ctatcagggc gatggcccac tacgtgaacc atcaccctaa tcaagttttt tggggtcgag    9120
gtgccgtaaa gcactaaatc ggaaccctaa agggagcccc cgatttagag cttgacgggg    9180
aaagccggcg aacgtggcga gaaaggaagg gaagaaagcg aaaggagcgg cgctagggc     9240
gctggcaagt gtagcggtca cgctgcgcgt aaccaccaca cccgccgcgc ttaatgcgcc    9300
gctacagggc gcgtccattc gccattcagg ctgcgcaact gttgggaagg gcgatcggtg    9360
cgggcctctt cgctattacg ccagctggcg aaagggggat gtgctgcaag gcgattaagt    9420
tgggtaacgc cagggttttc ccagtcacga cgttgtaaaa cgacggccag tgaattgtaa    9480
tacgactcac tatagggcga attgggcccg acgtcgcatg cgtcgagata tcgacattgt    9540
tccatctcca gtttaacccc aacttatcga gagtatttgt gagacacgca ataaatgaat    9600
ttataccaat caaatccata ttctacgctg tctacatata gatactttt gtcatctctt     9660
gccctactat ttcgtcgata tatgaaggat acgccaaccg aacccatact ccacgctaca    9720
cacgcgcctt ttcacgcatt tctggggaaa atagacaccc ttggtgtcac ctgaagaata    9780
tgaaagaaga tattcattgt attgagctgt agatctgtgt atttcttgac ctcatcaatg    9840
acttctgggc tctttacctc gaatcatggt ggtactgtac cacatctcaa caccttgtag    9900
cacacctatg ggaaaattga gactatgaat ggattcccgt gcccgtatta ctctactaat    9960
ttgatcttgg aacgcgaaaa tacgtttcta ggactccaaa gaatctcaac tcttgtcctt   10020
actaaatata ctacccatag ttgatggttt acttgaacag agaggacatg ttcacttgac   10080
ccaaagtttc tcgcatctct tggatatttg aacaacggcg tccactgacc gtcagttatc   10140
cagtcacaaa acccccacat tcatacattc ccatgtacgt ttacaaagtt ctcaattcca   10200
tcgtgcaaat caaaatcaca tctattcatt catcatatat aaacccatca tgtctactaa   10260
```

```
cactcacaac tccatagaaa acatcgactc agaacacacg ctccatctat tcctcgtcca   10320
gctcgcaaat gtcgtcatct taattaaaag gcgttgaaac agaatgagcc agacagcaag   10380
gacaaggtgg ccaacagcaa ggagtccaaa aagccctcta ttgacgagat ccacgatgtt   10440
attgctcatg aggtttccga gctcgatgct gggaagaaga agtgatttgt atataagaaa   10500
taaatgagat atagtaaagg agtgcaagag aatggcaagg tggtcaaatt ctatattact   10560
tgcagtcact ggttcctcgt tgacatgaat gaagttaccg ttggcatagc tgatttaata   10620
tataactgtc caactaactc tcacctagat ataacccatg tgtgtgtttc caatcatcaa   10680
tgcggccgct tagtcgctct tggccttggc tgcagcggca gactctttga gggtgaaaat   10740
ctgagcagtc tcgggcacag ctccgtagtt gacaaagagg tgagcggtct tgaagaaggc   10800
agtaatgatg ggctcgtcgt tacgtctcac gaggtgaggg taagcggcag caaagtgctt   10860
ggtggcttcg ttgagcttgt agtggggaat gatagggaac aagtgatgga cctggtgggt   10920
gccaatgtgg tgagacaggt tgtccacgaa agctccgtac gatcggtcga cggagctcag   10980
gttgcccttg acgtaggtcc actccgagtc accgtaccag ggagtagctt cgtcgttgtg   11040
atgcaagaag gtagtaatga cgaggaacga agcaaagaca aagagaggag catagtagta   11100
gaggcccatg acggcaaagc cgagcgagta tgtgaggtag gcgtaggcag cgaagaaggc   11160
agcccagact ccgagggaca cgatgacagc ggaggctcgt cgaagcagga gagggtccca   11220
ggggtcaaag tgggacatgg ttcgaggagc atatccgacc ttcaggtaga caaaccaagc   11280
acctccgagg gtgtagaccc attgtcgcac gtcctggagg tccttgacgg accgatgagg   11340
gtagaagatc tcgtccttat caatgttgcc agtgttcttg tgatggtgtc ggtgggtcac   11400
tcgccaggac tcgaagggag tcagaatggc agagtgcatg atgcagccaa tgatgaagtt   11460
gacggagtgg tatcgggaga aggcagagtg accacagtcg tgaccgacgg taaagaaacc   11520
ccagaagatg acaccctgca cgtagatgta ggtggcgcaa accagagcgt ggagcagaac   11580
gttatcggca atgaagggag tagatcgggc agcgtagagc agagcagcag aggcagatgc   11640
gttgaagatc gctcgggcag tgtagtagag cgagagtccg aggttggact caaagcaagc   11700
gttagggata gagtgcttca gctcagtcag ggtagggaac tcgaccttgg tcttatcctc   11760
agccatggta ccagagctgg gttagttttgt gtagagagtg tgtgttgcta gcgactttcg   11820
gattgtgtca ttacacaaaa cgcgtcgtct cgacactgat cttgtcgtgg atactcacgg   11880
ctcggaattc tgtgatgtgt agtttagatt tcgaatctgt ggggaaagaa aggaaaaaag   11940
agactggcaa ccgattggga gagccactgt ttatatatac cctagacaag cccccgctt   12000 gtaagatgtt ggtcaatgta aaccagtatt aaggttggca agtgcaggag aagcaaggtg   12060
tgggtaccga gcaatggaaa tgtgcggaag gcaaaaaaat gaggccacgg cctattgtcg   12120
gggctatatc caggggcga ttgaagtaca ctaacatgac atgtgtccac agaccctcaa   12180
tctggcctga tgagccaaat ccatacgcgc tttcgcagct ctaaaggcta taacaagtca   12240
caccaccctg ctcgacctca gcgccctcac tttttgttaa gacaaactgt acacgctgtt   12300
ccagcgtttt ctgcctgcac ctggtgggac atttggtgca acctaaagtg ctcggaacct   12360
ctgtggtgtc cagatcagcg cagcagttcc gaggtagttt tgaggccctt agatgatgca   12420
atggtgtcag tcgctggatc acgagtctta atggcagtat tcgttcttat ttgtgccatt   12480
gagccccgtt atcctcgtat cttctacccc ccatcccatc cctttgttgg tgcaacccta   12540
cccatttatt gttgggtgca gcccaaccga cgtgggagagc ttggcttggc catataaaaa   12600
ggcccccccc tagtggcaat ggcagaaagt cagctgtgag ttgttgaatt tgtcatctag   12660
```

```
gcggcctggc cgtcttctcc ggggcaattt                                    12690
```

<210> SEQ ID NO 108
<211> LENGTH: 1077
<212> TYPE: DNA
<213> ORGANISM: Saprolegnia diclina
<220> FEATURE:
<221> NAME/KEY: misc_feature
<223> OTHER INFORMATION: synthetic delta-17 desaturase (codon-optimized)

<400> SEQUENCE: 108

```
atggctgagg ataagaccaa ggtcgagttc cctaccctga ctgagctgaa gcactctatc      60
cctaacgctt gctttgagtc caacctcgga ctctcgctct actacactgc ccgagcgatc     120
ttcaacgcat ctgcctctgc tgctctgctc tacgctgccc gatctactcc cttcattgcc     180
gataacgttc tgctccacgc tctggtttgc gccacctaca tctacgtgca gggtgtcatc     240
ttctggggtt tctttaccgt cggtcacgac tgtggtcact ctgccttctc ccgataccac     300
tccgtcaact tcatcattgg ctgcatcatg cactctgcca ttctgactcc cttcgagtcc     360
tggcgagtga cccaccgaca ccatcacaag aacactggca acattgataa ggacgagatc     420
ttctaccctc atcggtccgt caaggacctc caggacgtgc acaatgggt ctacaccctc      480
ggaggtgctt ggtttgtcta cctgaaggtc ggatatgctc ctcgaaccat gtcccacttt     540
gaccctgg  accctctcct gcttcgacga gcctccgctg tcatcgtgtc cctcggagtc      600
tgggctgcct cttcgctgc ctacgcctac ctcacatact cgctcggctt tgccgtcatg      660
ggcctctact actatgctcc tctctttgtc tttgcttcgt tcctcgtcat tactaccttc     720
ttgcatcaca acgacgaagc tactccctgg tacggtgact cggagtggac ctacgtcaag     780
ggcaacctga ctccgtcga ccgatcgtac ggagctttcg tggacaacct gtctcaccac      840
attggcaccc accaggtcca tcacttgttc cctatcattc cccactacaa gctcaacgaa     900
gccaccaagc acttgctgc cgcttaccct cacctcgtga cgtaacga cgagcccatc       960
attactgcct tcttcaagac cgctcacctc tttgtcaact acggagctgt gcccgagact    1020
gctcagattt tcaccctcaa agagtctgcc gctgcagcca aggccaagag cgactaa       1077
```

<210> SEQ ID NO 109
<211> LENGTH: 358
<212> TYPE: PRT
<213> ORGANISM: Saprolegnia diclina (ATCC #56851)

<400> SEQUENCE: 109

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125
```

His Lys Asn Thr Gly Asn Ile Asp Lys Asp Glu Ile Phe Tyr Pro His
            130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 110
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 110
aaattgcccc ggagaagacg gccaggccgc ctagatgaca aattcaacaa ctcacagctg      60
actttctgcc attgccacta ggggggggcc tttttatatg gccaagccaa gctctccacg     120
tcggttgggc tgcacccaac aataaatggg tagggttgca ccaacaaagg gatgggatgg     180
ggggtagaag atacgaggat aacgggctc aatggcacaa ataagaacga atactgccat      240
taagactcgt gatccagcga ctgacaccat tgcatcatct aagggcctca aaactacctc     300
ggaactgctg cgctgatctg gacaccacag aggttccgag cactttaggt tgcaccaaat     360
gtcccaccag gtgcaggcag aaaacgctgg aacagcgtgt acagtttgtc ttaacaaaaa     420
gtgagggcgc tgaggtcgag cagggtggtg tgacttgtta tagcctttag agctgcgaaa     480
gcgcgtatgg atttggctca tcaggccaga ttgagggtct gtggacacat gtcatgttag     540
tgtacttcaa tcgcccctg gatatagccc cgacaatagg ccgtggcctc attttttgc      600 cttccgcaca tttccattgc tcggtaccca caccttgctt ctcctgcact tgccaacctt     660
aatactggtt tacattgacc aacatcttac aagcgggggg cttgtctagg gtatatataa     720

| | |
|---|---|
| acagtggctc tcccaatcgg ttgccagtct cttttttcct ttctttcccc acagattcga | 780 |
| aatctaaact acacatcaca gaattccgag ccgtgagtat ccacgacaag atcagtgtcg | 840 |
| agacgacgcg ttttgtgtaa tgacacaatc cgaaagtcgc tagcaacaca cactctctac | 900 |
| acaaactaac ccagctctgg tacc | 924 |

<210> SEQ ID NO 111
<211> LENGTH: 8194
<212> TYPE: DNA
<213> ORGANISM: Artificial Sequence
<220> FEATURE:
<223> OTHER INFORMATION: Plasmid pY37/F15

<400> SEQUENCE: 111

| | |
|---|---|
| ggccgcacaa tggcgactcg acagcgaact gccaccactg ttgtggtcga ggaccttccc | 60 |
| aaggtcactc ttgaggccaa gtctgaacct gtgttccccg atatcaagac catcaaggat | 120 |
| gccattcccg cgcactgctt ccagccctcg ctcgtcacct cattctacta cgtcttccgc | 180 |
| gattttgcca tggtctctgc cctcgtctgg gctgctctca cctacatccc cagcatcccc | 240 |
| gaccagaccc tccgcgtcgc agcttggatg gtctacggct tcgtccaggg tctgttctgc | 300 |
| accggtgtct ggattctcgg ccatgagtgc ggccacggtg ctttctctct ccacggaaag | 360 |
| gtcaacaatg tgaccggctg gttcctccac tcgttcctcc tcgtcccta cttcagctgg | 420 |
| aagtactctc accaccgcca ccaccgcttc accggccaca tggatctcga catggctttc | 480 |
| gtccccaaga ctgagcccaa gccctccaag tcgctcatga ttgctggcat tgacgtcgcc | 540 |
| gagcttgttg aggacacccc cgctgctcag atggtcaagc tcatcttcca ccagcttttc | 600 |
| ggatggcagg cgtacctctt cttcaacgct agctctggca agggcagcaa gcagtgggag | 660 |
| cccaagactg gcctctccaa gtggttccga gtcagtcact tcgagcctac cagcgctgtc | 720 |
| ttccgcccca acgaggccat cttcatcctc atctccgata tcggtcttgc tctaatggga | 780 |
| actgctctgt actttgcttc caagcaagtt ggtgtttcga ccattctctt cctctacctt | 840 |
| gttccctacc tgtgggttca ccactggctc gttgccatta cctacctcca ccaccaccac | 900 |
| accgagctcc ctcactacac cgctgagggc tggacctacg tcaagggagc tctcgccact | 960 |
| gtcgaccgtg agtttggctt catcggaaag cacctcttcc acggtatcat tgagaagcac | 1020 |
| gttgttcacc atctcttccc taagatcccc ttctacaagg ctgacgaggc caccgaggcc | 1080 |
| atcaagcccg tcattggcga ccactactgc cacgacgacc gaagcttcct gggccagctg | 1140 |
| tggaccatct tcggcacgct caagtacgtc gagcacgacc ctgcccgacc cggtgccatg | 1200 |
| cgatggaaca aggactaggc taggcggccg ccaccgcggc ccgaattccg gcctcttcgg | 1260 |
| ccgccaagcg acccgggtgg acgtctagag gtacctagca attaacagat agtttgccgg | 1320 |
| tgataattct cttaacctcc cacactcctt tgacataacg atttatgtaa cgaaactgaa | 1380 |
| atttgaccag atattgtgtc cgcggtggag ctccagcttt tgttcccttt agtgagggtt | 1440 |
| aatttcgagc ttggcgtaat catggtcata gctgtttcct gtgtgaaatt gttatccgct | 1500 |
| cacaattcca cacaacgtac gagccggaag cataaagtgt aaagcctggg gtgcctaatg | 1560 |
| agtgagctaa ctcacattaa ttgcgttgcg ctcactgccc gctttccagt cgggaaacct | 1620 |
| gtcgtgccag ctgcattaat gaatcggcca acgcgcgggg agaggcggtt tgcgtattgg | 1680 |
| gcgctcttcc gcttcctcgc tcactgactc gctgcgctcg gtcgttcggc tgcggcgagc | 1740 |
| ggtatcagct cactcaaagg cggtaatacg gttatccaca gaatcagggg ataacgcagg | 1800 |
| aaagaacatg tgagcaaaag gccagcaaaa ggccaggaac cgtaaaaagg ccgcgttgct | 1860 |

-continued

```
ggcgtttttc cataggctcc gccccccctga cgagcatcac aaaaatcgac gctcaagtca  1920
gaggtggcga aacccgacag gactataaag ataccaggcg tttccccctg gaagctccct  1980
cgtgcgctct cctgttccga ccctgccgct taccggatac ctgtccgcct ttctcccttc  2040
gggaagcgtg gcgctttctc atagctcacg ctgtaggtat ctcagttcgg tgtaggtcgt  2100
tcgctccaag ctgggctgtg tgcacgaacc ccccgttcag cccgaccgct gcgccttatc  2160
cggtaactat cgtcttgagt ccaacccggt aagacacgac ttatcgccac tggcagcagc  2220
cactggtaac aggattagca gagcgaggta tgtaggcggt gctacagagt tcttgaagtg  2280
gtggcctaac tacggctaca ctagaaggac agtatttggt atctgcgctc tgctgaagcc  2340
agttaccttc ggaaaaagag ttggtagctc ttgatccggc aaacaaacca ccgctggtag  2400
cggtggtttt tttgtttgca agcagcagat tacgcgcaga aaaaaggat ctcaagaaga  2460 tcctttgatc ttttctacgg ggtctgacgc tcagtggaac gaaaactcac gttaagggat  2520
tttggtcatg agattatcaa aaaggatctt cacctagatc cttttaaatt aaaaatgaag  2580
ttttaaatca atctaaagta tatatgagta aacttggtct gacagttacc aatgcttaat  2640
cagtgaggca cctatctcag cgatctgtct atttcgttca tccatagttg cctgactccc  2700
cgtcgtgtag ataactacga tacgggaggg cttaccatct ggccccagtg ctgcaatgat  2760
accgcgagac ccacgctcac cggctccaga tttatcagca ataaaccagc cagccggaag  2820
ggccgagcgc agaagtggtc ctgcaacttt atccgcctcc atccagtcta ttaattgttg  2880
ccgggaagct agagtaagta gttcgccagt taatagtttg cgcaacgttg ttgccattgc  2940
tacaggcatc gtggtgtcac gctcgtcgtt tggtatggct tcattcagct ccggttccca  3000
acgatcaagg cgagttacat gatcccccat gttgtgcaaa aaagcggtta gctccttcgg  3060
tcctccgatc gttgtcagaa gtaagttggc cgcagtgtta tcactcatgg ttatggcagc  3120
actgcataat tctcttactg tcatgccatc cgtaagatgc ttttctgtga ctggtgagta  3180
ctcaaccaag tcattctgag aatagtgtat gcggcgaccg agttgctctt gcccggcgtc  3240
aatacgggat aataccgcgc cacatagcag aactttaaaa gtgctcatca ttggaaaacg  3300
ttcttcgggg cgaaaactct caaggatctt accgctgttg agatccagtt cgatgtaacc  3360
cactcgtgca cccaactgat cttcagcatc ttttactttc accagcgttt ctgggtgagc  3420
aaaaacagga aggcaaaatg ccgcaaaaaa gggaataagg gcgacacgga aatgttgaat  3480
actcatactc ttccttttc aatattattg aagcatttat cagggttatt gtctcatgag  3540
cggatacata tttgaatgta tttagaaaaa taaacaaata ggggttccgc gcacatttcc  3600
ccgaaaagtg ccacctgacg cgccctgtag cggcgcatta agcgcggcgg gtgtggtggt  3660
tacgcgcagc gtgaccgcta cacttgccag cgccctagcg cccgctcctt tcgctttctt  3720
cccttccttt ctcgccacgt tcgccggctt tccccgtcaa gctctaaatc ggggctccc  3780 tttagggttc cgatttagtg ctttacggca cctcgacccc aaaaaacttg attagggtga  3840
tggttcacgt agtgggccat cgccctgata cggttttt cgccctttga cgttggagtc  3900
cacgttcttt aatagtggac tcttgttcca aactggaaca acactcaacc ctatctcggt  3960
ctattctttt gatttataag ggattttgcc gatttcggcc tattggttaa aaaatgagct  4020
gatttaacaa aaatttaacg cgaattttaa caaaatatta acgcttacaa tttccattcg  4080
ccattcaggc tgcgcaactg ttgggaaggg cgatcggtgc gggcctcttc gctattacgc  4140
cagctggcga aaggggatg tgctgcaagg cgattaagtt gggtaacgcc agggttttcc  4200
cagtcacgac gttgtaaaac gacggccagt gaattgtaat acgactcact ataggcgaa  4260
```

```
ttgggtaccg ggccccccct cgaggtcgat ggtgtcgata agcttgatat cgaattcatg    4320
tcacacaaac cgatcttcgc ctcaaggaaa cctaattcta catccgagag actgccgaga    4380
tccagtctac actgattaat tttcgggcca ataatttaaa aaaatcgtgt tatataatat    4440
tatatgtatt atatatatac atcatgatga tactgacagt catgtcccat tgctaaatag    4500
acagactcca tctgccgcct ccaactgatg ttctcaatat ttaaggggtc atctcgcatt    4560
gtttaataat aaacagactc catctaccgc ctccaaatga tgttctcaaa atatattgta    4620
tgaacttatt tttattactt agtattatta gacaacttac ttgctttatg aaaaacactt    4680
cctatttagg aaacaattta taatggcagt tcgttcattt aacaatttat gtagaataaa    4740
tgttataaat gcgtatggga atcttaaat atggatagca taaatgatat ctgcattgcc    4800
taattcgaaa tcaacagcaa cgaaaaaaat cccttgtaca acataaatag tcatcgagaa    4860
atatcaacta tcaaagaaca gctattcaca cgttactatt gagattatta ttggacgaga    4920
atcacacact caactgtctt tctctcttct agaaatacag gtacaagtat gtactattct    4980
cattgttcat acttctagtc atttcatccc acatattcct tggatttctc tccaatgaat    5040
gacattctat cttgcaaatt caacaattat aataagatat accaaagtag cggtatagtg    5100
gcaatcaaaa agcttctctg gtgtgcttct cgtatttatt tttattctaa tgatccatta    5160
aaggtatata tttatttctt gttatataat ccttttgttt attacatggg ctggatacat    5220
aaaggtattt tgatttaatt ttttgcttaa attcaatccc ccctcgttca gtgtcaactg    5280
taatggtagg aaaattaccat acttttgaag aagcaaaaaa aatgaaagaa aaaaaaaatc    5340
gtatttccag gttagacgtt ccgcagaatc tagaatgcgg tatgcggtac attgttcttc    5400
gaacgtaaaa gttgcgctcc ctgagatatt gtacattttt gcttttacaa gtacaagtac    5460
atcgtacaac tatgtactac tgttgatgca tccacaacag tttgttttgt ttttttttgt    5520
tttttttttt tctaatgatt cattaccgct atgtatacct acttgtactt gtagtaagcc    5580
gggttattgg cgttcaatta atcatagact tatgaatctg cacggtgtgc gctgcgagtt    5640 actttttagct tatgcatgct acttgggtgt aatattggga tctgttcgga aatcaacgga    5700
tgctcaaccg atttcgacag taattaatta agtcatacac aagtcagctt tcttcgagcc    5760
tcatataagt ataagtagtt caacgtatta gcactgtacc cagcatctcc gtatcgagaa    5820
acacaacaac atgccccatt ggacagatca tgcggataca caggttgtgc agtatcatac    5880
atactcgatc agacaggtcg tctgaccatc atacaagctg aacaagcgct ccatacttgc    5940
acgctctcta tatacacagt taaattacat atccatagtc taacctctaa cagttaatct    6000
tctggtaagc ctcccagcca gccttctggt atcgcttggc ctcctcaata ggatctcggt    6060 tctgccgta cagacctcgg ccgacaatta tgatatccgt tccggtagac atgacatcct    6120
caacagttcg gtactgctgt ccgagagcgt ctcccttgtc gtcaagaccc accccggggg    6180
tcagaataag ccagtcctca gagtcgccct taggtcggtt ctgggcaatg aagccaacca    6240
caaactcggg gtcggatcgg gcaagctcaa tggtctgctt ggagtactcg ccagtggcca    6300
gagagccctt gcaagacagc tcggccagca tgagcagacc tctggccagc ttctcgttgg    6360
gagaggggac taggaactcc ttgtactggg agttctcgta gtcagagacg tcctccttct    6420
tctgttcaga gacagtttcc tcggcaccag ctcgcaggcc agcaatgatt ccggttccgg    6480
gtacaccgtg ggcgttggtg atatcggacc actcggcgat tcggtgacac cggtactggt    6540
gcttgacagt gttgccaata tctgcgaact ttctgtcctc gaacaggaag aaaccgtgct    6600
taagagcaag ttccttgagg gggagcacag tgccggcgta ggtgaagtcg tcaatgatgt    6660
```

```
cgatatgggt tttgatcatg cacacataag gtccgacctt atcggcaagc tcaatgagct    6720
ccttggtggt ggtaacatcc agagaagcac acaggttggt tttcttggct gccacgagct    6780
tgagcactcg agcggcaaag gcggacttgt ggacgttagc tcgagcttcg taggagggca    6840
ttttggtggt gaagaggaga ctgaaataaa tttagtctgc agaactttt atcggaacct     6900 tatctgggc agtgaagtat atgttatggt aatagttacg agttagttga acttatagat     6960
agactggact atacggctat cggtccaaat tagaaagaac gtcaatggct ctctgggcgt    7020 cgccttgcc gacaaaaatg tgatcatgat gaaagccagc aatgacgttg cagctgatat     7080
tgttgtcggc caaccgcgcc gaaaacgcag ctgtcagacc cacagcctcc aacgaagaat    7140
gtatcgtcaa agtgatccaa gcacactcat agttggagtc gtactccaaa ggcggcaatg    7200
acgagtcaga cagatactcg tcgacgcagt aggatgtcct gcacgggtct ttttgtgggg    7260
tgtggagaaa ggggtgcttg gagatggaag ccggtagaac cgggctgctt gtgcttggag    7320
atggaagccg gtagaaccgg gctgcttggg gggatttggg gccgctgggc tccaaagagg    7380
ggtaggcatt tcgttggggt tacgtaattg cggcatttgg gtcctgcgcg catgtcccat    7440
tggtcagaat tagtccggat aggagactta tcagccaatc acagcgccgg atccacctgt    7500
aggttgggtt gggtgggagc accctccac agagtagagt caaacagcag cagcaacatg     7560
atagttgggg gtgtgcgtgt taaggaaaa aaagaagct tgggttatat tcccgctcta      7620
tttagaggtt gcgggataga cgccgacgga gggcaatggc gccatggaac cttgcggata    7680
tcgatacgcc gcggcggact gcgtccgaac cagctccagc agcgtttttt ccgggccatt    7740
gagccgactg cgaccccgcc aacgtgtctt ggcccacgca ctcatgtcat gttggtgttg    7800
ggaggccact ttttaagtag cacaaggcac ctagctcgca gcaaggtgtc cgaaccaaag    7860
aagcggctgc agtggtgcaa acggggcgga acggcggga aaaagccacg ggggcacgaa     7920
ttgaggcacg ccctcgaatt tgagacgagt cacggcccca ttcgcccgcg caatggctcg    7980
ccaacgcccg gtcttttgca ccacatcagg ttaccccaag ccaaaccttt gtgttaaaaa    8040
gcttaacata ttataccgaa cgtaggtttg ggcgggcttg ctccgtctgt ccaaggcaac    8100
atttatataa gggtctgcat cgccggctca attgaatctt ttttcttctt ctcttctcta    8160
tattcattct tgaattaaac acacatcaat ccgc                                8194

<210> SEQ ID NO 112
<211> LENGTH: 10448
<212> TYPE: DNA
<213> ORGANISM: Artificial Sequence
<220> FEATURE:
<223> OTHER INFORMATION: Plasmid pKO2UM26E

<400> SEQUENCE: 112
cgattgcccc ggagaagacg gccaggccgc ctagatgaca aattcaacaa ctcacagctg      60
actttctgcc attgccacta gggggggcc tttttatatg gccaagccaa gctctccacg      120
tcggttgggc tgcacccaac aataaatggg taggttgca ccaacaaagg gatgggatgg      180
ggggtagaag atacgaggat aacggggctc aatggcacaa ataagaacga atactgccat     240
taagactcgt gatccagcga ctgacaccat tgcatcatct aagggcctca aaactacctc     300
ggaactgctg cgctgatctg gacaccacag aggttccgag cactttaggt tgcaccaaat     360
gtcccaccag gtgcaggcag aaaacgctgg aacagcgtgt acagtttgtc ttaacaaaaa     420
gtgagggcgc tgaggtcgag cagggtggtg tgacttgtta tagcctttag agctgcgaaa     480
gcgcgtatgg atttggctca tcaggccaga ttgagggtct gtggacacat gtcatgttag     540
```

```
tgtacttcaa tcgcccctg gatatagccc cgacaatagg ccgtggcctc attttttgc     600
cttccgcaca tttccattgc tcggtaccca caccttgctt ctcctgcact tgccaacctt     660
aatactggtt tacattgacc aacatcttac aagcgggggg cttgtctagg gtatatataa     720
acagtggctc tcccaatcgg ttgccagtct cttttttcct ttctttcccc acagattcga     780
aatctaaact acacatcaca caatgcctgt tactgacgtc cttaagcgaa agtccggtgt     840
catcgtcggc gacgatgtcc gagccgtgag tatccacgac aagatcagtg tcgagacgac     900
gcgttttgtg taatgacaca atccgaaagt cgctagcaac acacactctc tacacaaact     960
aacccagctc tccatggtga agtccaagcg acaggctctg cccctcacca tcgacggaac    1020
tacctacgac gtctccgctt gggtgaactt ccaccctggt ggagctgaaa tcattgagaa    1080
ctaccaggga cgagatgcta ctgacgcctt catggttatg cactctcagg aagccttcga    1140
caagctcaag cgaatgccca agatcaaccc ctcctccgag ctgcctcccc aggctgccgt    1200
caacgaagct caggaggatt tccgaaagct ccgagaagag ctgatcgcca ctggcatgtt    1260
tgacgcctct cccctctggt actcgtacaa gatctccacc accctgggtc ttggcgtgct    1320
tggatacttc ctgatggtcc agtaccagat gtacttcatt ggtgctgtgc tgctcggtat    1380
gcactaccag caaatgggat ggctgtctca tgacatctgc caccaccaga ccttcaagaa    1440
ccgaaactgg aataacctcg tgggtctggt cttttggcaac ggactccagg gcttctccgt    1500
gacctggtgg aaggacagac acaacgccca tcattctgct accaacgttc agggtcacga    1560
tcccgacatt gataacctgc ctctgctcgc ctggtccgag gacgatgtca ctcgagcttc    1620
tcccatctcc cgaaagctca ttcagttcca acagtactat ttcctggtca tctgtattct    1680
cctgcgattc atctggtgtt tccagtctgt gctgaccgtt cgatccctca aggaccgaga    1740
caaccagttc taccgatctc agtacaagaa agaggccatt ggactcgctc tgcactggac    1800
tctcaagacc ctgttccacc tcttctttat gccctccatc ctgacctcgc tcctggtgtt    1860
ctttgtttcc gagctcgtcg gtggcttcgg aattgccatc gtggtcttca tgaaccacta    1920
ccctctggag aagatcggtg attccgtctg ggacggacat ggcttctctg tgggtcagat    1980
ccatgagacc atgaacattc gacgaggcat cattactgac tggttcttg gaggcctgaa    2040
ctaccagatc gagcaccatc tctgccccac cctgcctcga cacaacctca ctgccgtttc    2100
ctaccaggtg aacagctgt gccagaagca caacctcccc taccgaaacc ctctgcccca    2160
tgaaggtctc gtcatcctgc tccgatacct ggccgtgttc gctcgaatgg ccagaagca    2220
gcccgctggc aaggctctct aagcggccgc attgatgatt ggaaacacac acatgggtta    2280
tatctaggtg agagttagtt ggacagttat atattaaatc agctatgcca acggtaactt    2340
cattcatgtc aacgaggaac cagtgactgc aagtaatata gaatttgacc accttgccat    2400
tctcttgcac tcctttacta tatctcattt atttcttata tacaaatcac ttcttcttcc    2460
cagcatcgag ctcggaaacc tcatgagcaa taacatcgtg gatctcgtca atagagggct    2520
ttttggactc cttgctgttg gccaccttgt ccttgctgtc tggctcattc tgtttcaacg    2580
cctttaatt aagtcataca caagtcagct ttcttcgagc ctcatataag tataagtagt    2640
tcaacgtatt agcactgtac ccagcatctc cgtatcgaga aacacaacaa catgccccat    2700
tggacagatc atgcggatac acaggttgtg cagtatcata catactcgat cagacaggtc    2760
gtctgaccat catacaagct gaacaagcgc tccatacttg cacgctctct atatacacag    2820
ttaaattaca tatccatagt ctaacctcta acagttaatc ttctggtaag cctcccagcc    2880
agccttctgg tatcgcttgg cctcctcaat aggatctcgg ttctggccgt acagacctcg    2940
```

```
gccgacaatt atgatatccg ttccggtaga catgacatcc tcaacagttc ggtactgctg    3000
tccgagagcg tctcccttgt cgtcaagacc caccccgggg gtcagaataa gccagtcctc    3060
agagtcgccc ttaggtcggt tctgggcaat gaagccaacc acaaactcgg ggtcggatcg    3120
ggcaagctca atggtctgct tggagtactc gccagtggcc agagagccct tgcaagacag    3180
ctcggccagc atgagcagac ctctggccag cttctcgttg ggagagggga ctaggaactc    3240
cttgtactgg gagttctcgt agtcagagac gtcctccttc ttctgttcag agacagtttc    3300
ctcggcacca gctcgcaggc cagcaatgat tccggttccg ggtacaccgt gggcgttggt    3360
gatatcggac cactcggcga ttcggtgaca ccggtactgg tgcttgacag tgttgccaat    3420
atctgcgaac tttctgtcct cgaacaggaa gaaaccgtgc ttaagagcaa gttccttgag    3480
ggggagcaca gtgccggcgt aggtgaagtc gtcaatgatg tcgatatggg ttttgatcat    3540
gcacacataa ggtccgacct tatcggcaag ctcaatgagc tccttggtgg tggtaacatc    3600
cagagaagca cacaggttgg ttttcttggc tgccacgagc ttgagcactc gagcggcaaa    3660
ggcggacttg tggacgttag ctcgagcttc gtaggagggc attttggtgg tgaagaggag    3720
actgaaataa atttagtctg cagaactttt tatcggaacc ttatctgggg cagtgaagta    3780
tatgttatgg taatagttac gagttagttg aacttataga tagactggac tatacggcta    3840
tcggtccaaa ttagaaagaa cgtcaatggc tctctgggcg tcgcctttgc cgacaaaaat    3900
gtgatcatga tgaaagccag caatgacgtt gcagctgata ttgttgtcgg ccaaccgcgc    3960
cgaaaacgca gctgtcagac ccacagcctc caacgaagaa tgtatcgtca aagtgatcca    4020
agcacactca tagttggagt cgtactccaa aggcggcaat gacgagtcag acagatactc    4080
gtcgactcag gcgacgacgg aattcctgca gcccatctgc agaattcagg agagaccggg    4140
ttggcggcgt atttgtgtcc caaaaaacag ccccaattgc cccggagaag acggccaggc    4200
cgcctagatg acaaattcaa caactcacag ctgactttct gccattgcca ctaggggggg    4260
gcctttttat atggccaagc caagctctcc acgtcggttg ggctgcaccc aacaataaat    4320
gggtagggtt gcaccaacaa agggatggga tgggggtag aagatacgag gataacgggg    4380
ctcaatggca caaataagaa cgaatactgc cattaagact cgtgatccag cgactgacac    4440
cattgcatca tctaagggcc tcaaaactac ctccggaactg ctgcgctgat ctggacacca   4500
cagaggttcc gagcacttta ggttgcacca aatgtcccac caggtgcagg cagaaaacgc    4560
tggaacagcg tgtacagttt gtcttaacaa aaagtgaggg cgctgaggtc gagcagggtg    4620
gtgtgacttg ttatagcctt tagagctgcg aaagcgcgta tggatttggc tcatcaggcc    4680
agattgaggg tctgtggaca catgtcatgt tagtgtactt caatcgcccc ctggatatag    4740
ccccgacaat aggccgtggc ctcattttt tgccttccgc acatttccat tgctcggtac    4800
ccacaccttg cttctcctgc acttgccaac cttaatactg gtttacattg accaacatct    4860
tacaagcggg gggcttgtct agggtatata taaacagtgg ctctcccaat cggttgccag    4920 tctcttttt cctttctttc cccacagatt cgaaatctaa actacacatc acacaatgcc    4980
tgttactgac gtccttaagc gaaagtccgg tgtcatcgtc ggcgacgatg tccgagccgt    5040
gagtatccac gacaagatca gtgtcgagac gacgcgtttt gtgtaatgac acaatccgaa    5100
agtcgctagc aacacacact ctctacacaa actaacccag ctctccatgg ctctggccaa    5160
cgacgctggc gagcgaatct gggctgccgt caccgatccc gaaatcctca ttggcacctt    5220
ctcctacctg ctcctgaagc ctcctcctgcg aaactctggt ctcgtggacg agaagaaagg    5280
agcctaccga acctccatga tctggtacaa cgtcctcctg gctctcttct ctgccctgtc    5340
```

```
cttctacgtg actgccaccg ctctcggctg ggactacggt actggagcct ggctgcgaag    5400
acagaccggt gatactcccc agcctctctt tcagtgtccc tctcctgtct gggactccaa    5460
gctgttcacc tggactgcca aggccttcta ctattctaag tacgtggagt acctcgacac    5520
cgcttggctg gtcctcaagg gcaagcgagt gtcctttctg caggccttcc atcactttgg    5580
agctccctgg gacgtctacc tcggcattcg actgcacaac gagggtgtgt ggatcttcat    5640
gttctttaac tcgttcattc acaccatcat gtacacctac tatggactga ctgccgctgg    5700
ctacaagttc aaggccaagc ctctgatcac tgccatgcag atttgccagt cgtcggtgg    5760 cttttctcctg gtctgggact acatcaacgt tccctgcttc aactctgaca agggcaagct    5820
gttctcctgg gctttcaact acgcctacgt cggatctgtc tttctcctgt tctgtcactt    5880
cttttaccag gacaacctgg ccaccaagaa atccgctaag gctggtaagc agctttagcg    5940
gccgcaagtg tggatgggga agtgagtgcc cggttctgtg tgcacaattg caatccaag    6000 atggatggat tcaacacagg gatatagcga gctacgtggt ggtgcgagga tatagcaacg    6060
gatatttatg tttgacactt gagaatgtac gatacaagca ctgtccaagt acaatactaa    6120
acatactgta catactcata ctcgtacccg ggcaacggtt tcacttgagt gcagtggcta    6180
gtgctcttac tcgtacagtg tgcaatactg cgtatcatag tctttgatgt atatcgtatt    6240
cattcatgtt agttgcgtac gagccggaag cataaagtgt aaagcctggg gtgcctaatg    6300
agtgagctaa ctcacattaa ttgcgttgcg ctcactgccc gctttccagt cgggaaacct    6360
gtcgtgccag ctgcattaat gaatcggcca acgcgcgggg agaggcggtt tgcgtattgg    6420
gcgctcttcc gcttcctcgc tcactgactc gctgcgctcg gtcgttcggc tgcggcgagc    6480
ggtatcagct cactcaaagg cggtaatacg gttatccaca gaatcagggg ataacgcagg    6540
aaagaacatg tgagcaaaag gccagcaaaa ggccaggaac cgtaaaaagg ccgcgttgct    6600
ggcgtttttc cataggctcc gcccccctga cgagcatcac aaaaatcgac gctcaagtca    6660
gaggtggcga aacccgacag gactataaag ataccaggcg tttccccctg gaagctccct    6720
cgtgcgctct cctgttccga ccctgccgct taccggatac ctgtccgcct ttctcccttc    6780
gggaagcgtg gcgctttctc atagctcacg ctgtaggtat ctcagttcgg tgtaggtcgt    6840
tcgctccaag ctgggctgtg tgcacgaacc cccgttcag cccgaccgct gcgccttatc    6900
cggtaactat cgtcttgagt ccaacccggt aagacacgac ttatcgccac tggcagcagc    6960
cactggtaac aggattagca gagcgaggta tgtaggcggt gctacagagt tcttgaagtg    7020
gtggcctaac tacggctaca ctagaaggac agtatttggt atctgcgctc tgctgaagcc    7080
agttaccttc ggaaaaagag ttggtagctc ttgatccggc aaacaaacca ccgctggtag    7140
cggtggtttt tttgtttgca agcagcagat tacgcgcaga aaaaaggat ctcaagaaga    7200 tcctttgatc ttttctacgg ggtctgacgc tcagtggaac gaaaactcac gttaagggat    7260
tttggtcatg agattatcaa aaaggatctt cacctagatc cttttaaatt aaaaatgaag    7320
ttttaaatca atctaaagta tatatgagta aacttggtct gacagttacc aatgcttaat    7380
cagtgaggca cctatctcag cgatctgtct atttcgttca tccatagttg cctgactccc    7440
cgtcgtgtag ataactacga tacgggaggg cttaccatct ggccccagtg ctgcaatgat    7500
accgcgagac ccacgctcac cggctccaga tttatcagca ataaaccagc cagcggaag    7560 ggccgagcgc agaagtggtc ctgcaacttt atccgcctcc atccagtcta ttaattgttg    7620
ccgggaagct agagtaagta gttcgccagt taatagtttg cgcaacgttg ttgccattgc    7680
tacaggcatc gtggtgtcac gctcgtcgtt tggtatggct tcattcagct ccggttccca    7740
```

```
acgatcaagg cgagttacat gatcccccat gttgtgcaaa aaagcggtta gctccttcgg    7800
tcctccgatc gttgtcagaa gtaagttggc cgcagtgtta tcactcatgg ttatggcagc    7860
actgcataat tctcttactg tcatgccatc cgtaagatgc ttttctgtga ctggtgagta    7920
ctcaaccaag tcattctgag aatagtgtat gcggcgaccg agttgctctt gcccggcgtc    7980
aatacgggat aataccgcgc cacatagcag aactttaaaa gtgctcatca ttggaaaacg    8040
ttcttcgggg cgaaaactct caaggatctt accgctgttg agatccagtt cgatgtaacc    8100
cactcgtgca cccaactgat cttcagcatc ttttactttc accagcgttt ctgggtgagc    8160
aaaaacagga aggcaaaatg ccgcaaaaaa gggaataagg gcgacacgga aatgttgaat    8220
actcatactc ttccttttc aatattattg aagcatttat cagggttatt gtctcatgag    8280
cggatacata tttgaatgta tttagaaaaa taaacaaata ggggttccgc gcacatttcc    8340
ccgaaaagtg ccacctgacg cgccctgtag cggcgcatta agcgcggcgg gtgtggtggt    8400
tacgcgcagc gtgaccgcta cacttgccag cgccctagcg cccgctcctt tcgctttctt    8460
cccttccttt ctcgccacgt tcgccggctt tccccgtcaa gctctaaatc ggggggctccc    8520
tttagggttc cgatttagtg ctttacggca cctcgacccc aaaaaacttg attagggtga    8580
tggttcacgt agtgggccat cgccctgata cggttttt cgccctttga cgttggagtc    8640
cacgttcttt aatagtggac tcttgttcca aactggaaca acactcaacc ctatctcggt    8700
ctattctttt gatttataag ggattttgcc gatttcggcc tattggttaa aaaatgagct    8760
gatttaacaa aaatttaacg cgaattttaa caaaatatta acgcttacaa tttccattcg    8820
ccattcaggc tgcgcaactg ttgggaaggg cgatcggtgc gggcctcttc gctattacgc    8880
cagctggcga aggggggatg tgctgcaagg cgattaagtt gggtaacgcc agggttttcc    8940
cagtcacgac gttgtaaaac gacggccagt gaattgtaat acgactcact atagggcgaa    9000
ttgggtaccg gccccccct cgaggtcgat ggtgtcgata agcttgatat cgaattcatg    9060
tcacacaaac cgatcttcgc ctcaaggaaa cctaattcta catccgagag actgccgaga    9120
tccagtctac actgattaat tttcgggcca ataatttaaa aaaatcgtgt tatataat    9180
tatatgtatt atatatatac atcatgatga tactgacagt catgtcccat tgctaaatag    9240
acagactcca tctgccgcct ccaactgatg ttctcaatat ttaaggggtc atctcgcatt    9300
gtttaataat aaacagactc catctaccgc ctccaaatga tgttctcaaa atatattgta    9360
tgaacttatt tttattactt agtattatta gacaacttac ttgctttatg aaaaacactt    9420
cctatttagg aaacaattta taatggcagt tcgttcattt aacaatttat gtagaataaa    9480
tgttataaat gcgtatggga atcttaaat atggatagca taaatgatat ctgcattgcc    9540
taattcgaaa tcaacagcaa cgaaaaaaat cccttgtaca acataaatag tcatcgagaa    9600
atatcaacta tcaaagaaca gctattcaca cgttactatt gagattatta ttggacgaga    9660
atcacacact caactgtctt tctctcttct agaaatacag gtacaagtat gtactattct    9720
cattgttcat acttctagtc atttcatccc acatattcct tggatttctc tccaatgaat    9780
gacattctat cttgcaaatt caacaattat aataagatat accaaagtag cggtatagtg    9840
gcaatcaaaa agcttctctg gtgtgcttct cgtatttatt tttattctaa tgatccatta    9900
aaggtatata tttatttctt gttatataat cctttttgttt attacatggg ctggatacat    9960
aaaggtattt tgatttaatt ttttgcttaa attcaatccc ccctcgttca gtgtcaactg   10020
taatggtagg aaattaccat acttttgaag aagcaaaaaa aatgaaagaa aaaaaaaatc   10080
gtatttccag gttagacgtt ccgcagaatc tagaatgcgg tatgcggtac attgttcttc   10140
```

```
gaacgtaaaa gttgcgctcc ctgagatatt gtacattttt gcttttacaa gtacaagtac    10200
atcgtacaac tatgtactac tgttgatgca tccacaacag tttgttttgt ttttttttgt    10260
tttttttttt tctaatgatt cattaccgct atgtatacct acttgtactt gtagtaagcc    10320
gggttattgg cgttcaatta atcatagact tatgaatctg cacggtgtgc gctgcgagtt    10380
acttttagct tatgcatgct acttgggtgt aatattggga tctgttcgga aatcaacgga    10440
tgctcaat                                                             10448

<210> SEQ ID NO 113
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 113
cgtagttata tacaagaggt agatgcgtgc tggtgttaga ggggctctca ggattaggag      60
gaaaatttga cattggccct caacatataa cctcgggtgt gcctctgttt accctcagct     120
tttgcttgtc cccaagtcag tcacgccagg ccaaaaaggt tggtggattg acagggagaa     180
aaaaaaaagc ctagtgggtt taaactcgag gtaagacatt gaatatata ccggtcggca      240 tcctgagtcc ctttctcgta ttccaacaga ccgaccatag aa atg gat tcg acc        294
                                              Met Asp Ser Thr
                                                1 acg cag acc aac acc ggc acc ggc aag gtg gcc gtg cag ccc ccc acg       342
Thr Gln Thr Asn Thr Gly Thr Gly Lys Val Ala Val Gln Pro Pro Thr
  5              10                  15                  20 gcc ttc att aag ccc att gag aag gtg tcc gag ccc gtc tac gac acc       390
Ala Phe Ile Lys Pro Ile Glu Lys Val Ser Glu Pro Val Tyr Asp Thr
             25                  30                  35 ttt ggc aac gag ttc act cct cca gac tac tct atc aag gat att ctg       438
Phe Gly Asn Glu Phe Thr Pro Pro Asp Tyr Ser Ile Lys Asp Ile Leu
         40                  45                  50 gat gcc att ccc cag gag tgc tac aag cgg tcc tac gtt aag tcc tac       486
Asp Ala Ile Pro Gln Glu Cys Tyr Lys Arg Ser Tyr Val Lys Ser Tyr
     55                  60                  65 tcg tac gtg gcc cga gac tgc ttc ttt atc gcc gtt ttt gcc tac atg       534
Ser Tyr Val Ala Arg Asp Cys Phe Phe Ile Ala Val Phe Ala Tyr Met
 70                  75                  80 gcc tac gcg tac ctg cct ctt att ccc tcg gct tcc ggc cga gct gtg       582
Ala Tyr Ala Tyr Leu Pro Leu Ile Pro Ser Ala Ser Gly Arg Ala Val
 85                  90                  95                 100 gcc tgg gcc atg tac tcc att gtc cag ggt ctg ttt ggc acc ggt ctg       630
Ala Trp Ala Met Tyr Ser Ile Val Gln Gly Leu Phe Gly Thr Gly Leu
                 105                 110                 115 tgg gtt ctt gcc cac gag tgt ggc cac tct gct ttc tcc gac tct aac       678
Trp Val Leu Ala His Glu Cys Gly His Ser Ala Phe Ser Asp Ser Asn
             120                 125                 130 acc gtc aac aac gtc acc gga tgg gtt ctg cac tcc tcc atg ctg gtc       726
Thr Val Asn Asn Val Thr Gly Trp Val Leu His Ser Ser Met Leu Val
         135                 140                 145 cct tac tac gcc tgg aag ctg acc cac tcc atg cac cac aag tcc act       774
Pro Tyr Tyr Ala Trp Lys Leu Thr His Ser Met His His Lys Ser Thr
     150                 155                 160 ggt cac ctc acc cgt gat atg gtg ttt gtg ccc aag gac cga aag gag       822
Gly His Leu Thr Arg Asp Met Val Phe Val Pro Lys Asp Arg Lys Glu
165                 170                 175                 180
```

| | | |
|---|---|---|
| ttt atg gag aac cga ggc gcc cat gac tgg tct gag ctt gct gag gac<br>Phe Met Glu Asn Arg Gly Ala His Asp Trp Ser Glu Leu Ala Glu Asp<br>185 190 195 | 870 | |
| gct ccc ctc atg acc ctc tac ggc ctc atc acc cag cag gtg ttt gga<br>Ala Pro Leu Met Thr Leu Tyr Gly Leu Ile Thr Gln Gln Val Phe Gly<br>200 205 210 | 918 | |
| tgg cct ctg tat ctg ctg tct tac gtt acc gga cag aag tac ccc aag<br>Trp Pro Leu Tyr Leu Leu Ser Tyr Val Thr Gly Gln Lys Tyr Pro Lys<br>215 220 225 | 966 | |
| ctc aac aaa tgg gct gtc aac cac ttc aac ccc aac gcc ccg ctg ttt<br>Leu Asn Lys Trp Ala Val Asn His Phe Asn Pro Asn Ala Pro Leu Phe<br>230 235 240 | 1014 | |
| gag aag aag gac tgg ttc aac atc tgg atc tct aac gtc ggt att ggt<br>Glu Lys Lys Asp Trp Phe Asn Ile Trp Ile Ser Asn Val Gly Ile Gly<br>245 250 255 260 | 1062 | |
| atc acc atg tcc gtc atc gca tac tcc atc aac cga tgg ggc ctg gct<br>Ile Thr Met Ser Val Ile Ala Tyr Ser Ile Asn Arg Trp Gly Leu Ala<br>265 270 275 | 1110 | |
| tcc gtc acc ctc tac tac ctg atc ccc tac ctg tgg gtc aac cac tgg<br>Ser Val Thr Leu Tyr Tyr Leu Ile Pro Tyr Leu Trp Val Asn His Trp<br>280 285 290 | 1158 | |
| ctc gtg gcc atc acc tac ctg cag cac acc gac ccc act ctg ccc cac<br>Leu Val Ala Ile Thr Tyr Leu Gln His Thr Asp Pro Thr Leu Pro His<br>295 300 305 | 1206 | |
| tac cac gcc gac cag tgg aac ttc acc cga gga gcc gcc gcc acc atc<br>Tyr His Ala Asp Gln Trp Asn Phe Thr Arg Gly Ala Ala Ala Thr Ile<br>310 315 320 | 1254 | |
| gac cga gag ttt ggc ttc atc ggc tcc ttc tgc ttc cat gac atc atc<br>Asp Arg Glu Phe Gly Phe Ile Gly Ser Phe Cys Phe His Asp Ile Ile<br>325 330 335 340 | 1302 | |
| gag acc cac gtt ctg cac cac tac gtg tct cga att ccc ttc tac aac<br>Glu Thr His Val Leu His His Tyr Val Ser Arg Ile Pro Phe Tyr Asn<br>345 350 355 | 1350 | |
| gcc cga atc gcc act gag aag atc aag aag gtc atg ggc aag cac tac<br>Ala Arg Ile Ala Thr Glu Lys Ile Lys Lys Val Met Gly Lys His Tyr<br>360 365 370 | 1398 | |
| cga cac gac gac acc aac ttc atc aag tct ctt tac act gtc gcc cga<br>Arg His Asp Asp Thr Asn Phe Ile Lys Ser Leu Tyr Thr Val Ala Arg<br>375 380 385 | 1446 | |
| acc tgc cag ttt gtt gaa ggt aag gaa ggc att cag atg ttt aga aac<br>Thr Cys Gln Phe Val Glu Gly Lys Glu Gly Ile Gln Met Phe Arg Asn<br>390 395 400 | 1494 | |
| gtc aat gga gtc gga gtt gct cct gac ggc ctg cct tct aaa aag<br>Val Asn Gly Val Gly Val Ala Pro Asp Gly Leu Pro Ser Lys Lys<br>405 410 415 | 1539 | |
| tagagctaga aatgttattt gattgtgttt taactgaaca gcaccgagcc cgaggctaag | 1599 | |
| ccaagcgaag ccgagggggtt gtgtagtcca tggacgtaac gagtaggcga tatccgcca | 1659 | |
| ctcggcactg cgtgtctgcg ttcatgggcg aagtcacatt acgctgacaa ccgttgtagt | 1719 | |
| ttcccttag tatcaatact gttacaagta ccggtctcgt actcgtactg atacgaatct | 1779 | |
| gtgggaagaa gtcacccctta tcagaccttc atactgatgt ttcggatatc aatagaactg | 1839 | |
| gcatagagcc gttaaagaag tttcacttaa tcactccaac cctcctactt gtagattcaa | 1899 | |
| gcagatcgat aagatggatt tgatggtcag tgctagc | 1936 | |

<210> SEQ ID NO 114
<211> LENGTH: 419
<212> TYPE: PRT
<213> ORGANISM: Yarrowia lipolytica

<400> SEQUENCE: 114

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
                100                 105                 110

Gly Thr Gly Leu Trp Val Leu Ala His Glu Cys Gly His Ser Ala Phe
            115                 120                 125

Ser Asp Ser Asn Thr Val Asn Asn Val Thr Gly Trp Val Leu His Ser
130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
            195                 200                 205

Gln Val Phe Gly Trp Pro Leu Tyr Leu Leu Ser Tyr Val Thr Gly Gln
        210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
                260                 265                 270

Trp Gly Leu Ala Ser Val Thr Leu Tyr Tyr Leu Ile Pro Tyr Leu Trp
            275                 280                 285

Val Asn His Trp Leu Val Ala Ile Thr Tyr Leu Gln His Thr Asp Pro
        290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415
```

Ser Lys Lys

<210> SEQ ID NO 115
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter

<400> SEQUENCE: 115

```
caacttttct tgtcgacctg agataccgag gttgcgcagg ggatcaactt ttgtgtctca    60
gagggaccca agtgcgtacg gagagtacag tacatactgt agctaacggt agcaggcgaa   120
ctactggtac atacctcccc cggaatatgt acaggcataa tgcgtatctg tgggacatgt   180
ggtcgttgcg ccattatgta agcagcgtgt actcctctga ctgtccatat ggtttgctcc   240
atctcaccct catcgttttc attgttcaca ggcggccaca aaaaaactgt cttctctcct   300
tctctcttcg ccttagtcta ctcggaccag ttttagttta gcttggcgcc actggataaa   360
tgagacctca ggccttgtga tgaggaggtc acttatgaag catgttagga ggtgcttgta   420
tggatagaga agcacccaaa ataataagaa taataataaa acaggggggcg ttgtcatttc   480
atatcgtgtt ttcaccatca atacacctcc aaacaatgcc cttcatgtgg ccagccccaa   540
tattgtcctg tagttcaact ctatgcagct cgtatcttat tgagcaagta aaactctgtc   600
agccgatatt gcccgacccg cgacaagggt caacaaggtg gtgtaaggcc ttcgcagaag   660
tcaaaactgt gccaaacaaa catctagagt ctctttggtg tttctcgcat atatttaatc   720
ggctgtctta cgtatttggc ctcggtaccg gactaatttc ggatcatccc caatacgctt   780
tttcttcgca gctgtcaaca gtgtccatga tctatccacc taaatgggtc atatgaggcg   840
tataatttcg tggtgctgat aataattccc atatatttga cacaaaactt cccccccctag   900
acatacatct cacaatctca cttcttgtgc ttctgtcaca catctcctcc agctgacttc   960
aactcacacc tctgccccag ttggtctaca gcggtataag gtttctccgc atagaggtgc  1020
accactcctc ccgatacttg tttgtgtgac ttgtgggtca cgacatatat atctacacac  1080
attgcgccac cctttggttc ttccagcaca acaaaaacac gacacgctaa               1130
```

<210> SEQ ID NO 116
<211> LENGTH: 1203
<212> TYPE: DNA
<213> ORGANISM: Mortierella isabellina (GenBank Accession No. AF417245)
<220> FEATURE:
<221> NAME/KEY: CDS
<222> LOCATION: (1)..(1203)
<223> OTHER INFORMATION: delta-12 desaturase

<400> SEQUENCE: 116

```
atg gca cct ccc aac act atc gat gcc ggc ttg acc cag cgt cat atc     48
Met Ala Pro Pro Asn Thr Ile Asp Ala Gly Leu Thr Gln Arg His Ile
 1               5                  10                  15 acc acc acg gcc gcc cca acc tcg gcc aag ccc gct ttc gag cgc aac     96
Thr Thr Thr Ala Ala Pro Thr Ser Ala Lys Pro Ala Phe Glu Arg Asn
                 20                  25                  30 tac cag ctc ccc gag ttc act atc aag gag atc cga gag tgc atc cct    144
Tyr Gln Leu Pro Glu Phe Thr Ile Lys Glu Ile Arg Glu Cys Ile Pro
             35                  40                  45 gcc cac tgc ttt gag cgc tcc ggt ctt cgt ggt ctc tgc cac gtt gcc    192
Ala His Cys Phe Glu Arg Ser Gly Leu Arg Gly Leu Cys His Val Ala
         50                  55                  60
```

-continued

| | |
|---|---|
| att gat ctg acc tgg gcc tcg ctc ttg ttc ctg gct gca acc cag atc<br>Ile Asp Leu Thr Trp Ala Ser Leu Leu Phe Leu Ala Ala Thr Gln Ile<br>65                        70                    75                    80 | 240 |
| gac aag ttc gag aac ccc ttg atc cgc tat ctg gcc tgg cct gcg tac<br>Asp Lys Phe Glu Asn Pro Leu Ile Arg Tyr Leu Ala Trp Pro Ala Tyr<br>                    85                    90                    95 | 288 |
| tgg atc atg cag ggc att gtc tgc acc ggc ata tgg gtg ctg gcc cac<br>Trp Ile Met Gln Gly Ile Val Cys Thr Gly Ile Trp Val Leu Ala His<br>                  100                  105                110 | 336 |
| gag tgc ggt cac cag tcc ttc tcg acc tcc aag act ctc aac aac acc<br>Glu Cys Gly His Gln Ser Phe Ser Thr Ser Lys Thr Leu Asn Asn Thr<br>            115                  120                125 | 384 |
| gtc ggc tgg atc ctg cac tcg atg ctc ttg gtc ccc tac cac tcc tgg<br>Val Gly Trp Ile Leu His Ser Met Leu Leu Val Pro Tyr His Ser Trp<br>130                        135                    140 | 432 |
| aga atc tcg cac tcg aag cac cac aag gcc act ggc cac atg acc aag<br>Arg Ile Ser His Ser Lys His His Lys Ala Thr Gly His Met Thr Lys<br>145                        150                    155                    160 | 480 |
| gac cag gtc ttt gtt ccc aag acc cgc tcc cag gtt ggt ttg cct ccc<br>Asp Gln Val Phe Val Pro Lys Thr Arg Ser Gln Val Gly Leu Pro Pro<br>                  165                  170                175 | 528 |
| aag gag agc gct gct gct gcc gtt caa gag gag gac atg tcc gtg cac<br>Lys Glu Ser Ala Ala Ala Ala Val Gln Glu Glu Asp Met Ser Val His<br>            180                  185                190 | 576 |
| ctg gat gag gag gcc cct att gtg act ttg ttc tgg atg gtg atc cag<br>Leu Asp Glu Glu Ala Pro Ile Val Thr Leu Phe Trp Met Val Ile Gln<br>            195                  200                205 | 624 |
| ttc ctg ttc gga tgg cct gca tac ctg atc atg aac gcc tct ggt cag<br>Phe Leu Phe Gly Trp Pro Ala Tyr Leu Ile Met Asn Ala Ser Gly Gln<br>210                        215                    220 | 672 |
| gac tat ggc cgc tgg acc tcg cac ttc cac act tac tcg ccc atc ttt<br>Asp Tyr Gly Arg Trp Thr Ser His Phe His Thr Tyr Ser Pro Ile Phe<br>225                        230                    235                    240 | 720 |
| gag ccc cgc aac ttc ttc gac att atc atc tcg gat ctc ggt gtg ttg<br>Glu Pro Arg Asn Phe Phe Asp Ile Ile Ile Ser Asp Leu Gly Val Leu<br>                  245                  250                255 | 768 |
| gct gcc ctc ggt gcc ctg atc tac gct tcc atg cag ctg tcg ctc ttg<br>Ala Ala Leu Gly Ala Leu Ile Tyr Ala Ser Met Gln Leu Ser Leu Leu<br>            260                  265                270 | 816 |
| acc gtg acc aag tac tac atc atc ccg tac ctg ttt gtc aac ttt tgg<br>Thr Val Thr Lys Tyr Tyr Ile Ile Pro Tyr Leu Phe Val Asn Phe Trp<br>            275                  280                285 | 864 |
| ttg gtc ctg att act ttc ttg cag cac acc gac ccc aag ctg ccc cat<br>Leu Val Leu Ile Thr Phe Leu Gln His Thr Asp Pro Lys Leu Pro His<br>290                        295                    300 | 912 |
| tac cgt gag ggt gcc tgg aac ttc cag cgt gga gcc ctc tgc acc gtt<br>Tyr Arg Glu Gly Ala Trp Asn Phe Gln Arg Gly Ala Leu Cys Thr Val<br>305                        310                    315                    320 | 960 |
| gac cgc tcg ttt ggc aag ttc ttg gac cat atg ttc cac ggc atc gtc<br>Asp Arg Ser Phe Gly Lys Phe Leu Asp His Met Phe His Gly Ile Val<br>                  325                  330                335 | 1008 |
| cat acc cat gtg gcc cat cac ttg ttc tcg cag atg ccg ttc tac cat<br>His Thr His Val Ala His His Leu Phe Ser Gln Met Pro Phe Tyr His<br>            340                  345                350 | 1056 |
| gct gaa gaa gct acc tac cat ctc aag aaa ctg ctg gga gag tac tac<br>Ala Glu Glu Ala Thr Tyr His Leu Lys Lys Leu Leu Gly Glu Tyr Tyr<br>            355                  360                365 | 1104 |
| gtt tac gac cca tcc ccg atc gtc gtt gcg gtc tgg agg tcg ttc cgc<br>Val Tyr Asp Pro Ser Pro Ile Val Val Ala Val Trp Arg Ser Phe Arg<br>370                        375                    380 | 1152 |

-continued

```
gag tgc cga ttc gtg gag gat cat gga gac gtg gtc ttt ttc aag aag    1200
Glu Cys Arg Phe Val Glu Asp His Gly Asp Val Val Phe Phe Lys Lys
385                 390                 395                 400 taa                                                                1203
```

<210> SEQ ID NO 117
<211> LENGTH: 400
<212> TYPE: PRT
<213> ORGANISM: Mortieralla isabellina (GenBank Accession No. AF417245)

<400> SEQUENCE: 117

```
Met Ala Pro Pro Asn Thr Ile Asp Ala Gly Leu Thr Gln Arg His Ile
1               5                   10                  15

Thr Thr Thr Ala Ala Pro Thr Ser Ala Lys Pro Ala Phe Glu Arg Asn
                20                  25                  30

Tyr Gln Leu Pro Glu Phe Thr Ile Lys Glu Ile Arg Glu Cys Ile Pro
            35                  40                  45

Ala His Cys Phe Glu Arg Ser Gly Leu Arg Gly Leu Cys His Val Ala
        50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
            100                 105                 110

Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
130                 135                 140

Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Ser Ala Ala Ala Val Gln Glu Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ser Asp Leu Gly Val Leu
                245                 250                 255

Ala Ala Leu Gly Ala Leu Ile Tyr Ala Ser Met Gln Leu Ser Leu Leu
            260                 265                 270

Thr Val Thr Lys Tyr Tyr Ile Ile Pro Tyr Leu Phe Val Asn Phe Trp
        275                 280                 285

Leu Val Leu Ile Thr Phe Leu Gln His Thr Asp Pro Lys Leu Pro His
290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350
```

| | | | | | | | | | | | | |
|---|---|---|---|---|---|---|---|---|---|---|---|---|
|Ala|Glu|Glu|Ala|Thr|Tyr|His|Leu|Lys|Lys|Leu|Leu|Gly|Glu|Tyr|Tyr|
| | |355| | | |360| | | |365| | | | | |

Val Tyr Asp Pro Ser Pro Ile Val Val Ala Val Trp Arg Ser Phe Arg
    370                 375                 380

Glu Cys Arg Phe Val Glu Asp His Gly Asp Val Val Phe Phe Lys Lys
385             390                 395                 400

<210> SEQ ID NO 118
<211> LENGTH: 1521
<212> TYPE: DNA
<213> ORGANISM: Mortierella alpina (GenBank Accession No. AB070555)
<220> FEATURE:
<221> NAME/KEY: misc_feature
<223> OTHER INFORMATION: delta-6 desaturase

<400> SEQUENCE: 118

```
acaacgtgct cttgtcctca gaagactgtt gtgctcttcc ttccaccacc ccaagcactc      60
tctcacccca agcactgcct gccatgacca ccagcgaccc atctgtcaga gcgttcacac     120
gctcagaagt gttgcacgcc gatgccttga acagggcaa aaagaacgcc gaggcaccgt     180
ttctcatgat catcgacaac aaggtctacg atgtgcgcga gtttatcccc gaccatcctg     240
gtgggagcgt cattttgacc cacgtaggca aggacggcac cgacgttttc gagaccttcc     300
atcctgaggc tgcttgggag cgctcgcca attttatgt cggtgacatt gtagaatccg     360
atcgcgccat cgagaacgac gagtttgcag ctgaggttcg taagctgcgg acattgtttt     420
attctttggg ctactacgac tcatccaagg tttactacgc cttcaaggtc tcgttcaacc     480
tctgcatctg gggcctgtct gcattcattg ttgccaaatg gggccagacc tcgaccctcg     540
caaacgtgat atcagcctca ctcctgggtg tcttttggca acagtgcggt tggctcgccc     600
atgatttctt gcaccatcag gtctttcacg atcgattctg gggcgatctg ttcggtgcat     660
ttctcggcgg agtctgtcaa ggtttctcct cgtcctggtg gaaggacaaa cacaacaccc     720
accacgcggc gcccaatgtc catggagagg atccgatat cgacacacat ccgcttttga     780
cgtggagtga gcatgcgctc gagatgtttt cggatgtgcc cgatgaggag cttacccaaa     840
tgtggtcccg gtttatggtt ctgaaccagg cctggtttta cttcccatt ctgtcatttg     900
cccgcctgtc ctggtgcatc cagtcgattc tttttgtgct accgaacgga caggcacaca     960
aacctgcggg ggctcgggtt ccatctcgc tggtggagca attgtcgttg gcgatgcact    1020
ggacctggta cctggcaacc atgttcctgt tcatcaagga tcccgtcaac atgatggtgt    1080
atttcttggt ctcgcaagct gtctgcggca acctgttagc gattgtgttc tcgctgaacc    1140
ataacggtat gcctgtgatc tcgcaggagg aagcggtcga gatggattt ttcacaaagc    1200
agatcattac gggtcgtgat gtctacccgg gttggtttgc agactggttc acgggtggat    1260
tgaactatca gattgaacac catctgttcc cgtcgatgcc tcgacaccat ttctcaaaga    1320
tccagcccgc ggttgaatcg ctgtgcaaga agtacggggt ccgataccat acgacgggga    1380
tgattgctgg caccgcagag gtcttttcgc gactgaacga ggtgtcccag gctgcaagca    1440
agctcggcaa gtctgcttga gtctttcatg tcctcaagtt gattctagat acttattttc    1500
gcagacttct atcgataaat t                                                1521
```

<210> SEQ ID NO 119
<211> LENGTH: 458
<212> TYPE: PRT
<213> ORGANISM: Mortierella alpina (GenBank Accession No. AB070555)

<400> SEQUENCE: 119

-continued

```
Met Thr Thr Ser Asp Pro Ser Val Arg Ala Phe Thr Arg Ser Glu Val
1               5                   10                  15

Leu His Ala Asp Ala Leu Asn Glu Gly Lys Lys Asn Ala Glu Ala Pro
            20                  25                  30

Phe Leu Met Ile Ile Asp Asn Lys Val Tyr Asp Val Arg Glu Phe Ile
            35                  40                  45

Pro Asp His Pro Gly Gly Ser Val Ile Leu Thr His Val Gly Lys Asp
    50                  55                  60

Gly Thr Asp Val Phe Glu Thr Phe His Pro Glu Ala Ala Trp Glu Thr
65                  70                  75                  80

Leu Ala Asn Phe Tyr Val Gly Asp Ile Val Glu Ser Asp Arg Ala Ile
                85                  90                  95

Glu Asn Asp Glu Phe Ala Ala Glu Val Arg Lys Leu Arg Thr Leu Phe
                100                 105                 110

Tyr Ser Leu Gly Tyr Tyr Asp Ser Ser Lys Val Tyr Ala Phe Lys
            115                 120                 125

Val Ser Phe Asn Leu Cys Ile Trp Gly Leu Ser Ala Phe Ile Val Ala
    130                 135                 140

Lys Trp Gly Gln Thr Ser Thr Leu Ala Asn Val Ile Ser Ala Ser Leu
145                 150                 155                 160

Leu Gly Val Phe Trp Gln Gln Cys Gly Trp Leu Ala His Asp Phe Leu
                165                 170                 175

His His Gln Val Phe His Asp Arg Phe Trp Gly Asp Leu Phe Gly Ala
            180                 185                 190

Phe Leu Gly Gly Val Cys Gln Gly Phe Ser Ser Trp Trp Lys Asp
    195                 200                 205

Lys His Asn Thr His His Ala Ala Pro Asn Val His Gly Glu Asp Pro
210                 215                 220

Asp Ile Asp Thr His Pro Leu Leu Thr Trp Ser Glu His Ala Leu Glu
225                 230                 235                 240

Met Phe Ser Asp Val Pro Asp Glu Glu Leu Thr Gln Met Trp Ser Arg
            245                 250                 255

Phe Met Val Leu Asn Gln Ala Trp Phe Tyr Phe Pro Ile Leu Ser Phe
        260                 265                 270

Ala Arg Leu Ser Trp Cys Ile Gln Ser Ile Leu Phe Val Leu Pro Asn
    275                 280                 285

Gly Gln Ala His Lys Pro Ala Gly Ala Arg Val Pro Ile Ser Leu Val
    290                 295                 300

Glu Gln Leu Ser Leu Ala Met His Trp Thr Trp Tyr Leu Ala Thr Met
305                 310                 315                 320

Phe Leu Phe Ile Lys Asp Pro Val Asn Met Met Val Tyr Phe Leu Val
            325                 330                 335

Ser Gln Ala Val Cys Gly Asn Leu Leu Ala Ile Val Phe Ser Leu Asn
        340                 345                 350

His Asn Gly Met Pro Val Ile Ser Gln Glu Glu Ala Val Glu Met Asp
        355                 360                 365

Phe Phe Thr Lys Gln Ile Ile Thr Gly Arg Asp Val Tyr Pro Gly Trp
    370                 375                 380

Phe Ala Asp Trp Phe Thr Gly Gly Leu Asn Tyr Gln Ile Glu His His
385                 390                 395                 400

Leu Phe Pro Ser Met Pro Arg His Phe Ser Lys Ile Gln Pro Ala
            405                 410                 415

Val Glu Ser Leu Cys Lys Lys Tyr Gly Val Arg Tyr His Thr Thr Gly
            420                 425                 430
```

Met Ile Ala Gly Thr Ala Glu Val Phe Ser Arg Leu Asn Glu Val Ser
        435                 440                 445

Gln Ala Ala Ser Lys Leu Gly Lys Ser Ala
        450                 455

<210> SEQ ID NO 120
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 120

| | | | | | |
|---|---|---|---|---|---|
| taatcgagct | tggcgtaatc | atggtcatag | ctgtttcctg | tgtgaaattg | ttatccgctc | 60 |
| acaattccac | acaacatacg | agccggaagc | ataaagtgta | aagcctgggg | tgcctaatga | 120 |
| gtgagctaac | tcacattaat | tgcgttgcgc | tcactgcccg | ctttccagtc | gggaaacctg | 180 |
| tcgtgccagc | tgcattaatg | aatcggccaa | cgcgcgggga | gaggcggttt | gcgtattggg | 240 |
| cgctcttccg | cttcctcgct | cactgactcg | ctgcgctcgg | tcgttcggct | gcggcgagcg | 300 |
| gtatcagctc | actcaaaggc | ggtaatacgg | ttatccacag | aatcagggga | taacgcagga | 360 |
| aagaacatgt | gagcaaaagg | ccagcaaaag | gccaggaacc | gtaaaaaggc | cgcgttgctg | 420 |
| gcgtttttcc | ataggctccg | cccccctgac | gagcatcaca | aaaatcgacg | ctcaagtcag | 480 |
| aggtggcgaa | acccgacagg | actataaaga | taccaggcgt | ttccccctgg | aagctccctc | 540 |
| gtgcgctctc | ctgttccgac | cctgccgctt | accggatacc | tgtccgcctt | tctcccttcg | 600 |
| ggaagcgtgg | cgctttctca | tagctcacgc | tgtaggtatc | tcagttcggt | gtaggtcgtt | 660 |
| cgctccaagc | tgggctgtgt | gcacgaaccc | cccgttcagc | ccgaccgctg | cgccttatcc | 720 |
| ggtaactatc | gtcttgagtc | caacccggta | agacacgact | tatcgccact | ggcagcagcc | 780 |
| actggtaaca | ggattagcag | agcgaggtat | gtaggcggtg | ctacagagtt | cttgaagtgg | 840 |
| tggcctaact | acggctacac | tagaaggaca | gtatttggta | tctgcgctct | gctgaagcca | 900 |
| gttaccttcg | gaaaaagagt | tggtagctct | tgatccggca | aacaaaccac | cgctggtagc | 960 |
| ggtggttttt | ttgtttgcaa | gcagcagatt | acgcgcagaa | aaaaaggatc | tcaagaagat | 1020 |
| cctttgatct | tttctacggg | gtctgacgct | cagtggaacg | aaaactcacg | ttaagggatt | 1080 |
| ttggtcatga | gattatcaaa | aaggatcttc | acctagatcc | ttttaaatta | aaaatgaagt | 1140 |
| tttaaatcaa | tctaaagtat | atatgagtaa | acttggtctg | acagttacca | atgcttaatc | 1200 |
| agtgaggcac | ctatctcagc | gatctgtcta | tttcgttcat | ccatagttgc | ctgactcccc | 1260 |
| gtcgtgtaga | taactacgat | acgggagggc | ttaccatctg | gccccagtgc | tgcaatgata | 1320 |
| ccgcgagacc | cacgctcacc | ggctccagat | ttatcagcaa | taaaccagcc | agccggaagg | 1380 |
| gccgagcgca | gaagtggtcc | tgcaacttta | tccgcctcca | tccagtctat | taattgttgc | 1440 |
| cgggaagcta | gagtaagtag | ttcgccagtt | aatagtttgc | gcaacgttgt | tgccattgct | 1500 |
| acaggcatcg | tggtgtcacg | ctcgtcgttt | ggtatggctt | cattcagctc | cggttcccaa | 1560 |
| cgatcaaggc | gagttacatg | atcccccatg | ttgtgcaaaa | aagcggttag | ctccttcggt | 1620 |
| cctccgatcg | ttgtcagaag | taagttggcc | gcagtgttat | cactcatggt | tatggcagca | 1680 |
| ctgcataatt | ctcttactgt | catgccatcc | gtaagatgct | tttctgtgac | tggtgagtac | 1740 |
| tcaaccaagt | cattctgaga | atagtgtatg | cggcgaccga | gttgctcttg | cccggcgtca | 1800 |
| atacgggata | ataccgcgcc | acatagcaga | actttaaaag | tgctcatcat | ggaaaacgt | 1860 |
| tcttcggggc | gaaaactctc | aaggatctta | ccgctgttga | gatccagttc | gatgtaaccc | 1920 |

```
actcgtgcac ccaactgatc ttcagcatct tttactttca ccagcgtttc tgggtgagca    1980
aaaacaggaa ggcaaaatgc cgcaaaaaag ggaataaggg cgacacggaa atgttgaata    2040
ctcatactct tccttttca atattattga agcatttatc agggttattg tctcatgagc     2100
ggatacatat ttgaatgtat ttagaaaaat aaacaaatag gggttccgcg cacatttccc    2160
cgaaaagtgc cacctgacgc gcccgtagc ggcgcattaa gcgcggcggg tgtggtggtt     2220
acgcgcagcg tgaccgctac acttgccagc gccctagcgc ccgctccttt cgctttcttc    2280
ccttcctttc tcgccacgtt cgccggcttt ccccgtcaag ctctaaatcg ggggctccct    2340
ttagggttcc gatttagtgc tttacggcac ctcgacccca aaaaacttga ttagggtgat    2400
ggttcacgta gtgggccatc gccctgatag acggttttc gcccttgac gttggagtcc      2460 acgttctta atagtggact cttgttccaa actggaacaa cactcaaccc tatctcggtc     2520
tattcttttg atttataagg gattttgccg atttcggcct attggttaaa aaatgagctg    2580
atttaacaaa aatttaacgc gaattttaac aaaatattaa cgcttacaat ttccattcgc    2640
cattcaggct gcgcaactgt tgggaagggc gatcggtgcg ggcctcttcg ctattacgcc    2700
agctggcgaa aggggggatgt gctgcaaggc gattaagttg ggtaacgcca gggttttccc   2760
agtcacgacg ttgtaaaacg acggccagtg aattgtaata cgactcacta tagggcgaat    2820
tgggtaccgg gccccccctc gaggtcgacg agtatctgtc tgactcgtca ttgccgcctt    2880
tggagtacga ctccaactat gagtgtgctt ggatcacttt gacgatacat tcttcgttgg    2940
aggctgtggg tctgacagct gcgttttcgg cgcggttggc cgacaacaat atcagctgca    3000
acgtcattgc tggctttcat catgatcaca ttttgtcgg caaaggcgac gcccagagag     3060
ccattgacgt tctttctaat ttggaccgat agccgtatag tccagtctat ctataagttc    3120
aactaactcg taactattac cataacatat acttcactgc cccagataag gttccgataa    3180
aaagttctgc agactaaatt tatttcagtc tcctcttcac caccaaaatg ccctcctacg    3240
aagctcgagt gctcaagctc gtggcagcca agaaaaccaa cctgtgtgct tctctggatg    3300
ttaccaccac caaggagctc attgagcttg ccgataaggt cggaccttat gtgtgcatga    3360
tcaaacccca tatcgacatc attgacgact tcacctacgc cggcactgtg ctccccctca    3420
aggaacttgc tcttaagcac ggtttcttcc tgttcgagga cagaaagttc gcagatattg    3480
gcaacactgt caagcaccag taccggtgtc accgaatcgc cgagtggtcc gatatcacca    3540
acgcccacgg tgtacccgga accggaatcg attgctggcc tgcgagctgg tgcgtacgag    3600
gaaactgtct ctgaacagaa gaaggaggac gtctctgact acgagaactc ccagtacaag    3660
gagttcctag tcccctctcc caacgagaag ctggccagag gtctgctcat gctggccgag    3720
ctgtcttgca agggctctct ggccactggc gagtactcca agcagaccat tgagcttgcc    3780
cgatccgacc ccgagtttgt ggttggcttc attgcccaga accgacctaa gggcgactct    3840
gaggactggc ttattctgac ccccggggtg ggtcttgacg acaagggaga cgctctcgga    3900
cagcagtacc gaactgttga ggatgtcatg tctaccggaa cggatatcat aattgtcggc    3960
cgaggtctgt acgccagaa ccgagatcct attgaggagg ccaagcgata ccagaaggct     4020
ggctgggagg cttaccagaa gattaactgt tagaggttag actatggata tgtaatttaa    4080
ctgtgtatat agagagcgtg caagtatgga gcgcttgttc agcttgtatg atggtcagac    4140
gacctgtctg atcgagtatg tatgatactg cacaacctgt gtatccgcat gatctgtcca    4200
atggggcatg ttgttgtgtt tctcgatacg gagatgctgg gtacagtgct aatacgttga    4260
actacttata cttatatgag gctcgaagaa agctgacttg tgtatgactt aat           4313
```

<210> SEQ ID NO 121
<211> LENGTH: 23
<212> TYPE: DNA
<213> ORGANISM: Artificial Sequence
<220> FEATURE:
<223> OTHER INFORMATION: Primer P239

<400> SEQUENCE: 121
ccatgaacac tttgtcgtcc atc                                              23

<210> SEQ ID NO 122
<211> LENGTH: 23
<212> TYPE: DNA
<213> ORGANISM: Artificial Sequence
<220> FEATURE:
<223> OTHER INFORMATION: Primer P240

<400> SEQUENCE: 122
aatcgagctt gggctggaag aac                                              23

<210> SEQ ID NO 123
<211> LENGTH: 18
<212> TYPE: DNA
<213> ORGANISM: Artificial Sequence
<220> FEATURE:
<223> OTHER INFORMATION: Primer M13

<400> SEQUENCE: 123
tgtaaaacga cggccagt                                                    18

<210> SEQ ID NO 124
<211> LENGTH: 604
<212> TYPE: DNA
<213> ORGANISM: Mortierella alpina

<400> SEQUENCE: 124 gggggggcatg atgtactttt tagtcgagca gtacgccacc cccaccctgc agaactcggt     60
ccgagcattc gatgagttgg cgttcggcac cattctggag agagtgctga agctgagcac    120
caccagtgtc atcatctggc tactcatgtt ctacaccttt ttccactcgt tctttaatgc    180
tcttgcagag gcactgtact ttggagaccg tcgcttctat ctcgcctggt ggaatgccac    240
tggtgtcggc atgtactgga agacgtggaa ctcgcccgtc tacaccttct tcaaacgcca    300
cgtatacctg cccctgatca cctctggcac ctctcccatg gtcgcctcga tcgtcatctt    360
cctcatctcg gctgtcttgc acgagatctt gatcggcttc cccactcata tgatctatgg    420
atacgcattc gccggcatgt tcctccagat cccgctgatc attctgaccc gaccctcga    480
aaaatggcga ggcaccggat cgggtctcgg caacatgatc ttctgggtct cgttcaccat    540
cctgggccag ccagcgtgtg cgctgctcta ctactaccac tggaccaagc gccatatgga    600
tgtt                                                                 604

<210> SEQ ID NO 125
<211> LENGTH: 20
<212> TYPE: DNA
<213> ORGANISM: Artificial Sequence
<220> FEATURE:
<223> OTHER INFORMATION: Primer MARE2-N1

<400> SEQUENCE: 125
cctctgcaag agcattaaag                                                  20

<210> SEQ ID NO 126
<211> LENGTH: 21
<212> TYPE: DNA
<213> ORGANISM: Artificial Sequence
<220> FEATURE:
<223> OTHER INFORMATION: Primer MARE2-N2

<400> SEQUENCE: 126
ttcagcactc tctccagaat g                                              21

<210> SEQ ID NO 127
<211> LENGTH: 1683
<212> TYPE: DNA
<213> ORGANISM: Mortierella alpina
<220> FEATURE:
<221> NAME/KEY: misc_feature
<222> LOCATION: (1093)..(1093)
<223> OTHER INFORMATION: n is a, c, g, or t

<400> SEQUENCE: 127

```
actatagggc acgcgtggtc gacggcccgg gctggtaaag attcgcccac cccgcataca      60
ggtactcaca ctggcttcca tgcctacgct tacgagccaa ctcgattgca ctgttgcgtt     120
ccgtatcatg ccaacttgat gccataaaaa aaagatcctt tctttgcagc tcatgcttac     180
atgtctcatt gctcctccgt ttgctagggc atagtacagt tccccgccg ccatgacaga      240
gtcgacaaca acgacatgtg caaaggagga gggcattgcc aacagcgctg ctttgcctga     300
cattccccca agatggaag acctcaagtc ctccaggaag accggctctt cttacaagca      360
caccttcccc gtccatacaa aaaccatccc cagcccattg tctaaagagg cacctccaga     420
gagctatcgt ggattcgtca acctcggcag taagttccct ttcttatttt gcaccctgtt     480
cgataacact tcactctggg agtgaggagg tgtggccgtt gcgcacaact gggcggttcc     540
gttggaacaa gttgaatatg catgcatgca tgcagtgtga tacagtgtca tggagtcagt     600
acggcacagc ctcgctcagt ccttggatta ctcggacttc aacccaacca cagacggtgc     660
acacgttcag tttgagccgc gtctgaatgg cgatacacga gatagagagg cgccgtcgca     720
ttgaccccag agcagtgcaa acagcaatga ttggctgtgc agccccggta ccttcaattc     780
cttcgcttca tttcatgccg ctaaacatgt cactcctacg ttttccttg tggccgtcgc      840
ttagtgctcc tactttcgg caacaacatc cgattgatca tcgagaatta cctcaaatac      900
ggcttcctgc tctcaatccc tggatcaagc gtctcgaagc aggactggat cctggctgcc     960
ctcacccacg ccatcctacc cgtcaacctc atcctggcct acaagcttga gagctgggcc    1020
aaggagagag ccgtcggcta tcgcaagcgt cgatctgacg aacccattgc ccaggaatca    1080
accaaggccg tgncagcagg agataatgac gctatcaaaa ccacaaaacc cgccaaggcc    1140
caggatctca cacccgaggc ccttgcaagg aaggaacaat cgaccgtggg ctggctccat    1200
gtcttcaatc tgttcaccat cgttgcctgg ccctccttca tgtcctactt tatgatctac    1260
caccccttcg tggccatgtc ctgcctcatg aacggactta tcctcttcct caaaatgacc    1320
tcctttgcgc ttgtgaacca ggagctccga gcagcctaca tctttggaac accgtggac     1380
acgttccagc acatggctaa agtgcacgac atctctggca aggacctgac aaagaaggag    1440
atcttccagt atgacatcca gtaccccgac aacatcaccc tcaagaacat ggctatttc     1500
tggctcgccc ccacgctctg ctaccagcca tcatacccaa ggacgaccgt cttccgcaaa    1560
tccttcttcc tcaagcgtgt ggccgagatc gtgacctgtc tgggcatgat gtactttta    1620
gtcgagcagt acgccacccc cacctgcag aactcggtcc gagcattcga tgagttggcg     1680
ttc                                                                  1683
```

<210> SEQ ID NO 128
<211> LENGTH: 22
<212> TYPE: DNA
<213> ORGANISM: Artificial Sequence
<220> FEATURE:
<223> OTHER INFORMATION: Primer ARE-N3-1

<400> SEQUENCE: 128
agatcccgct gatcattctg ac                                              22

<210> SEQ ID NO 129
<211> LENGTH: 20
<212> TYPE: DNA
<213> ORGANISM: Artificial Sequence
<220> FEATURE:
<223> OTHER INFORMATION: Primer ARE-N3-2

<400> SEQUENCE: 129
gatcgggtct cggcaacatg                                                 20

<210> SEQ ID NO 130
<211> LENGTH: 184
<212> TYPE: DNA
<213> ORGANISM: Mortierella alpina

<400> SEQUENCE: 130
tttttttttt ttttgttct taaaaaaact atgcgttctc ccattatctt tatatctatt      60 caaaaaaat aataaagtcg gtcgtaagat tgaatcaaac atccatatgg cgcttggtcc     120
agtggtagta gtagagcagc gcacacgctg gctggcccag gatggtgaac gagacccaga    180
agat                                                                184

<210> SEQ ID NO 131
<211> LENGTH: 1578
<212> TYPE: DNA
<213> ORGANISM: Mortierella alpina
<220> FEATURE:
<221> NAME/KEY: misc_feature
<222> LOCATION: (466)..(466)
<223> OTHER INFORMATION: n is a, c, g, or t

<400> SEQUENCE: 131
atgacagagt cgacaacaac gacatgtgca aaggaggagg gcattgccaa cagcgctgct     60
ttgcctgaca ttcccccaaa gatggaagac ctcaagtcct ccaggaagac cggctcttct    120
tacaagcaca ccttccccgt ccatacaaaa accatcccca gcccattgtc taaagaggca    180
cctccagaga gctatcgtgg attcgtcaac ctcggcatgc tcctactttt cggcaacaac    240
atccgattga tcatcgagaa ttacctcaaa tacggcttcc tgctctcaat ccctggatca    300
agcgtctcga agcaggactg gatcctggct gccctcaccc acgccatcct acccgtcaac    360
ctcatcctgg cctacaagct tgagagctgg gccaaggaga gaccgtcgg ctatcgcaag    420 cgtcgatctg acgaacccat tgcccaggaa tcaaccaagg ccgtgncagc aggagataat    480
gacgctatca aaaccacaaa acccgccaag gcccaggatc tcacacccga ggcccttgca    540
aggaaggaac aatcgaccgt gggctggctc catgtcttca atctgttcac catcgttgcc    600
tggccctcct tcatgtccta ctttatgatc taccacccct tcgtggccat gtcctgcctc    660
atgaacggac ttatcctctt cctcaaaatg acctcctttg cgcttgtgaa ccaggagctc    720
cgagcagcct catctttgg aacacccgtg gacacgttcc agcacatggc taaagtgcac    780
gacatctctg gcaaggacct gacaaagaag gagatcttcc agtatgacat ccagtacccc    840

-continued

```
gacaacatca ccctcaagaa cattggctat ttctggctcg cccccacgct ctgctaccag      900
ccatcatacc caaggacgac cgtcttccgc aaatccttct tcctcaagcg tgtggccgag      960
atcgtgacct gtctgggcat gatgtacttt ttagtcgagc agtacgccac ccccaccctg     1020
cagaactcgg tccgagcatt cgatgagttg gcgttcggca ccattctgga gagagtgctg     1080
aagctgagca ccaccagtgt catcatctgg ctactcatgt tctacacctt tttccactcg     1140
ttctttaatg ctcttgcaga ggcactgtac tttggagacc gtcgcttcta tctcgcctgg     1200
tggaatgcca ctggtgtcgg catgtactgg aagacgtgga actcgcccgt ctacaccttc     1260
ttcaaacgcc acgtatacct gcccctgatc acctctggca cctctcccat ggtcgcctcg     1320
atcgtcatct tcctcatctc ggctgtcttg cacgagatct tgatcggctt ccccactcat     1380
atgatctatg gatacgcatt cgccggcatg ttcctccaga tcccgctgat cattctgacc     1440
cgacccctcg aaaaatggcg aggcaccgga tcgggtctcg gcaacatgat cttctgggtc     1500
tcgttcacca tcctgggcca gccagcgtgt gcgctgctct actactacca ctggaccaag     1560
cgccatatgg atgtttga                                                   1578
```

<210> SEQ ID NO 132
<211> LENGTH: 525
<212> TYPE: PRT
<213> ORGANISM: Mortierella alpina
<220> FEATURE:
<221> NAME/KEY: misc_feature
<222> LOCATION: (156)..(156)
<223> OTHER INFORMATION: Xaa can be any naturally occurring amino acid

<400> SEQUENCE: 132

```
Met Thr Glu Ser Thr Thr Thr Thr Cys Ala Lys Glu Glu Gly Ile Ala
1               5                   10                  15

Asn Ser Ala Ala Leu Pro Asp Ile Pro Pro Lys Met Glu Asp Leu Lys
            20                  25                  30

Ser Ser Arg Lys Thr Gly Ser Ser Tyr Lys His Thr Phe Pro Val His
        35                  40                  45

Thr Lys Thr Ile Pro Ser Pro Leu Ser Lys Glu Ala Pro Pro Glu Ser
    50                  55                  60

Tyr Arg Gly Phe Val Asn Leu Gly Met Leu Leu Leu Phe Gly Asn Asn
65                  70                  75                  80

Ile Arg Leu Ile Ile Glu Asn Tyr Leu Lys Tyr Gly Phe Leu Leu Ser
                85                  90                  95

Ile Pro Gly Ser Ser Val Ser Lys Gln Asp Trp Ile Leu Ala Ala Leu
            100                 105                 110

Thr His Ala Ile Leu Pro Val Asn Leu Ile Leu Ala Tyr Lys Leu Glu
        115                 120                 125

Ser Trp Ala Lys Glu Arg Ala Val Gly Tyr Arg Lys Arg Arg Ser Asp
    130                 135                 140

Glu Pro Ile Ala Gln Glu Ser Thr Lys Ala Val Xaa Ala Gly Asp Asn
145                 150                 155                 160

Asp Ala Ile Lys Thr Thr Lys Pro Ala Lys Ala Gln Asp Leu Thr Pro
                165                 170                 175

Glu Ala Leu Ala Arg Lys Glu Gln Ser Thr Val Gly Trp Leu His Val
            180                 185                 190

Phe Asn Leu Phe Thr Ile Val Ala Trp Pro Ser Phe Met Ser Tyr Phe
        195                 200                 205

Met Ile Tyr His Pro Phe Val Ala Met Ser Cys Leu Met Asn Gly Leu
    210                 215                 220
```

Ile Leu Phe Leu Lys Met Thr Ser Phe Ala Leu Val Asn Gln Glu Leu
225                 230                 235                 240

Arg Ala Ala Tyr Ile Phe Gly Thr Pro Val Asp Thr Phe Gln His Met
            245                 250                 255

Ala Lys Val His Asp Ile Ser Gly Lys Asp Leu Thr Lys Lys Glu Ile
                260                 265                 270

Phe Gln Tyr Asp Ile Gln Tyr Pro Asp Asn Ile Thr Leu Lys Asn Ile
            275                 280                 285

Gly Tyr Phe Trp Leu Ala Pro Thr Leu Cys Tyr Gln Pro Ser Tyr Pro
        290                 295                 300

Arg Thr Thr Val Phe Arg Lys Ser Phe Phe Leu Lys Arg Val Ala Glu
305                 310                 315                 320

Ile Val Thr Cys Leu Gly Met Met Tyr Phe Leu Val Glu Gln Tyr Ala
                325                 330                 335

Thr Pro Thr Leu Gln Asn Ser Val Arg Ala Phe Asp Glu Leu Ala Phe
            340                 345                 350

Gly Thr Ile Leu Glu Arg Val Leu Lys Leu Ser Thr Thr Ser Val Ile
        355                 360                 365

Ile Trp Leu Leu Met Phe Tyr Thr Phe Phe His Ser Phe Phe Asn Ala
370                 375                 380

Leu Ala Glu Ala Leu Tyr Phe Gly Asp Arg Arg Phe Tyr Leu Ala Trp
385                 390                 395                 400

Trp Asn Ala Thr Gly Val Gly Met Tyr Trp Lys Thr Trp Asn Ser Pro
                405                 410                 415

Val Tyr Thr Phe Phe Lys Arg His Val Tyr Leu Pro Leu Ile Thr Ser
            420                 425                 430

Gly Thr Ser Pro Met Val Ala Ser Ile Val Ile Phe Leu Ile Ser Ala
        435                 440                 445

Val Leu His Glu Ile Leu Ile Gly Phe Pro Thr His Met Ile Tyr Gly
450                 455                 460

Tyr Ala Phe Ala Gly Met Phe Leu Gln Ile Pro Leu Ile Ile Leu Thr
465                 470                 475                 480

Arg Pro Leu Glu Lys Trp Arg Gly Thr Gly Ser Gly Leu Gly Asn Met
                485                 490                 495

Ile Phe Trp Val Ser Phe Thr Ile Leu Gly Gln Pro Ala Cys Ala Leu
            500                 505                 510

Leu Tyr Tyr Tyr His Trp Thr Lys Arg His Met Asp Val
        515                 520                 525

<210> SEQ ID NO 133
<211> LENGTH: 533
<212> TYPE: PRT
<213> ORGANISM: Neurospora crassa strain OR74A [GenBank Accession No.
      XP_322121]

<400> SEQUENCE: 133

Met Ser Ser Ser Thr Ala Thr Thr Gly Leu Asp Pro Ala Val His
1               5                   10                  15

Thr Ser Asn Asp Asn Val Ile Arg Arg Thr His Gly Thr Glu Asn Gly
                20                  25                  30

Ser Thr Pro Asn Asp Lys Ala Asn Ala Gly Gly Glu Pro Glu Thr Glu
            35                  40                  45

Thr Lys Arg His Ser Lys Lys Val Val Arg Ser Lys Tyr Arg His Val
        50                  55                  60

Glu Ala Val His Ser Gln Ser Arg Pro Ser Cys Leu Ser His Asp Thr

```
              65                  70                  75                  80
Thr Glu Ser Pro Ser Phe Leu Gly Phe Arg Asn Leu Met Val Ile Val
                     85                  90                  95

Leu Ala Asn Asn Ser His Gln Tyr Gly Val Leu Ile Cys Ile Gly Cys
                100                 105                 110

His Asp Phe Arg Lys Ser Asp Ile Asn Leu Gly Leu Leu Tyr Phe
                115                 120                 125

Leu Ile Pro Cys His Leu Phe Ile Ala Tyr Ile Ile Glu Tyr Tyr Ala
            130                 135                 140

Ala Val Gln Ala Arg Ala Glu Arg Asn Val Ser Ala Ser Glu Gln Asn
145                 150                 155                 160

Ala Lys Glu His Gln His Gln Asp Gly Thr Asn Ser Pro Thr Glu Glu
                165                 170                 175

Gln His Arg Lys Phe Gln Ser Thr Trp Lys Leu Val Arg Leu Leu His
                180                 185                 190

Ala Ile Asn Val Thr Thr Ala Leu Val Leu Thr Ser Tyr Val Val Tyr
                195                 200                 205

Tyr His Ile His His Pro Leu Ile Gly Thr Leu Thr Glu Val His Ala
            210                 215                 220

Ile Val Val Trp Leu Lys Thr Ala Ser Tyr Ala Phe Thr Asn Arg Asp
225                 230                 235                 240

Leu Arg His Ala Tyr Leu His Pro Ala Arg Gly Glu Leu Asp Ala Leu
                245                 250                 255

Pro Gly Leu Tyr Ala Glu Cys Pro Tyr Pro Glu Asn Ile Thr Met Gly
                260                 265                 270

Asn Leu Cys Tyr Phe Trp Trp Ala Pro Thr Leu Val Tyr Gln Pro Val
                275                 280                 285

Tyr Pro Arg Thr Ala Lys Ile Arg Trp Ser Phe Val Ala Lys Arg Cys
            290                 295                 300

Gly Glu Val Ile Cys Leu Ser Val Phe Ile Trp Phe Leu Ser Ala Gln
305                 310                 315                 320

Tyr Ala Thr Pro Val Leu Arg Asn Ser Leu Asp Lys Ile Ala Ser Leu
                325                 330                 335

Asp Ile Pro Ser Ile Val Glu Arg Leu Leu Lys Leu Ser Thr Ile Ser
                340                 345                 350

Leu Ile Ile Trp Leu Ala Gly Phe Ala Leu Phe Gln Ser Phe Leu
            355                 360                 365

Asn Ala Leu Ala Glu Val Thr Arg Phe Ala Asp Arg Ser Phe Tyr Asp
            370                 375                 380

Glu Trp Trp Asn Ser Glu Ser Leu Gly Val Tyr Trp Arg Thr Trp Asn
385                 390                 395                 400

Lys Pro Val Tyr Gln Tyr Phe Lys Arg His Val Tyr Ser Pro Met Arg
                405                 410                 415

Ser Arg Gly Trp Ser Asn Ala Thr Ala Ser Leu Ala Val Phe Phe Leu
            420                 425                 430

Ser Ala Val Leu His Glu Leu Leu Val Gly Val Pro Thr His Asn Leu
            435                 440                 445

Ile Gly Val Ala Phe Leu Gly Met Phe Leu Gln Leu Pro Leu Ile Gln
            450                 455                 460

Phe Thr Lys Pro Leu Glu Lys Lys Thr Ser Pro Asn Gly Lys Leu Leu
465                 470                 475                 480

Gly Asn Ile Ile Phe Trp Val Ser Phe Thr Ile Phe Gly Gln Pro Phe
                485                 490                 495
```

```
Ala Ala Leu Met Tyr Phe Tyr Ala Trp Gln Ala Lys Tyr Gly Ser Val
            500                 505                 510

Ser Lys Met Thr Thr Ser Gln Gln Leu Val Gln Gln Gly Gln Gly Thr
            515                 520                 525

Cys Pro Pro Leu Val
            530

<210> SEQ ID NO 134
<211> LENGTH: 499
<212> TYPE: PRT
<213> ORGANISM: Gibberella zeae PH-1 [GenBank Accession No. EAA77624]

<400> SEQUENCE: 134

Met Asn Ser Ala Thr Thr Thr Ser Thr Glu Thr Ser Asn Gly Ser Thr
1               5                   10                  15

Ser Val Ser Lys Arg Asn Gly His Asp Val Thr Arg Thr Asn Gly Asn
            20                  25                  30

Gly Thr Thr Thr Thr Ser Pro Pro Lys Lys Ala Gly Gln Lys Tyr Arg
        35                  40                  45

His Val Ala Ala Val His Lys Lys Thr Arg Pro Ser Cys Leu Ser His
    50                  55                  60

Asp Ser Asp Ala Ala Pro Ser Phe Ile Gly Phe Arg Asn Leu Met Val
65                  70                  75                  80

Ile Val Leu Gly Ile Tyr His Ile Gly Met Ser Gln Phe Asp Ser Glu
                85                  90                  95

Gln Pro Ile Asp Thr Ala Ser Tyr Arg Gln Asp Ile Phe Leu Gly Leu
            100                 105                 110

Leu Leu Tyr Phe Leu Ile Pro Cys His Leu Leu Ala Ala Tyr Leu Ile
        115                 120                 125

Glu Leu Ala Ala Ala Gln Gln Ala Arg Gly Ser Leu Lys Arg Tyr Asn
130                 135                 140

Asp Ser Ala Ser Gly Gly Pro Ser Asp Gln Glu Arg Lys Lys Phe His
145                 150                 155                 160

Lys Thr Trp Val Ile Val Ala Trp Ala His Leu Phe Asn Ile Thr Leu
                165                 170                 175

Ala Leu Val Leu Thr Thr Trp Val Val Tyr Phe Lys Ile His His Pro
            180                 185                 190

Leu Ile Gly Thr Leu Thr Glu Met His Ala Ile Ala Val Trp Leu Lys
        195                 200                 205

Thr Ala Ser Tyr Ala Phe Thr Asn Arg Asp Leu Arg His Ala Tyr Leu
210                 215                 220

His Pro Val Glu Gly Glu Arg Glu Leu Val Pro Glu Leu Tyr Thr Gln
225                 230                 235                 240

Cys Pro Tyr Pro Gln Asn Ile Thr Phe Ser Asn Leu Ala Tyr Phe Trp
                245                 250                 255

Trp Ala Pro Thr Leu Val Tyr Gln Pro Val Tyr Pro Arg Thr Asp Lys
            260                 265                 270

Ile Arg Trp Gly Phe Val Ala Lys Arg Val Gly Glu Ile Phe Gly Leu
        275                 280                 285

Ser Val Phe Ile Trp Val Ala Ser Ala Gln Tyr Ala Ala Pro Val Leu
290                 295                 300

Arg Asn Ser Leu Asp Lys Ile Ala Ser Leu Asp Leu Met Ser Ile Leu
305                 310                 315                 320

Glu Arg Leu Leu Lys Leu Ser Thr Ile Ser Leu Ala Ile Trp Leu Ala
                325                 330                 335
```

```
Gly Phe Phe Ala Leu Phe Gln Ser Phe Leu Asn Ala Leu Ala Glu Val
                340                 345                 350

Leu Arg Phe Gly Asp Arg Ser Phe Tyr Asp Asp Trp Trp Asn Ser Glu
            355                 360                 365

Ser Leu Gly Ala Tyr Trp Arg Thr Trp Asn Lys Pro Val Tyr Thr Tyr
        370                 375                 380

Phe Lys Arg His Leu Tyr Met Pro Met Ile Gly Arg Gly Trp Ser Pro
385                 390                 395                 400

Gln Ala Ala Ser Phe Phe Val Phe Leu Val Ser Ala Ile Leu His Glu
                405                 410                 415

Ile Leu Val Gly Val Pro Thr His Asn Ile Ile Gly Val Ala Phe Leu
            420                 425                 430

Gly Met Phe Leu Gln Leu Pro Leu Ile His Leu Thr Lys Pro Leu Glu
        435                 440                 445

Asn Met Lys Leu Gly His Thr Gly Lys Ile Val Gly Asn Thr Ile Phe
    450                 455                 460

Trp Val Ser Phe Thr Ile Phe Gly Gln Pro Phe Ala Ala Leu Met Tyr
465                 470                 475                 480

Phe Tyr Ala Trp Gln Ala Lys Tyr Gly Ser Val Thr Asp Ser Gly Phe
                485                 490                 495

Ser Ile Ser

<210> SEQ ID NO 135
<211> LENGTH: 503
<212> TYPE: PRT
<213> ORGANISM: Magnaporthe grisea 70-15 [GenBank Accession No.
      EAA52634]

<400> SEQUENCE: 135

Met Ala Ala Ala Thr Ala Thr Gly Leu Asp Leu Ala Ala Gln Glu Gly
1               5                   10                  15

Ala Gln Gln Arg Arg Ser Thr Ala Thr Asn Gln Ser Ala Asp Asp Asp
            20                  25                  30

Val Thr Thr Asn Ala Asp Gly Ala Ala Ala Pro Ser Leu Lys Gly
        35                  40                  45

Thr Thr Ala Asp Thr Asn Gly Thr Ser Asn Gly Asn Gly Asn Gly Asn
    50                  55                  60

Gly Asn Val Asp Glu Asp Glu Gln Thr Lys Ala Leu Arg Lys Ala Phe
65                  70                  75                  80

Thr Arg Lys Tyr Arg His Val Ala Ala Leu His Ser Gln Ala Arg Pro
                85                  90                  95

Ser Thr Leu Ser His Asp Ser Glu Ala Ser Pro Ser Phe Val Gly Phe
            100                 105                 110

Arg Asn Leu Met Val Ile Val Leu Glu Leu Leu Ala Ala Gln Gln Ala
        115                 120                 125

Arg Asn Ser Arg Gly Tyr Phe Asn Arg Gly Arg Thr Gly Ser Ser Arg
    130                 135                 140

Asp Gly Ser Thr Ser Pro Thr Glu Asp Glu Ser Arg Arg Phe Val Ser
145                 150                 155                 160

Thr Trp Lys Leu Ile Ala Leu Val His Gly Ile Asn Val Asn Ser Ala
                165                 170                 175

Leu Leu Ile Thr Thr Tyr Thr Val Tyr Phe His Ile His Pro Leu
            180                 185                 190

Ile Gly Thr Leu Thr Glu Met His Ala Val Ile Val Trp Leu Lys Thr
        195                 200                 205
```

-continued

```
Ala Ser Tyr Ala Phe Thr Asn Arg Asp Leu Arg His Ala Tyr Leu His
    210                 215                 220

Pro Val Lys Gly Glu Leu Asp Ala Leu Pro Glu Leu Tyr Lys Gln Cys
225                 230                 235                 240

Pro Tyr Pro Asn Asn Ile Thr Met Lys Asn Leu Cys Tyr Phe Trp Trp
                245                 250                 255

Ala Pro Thr Leu Ile Tyr Gln Pro Val Tyr Pro Arg Ser Gly Arg Ile
            260                 265                 270

Arg Trp Val Phe Phe Lys Arg Val Ala Glu Val Phe Cys Leu Ser
        275                 280                 285

Val Cys Ile Trp Phe Leu Ser Ala Gln Tyr Ala Thr Pro Val Leu Val
    290                 295                 300

Asn Ser Leu Asp Lys Ile Ala Ser Leu Asp Met Pro Ala Ile Leu Glu
305                 310                 315                 320

Arg Leu Leu Lys Leu Ser Thr Ile Ser Leu Ala Ile Trp Leu Ala Gly
                325                 330                 335

Phe Phe Ala Leu Phe Gln Ser Phe Leu Asn Ala Leu Ala Glu Ile Thr
            340                 345                 350

Arg Phe Gly Asp Arg Ser Phe Tyr Glu Ala Trp Trp Asn Ser Glu Ser
        355                 360                 365

Leu Gly Val Tyr Trp Arg Thr Trp Asn Lys Pro Val Tyr Gln Tyr Phe
    370                 375                 380

Lys Arg His Val Tyr Ser Pro Met Leu Gly Arg Gly Trp Ala Pro Arg
385                 390                 395                 400

Thr Ala Ser Ala Ser Val Phe Leu Ile Ser Ala Val Leu His Glu Ile
                405                 410                 415

Leu Val Gly Val Pro Thr His Asn Ile Ile Gly Val Ala Phe Met Gly
            420                 425                 430

Met Phe Leu Gln Val Pro Leu Ile Ile Leu Thr Ala Pro Leu Glu Lys
        435                 440                 445

Arg Lys Ser Pro Thr Gly Lys Leu Ile Gly Asn Ser Ile Phe Trp Val
    450                 455                 460

Ser Phe Thr Ile Phe Gly Gln Pro Leu Ala Ala Leu Met Tyr Phe Tyr
465                 470                 475                 480

Ala Trp Gln Ala Lys Tyr Gly Ser Val Ser Lys Met Gly Tyr Ala Thr
                485                 490                 495

Ser Lys Ala Ala Leu Thr Asn
            500

<210> SEQ ID NO 136
<211> LENGTH: 458
<212> TYPE: PRT
<213> ORGANISM: Aspergillus nidulans FGSC A4 [GenBank Accession No.
      EAA57945]

<400> SEQUENCE: 136

Met Ala Thr Arg Lys Thr Ala Ile Tyr Arg His Ala Val Ala Val His
1               5                   10                  15

Ser Gln Val Gln His Ser Cys Leu Ser Arg Asp Ser Thr Lys Ala Thr
            20                  25                  30

Ser Phe Ile Gly Phe Arg Asn Leu Met Val Val Leu Val Ala Met
        35                  40                  45

Asn Leu Arg Leu Val Ile Glu Asn Phe Leu Lys Tyr Gly Val Leu Ile
    50                  55                  60

Cys Ile Arg Cys His Asp Tyr Arg Lys Gln Asp Val Val Ile Gly Ala
65                  70                  75                  80
```

Ile Leu Phe Ala Leu Val Pro Cys Gln Leu Cys Ser Tyr Phe Ile
            85                  90                  95

Glu Leu Ala Ala Ser Arg His Ala Gln Arg Val Ile Gly Arg Ala Lys
        100                 105                 110

Lys Gln Asp Lys Asp Arg Ile Leu Asn Glu Ser Lys Arg Thr Trp Phe
            115                 120                 125

Ala Ile Ala Leu Leu His Ser Ile Ile Ser Phe Phe Gly Leu Ala Ala
        130                 135                 140

Thr Ser Tyr Val Ile Phe Tyr Tyr Val Asn His Pro Gly Ile Gly Thr
145                 150                 155                 160

Val Cys Glu Val Gln Val Ile Ile Val Ser Leu Lys Ser Tyr Ser Tyr
            165                 170                 175

Ala Leu Thr Asn Arg Asp Leu Arg Arg Ala Met Leu Gly Ser Pro Ser
        180                 185                 190

Ala Asp Ser Asp Ile Pro Glu Leu Tyr Arg Ser Cys Pro Tyr Pro Arg
            195                 200                 205

Asn Ile Thr Leu Gly Asn Leu Ala Tyr Phe Leu Trp Ala Pro Thr Leu
        210                 215                 220

Val Tyr Gln Pro Val Tyr Pro Arg Thr Pro Arg Ile Arg Trp Ser Phe
225                 230                 235                 240

Val Gly Lys Arg Leu Phe Glu Phe Val Cys Leu Ser Val Val Met Trp
            245                 250                 255

Leu Leu Ser Ala Gln Tyr Ala Ala Pro Leu Leu Arg Asn Ala Thr Gln
        260                 265                 270

Lys Ile Ala Thr Leu Asp Ile Ala Ser Ile Leu Glu Arg Gly Leu Lys
            275                 280                 285

Leu Ser Thr Ile Ser Leu Val Ile Trp Leu Ala Gly Phe Tyr Ala Leu
        290                 295                 300

Phe Gln Ser Leu Leu Asn Gly Leu Ala Glu Ile Met Arg Phe Gly Asp
305                 310                 315                 320

Arg Glu Phe Tyr Thr Asp Trp Trp Asn Ser Pro Ser Phe Gly Val Tyr
            325                 330                 335

Trp Arg Ser Trp Asn Arg Pro Val Tyr Ile Phe Met Lys Arg His Val
        340                 345                 350

Tyr Met Pro Leu Val Thr Arg Gly Trp Asn Pro Thr Leu Ala Gly Thr
            355                 360                 365

Val Val Phe Ala Val Ser Ala Val Leu His Glu Ile Leu Val Gly Val
        370                 375                 380

Pro Thr His Asn Leu Ile Gly Val Ala Ser Ile Ala Met Met Phe Gln
385                 390                 395                 400

Leu Pro Leu Ile Leu Thr Ala Pro Phe Glu Arg Phe Lys Ser Pro
            405                 410                 415

Leu Gly Lys Ala Ile Gly Asn Ser Phe Phe Trp Val Thr Phe Cys Val
        420                 425                 430

Val Gly Gln Pro Leu Gly Ala Leu Leu Tyr Phe Phe Ala Trp Gln Ala
            435                 440                 445

Lys Tyr Gly Ser Val Ser Gln Thr His Pro
450                 455

<210> SEQ ID NO 137
<211> LENGTH: 388
<212> TYPE: PRT
<213> ORGANISM: Mus musculus (GenBank Accession No. AF384160)

<400> SEQUENCE: 137

Met Lys Thr Leu Ile Ala Ala Tyr Ser Gly Val Leu Arg Gly Glu Arg
1               5                   10                  15

Arg Ala Glu Ala Ala Arg Ser Glu Asn Lys Asn Lys Gly Ser Ala Leu
            20                  25                  30

Ser Arg Glu Gly Ser Gly Arg Trp Gly Thr Gly Ser Ser Ile Leu Ser
        35                  40                  45

Ala Leu Gln Asp Ile Phe Ser Val Thr Trp Leu Asn Arg Ser Lys Val
    50                  55                  60

Glu Lys Gln Leu Gln Val Ile Ser Val Leu Gln Trp Val Leu Ser Phe
65                  70                  75                  80

Leu Val Leu Gly Val Ala Cys Ser Val Ile Leu Met Tyr Thr Phe Cys
                85                  90                  95

Thr Asp Cys Trp Leu Ile Ala Val Leu Tyr Phe Thr Trp Leu Ala Phe
            100                 105                 110

Asp Trp Asn Thr Pro Lys Lys Gly Gly Arg Arg Ser Gln Trp Val Arg
        115                 120                 125

Asn Trp Ala Val Trp Arg Tyr Phe Arg Asp Tyr Phe Pro Ile Gln Leu
130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Asn Arg Asp Thr Ile Asp Tyr Leu
210                 215                 220

Leu Ser Lys Asn Gly Ser Gly Asn Ala Ile Ile Ile Val Val Gly Gly
225                 230                 235                 240

Ala Ala Glu Ser Leu Ser Ser Met Pro Gly Lys Asn Ala Val Thr Leu
                245                 250                 255

Lys Asn Arg Lys Gly Phe Val Lys Leu Ala Leu Arg His Gly Ala Asp
            260                 265                 270

Leu Val Pro Thr Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Val Pro Lys Leu Glu His Pro Thr Gln
            340                 345                 350

Lys Asp Ile Asp Leu Tyr His Ala Met Tyr Met Glu Ala Leu Val Lys
        355                 360                 365

Leu Phe Asp Asn His Lys Thr Lys Phe Gly Leu Pro Glu Thr Glu Val
370                 375                 380

Leu Glu Val Asn
385

<210> SEQ ID NO 138
<211> LENGTH: 504
<212> TYPE: PRT

```
<213> ORGANISM: Glycine max
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(504)

<400> SEQUENCE: 138
```

Met Ala Ile Ser Asp Glu Pro Glu Ser Val Ala Thr Ala Leu Asn His
1               5                   10                  15

Ser Ser Leu Arg Arg Pro Ser Ala Thr Ser Thr Ala Gly Leu Phe
            20                  25                  30

Asn Ser Pro Glu Thr Thr Thr Asp Ser Ser Gly Asp Leu Ala Lys
        35                  40                  45

Asp Ser Gly Ser Asp Asp Ser Ile Asn Ser Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Leu His Ile Ile Ile
            180                 185                 190

Thr Ser Thr Ser Leu Phe Tyr Pro Val Leu Val Ile Leu Arg Cys Asp
                195                 200                 205

Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
            275                 280                 285

Ile Arg Lys Gly Trp Leu Phe Arg Gln Leu Val Lys Leu Ile Ile Phe
        290                 295                 300

Thr Gly Val Met Gly Phe Ile Ile Asp Gln Tyr Ile Asn Pro Ile Val
305                 310                 315                 320

Gln Asn Ser Gln His Pro Leu Lys Gly Asn Leu Leu Tyr Ala Thr Glu
            325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Arg Phe Gly Asp Arg Glu Phe Tyr Lys Asp Trp Trp Asn Ala Lys Thr

```
                    370               375               380
Val Glu Asp Tyr Trp Arg Met Trp Asn Met Pro Val His Lys Trp Met
385                 390               395               400

Ile Arg His Leu Tyr Phe Pro Cys Leu Arg His Gly Leu Pro Lys Ala
                405               410               415

Ala Ala Leu Leu Ile Ala Phe Leu Val Ser Ala Leu Phe His Glu Leu
            420               425               430

Cys Ile Ala Val Pro Cys His Ile Phe Lys Leu Trp Ala Phe Gly Gly
                435               440               445

Ile Met Phe Gln Val Pro Leu Val Leu Ile Thr Asn Tyr Leu Gln Asn
            450               455               460

Lys Phe Arg Asn Ser Met Val Gly Asn Met Ile Phe Trp Phe Ile Phe
465             470                 475               480

Ser Ile Leu Gly Gln Pro Met Cys Val Leu Leu Tyr Tyr His Asp Leu
                485               490               495

Met Asn Arg Lys Gly Lys Leu Asp
            500

<210> SEQ ID NO 139
<211> LENGTH: 520
<212> TYPE: PRT
<213> ORGANISM: Arabidopsis thaliana
<300> PUBLICATION INFORMATION:
<302> TITLE: Plant diacyglycerol acyltransferases
<310> PATENT DOCUMENT NUMBER: US20040088759
<311> PATENT FILING DATE: 2003-10-21
<312> PUBLICATION DATE: 2004-05-06
<313> RELEVANT RESIDUES: (1)..(520)

<400> SEQUENCE: 139

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
                20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Gly Glu
                85                  90                  95

Gly Arg Gly Asn Ala Asp Ala Thr Phe Thr Tyr Arg Pro Ser Val Pro
                100                 105                 110

Ala His Arg Arg Ala Arg Glu Ser Pro Leu Ser Ser Asp Ala Ile Phe
            115                 120                 125

Lys Gln Ser His Ala Gly Leu Phe Asn Leu Cys Val Val Val Leu Ile
130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Trp Ile Ser Leu Ser Ile Phe Pro Leu Ala Ala
            180                 185                 190

Phe Thr Val Glu Lys Leu Val Leu Gln Lys Tyr Ile Ser Glu Pro Val
            195                 200                 205

Gly Ile Phe Leu His Ile Ile Ile Thr Met Thr Glu Val Leu Tyr Pro
```

-continued

```
               210                 215                 220
Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Val Ser Leu Lys Ser Leu Ala Tyr Phe
            275                 280                 285

Met Val Ala Pro Thr Leu Cys Tyr Gln Pro Ser Tyr Pro Arg Ser Ala
            290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
            370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
            435                 440                 445

Leu Cys Ile Ala Val Pro Cys Arg Leu Phe Lys Leu Trp Ala Phe Leu
            450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
            515                 520

<210> SEQ ID NO 140
<211> LENGTH: 500
<212> TYPE: PRT
<213> ORGANISM: Oryza sativa
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(500)

<400> SEQUENCE: 140

Met Val Gly Ser Asp Gly Asp Gly Asp Gly Gly Gly Glu Ala His
1               5                   10                  15

Ala Gly Gly Pro Arg Arg Arg Ala Gly Gln Leu Arg Gly Arg Leu Arg
                20                  25                  30

Asp Glu Ala Ala Pro Gly Ser Pro Pro Arg Pro Arg Pro Arg Pro Arg
```

-continued

```
            35                  40                  45
Pro Arg Gly Gly Asp Ser Asn Gly Arg Ser Val Leu Arg Pro Gly Gly
            50                  55                  60

Gly Gly Gly Arg Gly Gly Gly Asp Phe Ser Ala Phe Thr Phe Arg
65                  70                  75                  80

Ala Ala Ala Pro Val His Arg Lys Ala Lys Glu Ser Pro Leu Ser Ser
                85                  90                  95

Asp Ala Ile Phe Lys Gln Ser His Ala Gly Leu Phe Asn Leu Cys Ile
                100                 105                 110

Val Val Leu Val Ala Val Asn Ser Arg Leu Ile Ile Glu Asn Leu Met
                115                 120                 125

Lys Tyr Gly Leu Leu Ile Arg Ala Gly Phe Trp Phe Asn Asp Lys Ser
                130                 135                 140

Leu Arg Asp Trp Pro Leu Leu Met Cys Cys Leu Ser Leu Pro Ala Phe
145                 150                 155                 160

Pro Leu Gly Ala Phe Ala Val Glu Lys Leu Ala Phe Asn Asn Val Ile
                165                 170                 175

Thr Asp Ala Val Ala Thr Cys Leu His Ile Phe Leu Ser Thr Thr Glu
                180                 185                 190

Ile Val Tyr Pro Val Leu Val Ile Leu Lys Cys Asp Ser Ala Val Leu
                195                 200                 205

Ser Gly Phe Leu Leu Ile Phe Ile Ala Cys Ile Val Trp Leu Lys Leu
                210                 215                 220

Val Ser Phe Ala His Thr Asn His Asp Ile Arg Gln Leu Thr Met Gly
225                 230                 235                 240

Gly Lys Lys Val Asp Asn Glu Leu Ser Thr Val Asp Met Asp Asn Leu
                245                 250                 255

Gln Pro Pro Thr Leu Gly Asn Leu Ile Tyr Phe Met Met Ala Pro Thr
                260                 265                 270

Leu Cys Tyr Gln Pro Ser Tyr Pro Arg Thr Ser Cys Val Arg Lys Gly
                275                 280                 285

Trp Leu Ile Arg Gln Ile Ile Leu Tyr Leu Ile Phe Thr Gly Leu Gln
                290                 295                 300

Gly Phe Ile Ile Glu Gln Tyr Ile Asn Pro Ile Val Val Asn Ser Gln
305                 310                 315                 320

His Pro Leu Lys Gly Gly Leu Leu Asn Ala Val Glu Thr Val Leu Lys
                325                 330                 335

Leu Ser Leu Pro Asn Val Tyr Leu Trp Leu Cys Met Phe Tyr Ala Phe
                340                 345                 350

Phe His Leu Trp Leu Ser Ile Leu Ala Glu Ile Leu Arg Phe Gly Asp
                355                 360                 365

Arg Glu Phe Tyr Lys Asp Trp Trp Asn Ala Lys Thr Ile Asp Glu Tyr
                370                 375                 380

Trp Arg Lys Trp Asn Met Pro Val His Lys Trp Val Val Arg His Ile
385                 390                 395                 400

Tyr Phe Pro Cys Met Arg Asn Gly Ile Ser Lys Glu Val Ala Val Leu
                405                 410                 415

Ile Ser Phe Leu Val Ser Ala Val Leu His Glu Ile Cys Val Ala Val
                420                 425                 430

Pro Cys Arg Ile Leu Lys Phe Trp Ala Phe Leu Gly Ile Met Leu Gln
                435                 440                 445

Ile Pro Leu Ile Val Leu Thr Ala Tyr Leu Lys Ser Lys Phe Arg Asp
                450                 455                 460
```

```
Thr Met Val Gly Asn Met Ile Phe Trp Phe Phe Cys Ile Tyr Gly
465                 470                 475                 480

Gln Pro Met Cys Leu Leu Leu Tyr Tyr His Asp Val Met Asn Arg Ile
            485                 490                 495

Glu Lys Ala Arg
            500

<210> SEQ ID NO 141
<211> LENGTH: 534
<212> TYPE: PRT
<213> ORGANISM: Perilla frutescens (GenBank Accession No. AF298815)

<400> SEQUENCE: 141

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Gln Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
        275                 280                 285

Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335
```

-continued

```
Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
            355                 360                 365

Leu Lys Leu Ser Val Pro Asn Leu Tyr Val Trp Leu Cys Met Phe Tyr
        370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460

Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510

Phe Gly Gln Pro Met Cys Val Leu Leu Tyr Tyr His Asp Leu Met Asn
        515                 520                 525

Arg Lys Ala Ser Ala Arg
    530

<210> SEQ ID NO 142
<211> LENGTH: 508
<212> TYPE: PRT
<213> ORGANISM: Triticum aestivum
<300> PUBLICATION INFORMATION:
<302> TITLE: Plant diacyglycerol acyltransferases
<310> PATENT DOCUMENT NUMBER: US 20040088759
<311> PATENT FILING DATE: 2003-10-21
<312> PUBLICATION DATE: 2004-05-06
<313> RELEVANT RESIDUES: (1)..(508)

<400> SEQUENCE: 142

Met Ser Lys Gly Asn Pro Asp Pro His Leu Pro Gly Ser Phe Leu Pro
1               5                   10                  15

Ser His Gly Gly Pro Pro Pro Lys Pro Lys Thr Pro Arg Thr Phe
            20                  25                  30

Arg Asn Leu Pro Ser Ser Ser Thr His Gly Pro Ala Pro Ser Val Ala
        35                  40                  45

Ala Ala Thr Ile Ala Thr Thr Pro Pro Ser Ala Ser Ala Ala Pro Leu
    50                  55                  60

Pro Pro Thr Val His Gly Glu Ala Ala His Gly Ala Ala Ala Ala Ala
65                  70                  75                  80

Arg Arg Asp Ala Leu Leu Pro Gly Val Gly Ala Ala His Arg Arg Val
                85                  90                  95

Lys Glu Ser Pro Leu Ser Ser Asp Ala Ile Phe Arg Gln Ser His Ala
            100                 105                 110

Gly Leu Leu Asn Leu Cys Ile Val Val Leu Ile Ala Val Asn Ser Arg
        115                 120                 125

Leu Ile Ile Glu Asn Leu Met Lys Tyr Gly Leu Leu Ile Arg Ala Gly
    130                 135                 140
```

```
Phe Trp Phe Ser Ala Arg Ser Leu Gly Asp Trp Pro Leu Leu Met Cys
145                 150                 155                 160

Cys Leu Thr Leu Pro Ile Phe Pro Leu Ala Leu Met Thr Glu Lys
            165                 170                 175

Trp Ala Gln Arg Lys Leu Ile Arg Asp His Val Ser Ile Leu Leu His
            180                 185                 190

Ile Ile Ile Thr Thr Val Leu Ile Tyr Pro Val Val Ile Leu
        195                 200                 205

Lys Cys Glu Ser Ala Val Leu Ser Gly Phe Val Leu Met Phe Ile Ala
210                 215                 220

Ser Ile Thr Trp Leu Lys Leu Val Ser Phe Ala His Thr Asn Tyr Asp
225                 230                 235                 240

Ile Arg Ile Leu Ser Gln Ser Ile Glu Lys Gly Ala Thr His Gly Ser
            245                 250                 255

Ser Ile Asp Glu Glu Asn Ile Lys Gly Pro Thr Ile Asn Ser Val Val
            260                 265                 270

Tyr Phe Met Leu Ala Pro Thr Leu Cys Tyr Gln Pro Ser Tyr Pro Arg
            275                 280                 285

Thr Ala Phe Ile Arg Lys Gly Trp Val Thr Arg Gln Leu Ile Lys Cys
290                 295                 300

Val Val Phe Thr Gly Leu Met Gly Phe Ile Ile Glu Gln Tyr Ile Asn
305                 310                 315                 320

Pro Ile Val Gln Asn Ser Lys His Pro Leu Asn Gly Asn Phe Leu Asp
                325                 330                 335

Ala Ile Glu Arg Val Leu Lys Leu Ser Val Pro Thr Leu Tyr Val Trp
            340                 345                 350

Leu Cys Met Phe Tyr Ser Phe Phe His Leu Trp Leu Asn Ile Leu Ala
            355                 360                 365

Glu Leu Leu Arg Phe Gly Asp Arg Glu Phe Tyr Lys Asp Trp Trp Asn
370                 375                 380

Ala Lys Thr Val Glu Glu Tyr Trp Arg Met Trp Asn Met Pro Val His
385                 390                 395                 400

Lys Trp Ile Val Arg His Ile Tyr Phe Pro Cys Ile Arg Asn Gly Leu
                405                 410                 415

Ser Lys Gly Cys Ala Ile Leu Ile Ala Phe Leu Val Ser Ala Val Phe
            420                 425                 430

His Glu Leu Cys Ile Ala Val Pro Cys His Ile Phe Lys Leu Trp Ala
            435                 440                 445

Phe Ser Gly Ile Met Phe Gln Ile Pro Leu Leu Phe Leu Thr Lys Tyr
            450                 455                 460

Leu Gln Asp Lys Phe Lys Asn Thr Met Val Gly Asn Met Ile Phe Trp
465                 470                 475                 480

Phe Phe Phe Ser Ile Val Gly Gln Pro Met Cys Val Leu Leu Tyr Tyr
                485                 490                 495

His Asp Val Met Asn Arg Gln Ala Gln Thr Asn Gly
            500                 505

<210> SEQ ID NO 143
<211> LENGTH: 8
<212> TYPE: PRT
<213> ORGANISM: Artificial Sequence
<220> FEATURE:
<223> OTHER INFORMATION: Fungal DGAT1 motif #1
<220> FEATURE:
<221> NAME/KEY: MISC_FEATURE
<222> LOCATION: (1)..(1)
<223> OTHER INFORMATION: Xaa = F or Y
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = L or I
<220> FEATURE:
<221> NAME/KEY: MISC_FEATURE
<222> LOCATION: (8)..(8)
<223> OTHER INFORMATION: Xaa = M or G

<400> SEQUENCE: 143

Xaa Xaa Gly Phe Xaa Asn Xaa Xaa
1               5

<210> SEQ ID NO 144
<211> LENGTH: 7
<212> TYPE: PRT
<213> ORGANISM: Artificial Sequence
<220> FEATURE:
<223> OTHER INFORMATION: Fungal DGAT1 motif #2
<220> FEATURE:
<221> NAME/KEY: MISC_FEATURE
<222> LOCATION: (1)..(1)
<223> OTHER INFORMATION: Xaa = P or Q
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = I or V

<400> SEQUENCE: 144

Xaa Tyr Pro Xaa Asn Xaa Thr
1               5

<210> SEQ ID NO 145
<211> LENGTH: 7
<212> TYPE: PRT
<213> ORGANISM: Artificial Sequence
<220> FEATURE:
<223> OTHER INFORMATION: Fungal DGAT1 motif #3
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = L or M

<400> SEQUENCE: 145

Gln Tyr Ala Xaa Pro Xaa Xaa
1               5

<210> SEQ ID NO 146
<211> LENGTH: 11
<212> TYPE: PRT
<213> ORGANISM: Artificial Sequence
<220> FEATURE:
<223> OTHER INFORMATION: Fungal DGAT1 motif #4
<220> FEATURE:
```

```
<221> NAME/KEY: MISC_FEATURE
<222> LOCATION: (3)..(3)
<223> OTHER INFORMATION: Xaa = A or S
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = can not be P
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = I or V

<400> SEQUENCE: 146

Lys Leu Xaa Xaa Xaa Ser Xaa Xaa Xaa Trp Leu
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Fungal DGAT1 motif #5
<220> FEATURE:
<221> NAME/KEY: MISC_FEATURE
<222> LOCATION: (3)..(3)
<223> OTHER INFORMATION: Xaa = Y or N
<220> FEATURE:
<221> NAME/KEY: MISC_FEATURE
<222> LOCATION: (4)..(4)
<223> OTHER INFORMATION: Xaa = Q or T or I
<220> FEATURE:
<221> NAME/KEY: MISC_FEATURE
<222> LOCATION: (5)..(5)
<223> OTHER INFORMATION: Xaa = Y or F
<220> FEATURE:
<221> NAME/KEY: MISC_FEATURE
<222> LOCATION: (6)..(6)
<223> OTHER INFORMATION: Xaa = F or M
<220> FEATURE:
<221> NAME/KEY: MISC_FEATURE
<222> LOCATION: (7)..(7)
<223> OTHER INFORMATION: Xaa = K or R

<400> SEQUENCE: 147

Pro Val Xaa Xaa Xaa Xaa Xaa
1               5

<210> SEQ ID NO 148
<211> LENGTH: 10
<212> TYPE: PRT
<213> ORGANISM: Artificial Sequence
<220> FEATURE:
<223> OTHER INFORMATION: Fungal DGAT1 motif #6
<220> FEATURE:
<221> NAME/KEY: MISC_FEATURE
<222> LOCATION: (3)..(3)
<223> OTHER INFORMATION: Xaa = K or R or S
<220> FEATURE:
<221> NAME/KEY: MISC_FEATURE
<222> LOCATION: (6)..(6)
<223> OTHER INFORMATION: Xaa = Y or N
<220> FEATURE:
<221> NAME/KEY: MISC_FEATURE
<222> LOCATION: (7)..(7)
<223> OTHER INFORMATION: Xaa can not be K
<220> FEATURE:
<221> NAME/KEY: MISC_FEATURE
<222> LOCATION: (8)..(8)
```

```
<223> OTHER INFORMATION: Xaa = Y or F
<220> FEATURE:
<221> NAME/KEY: MISC_FEATURE
<222> LOCATION: (9)..(9)
<223> OTHER INFORMATION: Xaa = F or M
<220> FEATURE:
<221> NAME/KEY: MISC_FEATURE
<222> LOCATION: (10)..(10)
<223> OTHER INFORMATION: Xaa = K or R

<400> SEQUENCE: 148

Trp Asn Xaa Pro Val Xaa Xaa Xaa Xaa Xaa
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Fungal DGAT1 motif #7
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa = I or Y

<400> SEQUENCE: 149

Leu Xaa Gly Xaa Pro Thr His Xaa Xaa Xaa Gly
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Fungal DGAT1 motif #8
<220> FEATURE:
<221> NAME/KEY: MISC_FEATURE
<222> LOCATION: (2)..(2)
<223> OTHER INFORMATION: Xaa = L or F
<220> FEATURE:
<221> NAME/KEY: MISC_FEATURE
<222> LOCATION: (3)..(3)
<223> OTHER INFORMATION: Xaa = L or M
<220> FEATURE:
<221> NAME/KEY: MISC_FEATURE
<222> LOCATION: (5)..(5)
<223> OTHER INFORMATION: Xaa = F or Y
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = A or H

<400> SEQUENCE: 150

Ala Xaa Xaa Tyr Xaa Xaa Xaa
1               5

<210> SEQ ID NO 151
<211> LENGTH: 8
```

```
<212> TYPE: PRT
<213> ORGANISM: Artificial Sequence
<220> FEATURE:
<223> OTHER INFORMATION: Universal DGAT1 motif #1
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 151

Xaa Xaa Gly Xaa Xaa Asn Xaa Xaa
1               5

<210> SEQ ID NO 152
<211> LENGTH: 7
<212> TYPE: PRT
<213> ORGANISM: Artificial Sequence
<220> FEATURE:
<223> OTHER INFORMATION: Universal DGAT1 motif #3
<220> FEATURE:
<221> NAME/KEY: MISC_FEATURE
<222> LOCATION: (2)..(2)
<223> OTHER INFORMATION: Xaa = Y or W
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 152

Gln Xaa Xaa Xaa Pro Xaa Xaa
1               5

<210> SEQ ID NO 153
<211> LENGTH: 11
<212> TYPE: PRT
<213> ORGANISM: Artificial Sequence
<220> FEATURE:
<223> OTHER INFORMATION: Universal DGAT1 motif #4
<220> FEATURE:
<221> NAME/KEY: MISC_FEATURE
<222> LOCATION: (3)..(3)
<223> OTHER INFORMATION: Xaa = A or S
<220> FEATURE:
<221> NAME/KEY: misc_feature
<222> LOCATION: (4)..(9)
<223> OTHER INFORMATION: Xaa can be any naturally occurring amino acid

<400> SEQUENCE: 153

Lys Leu Xaa Xaa Xaa Xaa Xaa Xaa Xaa Trp Leu
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Universal DGAT1 motif #5
<220> FEATURE:
<221> NAME/KEY: misc_feature
<222> LOCATION: (3)..(7)
<223> OTHER INFORMATION: Xaa can be any naturally occurring amino acid
```

```
<400> SEQUENCE: 154

Pro Val Xaa Xaa Xaa Xaa Xaa
1               5

<210> SEQ ID NO 155
<211> LENGTH: 10
<212> TYPE: PRT
<213> ORGANISM: Artificial Sequence
<220> FEATURE:
<223> OTHER INFORMATION: Universal DGAT1 motif #6
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 155

Trp Asn Xaa Pro Val Xaa Xaa Xaa Xaa Xaa
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Universal DGAT1 motif #7
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid

<400> SEQUENCE: 156

Xaa Xaa Xaa Xaa Pro Xaa Xaa Xaa Xaa Xaa
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Universal DGAT1 motif #8
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa = L or F
<220> FEATURE:
<221> NAME/KEY: MISC_FEATURE
<222> LOCATION: (3)..(3)
<223> OTHER INFORMATION: Xaa = L or M
<220> FEATURE:
<221> NAME/KEY: misc_feature
<222> LOCATION: (5)..(7)
<223> OTHER INFORMATION: Xaa can be any naturally occurring amino acid

<400> SEQUENCE: 157

Xaa Xaa Xaa Tyr Xaa Xaa Xaa
1               5

<210> SEQ ID NO 158
<211> LENGTH: 7
<212> TYPE: PRT
```

```
<213> ORGANISM: Artificial Sequence
<220> FEATURE:
<223> OTHER INFORMATION: Fungal DGAT2 motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<300> PUBLICATION INFORMATION:
<302> TITLE: Diacylglycerol acyltransferase nucleic acid sequences and
       associated products
<310> PATENT DOCUMENT NUMBER: US 2004/0107459 A1
<311> PATENT FILING DATE: 2003-07-31
<312> PUBLICATION DATE: 2004-06-03
<313> RELEVANT RESIDUES: (1)..(7)

<400> SEQUENCE: 158

Phe Xaa Xaa Pro Xaa Tyr Arg
1               5

<210> SEQ ID NO 159
<211> LENGTH: 14
<212> TYPE: PRT
<213> ORGANISM: Artificial Sequence
<220> FEATURE:
<223> OTHER INFORMATION: Plant DGAT2 motif
<220> FEATURE:
<221> NAME/KEY: misc_feature
<222> LOCATION: (12)..(12)
<223> OTHER INFORMATION: Xaa can be any naturally occurring amino acid
<300> PUBLICATION INFORMATION:
<302> TITLE: Diacylglycerol acyltransferase nucleic acid sequences and
       associated products
<310> PATENT DOCUMENT NUMBER: US 2004/0107459 A1
<311> PATENT FILING DATE: 2003-07-31
<312> PUBLICATION DATE: 2004-06-03
<313> RELEVANT RESIDUES: (1)..(14)

<400> SEQUENCE: 159

Ala Tyr Val Phe Gly Tyr Glu Pro His Ser Val Xaa Pro Ile
1               5                   10
```

ACYLTRANSFERASE REGULATION TO INCREASE THE PERCENT OF POLYUNSATURATED FATTY ACIDS IN TOTAL LIPIDS AND OILS OF OLEAGINOUS ORGANISMS

This application is a Continuation-In-Part of U.S. patent application Ser. No. 11/024544, filed Dec. 29, 2004, and claims the benefit of U.S. Provisional Application 60/624812, filed Nov. 4, 2004.

FIELD OF THE INVENTION

This invention is in the field of biotechnology. More specifically, this invention pertains to methods useful for manipulating the percent of polyunsaturated fatty acids in the lipids and oil fractions of oil-producing (i.e., oleaginous) organisms.

BACKGROUND OF THE INVENTION

The importance of polyunsaturated fatty acids (or "PUFAs") are undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2) or α-linolenic acid (ALA; 18:3); constituents of plasma membranes of cells, where they may be found in such forms as phospholipids or TAGs; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of ω-3 PUFAs such as eicosapentaenoic acid (EPA) and docosahexaenoic acid (DHA) produce cardiovascular protective effects (Dyerberg, J. et al., *Amer. J. Clin Nutr.* 28:958-966 (1975); Dyerberg, J. et al., *Lancet* 2(8081):117-119 (Jul. 15, 1978); Shimokawa, H., *World Rev Nutr Diet*, 88:100-108 (2001); von Schacky, C., and Dyerberg, J., *World Rev Nutr Diet*, 88:90-99 (2001)). Furthermore, numerous other studies document wide-ranging health benefits conferred by administration of ω-3 and/or ω-6 fatty acids against a variety of symptoms and diseases (e.g., asthma, psoriasis, eczema, diabetes, cancer).

Based on the tremendous scientific knowledge in support of the benefits of a diet comprising long-chain PUFAs for humans and other animals, considerable research has been directed toward the understanding and discovery of genes encoding the biosynthetic pathways that permit synthesis of lipids and fatty acids. As a result, numerous studies have attempted to introduce pathways that enable ω-3/ω-6 PUFA biosynthesis into organisms that do not natively produce (ω-3/ω-6 PUFAs as a preliminary means to demonstrate the feasibility of this approach. One such organism that has been extensively manipulated is the non-oleaginous yeast, *Saccharomyces cerevisiae*. Specifically, Dyer, J. M. et al. (*Appl. Envi. Microbiol.*, 59:224-230 (2002)) reported synthesis of ALA upon expression of two plant fatty acid desaturases (FAD2 and FAD3); Knutzon et al. (U.S. Pat. No. 6,136,574) expressed one desaturase from *Brassica napus* and two desaturases from the fungus *Mortierella alpina* in *S. cerevisiae*, leading to the production of LA, γ-linolenic acid (GLA), ALA and stearidonic acid (STA); and Domergue, F. et al. (*Eur. J. Biochem.* 269:4105-4113 (2002)) expressed two desaturases from the marine diatom *Phaeodactylum tricornutum* in *S. cerevisiae*, leading to the production of EPA (0.23% with respect to total fatty acids). However, none of these preliminary results are suitable for commercial exploitation.

Other efforts to produce large-scale quantities of ω-3/(ω-6 PUFAs have relied on the cultivation of microbial organisms that natively produce the fatty acid of choice [e.g., EPA is produced via: heterotrophic diatoms *Cyclotella* sp. and *Nitzschia* sp. (U.S. Pat. No. 5,244,921); *Pseudomonas, Alteromonas* or *Shewanella* species (U.S. Pat. No. 5,246,841); filamentous fungi of the genus *Pythium* (U.S. Pat. No. 5,246,842); or *Mortierella elongata*, *M. exigua* or *M. hygrophila* (U.S. Pat. No. 5,401,646)]. However, these methods all suffer from an inability to substantially improve the yield of oil or to control the characteristics of the oil composition produced, since the fermentations rely on the natural abilities of the microbes themselves. Furthermore, large-scale fermentation of some organisms (e.g., *Porphyridium, Mortierella*) can also be expensive and/or difficult to cultivate on a commercial scale.

A recent alternative to the strategies above is that of Picataggio et al. (see WO 2004/101757 and co-pending U.S. patent application Ser. No. 60/624812, each herein incorporated entirely by reference), wherein the utility of the oleaginous yeast *Yarrowia lipolytica* (formerly classified as *Candida lipolytica*) has been explored as a preferred class of microorganisms for production of ω-3/(ω-6 PUFAs such as arachidonic acid (ARA), EPA and DHA. Oleaginous yeast are defined as those yeast that are naturally capable of oil synthesis and accumulation, wherein oil accumulation can be up to about 80% of the cellular dry weight. Despite a natural deficiency in the production of ω-6 and ω-3 fatty acids in these organisms (since naturally produced PUFAs are limited to 18:2 fatty acids (and less commonly, 18:3 fatty acids)), Picataggio et al. (supra) have demonstrated production of up to 28% EPA (of total fatty acids) by introduction of PUFA desaturases, elongases and acyltransferases. Despite this success, a general method of up-regulating ω-3/ω-6 fatty acids synthesis and accumulation in the lipid and oil fractions has not been previously taught.

With respect to plants, annual and perennial oilseed crops produce a yearly output of greater than 87 million tonnes in traded vegetable oils that is worth about US $45-50 billion (Murphy, D. J. *Appl. Biotech, Food Sci. and Policy*, 1(1):25-38 (2003)). Although many modifications could improve the edible quality of plant oils, the introduction of long-chain (ω-3 PUFAs is one of the top two targets for those working in agricultural biotechnology (since mosses and algae are the only known plant systems that produce considerable amounts of ω-3 PUFAs such as EPA and DHA). As such, seed oil content and composition has been manipulated by introduction of PUFA desaturases, elongases and acyltransferases into several well-studied oilseed crop plants (e.g., flax, rape, soybean [as described in e.g., WO 2003/093482; WO 2004/057001; WO 2004/090123; WO 2004/087902; U.S. Pat. Nos. 6,140,486; 6,459,018; U.S. 2003/0172399; U.S. 2004/0172682; U.S. 2004/098762; U.S. 2004/0111763; Qi, B. et al., *Nature Biotech*. 22:739-745 (2004); Abbadi et al., *The Plant Cell*, 16:2734-2748 (2004)]). The greatest accumulation of EPA in these studies is 19.6% of total fatty acids in transformant soybean seeds, by expression of various PUFA desaturases and elongases (U.S. 2004/0172682). However, despite the extensive work described above, none of these studies have set forth a means to increase the percent of PUFAs in the total lipid and oil by regulation of the host organism's native acyltransferases.

Acyltransferases are intimately involved in the process of triacylglycerol (TAG) biosynthesis, wherein newly synthesized PUFAs are transferred into a host organism's storage lipid pools. This is possible since most free fatty acids become esterified to coenzyme A (CoA) to yield acyl-CoAs. These molecules are then substrates for glycerolipid synthesis in the endoplasmic reticulum of the cell, where phosphatidic acid and 1,2-diacylglycerol (DAG) are produced. Either of these metabolic intermediates may be directed to membrane phospholipids or DAG may be converted to TAG by the addition of a fatty acid to the sn-3 position of DAG. This reaction is catalyzed by a diacylglycerol acyltransferase enzyme (DAG AT), such as a diacylglycerol acyltransferase 1 (DGAT1), diacylglycerol acyltransferase 2 (DGAT2) or a phospholipid:diacylglycerol acyltransferase (PDAT).

In the present disclosure, the Applicants describe methods to regulate the percent of PUFAs within the lipids and oils of PUFA-producing oleaginous organisms, by regulating the activity of a host organism's native DAG ATs. Specifically, since oil biosynthesis is expected to compete with polyunsaturation during oleaginy, it is possible to reduce or inactivate the activity of an organism's one or more DAG ATs (e.g., PDAT and/or DGAT1 and/or DGAT2), to thereby reduce the overall rate of oil biosynthesis while concomitantly increasing the percent of PUFAs that are incorporated into the lipid and oil fractions.

Thus, the Applicants have solved the stated problem wherein methods to increase the percent of PUFAs in the total lipid and oil fractions of oleaginous organisms were previously lacking, by enabling one to engineer a wide variety of oleaginous organisms (e.g., bacteria, algae, moss, yeast, fungi, plants) to produce lipids and oils with very specific fatty acid compositions using techniques that rely on manipulation of the host organism's native DAG ATs.

SUMMARY OF THE INVENTION

The invention relates to the regulation of diacylglycerol acyltransferase enzymes (DAG ATs) as a means to alter the percent of polyunsaturated fatty acids (relative to the total fatty acids) that accumulate in the lipid and oil fractions of oleaginous organisms.

In a preferred embodiment the invention provides a method for increasing the percent of polyunsaturated fatty acids in the total lipid or oil of an oleaginous organism, comprising:
a) providing an oleaginous organism, comprising:
(i) native genes encoding at least one acyltransferase selected from the group consisting of: a phospholipid:diacylglycerol acyltransferase, a diacylglycerol acyltransferase 1 and a diacylglycerol acyltransferase 2; and
(ii) genes encoding a functional polyunsaturated fatty acid biosynthetic pathway;
b) reducing the activity of at least one native acyltransferase enzyme, wherein the organism's overall rate of oil biosynthesis is reduced and the percent of polyunsaturated fatty acids in the total lipid or oil is increased as compared with the oleaginous organism where the activity of at least one native acyltransferase enzyme is not reduced.

In additional embodiments, the activity of the diacylglycerol acyltransferase 1, diacylglycerol acyltransferase 2 and/or phospholipid:diacylglycerol acyltransferase is diminished or eliminated by a means selected from the group consisting of: disruption of the gene through insertion, substitution and/or deletion of all or part of the target gene; antisense or iRNA technology; use of a mutant host cell having diminished activity; over-expression of a mutagenized hereosubunit; and manipulation of the regulatory sequences controlling expression of the protein.

In an alternate embodiment, the oleaginous organism comprises at total of "n" native acyltransferases selected from the group consisting of: a phospholipid:diacylglycerol acyltransferase, a diacylglycerol acyltransferase 1 and a diacylglycerol acyltransferase 2; and the activity of a total of "n-1" acyltransferases are modified to result in a reduced rate of oil biosynthesis, while the remaining acyltransferase retains its wild-type activity.

In similar fashion, the invention provides a method for increasing the percent of polyunsaturated fatty acids in the lipid or oil fraction of an oleaginous organism, wherein the diacylglycerol acyltransferase 1 enzyme is selected from the group consisting of:
a) a diacylglycerol acyltransferase 1 enzyme comprising all of the amino acid motifs as set forth in: SEQ ID NO:151; SEQ ID NO:152; SEQ ID NO:153; SEQ ID NO:154; SEQ ID NO:155; SEQ ID NO:156; and SEQ ID NO:157;
b) a diacylglycerol acyltransferase 1 enzyme comprising all of the amino acid motifs as set forth in: SEQ ID NO:143; SEQ ID NO:144; SEQ ID NO:145; SEQ ID NO:146; SEQ ID NO:147; SEQ ID NO:148; SEQ ID NO:149; and SEQ ID NO:150;
c) a diacylglycerol acyltransferase 1 enzyme selected from the group consisting of: SEQ ID NOs:84, 132, 133, 134, 135, 136, 137, 138, 139, 140,141 and 142; and
d) a diacylglycerol acyltransferase 1 enzyme selected from the group consisting of GenBank Accession Nos: AY445635, AF384160, NM_053437, NM_174693, AY116586, AY327327, AY327326, AF298815, AF164434 and NM_010046.

Similarly, the invention provides a method for increasing the percent of polyunsaturated fatty acids in the lipid or oil fraction of an oleaginous organism, wherein the diacylglycerol acyltransferase 2 enzyme is selected from the group consisting of:
a) a diacylglycerol acyltransferase 2 enzyme comprising an amino acid motif selected from the group consisting of: SEQ ID NO:158 and SEQ ID NO:159;
b) a diacylglycerol acyltransferase 2 enzyme selected from the group consisting of: SEQ ID NO:30, 44, 74 and 76; and
c) a diacylglycerol acyltransferase 2 enzyme selected from the group consisting of GenBank Accession Nos: NC_001147 (locus NP_014888), NM_012079, NM_127503, AF051849, AJ238008, NM_026384, AF384160, AB057816, AY093657, AB062762, AF221132, AF391089, AF391090, AF129003, AF251794 and AF164434.

Additionally the invention provides a method for increasing the percent of polyunsaturated fatty acids in the lipid or oil fraction of an oleaginous organism, wherein the phospholipid:diacylglycerol acyltransferase enzyme is selected from the group consisting of: SEQ ID NO:59 and GenBank Accession Nos: P40345, O94680, NP_596330, NP_190069 and AB006704 [gi:2351069].

In another embodiment, the invention relates to the oleaginous organisms produced by the method of the invention herein, lipids and oils obtained from the oleaginous organisms of the invention and the use of those lipids and oils in foods, animal feeds and industrial applications.

BRIEF DESCRIPTION OF THE DRAWINGS AND SEQUENCE DESCRIPTIONS

FIG. 1 illustrates the (ω-3 and ω-6 fatty acid biosynthetic pathways.

Figure 2:
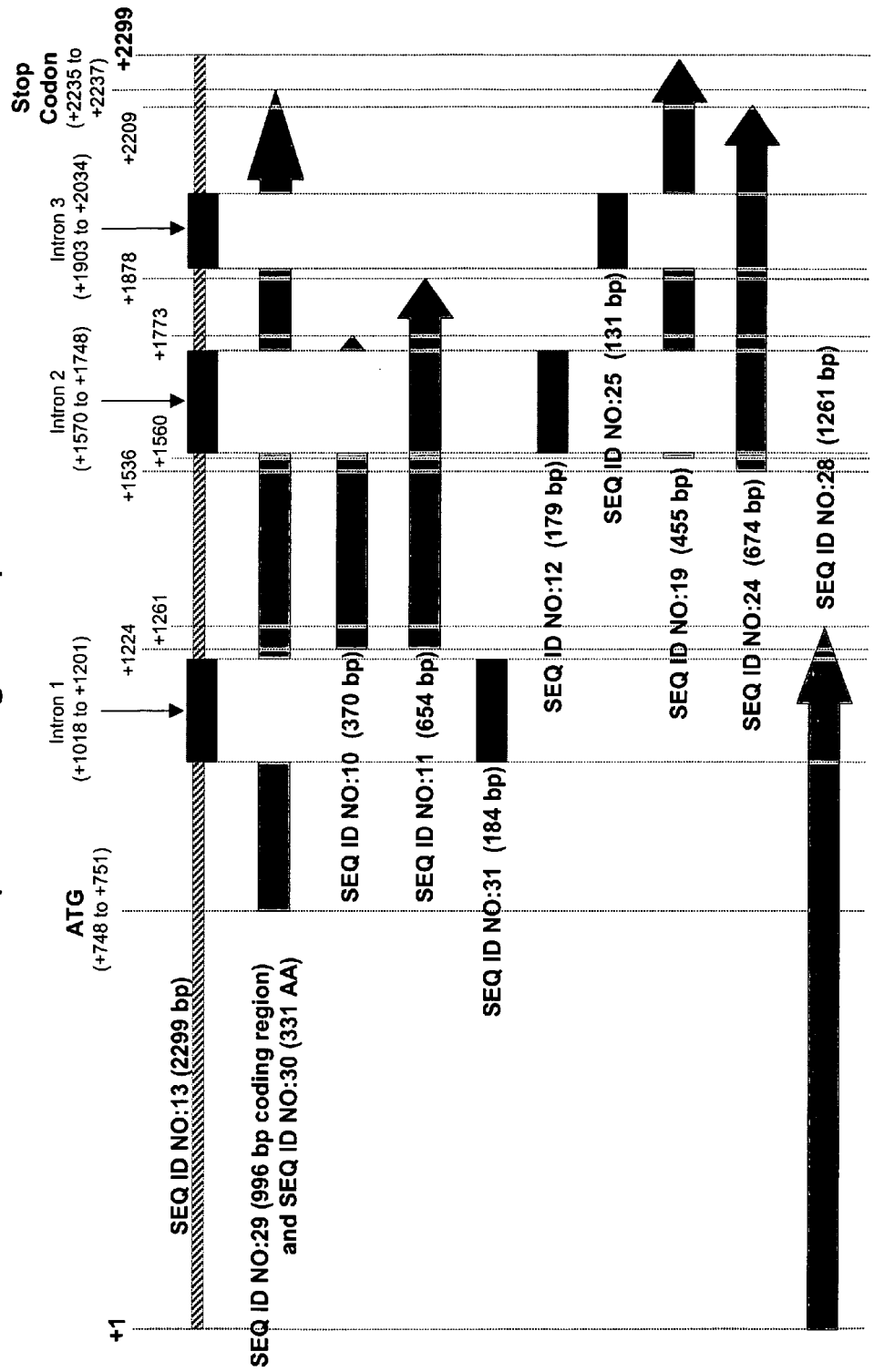

FIG. 2 graphically represents the relationship between SEQ ID NOs:10, 11, 12, 13, 19, 24, 25, 28, 29, 30 and 31, each of which relates to the diacylglycerol acyltransferase 2 (dgat2) gene in *Mortierella alpina*.

Figure 3:
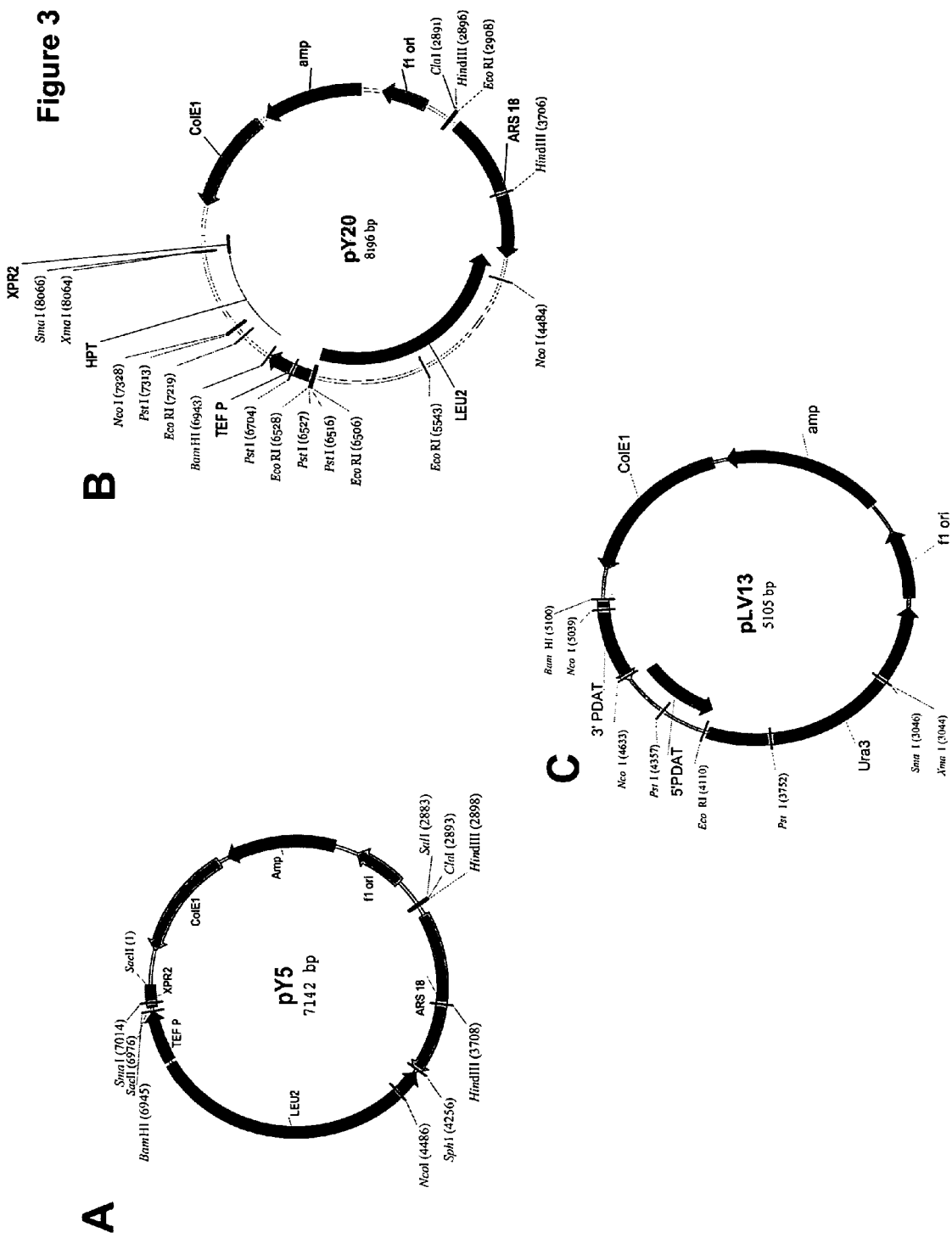

FIG. 3 provides plasmid maps for the following plasmids: (A) pY5; (B) pY20; and (C) pLV13.

Figure 4:
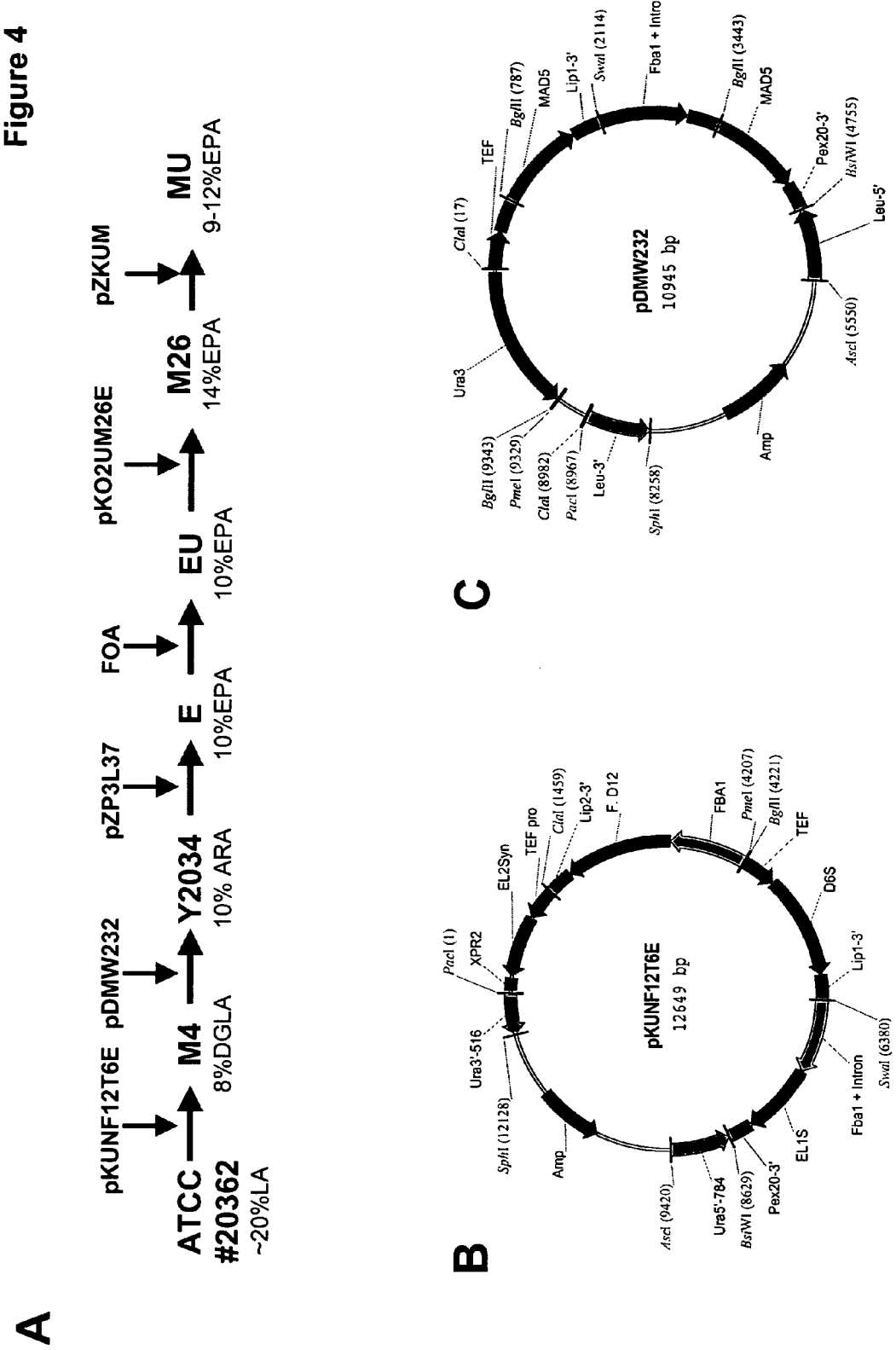

FIG. 4A diagrams the development of *Yarrowia lipolytica* strain MU producing up to about 12% EPA in the total lipid fraction. FIG. 4B provides a plasmid map for pKUNF12T6E, while FIG. 4C provides a plasmid map for pDMW232.

Figure 5:
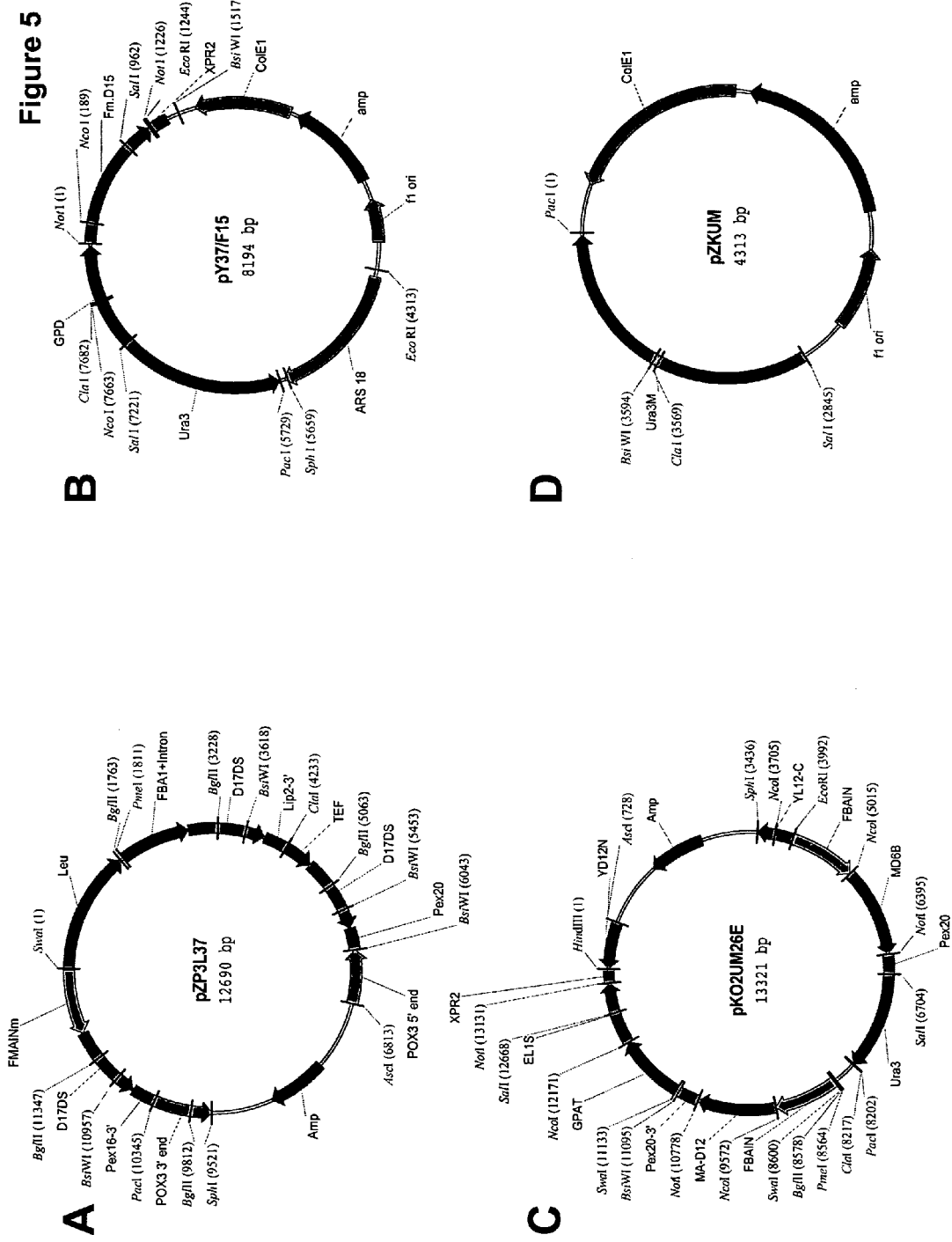
Figure 6F:
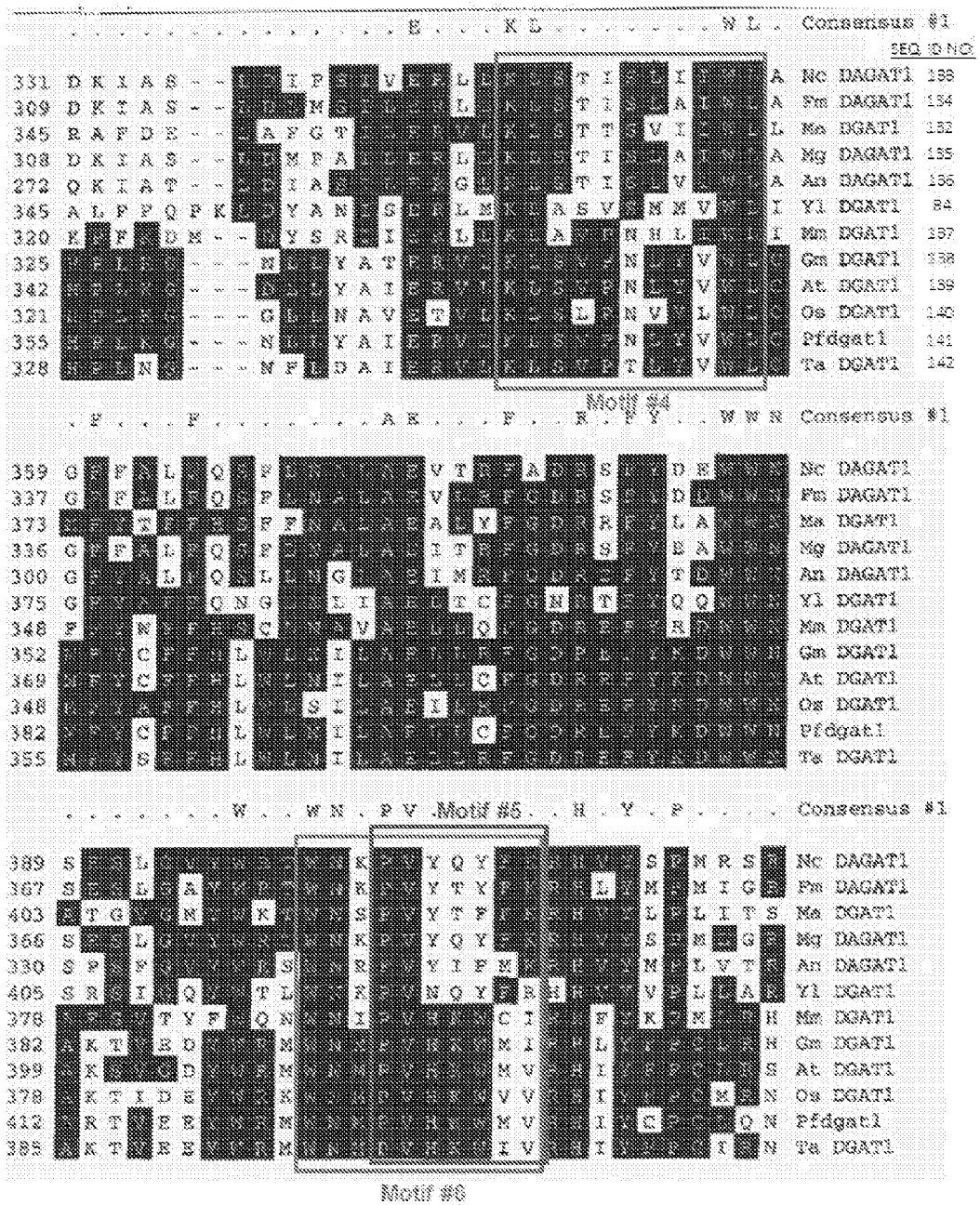
Figure 6G:
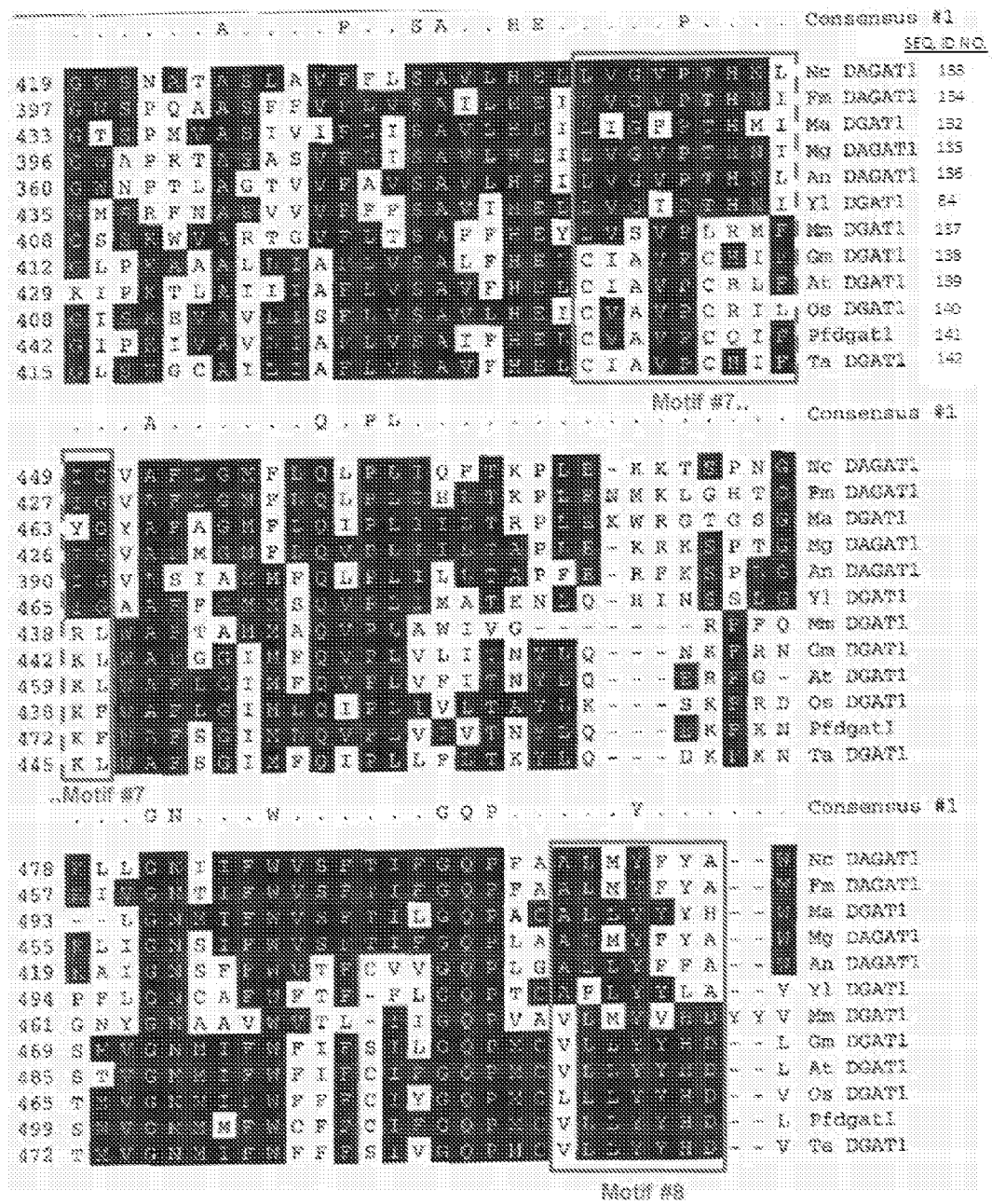

FIG. 5 provides plasmid maps for the following plasmids: (A) pZP3L37; (B) pY37/F15; (C) pKO2UM26E; and (D) PZKUM.

FIG. 6a, 6b, 6c, 6d, 6e, 6f, 6g and 6h are an alignment of DGAT1 proteins using the Megalign program of DNASTAR using Clustal W.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:10-13, 19, 24, 25, 28-31, 43, 44, 59, 60, 73-80, 83, 84, 95-98, 100-103, 105, 106, 108, 109, 113, 114, 116-119, 124, 127 and 130-159 are ORFs encoding genes or proteins (or portions thereof) or protein motifs, as identified in Table 1.

TABLE 1

Summary of Gene and Protein SEQ ID Numbers

| Description and Abbreviation | Nucleic acid SEQ ID NO. | Protein SEQ ID NO. |
|---|---|---|
| *Mortierella alpina* DGAT2 - partial cDNA sequence | 10 (370 bp) | — |
| *Mortierella alpina* DGAT2 - internal genomic fragment | 11 (654 bp) | — |
| *Mortierella alpina* DGAT2 - intron 2 | 12 (179 bp) | — |
| *Mortierella alpina* DGAT2 - genomic fragment | 13 (2299 bp) | — |
| *Mortierella alpina* DGAT2 - 3' fragment | 19 (455 bp) | — |
| *Mortierella alpina* DGAT2 - 3' fragment | 24 (674 bp) | — |
| *Mortierella alpina* DGAT2 - intron 3 | 25 (131 bp) | — |
| *Mortierella alpina* DGAT2 - 5' fragment | 28 (1261 bp) | — |
| *Mortierella alpina* diacylglycerol acyltransferase 2 (DGAT2) coding region | 29 (996 bp) | 30 (331 AA) |
| *Mortierella alpina* DGAT2 - intron 1 | 31 (184 bp) | — |
| *Yarrowia lipolytica* DGAT2 ("Yl DGAT2") | 43 (2119 bp) | 44 (514 AA) |
| | 73 (1380 bp) | 74 (459 AA) |
| | 75 (1068 bp) | 76 (355 AA) |
| *Yarrowia lipolytica* PDAT ("Yl PDAT") | 59 (2326 bp) | 60 (648 AA) |
| *Yarrowia lipolytica* YALI-CDS2011.1 (see also GenBank Accession No. NC_006072, bases 974607-976238, locus_tag = "YALI0F06578g") | 77 (1632 bp) | 78 (543 AA) |
| *Yarrowia lipolytica* YALI-CDS2141.1 (see also GenBank Accession No. CR382130, bases 1026155-1027735, locus_tag = "YALI0D07986g") | 79 (1581 bp) | 80 (526 AA) |

TABLE 1-continued

Summary of Gene and Protein SEQ ID Numbers

| Description and Abbreviation | Nucleic acid SEQ ID NO. | Protein SEQ ID NO. |
|---|---|---|
| *Yarrowia lipolytica* DGAT1 ("Yl DGAT1") | 83 (1578 bp) | 84 (526 AA) |
| Synthetic elongase gene derived from *Mortierella alpina*, codon-optimized for expression in *Yarrowia lipolytica* | 95 (957 bp) | 96 (318 AA) |
| Synthetic Δ6 desaturase, derived from *Mortierella alpina*, codon-optimized for expression in *Yarrowia lipolytica* | 97 (1374 bp) | 98 (457 AA) |
| *Fusarium moniliforme* Δ12 desaturase | 100 (1434 bp) | 101 (477 AA) |
| Synthetic elongase gene derived from *Thraustochytrium aureum*, codon-optimized for expression in *Yarrowia lipolytica* | 102 (819 bp) | 103 (272 AA) |
| *Mortierella alpina* Δ5 desaturase | 105 (1341 bp) | 106 (446 AA) |
| Synthetic Δ17 desaturase gene derived from *Saprolegnia diclina*, codon-optimized for expression in *Yarrowia lipolytica* | 108 (1077 bp) | 109 (358 AA) |
| *Yarrowia lipolytica* Δ12 desaturase | 113 (1936 bp) | 114 (419 AA) |
| *Mortieralla isabellina* Δ12 desaturase | 116 (1203 bp) | 117 (400 AA) |
| *Mortierella alpina* Δ6 desaturase "B" | 118 (1521 bp) | 119 (458 AA) |
| *Mortierella alpina* DGAT1 - internal cDNA fragment | 124 (604 bp) | — |
| *Mortierella alpina* DGAT1 - 5'-end sequence of cDNA fragment | 127 (1683 bp) | — |
| *Mortierella alpina* DGAT1 - 3'-end sequence of cDNA fragment | 130 (184 bp) | — |
| *Mortierella alpina* DGAT1 ("Ma DGAT1") | 131 (1578 bp) | 132 (525 AA) |
| *Neurospora crassa* DGAT1 ("Nc DAGAT1") | — | 133 (533 AA) |
| *Gibberella zeae* DGAT1 ("Fm DAGAT1") | — | 134 (499 AA) |
| *Magnaporthe grisea* DGAT1 ("Mg DAGAT1") | — | 135 (503 AA) |
| *Aspergillus nidulans* DGAT1 ("An DAGAT1") | — | 136 (458 AA) |
| *Mus musculus* DGAT2 ("Mm DGAT1") | — | 137 (388 AA) |
| *Glycine max* DGAT1 ("Gm DGAT1") | — | 138 (504 AA) |
| *Arabidopsis thaliana* DGAT1 ("At DGAT1") | — | 139 (520 AA) |
| *Oryza sativa* DGAT1 ("Os DGAT1") | — | 140 (500 AA) |
| *Perilla frutescens* DGAT1 ("Pf DGAT1") | — | 141 (534 AA) |
| *Triticum aestivum* DGAT1 (Ta DGAT1") | — | 142 (508 AA) |
| Fungal DGAT1 motif #1 | — | 143 |
| Fungal DGAT1 motif #2 | — | 144 |
| Fungal DGAT1 motif #3 | — | 145 |
| Fungal DGAT1 motif #4 | — | 146 |
| Fungal DGAT1 motif #5 | — | 147 |
| Fungal DGAT1 motif #6 | — | 148 |
| Fungal DGAT1 motif #7 | — | 149 |
| Fungal DGAT1 motif #8 | — | 150 |
| Universal DGAT1 motif #1 | — | 151 |
| Universal DGAT1 motif #3 | — | 152 |
| Universal DGAT1 motif #4 | — | 153 |
| Universal DGAT1 motif #5 | — | 154 |
| Universal DGAT1 motif #6 | — | 155 |
| Universal DGAT1 motif #7 | — | 156 |
| Universal DGAT1 motif #8 | — | 157 |
| Fungal DGAT2 motif | — | 158 |
| Plant DGAT2 motif | — | 159 |

SEQ ID NOs:32, 63, 93, 104, 107, 111, 112 and 120 are plasmids as identified in Table 2.

TABLE 2

Summary of Plasmid SEQ ID Numbers

| Plasmid | Corresponding FIG. | SEQ ID NO |
|---|---|---|
| pY20 | 4B | 32 (8,196 bp) |
| pLV13 | 4C | 63 (5,105 bp) |
| pKUNF12T6E | 5B | 93 (12,649 bp) |
| pDMW232 | 5C | 104 (10,945 bp) |
| pZP3L37 | 6A | 107 (12,690 bp) |
| pY37/F15 | 6B | 111 (8,194 bp) |
| pKO2UM26E | 6C | 112 (10,448 bp) |
| pZKUM | 6D | 120 (4,313 bp) |

SEQ ID NOs:1, 2 and 3 correspond to BD-Clontech's Creator Smart® cDNA library kit primers SMART IV oligonucleotide, CDSIII/3' PCR primer and 5'-PCR primer, respectively.

SEQ ID NOs:4, 6 and 8 are the degenerate primers identified as MDGAT-FN1, MDGAT-RN1 and MDGAT-RN2, respectively, used for the amplification of a partial putative *Mortierella alpina* DGAT2.

SEQ ID NOs:5, 7 and 9 are the amino acid consensus sequences that correspond to the degenerate primers MDGAT-FN1, MDGAT-RN1 and MDGAT-RN2, respectively.

SEQ ID NOs:14-18 correspond to primers AP, MDGAT-3-1, UAP, MDGAT-3-2 and MDGAT-3-3, respectively, used for genome-walking to isolate the 3'-end region of the *M. alpina* DGAT2.

SEQ ID NOs:20 and 21 correspond to the Genome Walker adaptor from ClonTech's Universal GenomeWalker™ Kit, used for genome-walking to isolate the 3'-end region of the *M. alpina* DGAT2.

SEQ ID NOs:22 and 23 correspond to primers AP1 and AP2, respectively, used for genome-walking to isolate the 3'-end region of the *M. alpina* DGAT2.

SEQ ID NOs:26 and 27 correspond to primers MDGAT-5-1 and MDGAT-5-2, respectively, used for genome-walking to isolate the 5'-end region of the *M. alpina* DGAT2.

SEQ ID NO:33 corresponds to a 1 kB DNA fragment (amino acid sequence provided as SEQ ID NO:34) containing the *E. coli* hygromycin resistance gene.

SEQ ID NO:35 corresponds to a 1.7 kB DNA fragment containing the *Yarrowia* Ura3 gene (amino acid sequence provided as SEQ ID NO:36), which was amplified with primers KU5 and KU3 (SEQ ID NOs:37 and 38, respectively).

SEQ ID NOs:39 and 41 are the degenerate primers identified as P7 and P8, respectively, used for the isolation of a *Yarrowia lipolytica* DGAT2.

SEQ ID NOs:40 and 42 are the amino acid consensus sequences that correspond to the degenerate primers P7 and P8, respectively.

SEQ ID NOs:45-47 correspond to primers P80, P81 and LinkAmp Primer1, respectively, used for chromosome walking.

SEQ ID NOs:48-51 correspond to primers P95, P96, P97 and P98, respectively, used for targeted disruption of the *Y. lipolytica* DGAT2 gene.

SEQ ID NOs:52-54 correspond to primers P115, P116 and P112, respectively, used to screen for targeted integration of the disrupted *Y. lipolytica* DGAT2 gene.

SEQ ID NOs:55 and 57 are the degenerate primers identified as P26 and P27, respectively, used for isolation of the *Y. lipolytica* PDAT.

SEQ ID NOs:56 and 58 are the amino acid consensus sequences that correspond to degenerate primers P26 and P27, respectively.

SEQ ID NOs:61, 62, 64 and 65 correspond to primers P39, P42, P41 and P40, respectively, used for targeted disruption of the *Y. lipolytica* PDAT gene.

SEQ ID NOs:66-69 correspond to primers P51, P52, P37 and P38, respectively, used to screen for targeted integration of the disrupted *Y. lipolytica* PDAT gene.

SEQ ID NO:70 corresponds to primer P79, used to amplify the full-length *Y. lipolytica* DGAT2 gene from rescued plasmids.

SEQ ID NOs:71 and 72 correspond to primers P84 and P85, respectively, used to amplify the full-length *Y. lipolytica* PDAT gene from rescued plasmids.

SEQ ID NOs:81 and 82 are the degenerate primers identified as P201 and P203, respectively, used for isolation of the *Y. lipolytica* DGAT1.

SEQ ID NOs:85-90 correspond to primers P214, P215, P216, P217, P218 and P219, respectively, used for targeted disruption of the *Y. lipolytica* DGAT1 gene.

SEQ ID NOs:91 and 92 correspond to primers P226 and P227, respectively, used to screen for targeted integration of the disrupted *Y. lipolytica* DGAT1 gene.

SEQ ID NOs:94, 99, 110 and 115 correspond to the following *Yarrowia lipolytica* promoters, respectively: fructose-bisphosphate aldolase+intron (FBAIN; 973 bp), fructose-bisphosphate aldolase (FBA; 1001 bp), fructose-bisphosphate aldolase+modified intron (FBAINm; 924 bp) and glycerol-3-phosphate acyltransferase (GPAT; 1130 bp).

SEQ ID NOs:121 and 122 correspond to primers P239 and P240, respectively, used for sequencing of the *Y. lipolytica* DGAT1 ORF.

SEQ ID NO:123 corresponds to the M13 forward primer used for sequencing of the *M. alpina* cDNA library.

SEQ ID NOs:125 and 126 correspond to primers MARE2-N1 and MARE2-N2, respectively, used for cloning the 5'-end region of the putative *M. alpina* DGAT1 gene.

SEQ ID NOs:128 and 129 correspond to primers ARE-N3-1 and ARE-N3-2, respectively, used for cloning the 3'-end region of the putative *M. alpina* DGAT1 gene.

DETAILED DESCRIPTION OF THE INVENTION

In accordance with the subject invention, Applicants have demonstrated a generalized method to manipulate the percent of polyunsaturated fatty acids (PUFAs) within the lipid and oil fractions of PUFA-producing oleaginous organisms. This method relies on the down-regulation of a host organism's native diacylglycerol acyltransferase(s) [DAG AT(s)] such that the overall rate of oil biosynthesis is reduced. As a result, the competition between oil biosynthesis and polyunsaturation is reduced, therein permitting increased polyunsaturation of fatty acids in the total lipid and oil fractions. This method will have wide-spread applicability to a variety of oleaginous organisms (e.g., algae, moss, yeast, fungi, plants) that have the native or genetically-engineered ability to produce PUFAs.

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

In alternate embodiments, the PUFAs accumulated by the methodology disclosed herein can be used for the production of industrial oleochemicals (e.g., adhesives, paints, detergents, lubricants, nylons and cosmetics).

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Diacylglycerol acyltransferase" is abbreviated DAG AT or DGAT.

"Diacylglycerol" is abbreviated DAG.

"Phospholipid:diacylglycerol acyltransferase" is abbreviated PDAT.

"Triacylglycerols" are abbreviated TAGs.

"Co-enzyme A" is abbreviated CoA.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)). "PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 3, in the column titled "Shorthand Notation". The remainder of the Table summarizes the common names of ω-3 and ω-6 fatty acids, the abbreviations that will be used throughout the specification and each compounds' chemical name.

TABLE 3

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Although the ω-3/ω-6 PUFAs described above in Table 3 will likely be considered most preferred for accumulation in the oil of oleaginous organisms according to the invention herein, these PUFAs should not be construed as limiting.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

"Microbial oils" or "single cell oils" are those oils naturally produced by microorganisms (e.g., algae, oleaginous yeasts and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

The term "oleaginous" refers to those organisms that tend to store their energy source in the form of lipid (or "oil") (Weete, In: Fungal Lipid Biochemistry, $2^{nd}$ Ed., Plenum, 1980). And, for the purposes herein, oleaginous organisms include bacteria, algae, moss, yeast, fungi and plants that have the ability to produce oils.

The term "oleaginous yeast" refers to those microorganisms classified as yeasts that can make oils. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "oleaginous plant" refers to an oil-producing plant species (i.e., oilseed plant) that produces and stores triacylglycerol in specific organs (e.g., seeds). Preferred oilseeds of the invention are those plants cultivated in fields from which a harvest is taken, although non-agronomic species and wild species may also be useful in some embodiments.

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The generic usage of the term "diacylglycerol acyltransferase" and "DAG AT" will refer to any enzyme involved in oil biosynthesis, including the three enzymes identified herein as DGAT1, DGAT2 and PDAT, each of whom reacts with a molecule of diacylglycerol (DAG) to produce TAG.

The terms "DGAT1" and "DGAT2" refer to a specific diacylglycerol acyltransferase (also known as an acyl-CoA-diacylglycerol acyltransferase or a diacylglycerol O-acyltransferase) (EC 2.3.1.20) that is responsible for the conversion of acyl-CoA and 1,2-diacylglycerol to TAG and CoA (thereby involved in the terminal step of TAG biosynthesis). The DGAT1 family shares homology with the acyl-CoA:cholesterol acyltransferase (ACAT) gene family, while the DGAT2 family is unrelated (Lardizabal et al., *J. Biol. Chem.* 276(42):38862-28869 (2001)).

The term "PDAT" refers to a phospholipid:diacylglycerol acyltransferase enzyme (EC 2.3.1.158), classified herein as a DAG AT. This enzyme is responsible for the transfer of an acyl group from the sn-2 position of a phospholipid to the sn-3 position of 1,2-diacylglycerol, thus resulting in lysophospholipid and TAG (thereby involved in the terminal step of TAG biosynthesis). This enzyme differs from DGAT1 and DGAT2 (EC 2.3.1.20) by synthesizing TAG via an acyl-CoA-independent mechanism.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s).

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase(s), Δ5 desaturase, Δ17 desaturase, Δ15 desaturase, Δ9 desaturase, Δ8 desaturase and Δ4 desaturase. A representative pathway is illustrated in FIG. 1, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the PUFA and/or ω-3/ω-6 fatty acid biosynthetic pathway means that some (or all of) the genes in the pathway express active enzymes. It should be understood that e.g., "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms).

Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA, and EPA to DPA. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to EDA and ETrA, respectively.

The term "fermentable carbon source" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

The terms "isolated nucleic acid fragment" and "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, NY (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms) to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min., and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular yeast and fungal proteins. The skilled artisan, having the benefit of the sequences as reported herein, may now use all or a substantial portion of the disclosed sequences for purposes known to those skilled in this art.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data. Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences are described, for example, in Turner, R. and Foster, G. D. *Mol. Biotechnol*. 3:225-236 (1995)).

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

"Antisense inhibition" refers to the production of antisense RNA transcripts capable of suppressing the expression of a target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on over-expression of a nucleic acid sequence having homology to an endogenous mRNA, in the sense orientation, which results in the reduction of all RNA having homology to the over-expressed sequence (see Vaucheret et al., *Plant J.* 16:651-659 (1998); and Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (see WO 99/53050 and WO 02/00904). This increases the frequency of co-suppression in the recovered transgenic plants. Another variation describes the use of plant viral sequences to direct the suppression (or "silencing") of proximal mRNA encoding sequences (WO 98/36083). Both of these co-suppressing phenomena have not been elucidated mechanistically, although genetic evidence has begun to unravel this complex situation (Elmayan et al. *Plant Cell*, 10:1747-1757 (1998)).

The polynucleotide sequences used for suppression do not necessarily have to be 100% complementary to the polynucleotide sequences found in the gene to be suppressed. Thus, polynucleotides that are at least 75% identical to a region of the polynucleotide that is target for suppression have been shown to be effective in suppressing the desired target (U.S. Pat. No. 6,362,399). The polynucleotide should be at least 80% identical, preferably at least 90% identical, most preferably at least 95% identical, or the polynucleotide may be 100% identical to the desired target.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The terms "construct" and "cassette" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising DAG AT nucleic acid fragments. The, skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)); thus, multiple events must be screened in order to obtain cells or lines displaying the desired expression level and pattern. Such screening may be accomplished by Southern analysis of DNA, Northern analysis of mRNA expression, immunoblotting analysis of protein expression or phenotypic analysis, among others. "Transformation cassette" refers to a specific vector containing a foreign gene(s) and having elements in addition to the foreign gene(s) that facilitate transformation of a particular host cell. "Expression cassette" refers to a specific vector containing a foreign gene(s) and having elements in addition to the foreign gene(s) that allow for enhanced expression of that gene in a foreign host.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" or "reduced activity" is an altered activity that is less than that associated with the native sequence.

The term "homologous recombination" refers to the exchange of DNA fragments between two DNA molecules (during cross over). The fragments which are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Motifs that are universally found in DGAT1 enzymes (i.e., animal, plants and fungi) are provided as SEQ ID NOs:151-157; motifs found in DGAT1 s that are specific to fungal organisms are provided as SEQ ID NOs: 143-150. Similarly, a fungal-specific DGAT2 motif and a plant-specific DGAT2 motif are provided as SEQ ID NOs: 158 and 159, respectively.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, NY (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, NY (1984); and by Ausubel, F. M. et al., *Current Protocols in Molecular Biology*, published by Greene Publishing Assoc. and Wiley-lnterscience (1987).

An Overview: Biosynthesis of Fatty Acids and Triacylglycerols

The process of de novo synthesis of palmitate (16:0) in oleaginous microorganisms is described in WO 2004/101757 (published Nov. 25, 2004). This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a Δ9 desaturase; similarly, palmitate is elongated to form stearic acid (18:0), which can be converted to its unsaturated derivative by a Δ9 desaturase to thereby yield oleic (18:1) acid.

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of a DAG AT (e.g., PDAT, DGAT1 or DGAT2) to forrn TAG.

A wide spectrum of fatty acids can be incorporated into TAGs, including saturated and unsaturated fatty acids and short-chain and long-chain fatty acids. Some non-limiting examples of fatty acids that can be incorporated into TAGs by DAG ATs include: capric (10:0), lauric (12:0), myristic (14:0), palmitic (16:0), palmitoleic (16:1), stearic (18:0), oleic (18:1), vaccenic (18:1), LA (18:2), eleostearic (18:3), GLA (18:3), ALA (18:3), STA (18:4), arachidic (20:0), EDA (20:2), DGLA (20:3), ETrA (20:3), ARA (20:4), ETA (20:4), EPA (20:5), behenic (22:0), DPA (22:5), DHA (22:6), lignoceric (24:0), nervonic (24:1), cerotic (26:0) and montanic (28:0) fatty acids.

In preferred embodiments of the present invention, however, incorporation of "long-chain" PUFAs into TAG is most desirable, wherein long-chain PUFAs include any fatty acid derived from an 18:1 substrate having at least 18 carbons in length (i.e., $C_{18}$ or greater). This also includes hydroxylated fatty acids, expoxy fatty acids and conjugated linoleic acid.

Although most PUFAs are incorporated into TAGs as neutral lipids and are stored in lipid bodies, it is important to note that a measurement of the total lipids within an oleaginous organism should include those lipids that are located in the phosphatidylcholine (PC) fraction, phosphatidyletanolamine (PE) fraction, and triacylglycerol (TAG or oil) fraction. For example, plant seed oils comprise both neutral (i.e., comprising TAGs primarily) and polar lipids. The polar lipids are mainly found in the various membranes of the seed cells, e.g. the endoplasmic reticulum, microsomal membranes and the cell membrane. The fatty acid composition of membrane lipids is highly regulated and only a select number of fatty acids are found in membrane lipids; on the other hand, a large number of unusual fatty acids can be incorporated into the neutral storage lipids in seeds of many plant species.

Acyltransferases and their Role in the Terminal Step of TAG Biosynthesis

A variety of acyltransferases are intimately involved in the biosynthesis of TAGs, including acyl-CoA:cholesterol acyltransferases (ACATs), diacylglycerol acyltransferases (i.e., DGAT1s and DGAT2s), lecithin:cholesterol acyltransferases (LCATs), phospholipid:diacylglycerol acyltransferases (PDATs), glycerol-3-phosphate acyltransferases (GPATs) and acyl-CoA lysophosphatidic acid acyltransferases (LPAATs). Two comprehensive mini-reviews on TAG biosynthesis in yeast, including details concerning the genes involved and the metabolic intermediates that lead to TAG synthesis are: D. Sorger and G. Daum, *Appl. Microbiol. Biotechnol.* 61:289-299 (2003); and H. Müllner and G. Daum, *Acta Biochimica Polonica,* 51 (2):323-347 (2004). However, the authors of these reviews clearly acknowledge that regulatory aspects of TAG synthesis and formation of neutral lipids in lipid particles remain far from clear. Similar confusion concerning these mechanisms exists in other organisms as well (e.g., plants, fungi, etc.).

Focusing on the terminal step in the synthesis of TAG (wherein a third fatty acid is added to the sn-3 position of 1,2-diacylglycerol (DAG)), however, limits the acyltransferases of primary importance to the DAG ATs, i.e., DGAT1, DGAT2 and PDAT. Together, these 3 enzymes appear to represent overlapping biosynthetic systems for neutral lipid formation that have differential regulation, alternative localization and/or different substrate specifities (H. Müllner and G. Daum, supra).

Historically, DGAT1 (responsible for the transfer of an acyl-CoA group from acyl-CoA to the sn-3 position of DAG to form TAG) was thought to be the only enzyme specifically involved in TAG synthesis. This enzyme was known to be homologous to acyl-CoA:cholesterol acyltransferases (ACATs); however, recent studies have identified a new family of DAG AT enzymes that are unrelated to the ACAT gene family. Thus, nomenclature now distinguishes between the DAG AT enzymes that are related to the ACAT gene family (DGAT1 family) versus those that are unrelated (DGAT2 family) (Lardizabal et al., *J. Biol. Chem.* 276(42):38862-28869 (2001)). And, recently Dahlqvist et al. (*Proc. Nat. Acad. Sci.* (*USA*) 97:6487-6492 (2000)) and Oelkers et al. (*J. Biol. Chem.* 275:15609-15612 (2000)) discovered that TAG synthesis can also occur in the absence of acyl-CoA, via the acyl-CoA-independent PDAT enzyme.

PDAT (structurally related to the LCAT family of proteins) removes an acyl group from the sn-2 position of a phosphotidylcholine substrate for transfer to the sn-3 position of DAG to produce TAG. Although the function of PDAT is not as well characterized as DGAT2, PDAT has been postulated to play a major role in removing "unusual" fatty acids from phospholipids in some oilseed plants (Banas, A. et al., *Biochem. Soc. Trans.* 28(6):703-705 (2000)).

Publicly Available Genes Encoding DGAT1. DGAT2 and PDAT

Many genes encoding DAG AT enzymes for use in the present invention have been identified through genetic means and the DNA sequences of some of these genes are publicly available; alternatively, the patent literature provides many additional DNA sequences of DAG AT genes (and/or details concerning several of the genes provided via GenBank and their methods of isolation) (non-limiting examples are shown below in Table 4):

TABLE 4

Some Publicly Available DAG AT Genes

| Gene | GenBank Accession No. | Patent Literature |
| --- | --- | --- |
| DGAT1 | AY445635 (olive); AF384160 (*Mus musculus*); NM_053437 (Norway rat); NM_174693 (cow); AY116586 (pig); AY327327 and AY327326 (*Toxoplasma gondii*); AF298815 (*Perilla frutescens*); AF164434 (*Brassica napus*); NM_010046 (mouse) | U.S. Pat. No. 6,100,077 (human); U.S. Pat. No. 6,552,250 (*Brassica*); U.S. Pat. No. 6,344,548 (human, mouse, *Arabidopsis*); U.S. 2004/0088759A1 (soy, *Arabidopsis*, wheat, rice); U.S. 2004/0078836A1 (Farese et al.); U.S. patent application Ser. No. 11/024544 (*Yarrowia lipolytica*, *Mortierella alpina*, *Neurospora crassa*, *Gibberella zeae* PH-1, *Magnaporthe grisea* and *Aspergillus nidulans*) |
| DGAT2 | NC_001147 (locus NP_014888; *Saccharomyces cerevisiae*); NM_012079 (human); NM_127503, AF051849 and AJ238008 (*Arabidopsis thaliana*); NM_026384, AF384160 and AB057816 (mouse); AY093657 (pig); | U.S. 2003/124126; WO 2001/034814; U.S. 2003/115632, U.S. 2003/0028923 and U.S. 2004/0107459 (*Mortierella ramanniana*, *Neurospora crassa*, *Saccharomyces cerevisiae*, *Hordeum vulgare*, *Zea mays*, *Glycine max*, |

TABLE 4-continued

Some Publicly Available DAG AT Genes

| Gene | GenBank Accession No. | Patent Literature |
| --- | --- | --- |
| | AB062762 (rat); AF221132 (*Caenorhabditis elegans*); AF391089 and AF391090 (*Mortierella ramanniana*); AF129003 (*Nicotiana tabacum*); AF251794 and AF164434 (*Brassica napus*) | *Triticum aestivum*, *Drosophilia*, *Homo sapiens*, *Schizosaccharomyces pombe*, *Candida albicans* and *Arabidopsis thaliana*); U.S. patent application Ser. No. 10/882760 (*Yarrowia lipolytica*); U.S. patent application Ser. No. 11/024545 (*Mortierella alpina*) |
| PDAT | P40345 (*Saccharomyces cerevisiae*); O94680 and NP_596330 (*Schizosaccharomyces pombe*); NP_190069 and AB006704 [gi: 2351069] (*Arabidopsis thaliana*) | WO 2000/060095; WO 2003/083100 (*Physcomitrella patens*); U.S. patent application Ser. No. 10/882760 (*Yarrowia lipolytica*) |

Isolation of DAG AT Homologs

When the sequence of a host organism's native DGAT1, DGAT2 and/or PDAT are not known, one skilled in the art will recognize that it will be most desirable to isolate these genes (or portions thereof) prior to regulating the activity of the encoded proteins and thereby altering the percent of PUFAs (of the total fatty acids) that are incorporated in the total lipid and oil fractions in a particular oleaginous host organism. Sequence knowledge of the preferred host organism's DAG ATs also facilitates disruption of the homologous chromosomal genes by targeted disruption.

Using the publicly disclosed sequence information described above, it is readily possible to isolate homologs.

For example, the Applicants have recently isolated and characterized the PDAT, DGAT1 and DGAT2 of *Yarrowia lipolytica* (see commonly owned WO 2005/003322 and co-pending commonly owned U.S. patent application Ser. No. 11/024544, each incorporated entirely herein by reference). This was accomplished by cloning of partial putative DAG AT DNA fragments from *Y. lipolytica* (using degenerate primers designed to encode conserved amino acid sequences among different known DGAT2s, DGAT1 or PDATs, respectively), followed by targeted disruption of the endogenous *Y. lipolytica* gene to test the identity of the fragment. Lower oil content in the disrupted strain confirmed that the native DGAT2, DGAT1 or PDAT activity, respectively, was eliminated. Subsequently, the full-length *Y. lipolytica* DGAT2, DGAT1 (1578 bp; SEQ ID NO:83) and PDAT (2326 bp; SEQ ID NO:59) genes were assembled. The DGAT2 (2119 bp; SEQ ID NO:43) included three nested open reading frames: 1.) ORF 1: nucleotides +291 to +1835 of SEQ ID NO:43, corresponding to the protein encoded by SEQ ID NO:44 (514 amino acid residues); 2.) ORF 2: nucleotides +456 to +1835 of SEQ ID NO:43, corresponding to SEQ ID NO:73 (1380 bases) and the protein encoded by SEQ ID NO:74 (459 amino acid residues); and 3.) ORF 3: nucleotides +768 to +1835 of SEQ ID NO:43, corresponding to SEQ ID NO:75 (1068 bases) and the protein encoded by SEQ ID NO:76 (355 amino acid residues).

Comparison of the *Yarrowia lipolytica* DGAT1 deduced amino acid (SEQ ID NO:83) sequence to public databases revealed that the most similar known sequences were about 55% identical over a length of 526 amino acids using the BLASTP method of alignment with a low complexity filter and the following parameters: Expect value=10, matrix=Blosum 62 (Altschul, et al., *Nucleic Acids Res.*

25:3389-3402 (1997))). Thus, the method described above is suitable for the isolation of homologs having a relatively a low percent identity to publicly available sequences. It would be expected that isolation of DAG AT homologs having about 70%-80% identity to publicly available DAG AT sequences would be even easier to isolate, those sequences that are 85%-90% identical would be particularly suitable for isolation and those sequences that are about 95% identical are most preferred.

DAG AT homologs have also been isolated by the use of motifs unique to DGAT1 and DGAT2 enzymes. These regions of "conserved domains" are sets of amino acids that are highly conserved at specific positions and likely correspond to a region of the DAG AT protein that is essential to the structure, stability or activity of the protein. Motifs are identified by their high degree of conservation in aligned sequences of a family of protein homologues, and thus also can be used as unique "signatures" to determine if a protein with a newly determined sequence belongs to a previously identified protein family. Motifs that are universally found in DGAT1 enzymes (i.e., animal, plants and fungi) are provided as SEQ ID NOs:151-157; motifs found in DGAT1s that are specific to fungal organisms (and absent in DGAT1 s from non-fungal organisms) are provided as SEQ ID NOs:143-150 (see U.S. patent application Ser. No. 11/024544). Similarly, a plant-specific DGAT2 motif (SEQ ID NO:159) and a fungal-specific DGAT2 motif (SEQ ID NO:158) are taught by Lardizabal et al. (U.S. Ser. No. 04/0107459). As is well known to one of skill in the art, these motifs are useful as diagnostic tools for the rapid identification of novel DGAT1 s and DGAT2s, respectively.

Although one of skill in the art could readily apply the means utilized for isolation of the *Yarrowia lipolytica* DAG ATs to enable isolation of DAG ATs from any preferred organism, a more generalized description of methods for isolation of DAG AT homologs will be presented below for clarity and completeness. In general, isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to publicly available DGAT1s, DGAT2s and/or PDATs (or motifs thereof) could be isolated directly by using all or a portion of those publicly available nucleic acid fragments as DNA hybridization probes to screen libraries from any desired organism using methodology well known to those skilled in the art. Specific oligonucleotide probes based upon the publicly available nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the publicly available sequences (or motifs thereof). The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the publicly available sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the publicly available nucleic acid fragments (or motifs thereof), and the sequence of the other primer takes advantage of the presence of the polyadenylic acid tracts to the 3' end of the mRNA precursor encoding genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the publicly available sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the publicly available DGAT1, DGAT2 and/or PDAT sequences (or motifs thereof) may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Based on any of the methods described above, it should be possible to isolate DAG AT homologs (e.g., DGAT1, DGAT2 and/or PDAT) in any organism of choice. The identity of any putative DAG AT can readily be confirmed by targeted disruption of the endogenous gene within the host organism, since lower oil content in the disrupted strain will result when a native DAG AT (e.g., DGAT2, DGAT1 and/or PDAT) is eliminated or down-regulated.

Interaction Between DAG ATs and other Acyltransferases

In *S. cerevisiae*, four genes (i.e., ARE1 and ARE2 [encoding acyl-CoA:sterol-acyltransferases], DGA1 [encoding DGAT2] and LRO1 [encoding PDAT]), contribute to oil biosynthesis; however, PDAT and DGAT2 are the major DAG ATs, having responsibility for up to approximately 95% of oil biosynthesis (Sandager, L. et al., *J. Biol. Chem.* 277(8):6478-6482 (2002); Oelkers et. al. *J. Biol. Chem.* 277:8877 (2002)). In contrast, oil biosynthesis in the yeast *Yarrowia lipolytica* requires the activity of PDAT, DGAT1 and DGAT2, while ARE2 may additionally be a minor contributor to oil biosynthesis (WO 05/003322 and co-pending U.S. patent application Ser. No.11/024544).

Based on the findings described above, one should not assume that all organisms will comprise a suite of DAG AT genes encoding a DGAT1, a DGAT2 and a PDAT, wherein each enzyme plays an equal role in oil biosynthesis. Thus, some variation in the number of DAG ATs that an organism may possess is expected, in addition to significant variation concerning the contribution that each enzyme plays in oil biosynthesis. Since these enzymes appear to represent overlapping biosynthetic systems for neutral lipid formation that have differential regulation, alternative localization and/or different substrate specifities (H. Müllner and G. Daum, supra), some organisms may have enzymes encoding only a DGAT1 and DGAT2, a DGAT1 and PDAT or a DGAT2 and PDAT; the contribution of each of these enzymes to oil biosynthesis may range from an equal, shared contribution to a significantly skewed ratio of activity. In alternate embodiments, some specialized organisms may possess only a single DAG AT enzyme, while in other embodiments, some organisms may have multiple isozymes encoding DGAT1, DGAT2 and/or PDAT. This variability by no means limits the applicability of the invention, as a key aspect to the invention herein is reduction of the overall rate of oil biosynthesis as a means to concomitantly increase the percent of PUFAs of the total fatty acids that are incorporated into the total lipid and/or oil fraction. Furthermore, although this application is directed towards methods of increasing the percent of PUFAs in the total lipid and oil by reducing the overall rate of oil biosynthesis by down-regulating the activity of one or more DAG ATs, it will be apparent to one of skill in the art that the same goal can be accomplished by down-regulating the first two steps of oil biosynthesis (e.g., GPAT and LPAAT).

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 1). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the action of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to EDA and ETrA, respectively. A Δ8 desaturase then converts these products to DGLA and ETA, respectively.

The host organism of the invention must possess the ability to produce PUFAs, either naturally or via techniques of genetic engineering. Specifically, although many microorganisms can synthesize PUFAs (including ω-3/ω-6 fatty acids) in the ordinary course of cellular metabolism, some of whom could be commercially cultured, few to none of these organisms produce oils having the specific oil content and composition that is sought for e.g., pharmaceuticals, dietary substitutes, medical foods, nutritional supplements, other food products, industrial oleochemicals and/or other end-use applications. Thus, there is increasing emphasis on the ability to engineer microorganisms for production of "designer" lipids and oils, wherein the fatty acid content and composition are carefully specified by genetic engineering. Likewise, much scientific effort is targeted toward the creation of various oilseed crop plants having a specific (ω-3 PUFA content, since mosses and algae are the only known plant systems that produce considerable amounts of ω-3 PUFAs such as EPA and DHA. On this basis, it is expected that the host organism of the invention will likely comprise heterologous genes encoding a functional PUFA biosynthetic pathway (although this should not be construed as a limitation herein).

If the host organism of choice does not natively produce the desired PUFAs (or possess the desired lipid profile), one skilled in the art will be familiar with the considerations and techniques necessary to introduce an expression cassette encoding appropriate enzymes for PUFA biosynthesis into the host organism of choice. Although these issues are not elaborated in detail herein, numerous teachings are provided in the literature; and, some illustrative references are provided as follows, although these should not be construed as limiting: WO 98/46763; WO 98/46764; WO 98/46765; WO 99/64616; WO 02/077213; WO 03/093482; WO 04/057001; WO 04/090123; WO 04/087902; U.S. Pat. Nos. 6,140,486; 6,459,018; 6,136,574; U.S. Ser. Nos. 03/0172399; 04/0172682; 04/098762; 04/0111763; 04/0053379; 4/0049805; 04/0237139; 04/0172682; Beaudoin F. et al., *PNAS USA*, 97(12):6421-6426 (2000); Dyer, J. M. et al., *Appl. Envi. Microbiol.*, 59:224-230 (2002); Domergue, F. et al. *Eur. J. Biochem.* 269:4105-4113 (2002); Qi, B. et al., *Nature Biotech.* 22:739-745 (2004); and Abbadi et al., *The Plant Cell*, 16:2734-2748 (2004)).

Briefly, however, a variety of ω-3/ω-6 PUFA products can be produced (prior to their transfer to TAGs), depending on the fatty acid substrate and the particular genes of the ω-3/ω-6 fatty acid biosynthetic pathway that are present in (or transformed into) the host cell. As such, production of the desired fatty acid product can occur directly (wherein the fatty acid substrate is converted directly into the desired fatty acid product without any intermediate steps or pathway intermediates) or indirectly (wherein multiple genes encoding the PUFA biosynthetic pathway may be used in combination, such that a series of reactions occur to produce a desired PUFA). Specifically, for example, it may be desirable to transform an oleaginous yeast with an expression cassette comprising a Δ12 desaturase, Δ6 desaturase, an elongase, a Δ5 desaturase and a Δ17 desaturase for the overproduction of EPA. As is well known to one skilled in the art, various other combinations of the following enzymatic activities may be useful to express in an oleaginous organism: a Δ15 desaturase, a Δ4 desaturase, a Δ5 desaturase, a Δ6 desaturase, a Δ17 desaturase, a Δ9 desaturase, a Δ8 desaturase and/or an elongase(s) (see FIG. 1). The particular genes included within a particular expression cassette will depend on the oleaginous organism (and its PUFA profile and/or desaturase/elongase profile), the availability of substrate and the desired end product(s).

A tremendous number of candidate genes having the desired desaturase and/or elongase activities can be identified according to publicly available literature (e.g., GenBank), the patent literature, and experimental analysis of organisms having the ability to produce PUFAs. Following the identification of these candidate genes, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) cofactors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired fatty acid substrate.

Increasing the Percent of PUFAs in the Total Lipid and Oil Fractions Via Regulation of DAG ATs According to the invention herein, a method for increasing the percent of PUFAs in the total lipid and oil fractions of an oleaginous organism is provided, wherein:
 a) the oleaginous organism comprises: at least one gene encoding a native DAG AT; and genes encoding a functional PUFA biosynthetic pathway; and,
 b) the overall rate of oil biosynthesis is reduced by down-regulating the activity of the host organism's native DAG AT(s), thereby permitting an increased percent of PUFAs (relative to the total fatty acids) to be incorporated into the total lipid and oil fractions during growth under conditions that permit the synthesis of PUFAs.

This results since polyunsaturation is permitted to occur more efficiently. In other words, by down-regulating the activity of specific DAG ATs, the substrate competition between oil biosynthesis and polyunsaturation is reduced in favor of polyunsaturation during oleaginy.

In alternate embodiments, the invention is also directed toward oleaginous organisms produced by the methodology of the invention herein. This therefore includes oleaginous bacteria, algae, moss, fungi, yeast, plants, plant cells, plant tissues and/or plant parts (e.g., seeds) comprising in their genome a recombinant construct of the invention that results in down-regulation of at least one DAG AT. In futher embodiments, the present invention concerns lipids and oils obtained from these oleaginous organisms, products obtained from the processing of the lipids and oil, use of these lipids and oil in foods, animal feeds or industrial applications and/or use of the by-products in foods or animal feeds.

One aspect of the invention requires metabolic engineering of the host organism's DAG ATs to down-regulate (but not halt) the rate of oil biosynthesis. Although numerous techniques are available to one of skill in the art to achieve this, generally the endogenous activity of a particular gene can be reduced or eliminated by, for example: 1.) disrupting the gene through insertion, substitution and/or deletion of all or part of the target gene; 2.) using antisense or iRNA technology; 3.) using a host cell which naturally has [or has been mutated to have] little or none of the specific gene's activity; 4.) overexpressing a mutagenized heterosubunit (i.e., in an enzyme that comprises two or more heterosubunits) to thereby reduce the enzyme's activity as a result of the "dominant negative effect"; and 5.) manipulating the regulatory sequences controlling the expression of the protein. In some cases, inhibition of undesired gene pathways can also be accomplished through the use of specific inhibitors (e.g., desaturase inhibitors such as those described in U.S. Pat. No. 4,778,630). Each of these techniques will be discussed briefly below; however, one skilled in the art should recognize that these techniques are well described in the existing literature and are not limiting to the invention herein. Furthermore, one skilled in the art will be well equipped to ascertain the most appropriate technique to be utilized with any particular oleaginous organism.

Disruption Via Insertion, Substitution and/or Deletion

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617-4622 (1989); Balbas et al., *Gene* 136:211-213 (1993); Gueldener et al., *Nucleic Acids Res.* 24:2519-2524 (1996); and Smith et al., *Methods Mol. Cell. Biol.* 5:270-277(1996)). One skilled in the art will be familiar with the many variations that exist on the generalized method of gene targeting, thereby permitting positive or negative selection, creation of gene knockouts, and insertion of exogenous DNA sequences into specific genome sites in mammalian systems, plant cells, filamentous fungi, and/or microbial systems.

In contrast, a non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

In alternate embodiments, the phenomenum of co-suppression can result in reduced activity (or silencing) of an endogenous target gene. This method relies on the insertion of additional copies of all (or part of) the target gene in the sense orientation into the genome, by the introduction of a transgene or by a viral infection, with the result that expression of all copies of the gene are inhibited. Co-suppression can refer to silencing at the post-transcriptional or transcriptional level. See, for example: van der Krol et al., *The Plant Cell* 2:291-299 (1990); Napoli et al., *The Plant Cell* 2: 279-289 (1990); Zhang et al., *The Plant Cell* 4:1575-1588 (1992); and U.S. Pat. No. 5,231,020. Further refinements of the co-suppression technology may be found in: WO 95/34668; Angell & Baulcombe. The EMBO Journal, 16(12):3675-3684 (1997); and Voinnet & Baulcombe. Nature, 389:553 (1997).

RNA Technologies (Antisense And RNA Interference)

Antisense technology and RNA interference are two methods that rely on use of RNA to down-regulate the activity of a gene when the sequence of the target gene (or a portion thereof) is known. Specifically, antisense technology is accomplished by cloning a nucleic acid segment from the desired gene (i.e., operably linked to a promoter) in a manner such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes (e.g., a DAG AT). For example, the proper level of expression of antisense genes may require the use of different chimeric genes utilizing different regulatory elements known to the skilled artisan.

In alternate embodiments, an antisense molecule may be designed to hybridize with a regulatory region of the DAG AT gene of interest (e.g., promoter, enhancer or transcription initiation site) and thereby block transcription of the gene. Or, the antisense molecule can block translation by inhibiting binding of a transcript to ribosomes. Methods of designing and producing antisense molecules to disrupt expression through a particular sequence element are well known in the art.

One can also down-regulate the activity of a DAG AT by relying on double-stranded RNA interference (RNAi) to inhibit expression of a specific endogenous gene. Briefly, the presence of double-stranded RNA (dsRNA) silences gene expression in a sequence-specific manner by causing the corresponding endogenous RNA to be degraded. The mechanism behind RNA interference is still not entirely understood, but it appears that a dsRNA is cleaved into short fragments by a ribonuclease (e.g., DICER). These fragments are referred to as "short interfering RNAs" (i.e., siRNA) and are typically about 21-23 nucleotides in length. The siRNAs subsequently assemble with protein components into an RNA- induced silencing complex, which binds to and tags the complementary portion of the target mRNA for nuclease digestion. Thus, the siRNA triggers the degradation of mRNA that matches its sequence, thereby repressing expression of the corresponding gene (see, e.g., Bass, B., *Nature* 411:428429 (2001); Sharp, P. A., *Genes Dev.* 15:485-490 (2001); WO 01/68836; WO 01/29058; WO 02/44321; WO 01/75164). According to the invention herein, dsRNA comprising the sequence of a target DAG AT gene can be used to prevent expression of that gene.

Advantageously, neither antisense technology or RNA interference methods require the complete DAG AT coding sequence to be known or used; and, it is a routine matter for the person skilled in the art to screen fragments of various sizes and from various parts of the coding sequence to optimize the level of resulting inhibition. The sequence employed may be as short as about 14-23 nucleotides or may be even longer than about 1000 nucleotides. Likewise, complete sequence identity between the coding sequence to be used and the target sequence is not essential (although may be preferable in some cases). One or more nucleotides may differ in the sequence used from the target gene. Thus, a sequence used for down-regulation of gene expression in accordance with the present invention may be a wild-type sequence or a mutant, derivative, variant or allele of such a sequence. The sequence need not include an open reading frame or specify an RNA that would be translatable.

Mutagenesis

In vitro mutagenesis and selection, site-directed mutagenesis, error prone PCR (Melnikov et al., *Nucleic Acids Research*, 27(4):1056-1062 (Feb. 15, 1999)), "gene shuffling" or other means can be employed to obtain mutations of naturally occurring DAG AT genes. This would permit production of a polypeptide having acyltransferase activity in vivo with less desirable physical and kinetic parameters for function in the host cell (e.g., a lower rate of synthesis of TAGs from fatty acids).

If desired, the regions of a DAG AT polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of an acyltransferase polypeptide important for activity, to thereby enable selection of a DAG AT that functions with reduced efficiency when compared to the wildtype enzyme. A mutated construct is expressed, and the ability of the resulting altered protein to function as an acyltransferase is assayed. Such structure-function analysis can determine which regions may be deleted, which regions tolerate insertions, and which point mutations allow the mutant protein to function in substantially the same way as the native acyltransferase.

In alternate embodiments, when the sequence of the DAG AT is not known, host cells may be exposed to UV radiation and then screened for the desired phenotype (i.e., a decreased rate of oil biosynthesis). Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

The Dominant Negative Effect

Dominant negative inhibition is most commonly seen when a mutant subunit of a multisubunit protein is coexpressed with the wild-type protein so that assembly of a functional oligomer is impaired (Herskowitz, I. *Nature*. 329 (6136):219-22 (1987)). Thus, dominant negative inhibition is a phenomenon in which the function of a wild-type gene product is impaired as a result of a coexpressed mutant variant of the same gene product. Using means well known to one of skill in the art, dominant negative inhibition of an oleaginous organism's native DAG ATs could be created to thereby result in a reduced rate of oil biosynthesis.

Manipulation of DAG AT Regulatory Sequences

As is well known in the art, the regulatory sequences associated with a coding sequence include transcriptional and translational "control" nucleotide sequences located upstream (5' non-coding sequences), within, or downstream (3' non-coding sequences) of coding sequence, and which influence the transcription, RNA processing or stability, or translation of the associated coding sequence. Thus, manipulation of a DAG AT's regulatory sequences may refer to manipulation of the DAG AT's promoters, translation leader sequences, introns, enhancers, initiation control regions, polyadenylation recognition sequences, RNA processing sites, effector binding sites and stem-loop structures. In all cases, however, the result of the manipulation is a reduced rate of lipid and oil biosynthesis due to down-regulation of the DAG AT's expression.

Thus, for example, the promoter of a DAG AT could be deleted or disrupted. Alternatively, the native promoter driving expression of a DAG AT could be substituted with a heterologous promoter having diminished promoter activity with respect to the native promoter. Methods useful for manipulating regulatory sequences are well known to those skilled in the art.

In summary, any of the above described methods (i.e., gene disruption, antisense/iRNA technology, use of mutant hosts, over-expression of a mutagenized heterosubunit, and manipulation of DAG AT regulatory sequences) may be utilized to down-regulate the rate of oil biosynthesis in an oleaginous organism of choice. And, one skilled in the art will have the skills necessary to elucidate the optimum level of down-regulation and the means required to achieve such inhibition. For example, in some preferred embodiments, it may be desirable to manipulate the activity of a single DAG AT (e.g., create a DGAT1 knockout, while the activity of PDAT and DGAT2 are not altered). In alternate embodiments, the oleaginous organism comprises at total of "n" native DAG ATs and the activity of a total of "n-1" acyltransferases are modified to result in a reduced rate of oil biosynthesis, while the remaining acyltransferase retains its wildtype activity. And, in some situations, it may be desirable to manipulate the activity of all of the native DAG ATs in some preferred oleaginous organisms, to achieve the optimum rate of oil biosynthesis with respect to the rate of polyunsaturation.

Preferred Oleaginous Organisms

A variety of oleaginous organisms are suitable for manipulation according to the invention herein, to thereby yield a transformant host organism having an increased percent of PUFAs (relative to the total fatty acids) incorporated into the total lipid and oil fractions. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Various algae, moss, fungi, yeast and plants are classified as oleaginous.

Although not to be construed as limiting herein, preferred oleaginous microbes include those bacterial, algal and fungal organisms that naturally produce ω-3/ω-6 PUFAs. For example, ARA, EPA and/or DHA is produced via *Cyclotella* sp., *Nitzschia* sp., *Pseudomonas*, *Alteromonas*, *Shewanella*, *Pythium*, *Thraustochytrium* sp., *Schizochytrium* sp. and *Mortierella*. More specifically, *M. elongata*, *M. exigua*, *M. hygrophila* and *M. alpina* are especially preferred; and, the method of transformation of *M. alpina* has been described by Mackenzie et al. (Applied and Environmental Microbiology 66:4655 (2000)).

In other embodiments, oleaginous yeast produce (or can be genetically engineered to produce) PUFAs. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida*

*revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). Concerning *Yarrowia lipolytica*, there is basis for the use of these organisms for the production of PUFAs, as seen in WO 04/101757 and co-pending U.S. Patent Application No. 60/624812, each herein incorporated entirely by reference.

Preferred oleaginous plants of the invention are oilseed plants that produce and store triacylglycerol in specific organs (e.g., seeds). These include both monocotyledonous and dicotyledonous plants. Examples of such plants include, for example: cacao bean, colza, borage, *Helianthus* (sunflower), Arachis (peanut), soya, rapeseed, copra, tobacco, oat, *Olea* (olive), *Elaeis* (oil palm), *Secale* (rye), barley, *Triticum* (wheat), pepper, primrose, *Tagetes* (marigold), linseed, *Brassica* species (canola), *Arabidopsis thaliana, Acrocomia, Aiphanes, Apeiba, Attalea, Beilschmiedia, Bertholettia, Cannabis* (hemp), *Ceiba, Cocos* (coconut palm), *Corozo, Dialyanthera, Elaeia, Hibiscus* (e.g., kenaf), *Jessenia, Lecythis, Lepidium, Licania, Moringa, Papaver, Pentaclethra, Ricinus* (castor), *Scheelia, Sesamum* (sesame), *Simarouba, Tamarindus* (tamarind), *Terminalia, Virola, Ximenia, Zea* (corn and maize), *Carthamus* (safflower), *Glycine* (soybean), *Soja* sp. (soybean), *Gossypium* (cotton), *Linum* (flax), *Cuphea, Euphorbia* (spurges), *Limnanthes* (meadowfoam), *Crambe, Lesquerella, Vernonia* and *Simmondsia*. Again, it is important to note that the preferred plant organisms of the invention are not necessarily required to produce PUFAs as a wildtype organism; plants that have been genetically engineered to produce these PUFAs are suitable for the invention herein.

Recombinant Constructs for DAG AT Down-Requlation

Following the identification of a specific oleaginous organism, its native DAG ATs and a preferred means for down-regulating the activity of at least one native DAG AT, an appropriate recombinant construct (comprising a DAG AT(s) under the control of suitable regulatory sequences such as promoters and 3' transcription terminators, which lead to down-regulation of the gene's activity) must generally be created to result in a reduced rate of oil biosynthesis. Then, this construct is transformed into the appropriate PUFA-producing oleaginous organism. Those of skill in the art are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones (see for example, Sambrook et al., *Molecular Cloning: A Laboratory Manual, 2nd* ed., Cold Spring Harbor Laboratory: Cold Spring Harbor, NY (1989); Maliga et al., Methods in Plant Molecular Biology, Cold Spring Harbor, NY (1995); Birren et al., Genome Analysis: Detecting Genes, v. 1, Cold Spring Harbor, NY (1998); Birren et al., Genome Analysis: Analyzing DNA, v. 2, Cold Spring Harbor: NY (1998); *Plant Molecular Biology: A Laboratory Manual*, Clark, ed. Springer: NY (1997)).

In general, however, the specific choice of sequences present in the construct is dependent upon the desired expression products, the nature of the host cell and the proposed means of separating transformed cells versus non-transformed cells. The skilled artisan is well aware of the genetic elements that must be present on the plasmid vector in order to successfully transform, select and propagate host cells containing the chimeric gene. Typically, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions which are useful to drive expression of the instant DAG ATs (or portions thereof) in the desired host cell are numerous and familiar to those skilled in the art. These control regions may comprise a promoter, enhancer, silencer, intron sequences, 3'UTR and/or 5'UTR regions, and protein and/or RNA stabilizing elements. Such elements may vary in their strength and specificity. Virtually any promoter capable of directing expression of these genes in the selected host cell may be suitable for the present invention. Expression in a host cell can be accomplished in a transient or stable fashion. Transient expression can be accomplished by inducing the activity of a regulatable promoter operably linked to the DAG AT gene of interest. Stable expression can be achieved by the use of a constitutive promoter operably linked to the gene of interest.

As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (U.S. patent application Ser. No. 10/869630), phosphoglycerate mutase (U.S. patent application Ser. No. 10/869630), fructose-bisphosphate aldolase (U.S. patent application Ser. No. 10/987548), phosphoglucose-isomerase, phosphoglycerate kinase, glycerol-3-phosphate O-acyltransferase (U.S. Patent Application No. 60/610060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Similarly, any promoter functional in a plant may be suitable for the purposes herein, including (but not limited to): constitutive plant promoters, plant tissue-specific promoters, plant development-stage specific promoters, inducible plant promoters, viral promoters, male germline-specific promoters, female germline-specific promoters, flower-specific promoters and vegetative shoot apical meristem-specific promoters. Either heterologous or non-heterologous (i.e., endogenous) promoters can be used to practice the invention. Thus, examples of suitable promoters include, but are not limited to: either the α' subunit of the β-conglycinin promoter or the β subunit thereof, the Kunitz trypsin inhibitor 3 promoter, the annexin promoter, the Glyl promoter, the P34/Gly Bd m 30K promoter, the albumin promoter and the Leg promoters (A1 and A2). The level of activity of the annexin (or "P34") promoter is comparable to that of many known strong promoters, such as the CaMV 35S promoter [Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)], the *Arabidopsis oleosin* promoters [Plant et al., *Plant Mol. Biol.* 25:193-205 (1994); Li, Texas A&M University Ph.D. dissertation, pp.107-128 (1997)], the *Arabidopsis* ubiquitin extension protein promoters [Callis et al., *J Biol*

*Chem.* 265(21):12486-93 (1990)], a tomato ubiquitin gene promoter [Rollfinke et al., *Gene.* 211 (2):267-76 (1998)], a soybean heat shock protein promoter [Schoffl et al., *Mol Gen Genet.* 217(2-3):246-53 (1989)] and a maize H3 histone gene promoter [Atanassova et al., *Plant Mol Biol.* 37(2):275-85 (1998)].

Expression of chimeric genes in most plant cells makes the P34 promoter especially useful when seed specific expression of a target heterologous nucleic acid fragment is required (see WO 04/071178). Another useful feature of the P34 promoter is its expression profile in developing seeds, wherein the activity is greatest in developing seeds at early stages (before 10 days after pollination) and is largely quiescent in later stages. The expression profile of the P34 promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., *Plant Mol. Biol.* 25:193-205 (1994); Li, (supra)). A plant translational enhancer often used is the tobacco mosaic virus (TMV) omega sequences; additionally, the inclusion of an intron (e.g., lntron-1 from the Shrunken gene of maize) has been shown to increase expression levels by up to 100-fold (Mait, Transgenic Res. 6:143-156 (1997); Ni, *Plant Journal,* 7:661-676 (1995)).

3' Non-coding sequences encoding transcription termination signals must also be provided in a recombinant construct. The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Particularly useful termination regions for use in yeast are those derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. In plants, the termination signals usually employed are from the Nopaline Synthase promoter or from the CAMV 35S promoter. Optionally, a termination site may be unnecessary; however, it is most preferred if included.

In addition to the regulatory elements described above for a recombinant construct, it is also useful for the vector to comprise a selectable and/or scorable marker. Preferably, the marker gene is an antibiotic resistance gene whereby the appropriate antibiotic can be used to select for transformed cells from among those cells that were not transformed. For selection of yeast transformants, any marker that functions in yeast may be used. Desirably, resistance to kanamycin, hygromycin and the amino glycoside G418 are of interest, as well as ability to grow on media lacking uracil or leucine. Selectable marker genes useful for the selection of transformed plant cells, callus, plant tissue and plants are also well known to those skilled in the art. Examples include, but are not limited to: npt, which confers resistance to the aminoglycosides neomycin, kanamycin and paromycin; hygro, which confers resistance to hygromycin; trpB, which allows cells to utilize indole in place of tryptophan; hisD, which allows cells to utilize histinol in place of histidine (Hartman, *Proc. Natl. Acad. Sci. USA* 85:8047 (1988)); mannose-6- phosphate isomerase, which allows cells to utilize mannose (WO 94/20627); ODC (ornithine decarboxylase), which confers resistance to the ornithine decarboxylase inhibitor, 2-(difluoromethyl)-DL-ornithine (or "DFMO"; McConlogue, In: *Current Communications in Molecular Biology*, Cold Spring Harbor Laboratory: Cold Spring Harbor, NY (1987)); and deaminase from Aspergillus terreus, which confers resistance to blasticidin S (Tamura, *Biosci. Biotechnol. Biochem.* 59 2336-2338 (1995)). Useful scorable markers are also known to those skilled in the art and are commercially available, such as the genes encoding luciferase (Giacomin, *Pl. Sci.* 116:59-72 (1996); Scikantha, *J. Bact.* 178:121 (1996)), green fluorescent protein (Gerdes, *FEBS Lett.* 389:44- 47 (1996)) or R-glucuronidase (Jefferson, *EMBO J.* 6:3901-3907 (1987)).

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene. Each of these types of modifications are encompassed in the present invention, as means to further manipulate expression of an organism's DAG ATs.

Transformation of Microbial Oleaginous Organisms

Once a recombinant construct suitable for down-regulating the activity of an oleaginous microbial organism's native DAG AT(s) has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extra-chromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies.

Transformation of Plant Oleaginous Organisms

A variety of techniques are available and known to those skilled in the art for introduction of recombinant constructs into an oilseed plant, such that the plant's native DAG AT(s) is ultimately down-regulated. These techniques include transformation with DNA employing *Agrobacterium tumefaciens* or *A. rhizogenes* as the transforming agent. It is particularly preferred to use the binary type vectors of Ti and Ri plasmids of *Agrobacterium* spp. Ti-derived vectors transform a wide variety of higher plants, including monocotyledonous and dicotyledonous plants such as soybean, cotton, rape, tobacco and rice (Pacciotti et al., *Bio/Technology*, 3:241 (1985); Byrne et al., *Plant Cell, Tissue and Organ Culture*, 8:3 (1987); Sukhapinda et al., *Plant Mol. Biol.* 8:209-216 (1987); Lorz et al., *Mol. Gen. Genet.* 199:178 (1985); Potrykus, *Mol. Gen. Genet.* 199:183 (1985); Park et al., *J. Plant Biol.* 38(4):365-71 (1995); Hiei et al., *Plant J.* 6:271-282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf et al., *Genetic Analysis of Host Range Expression by Agrobacterium*, In: *Molecular Genetics of the Bacteria-Plant Interaction*, Puhler, A. Ed.; Springer-Verlag: NY, 1983, p 245; and An et al., *EMBO J.* 4:277-284 (1985)).

Other transformation methods are also available to those skilled in the art, such as: 1.) direct uptake of foreign DNA constructs (see EP 295959); 2.) techniques of electroporation (see Fromm et al., *Nature* (London) 319:791 (1986)); 3.) high-velocity ballistic bombardment with metal particles coated with the nucleic acid constructs (see Kline et al., *Nature* (London) 327:70 (1987) and U.S. Pat. No. 4,945,050); or 4.) microinjection (see *Gene Transfer To Plants*, Potrykus and Spangenberg, Eds., Springer Verlag: Berlin, NY (1995)). For a review of commonly used methods of plant transformation see Newell, C. A. (*Mol. Biotechnol.* 16:53-65 (2000)). The transformation of most dicotyledonous plants is possible with the methods described above; however, additional transformation techniques have been developed for the successful transformation of monocotyledonous plants. These include protoplast transformation and transformation by an in planta method using *Agrobacterium tumefaciens*. This in planta method (Bechtold and Pelletier, C. R. *Acad. Sci. Paris*, 316: 1194 (1993); or Clough S. J., Bent A. F., *Plant Journal*, 16(6):735-43 (1998)) involves the application of A. tumefaciens to the outside of the developing flower bud and then introduction of the binary vector DNA to the developing microspore and/or macrospore and/or developing seed, so as to produce a transformed seed without the exogenous application of cytokinin and/or gibberellin.

Of particular relevance are methods to transform foreign constructs into commercially important oilseed crops, such as rapeseed (De Block et al., *Plant Physiol.* 91:694-701 (1989); U.S. Pat. No. 5,463,174), sunflower (Everett et al., *Bio/Technology* 5:1201 (1987)), corn (Gordon-Kamm et al., *Plant Cell* 2:603-618 (1990); Fromm et al., Biotechnology 8:833-839 (1990)), cotton (U.S. Pat. Nos. 5,004,863; 5,159,135), peanut (Cheng et al., *Plant Cell Rep.* 15:653-657 (1996); McKently et al., *Plant Cell Rep.* 14:699-703 (1995)), pea (Grant et al., *Plant Cell Rep.* 15:254-258 (1995)) and soybean (McCabe et al., *Bio/Technology* 6:923 (1988); Hinchee et al., *Bio/Technology* 6:915 (1988); Chee et al., *Plant Physiol.* 91:1212-1218 (1989); Chowrira, G. M. et al., *Mol. Biotechnol.* 3:17-23 (1995); Christou, P. et al., *Proc. Natl. Acad. Sci. U.S.A.* 84:3962-3966 (1987); Christou et al., *Plant Physiol.* 87:671-674 (1988); Christou et al., *Proc. Natl. Acad. Sci USA* 86:7500-7504 (1989); WO 92/17598; EP 301749; U.S. Pat. Nos. 5,569,834; 5,416,011).

Those skilled in the art will be aware that the selection of tissue (e.g., leaves, hypocotyls, cotyledons, stems, calluses, single cells, protoplasts) for use in transformation procedures may vary; however, it is preferable generally to use plant material at the zygote formation stage for in planta transformation procedures.

Once transformed, there are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Methods for Plant Molecular Biology; Weissbach and Weissbach, Eds., Academic: San Diego, Calif. (1988)). This regeneration and growth process typically includes the steps of selection of transformed cells using an appropriate selective medium, culturing those individualized cells through the usual stages of embryonic development and through the rooted plantlet stage (i.e., transgenic cells are grown to callus, shoots are grown from callus and plantlets generated from the shoot). Transgenic embryos and seeds are similarly regenerated. The resulting transgenic rooted shoots are thereafter planted in an appropriate plant growth medium (e.g., soil). Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing PUFAs is cultivated using methods well known to one skilled in the art.

One skilled in the art recognizes that the expression level and regulation of a transgene in a plant can vary significantly from line to line. Thus, one has to test several lines to find one with the desired expression level and regulation. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA blots (Southern, *J. Mol. Biol.* 98: 503 (1975)), Northern analysis of mRNA expression (Kroczek, *J. Chromatogr. Biomed. Appl.*, 618(1-2):133-145 (1993)), Western analysis of protein expression or phenotypic analysis. One particularly useful way to quantitate protein expression and to detect replication in different plant tissues is to use a reporter gene (e.g., GUS).

Once transgenic plants have been obtained, they may be grown to produce plant tissues or parts having the desired phenotype. The plant tissue or plant parts may be harvested and/or the seed collected. The seed may serve as a source for growing additional plants with tissues or parts having the desired characteristics.

Fermentation Processes For Microbial Triacylglycerol Biosynthesis and Accumulation The engineered oleaginous microbe is grown under conditions that optimize activity of fatty acid biosynthetic genes. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea, glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids arid PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. This approach is described in WO 2004/101757, as are various suitable fermentation process designs (i.e., batch, fed-batch and continuous) and considerations during growth.

Purification of Microbial Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of fatty acids (including PUFAs) may include extraction with organic solvents, sonication, supercritical fluid extraction (e.g., using carbon dioxide), saponification and physical means such as presses, or combinations thereof. One is referred to the teachings of WO 2004/101757 for additional details.

Purification of Seed Oils

Methods of isolating seed oils are well known in the art (Young et al., In *The Lipid Handbook*, Gunstone et al., eds., Chapter 5, pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in the Table below.

TABLE 5

Generalized Steps For Soybean Oil And Byproduct Production

| Process Step | Process | Impurities Removed And/Or By-Products Obtained |
| --- | --- | --- |
| #1 | Soybean seed | |
| #2 | Oil extraction | Meal |
| #3 | Degumming | Lecithin |
| #4 | Alkali or physical refining | Gums, free fatty acids, pigments |
| #5 | Water washing | Soap |

TABLE 5-continued

Generalized Steps For Soybean Oil And Byproduct Production

| Process Step | Process | Impurities Removed And/Or By-Products Obtained |
|---|---|---|
| # 6 | Bleaching | Color, soap, metal |
| # 7 | (Hydrogenation) | |
| # 8 | (Winterization) | Stearine |
| # 9 | Deodorization | Free fatty acids, tocopherols, sterols, volatiles |
| # 10 | Oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. The term lecithin itself has different meanings when used in chemistry and biochemistry than when used commercially: specifically, chemically, lecithin is phosphatidylcholine; commercially, however, it refers to a natural mixture of neutral and polar lipids. Phosphatidylcholine, which is a polar lipid, is present in commercial lecithin in concentrations of 20 to 90%. Lecithins containing phosphatidylcholine are produced from vegetable, animal and microbial sources, but mainly from vegetable sources. Soybean, sunflower and rapeseed are the major plant sources of commercial lecithin, with soybean the most common source. Plant lecithins are considered to be GRAS (generally regarded as safe). Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated to result in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds that impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Soybean oil is liquid at room temperature because it is relatively low in saturated fatty acids when compared with oils such as coconut, palm, palm kernel and cocoa butter. Many processed fats, including spreads, confectionary fats, hard butters, margarines, baking shortenings, etc., require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, linoleic and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables that affect the hydrogenation reaction which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial frying and roasting operations and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have also become controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

Commercial uses for the PUFA-Containing Lipids of the Invention

In a preferred embodiment, the present invention concerns a method for increasing the percent of PUFAs in the total lipid and oil fraction of an oleaginous organism by down-regulating the activity of at the least one native DAG AT. In alterate embodiments, the invention is also directed to microbes, oilseed plants, plant cells, plant tissues, or plant parts (e.g., seeds, oils obtained from the seeds) produced by the method thereof. Thus, the invention also concerns the use of lipids and oils produced in an oleaginous organism using the methodology described herein, wherein the altered lipids and oils are incorporated into various nutritional compositions. Specifically, the altered microbial and/or seed oils can be added to nutritional compositions such as a nutritional supplement, food products, infant formula, animal feed, pet food and the like. Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

Food analogs can be classified as "imitation" or "substitutes", depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheeses will often have higher protein levels than imitation cheeses and be fortified with vitamins and minerals.

Food analogs can be made use processes well known to those skilled in the art. For example, U.S. Pat. Nos. 6,355,296 and 6,187,367 describe emulsified meat analogs and emulsified meat extenders; U.S. Pat. No. 5,206,050 describes soy protein curd useful for cooked food analogs (and a process thereof); U.S. Pat. No. 4,284,656 describes a soy protein curd useful for food analogs; U.S. Pat. No. 3,988,485 describes a meat-like protein food formed from spun vegetable protein fibers; U.S. Pat. No. 3,950,564 describes a process of making a soy-based meat substitute; and U.S. Pat. No. 3,925,566 describes a simulated meat product. Soy protein that has been processed to impart a structure, chunk or fiber for use as a food ingredient is called "textured soy protein" (TSP). TSPs are frequently made to resemble meat, seafood, or poultry in structure and appearance when hydrated.

Examples of food products or food analogs into which altered oils of the invention may be incorporated include: a meat product (e.g., a processed meat product), a cereal food product, a snack food product, a baked goods product, a fried food product, a health food product, an infant formula, a beverage, a nutritional supplement, a dairy product, a pet food product, animal feed and/or an aquaculture food product.

Meat products encompass a broad variety of products. In the United States "meat" includes "red meats" produced from cattle, hogs and sheep. In addition to the red meats there are poultry items that include chickens, turkeys, geese, guineas, ducks and fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs and the like.

A dairy product is a product derived from milk. A milk analog or nondairy product is derived from a source other than milk, e.g., soymilk. These products include, but are not limited to, whole milk, skim milk, fermented milk products such as yogurt or sour milk, cream, butter, condensed milk, dehydrated milk, coffee whitener, coffee creamer, ice cream, cheese, etc. Milk analogs or nondairy food products include, but are not limited to: imitation milk and nondairy frozen desserts (e.g., those made from soybeans and/or soy protein products).

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas and the like.

A baked goods product comprises any of the cereal food products mentioned above and that has been baked or processed in a manner comparable to baking, i.e., to dry or harden by subjecting to heat. Examples of a baked good product include, but are not limited to: breads, cakes, doughnuts, breadcrumbs, baked snacks, mini-biscuits, mini-crackers, mini-cookies and mini-pretzels. As was mentioned above, oils of the invention can be used as an ingredient.

A snack food product comprises any of the above or below described food products. A fried food product comprises any of the above or below described food products that has been fried. A health food product is any food product that imparts a health benefit. Many oilseed-derived food products may be considered as health foods.

The beverage can be in a liquid or in a dry powdered form. For example, there can be mentioned non-carbonated drinks, fruit juices (e.g., fresh, frozen, canned, concentrate), and flavored or plain milk drinks, etc. Adult and infant nutritional formulas are well known in the art and commercially available (e.g., Similac®, Ensure®, Jevity® and Alimentum® from Ross Products Division, Abbott Laboratories). Infant formulas are liquids or reconstituted powders fed to infants and young children. They serve as substitutes for human milk. Infant formulas have a special role to play in the diets of infants because they are often the only source of nutrients for infants. Although breast-feeding is still the best nourishment for infants, infant formula is a close enough second that babies not only survive but thrive. Infant formula is becoming more and more increasingly close to breast milk.

A pet food product is a product intended to be fed to a pet such as a dog, cat, bird, reptile, fish, rodent and the like. These products can include the cereal and health food products above, as well as meat and meat byproducts, soy protein products and grass and hay products (including, but not limited to: alfalfa, timothy, oat or brome grass, vegetables and the like). Animal feed is a product intended to be fed to animals such as turkeys, chickens, cattle and swine and the like. As with the pet foods above, these products can include cereal and health food products, soy protein products, meat and meat byproducts, and grass and hay products. Aquaculture feed is a product intended to be used in aquafarming that concerns the propagation, cultivation or farming of aquatic organisms, animals and/or plants in fresh or marine waters.

DESCRIPTION OF PREFERRED EMBODIMENTS

While working toward the development of an oleaginous yeast that accumulates high concentrations of TAGs enriched in ω-3 and/or ω-6 PUFAs, the Applicants discovered a generalized mechanism useful for increasing the percent of PUFAs (relative to the total fatty acids) in the total lipid and oil fractions of an oleaginous organism.

Briefly, the TAG content and composition in several strains of mutant and wildtype *Yarrowia lipolytica* containing various single, double, and triple disruptions in DAG ATs were analyzed, as described below in Table 6 and elaborated in the Examples. Although the PUFA of primary interest in these particular studies with *Y. lipolytica* was EPA, one skilled in the art will understand that the teachings provided in the invention herein should not be so limited.

TABLE 6

Summary Of Experiments Analyzing TAG Content And Composition In Various *Yarrowia lipolytica* Strains Comprising DAG AT Knockouts

| Strains Analyzed | Interpretation Of Results | Example |
|---|---|---|
| Mutant and wildtype *Y. lipolytica* containing single, double and triple disruptions in PDAT, DGAT2 and/or DGAT1 | DGAT2 contributes the most to oil biosynthesis in *Y. lipolytica*, while PDAT and DGAT1 contribute equally (but less than) DGAT2 | 11 |
| Mutant and wildtype strains of an EPA-producing *Y. lipolytica* (strain EU, producing 10% EPA), containing a single disruption in DGAT2 | TAG content is decreased (50% reduction, measured as % dcw) and EPA content is increased (% EPA of total fatty acids doubled) in strain EU with a disrupted DGAT2 gene | 13 |
| Mutant and wildtype strains of an EPA-producing *Y. lipolytica* (strain MU, producing 9-12% EPA), containing single disruptions in PDAT, DGAT2 and/or DGAT1 and double disruptions in PDAT and DGAT2 | Lipid content, and the contribution of each DAG AT on lipid content, varies according to growth conditions. Knockout of DGAT1, DGAT2, or PDAT resulted in lowered oil content and increased EPA content. Knockout of both DAGT2 and PDAT resulted in the least oil and the most % EPA. | 14 |

Based on the results of these studies in *Y. lipolytica*, the broadly applicable methodology of the present invention was conceived wherein down-regulation of the expression levels of specific DAG ATs permits a reduction in the substrate competition that occurs between oil biosynthesis and polyunsaturation during oleaginy. Thus, fatty acids have an increased opportunity to become polyunsaturated, prior to their incorporation into TAG. And, since an increased percentage of PUFAs are synthesized, the resulting lipid and oil fractions have an increased percentage of PUFAs.

Additionally, in conjunction with the experimental work above, the Applicants also describe herein: 1.) the identification and cloning of the *Yarrowia lipolytica* PDAT [Examples 6 and 8], DGAT2 [Examples 5 and 8] and DGAT1 [Examples 9 and 10]; 2.) the identification and cloning of the *Mortierella alpina* DGAT2 [Examples 1, 2 and 3] and DGAT1 [Examples 16 and 17]; 3.) the identification of DGAT1 homologs from *Neurospora crassa*, *Gibberella zeae* PH-1, *Magnaporthe grisea* and *Aspergillus nidulans* [Example 18]; and, 4.) the identification of universal and fungal DGAT1 motifs [Example 19].

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, NY (1989) (Maniatis); 2.) T. J. Silhavy, M. L. Bennan, and L. W. Enquist, *Experiments with Gene Fusions*; Cold Spring Harbor Laboratory: Cold Spring Harbor, NY (1984); and 3.) Ausubel, F. M. et al., *Current Protocols in Molecular Biology*, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). *E. coli* strains were typically grown at 37° C. on Luria Bertani (LB) plates. General molecular cloning was performed according to standard methods (Sambrook et al., supra). Oligonucleotides were synthesized by Sigma-Genosys (Spring, Tex.).

All polymerase chain reactions (PCRs) were performed in a thermocyler using DNA polymerase in a buffer recommended by the manufacturer of the polymerase. Unless specified otherwise, amplification was carried out as follows: initial denaturation at 95° C. for 1 min, followed by 30 cycles of denaturation at 95° .C for 30 sec, annealing at 55° C. for 1 min, and elongation at 72° C. for 1 min. A final elongation cycle at 72° C. for 10 min was carried out, followed by reaction termination at 4° C. PCR products were cloned into Promega's pGEM-T-easy vector (Madison, Wis.), unless otherwise noted.

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., Madison, Wis.). The percent identities between these proteins were determined by the Megalign program of DNASTAR using Clustal W with the following parameters: gap penalty=10, gap length penalty=0.2, delay divergent seqs (%)=30, DNA transition weight=0.5 and protein weight matrix by Gonnet series.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains ATCC #20362, #76982 and #90812 were purchased from the American Type Culture Collection (Rockville, Md.). *Y. lipolytica* strains were usually grown at 28° C. on YPD agar (1 % yeast extract, 2% bactopeptone, 2% glucose, 2% agar).

Transformation of *Yarrowia lipolytica* was performed according to the method of Chen, D. C. et al. (*Appl. Microbiol Biotechnol*. 48(2):232-235 (1997), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of adenine, leucine, lysine and/or uracil were added as appropriate to a final concentration of 0.01% (thereby producing "MMA", "MMLe", "MMLy" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

To promote oleaginous conditions, High Glucose Media ("HGM") was prepared as follows: 14 g/L $KH_2PO_4$, 4 g/L $K_2HPO_4$, 2 g/L $MgSO_4.7H_2O$, 80 g/L glucose (pH 6.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol*. 37:911-917 (1959)). Fatty acid methyl esters were prepared by transesterification of the lipid extract with sodium methoxide (Roughan, G., and Nishida I. *Arch Biochem Biophys*. 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Preparation of *Mortierella alpina* Genomic DNA and cDNA

The present Example describes the preparation of genomic DNA and cDNA from Mortierella alpina (ATCC #16266).

Preparation of Genomic DNA from *Mortierella alpina*

Genomic DNA was isolated from Mortierella alpina (ATCC #16266) using a QiaPrep Spin Miniprep Kit (Qiagen, Catalog #627106). Cells grown on a YPD agar plate (2% Bacto-yeast extract, 3% Bactor-peptone, 2% glucose, 2.5% bacto-agar) were scraped off and resuspended in 1.2 mL of kit buffer P1. The resuspended cells were placed in two 2.0 mL screw cap tubes, each containing 0.6 mL glass beads (0.5 mm diameter). The cells were homogenized at the HOMOGENIZE setting on a Biospec (Bartlesville, Okla.) mini bead beater for 2 min. The tubes were then centrifuged at 14,000 rpm in an Eppendorf microfuge for 2 min. The supernatant (0.75 mL) was transferred to three 1.5 mL microfuge tubes. Equal volumes of kit buffer P2 were added to each tube. After mixing the tubes by inversion three times, 0.35 mL of buffer N3 was added to each tube. The contents of each tube were again mixed by inversion for a total of five times. The mixture was centrifuged at 14,000 rpm in an Eppendorf microfuge for 5 min. The supernatant from each tube was transferred individually into 3 separate kit spin columns. The columns were then subjected to the following steps: centrifugation (1 min at 14,000 rpm), wash once with buffer PE, centrifugation (1 min at 14,000 rpm), and then a final centrifugation (1 min at 14,000 rpm). Buffer EB (50 µl) was added to each column and let stand for 1 min. The genomic DNA was then eluted by centrifugation at 14,000 rpm for 1 min.

Preparation of cDNA from *Mortierella alpina* cDNA of *Mortierella alpina* was prepared using the BD-Clontech Creator Smart® cDNA library kit (Mississauga, ON, Canada), according to the manufacturer's protocol.

Specifically, *M. alpina* strain ATCC #16266 was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform:isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol, made with RNase free water and air-dried. The total RNA sample was then redissolved in 500 µl of water, and the amount of RNA was measured by A260 nm using a 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 µl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 µl of RNase free water to each column, waiting for 1 min and centrifuging at 4500×g for 3 min.

PolyA(+)RNA was then isolated from the above total RNA sample, following Pharmacia's kit protocol. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly(A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/µl.

cDNA was generated, using the LD-PCR method specified by BD-Clontech and 0.1 µg of polyA(+) RNA sample. Specifically, for $1^{st}$ strand cDNA synthesis, 3 µl of the poly(A)+ RNA sample was mixed with 1 µl of SMART IV oligo nucleotide (SEQ ID NO:1) and 1 µl of CDSIII/3' PCR primer (SEQ ID NO:2). The mixture was heated at 72° C. for 2 min and cooled on ice for 2 min. To the tube was added the following: 2 µl first strand buffer, 1 µl 20 mM DTT, 1 µl 10 mM dNTP mix and 1 µl Powerscript reverse transcriptase. The mixture was incubated at 42° C. for 1 hr and cooled on ice.

The $1^{st}$ strand cDNA synthesis mixture was used as template for the PCR reaction. Specifically, the reaction mixture contained the following: 2 µl of the $1^{st}$ strand cDNA mixture, 2 µl 5'-PCR primer (SEQ ID NO:3), 2 µl CDSIII/3'-PCR primer (SEQ ID NO:2), 80 µl water, 10 µl 10×Advantage 2 PCR buffer, 2 µl 50×dNTP mix and 2 µl 50×Advantage 2 polymerase mix. The thermocycler conditions were set for 95° C. for 20 sec, followed by 20 cycles of 95° C. for 5 sec and 68° C. for 6 min on a GenAmp 9600 instrument. PCR product was quantitated by agarose gel electrophoresis and ethidium bromide staining.

Example 2

Cloning of a Partial Putative DGAT2 Sequence from *Mortierella alpina* by PCR using Degenerate PCR Primers PCR amplifications were performed using either *M. alpina* genomic DNA or cDNA as template and several sets of degenerate primers (see Table 7 below) designed to encode conserved amino acid sequences among different known DGAT2s (i.e., GenBank Accession Nos. NC_001147 *[Saccharomyces cerevisiae]* and AF391089 and AF391090 *[Mortierella ramanniana]*). The best results were obtained with degenerate primers MDGAT-FN1 and MDGAT-RN1.

The PCR was carried out in a Perkin Elmer GeneAmp 9600 PCR machine using TaKaRa ExTaq premix Taq polymerase (TaKaRa Bio Inc., Otsu, Shiga, Japan). Amplification was carried out as follows: 30 cycles of denaturation at 94° C. for 30 sec, annealing at 55° C. for 30 sec and elongation at 72° C. for 90 sec, followed by a final elongation cycle at 72° C. for 7 min.

Using cDNA as template, and MDGAT-FN1 and MDGAT-RN1 as primers, a fragment with a size of ca. 370 bp was obtained (SEQ ID NO:10). This fragment was purified with a Qiagen QiaQuick PCR purification kit, cloned into the TOPO® cloning vector pCR2.1-TOPO (Invitrogen), and sequenced. The resultant sequence, when translated, had homology to known DGAT2s, based on BLAST program analysis (Basic Local Alignment Search Tool; Altschul, S. F., et al., *J. Mol. Biol.* 215:403-410 (1993)).

Using genomic DNA as template, and MDGAT-FN1 and MDGAT-RN2 as primers, a fragment of ca 670 bp was obtained. The fragment was purified, cloned into pCR2.1-TOPO and sequenced, as above. 654 bp of sequence was obtained (SEQ ID NO:11). Again, when translated, the sequence had homology to known DGAT2s, based on the BLAST program analysis. Comparison of the genomic sequence and the cDNA sequence revealed the presence of an intron of 179 bp (SEQ ID NO:12).

Example 3

Isolation of the Full-Length DGAT2 Sequence from *Mortierella alpina*

Based on the sequence of the 370 bp fragment, the 5' and 3' end regions of the *M. alpina* DGAT2 were cloned using genome walking techniques. This enabled assembly of a contig, corresponding to the −747 bp to +1552 bp region of the *M. alpina* DGAT2 (SEQ ID NO:13). This contig included the entire coding region of DGAT2 and three introns.

InVitrogen's 3'-end RACE Protocol

3'-end RACE was carried out using the InVitrogen 3'-end RACE kit, following the manufacturer's protocol. Briefly, 90 ng of *M. alpina* polyA(+)RNA in 11 µl of water was mixed with 1 µl of 10 µM Adaptor primer ("AP"; SEQ ID NO:14) solution. The mixture was heated at 70° C. for 10 min and cooled on ice for 2 min. To this, 2 µl 10×PCR buffer, 2 µl 25 mM $MgCl_2$, 2 µl 0.1 M DTT, and 1 µl of 10 mM dNTP mix were added (from the kit). The reaction mixture was heated to 42° C. for 3 min and then 1 µl of Superscript II reverse

TABLE 7

Degenerate Primers Used For Amplification Of A Partial Putative DGAT2

| Primer Set | Description | Degenerate Nucleotide Sequence | Corresponding Amino Acid Sequence |
|---|---|---|---|
| MDGAT-FN1 | (16) 20-mers | 5'-GAACTACATCTTYG GNTAYCA-3' (SEQ ID NO:4) | NYIFGYH (SEQ ID NO:5) |
| MDGAT-RN1 | (32) 20-mers | 5'-TACAGCTCRTTYTC NCCRAA-3' (SEQ ID NO:6) | Complement of FGENELY (SEQ ID NO:7) |
| MDGAT-RN2 | (32) 20-mers | 5'-CCAAAGTCRTARTT RAANAC-3' (SEQ ID NO:8) | Complement of VFNYDFG (SEQ ID NO:9) |

[Note:
Abbreviations are standard for nucleotides and proteins. The nucleic acid degeneracy code used is as follows: Y = C/T; R = A/G; and N = A/C/G/T.]

transcriptase was added. The reaction was allowed to proceed for 50 min at 42° C., then was heated to 70° C. for 15 min and cooled on ice for 2 min. 1 μl of RNaseH from the kit was added. The entire mixture was then incubated at 37° C. for 20 min.

The above reaction mixture (2 μl) was used directly as a PCR template, while the remainder of the PCR reaction mixture contained 1 μl of 20 μM primer MDGAT-3-1 (SEQ ID NO:15, nested at the 3' end), 2 μl of 10 μM kit primer UAP (SEQ ID NO:16), 25 μl of ExTaq premix Taq 2×PCR solution (TaKaRa Bio Inc., Otsu, Shiga, Japan) and 20 μl of water. PCR amplification was carried out for 30 cycles using the following conditions: denaturation at 94° C. for 30 sec, annealing at 55° C. for 30 sec, and elongation at 72° C. for 90 sec. A final elongation cycle at 72° C. for 7 min was carried out, followed by reaction termination at 4° C.

A second round of PCR was carried out using the same conditions described above, with the exception that the template used was 1 μl of 1:10 diluted PCR reaction mixture and primer MDGAT-3-2 (SEQ ID NO:17, nested at the 3' end) was used in place of primer MDGAT-3-1. This was followed by a third round of PCR using primers MDGAT-3-3 (SEQ ID NO:18, nested at the 3' end) and UAP.

A ca 455 bp fragment was obtained from the PCR. After purification with a Qiagen QiaQuick PCR purification kit, the fragment was cloned into pCR2.1-TOPO and sequenced. Sequence analysis showed that the fragment was the 3'-end of the *M. alpina* DGAT2 cDNA and it included the polyA tail (SEQ ID NO:19).

Genome Walking to Isolate the 3'-End Region of the *M. alpina* DGAT2

A Clontech Universal GenomeWalker™ kit was used to obtain a piece of genomic DNA corresponding to the 3'-end region of the *M. alpina* DGAT2. Briefly, 2.5 μg each of *M. alpina* genomic DNA was digested with DraI, EcoRV, PvuII or StuI individually, the digested DNA samples were purified using Qiagen Qiaquick PCR purification kits and eluted with 30 μl each of kit buffer EB, and the purified samples were then ligated with Genome Walker adaptor (SEQ ID NOs:20 [top strand] and 21 [bottom strand]), as shown below:

```
5'-GTAATACGACTCACTATAGGGCACGCGTGGTCGACGGCCCGGGCTGGT-3'

3'-H2N-CCCGACCA-5'
```

Each ligation reaction mixture contained 1.9 μl of 25 μM Genome Walker adaptor, 1.6 μl 10×ligation buffer, 0.5 μl T4 DNA ligase and 4 μl of one of the purified digested genomic DNA samples. The reaction mixtures were incubated at 16° C. overnight. The reaction was terminated by incubation at 70° C. for 5 min. Then, 72 μl of 10 mM TrisHCl, 1 mM EDTA, pH 7.4 buffer was added to each ligation reaction mix.

Four separate PCR reactions were performed, each using one of the four ligation mixtures as template. The PCR reaction mixtures contained 1 μl of ligation mixture, 1 μl of 20 μM MDGAT-3-1 (SEQ ID NO:15), 2 μl of 10 μM kit primer AP1 (SEQ ID NO:22), 21 μl water, and 25 μl ExTaq premix Taq 2×PCR solution (TaKaRa). The PCR reactions were carried out for 30 cycles using the following conditions: denaturation at 94° C. for 30 sec, annealing at 55° C. for 30 sec, and elongation at 72° C. for 90 sec. A final elongation cycle at 72° C. for 7 min was carried out, followed by reaction termination at 4° C.

The products of each PCR reaction were diluted 1:50 individually and used as templates for a second round of PCR. Each reaction mixture contained 1 μl of one of the diluted PCR product as template, 1 μl of 20 μM MDGAT-3-2 (SEQ ID NO:17), 2 μl of 10 μM kit primer AP2 (SEQ ID NO:23), 21 μl water and 25 μl of ExTaq premix Taq 2×PCR solution (TaKaRa). PCR reactions were carried out for 30 cycles using the same thermocycler conditions described above.

A 674 bp DNA fragment was obtained from the second round of PCR. This fragment was purified and cloned into pCR2.1-TOPO and sequenced. Sequence analysis showed that the fragment was the 3'-end of the *M. alpina* DGAT2 gene (SEQ ID NO:24). Additionally, this fragment was identical to the cDNA fragment (SEQ ID NO:19), with two exceptions: (1) the 3'-end did not extend as far as the cDNA fragment; and (2) two additional regions were present, representing introns that had been spliced off from the cDNA (wherein one intron [SEQ ID NO:12] was located between bases 35-213 of SEQ ID NO:24 and the second intron [SEQ ID NO:25] was located between bases 369-499 of SEQ ID NO:24).

Genome Walking to Isolate the 5'-End Region of the *M. alpina* DGAT2

The same set of four ligation mixtures used in the Clontech 3'-end RACE protocol were also used to obtain the 5'-end region of the *M. alpina* DGAT2. Specifically, a first round of PCR using the same components and conditions as described above was conducted, with the exception that MDGAT-5-1 (SEQ ID NO:26, nested at the 5' end) and AP1 were used as primers. The second round of PCR used MDGAT-5-2 (SEQ ID NO:27, nested at the 5' end) and AP2 as primers. A DNA fragment with 1261 bp was obtained. It was purified and cloned into pCR2.1-TOPO and sequenced. Analysis of the sequence showed that it was the 5'-region of the DGAT2 gene (SEQ ID NO:28).

Assembly of the Full-Length DGAT2 Sequence from *Mortierella alpina*

A 2299 bp sequence (SEQ ID NO:13) containing the complete DGAT2 gene (comprising a region extending 747 bases upstream of the DGAT2 translation initiation 'ATG' codon and extending 62 bases beyond the DGAT2 termination codon) was assembled from the original partial CDNA fragment (SEQ ID NO:10), the partial genomic fragment (SEQ ID NO:11), the 3' cDNA fragment (SEQ ID NO:19) and 3' and 5' genomic sequences (SEQ ID NOs:24 and 28) described above (graphically illustrated in FIG. 2). The complete nucleotide sequence of the *M. alpina* DGAT2 cDNA from 'ATG' to the stop codon 'TAG' is provided as SEQ ID NO:29 (corresponding to bases 748 to 2237 of SEQ ID NO:13, excluding the three introns (i.e., intron 1 [SEQ ID NO:31], corresponding to bases 1018 to 1201 of SEQ ID NO:13; intron 2 [SEQ ID NO:12], corresponding to bases 1570 to 1748 of SEQ ID NO:13; and intron 3 [SEQ ID NO:25], corresponding to bases 1903 to 2034 of SEQ ID NO:13). The translated amino acid sequence (SEQ ID NO:30) showed homology with a number of fungal, plant and animal DGAT2s.

More specifically, identity of the sequence was determined by conducting BLAST (Basic Local Alignment Search Tool; Altschul, S. F., et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. Nature Genetics 3:266-272 (1993)) provided by the NCBI. The results of the BLAST comparison summarizing the sequence to which SEQ ID NO:30 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the amino acid fragment described herein as SEQ ID NO:30 had 47% identity and 66% similarity with the protein sequence of *Mortierella ramanniana* DGAT2A (GenBank Accession No. MK84179.1), with an expectation value of 1e-87; additionally, SEQ ID NO:30 had 47% identity and 65% similarity with hypothetical protein CNBF4150 from *Cryptococcus neoformans* var. *neoformans* B-3501A (GenBank Accession No. EAL20089), with an expectation value of 6e-89.

Example 4

Construction of Plasmids Suitable for Gene Expression in *Y. lipolytica*

The present Example describes the construction of plasmids pY5, pY5-13, pY20 and pLV5.
Construction of Plasmid pY5
The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as described in WO 2004/101757 (herein incorporated by reference in its entirety). As shown in FIG. 3A, pY5 is useful as a *Yarrowia*—*E. coli* shuttle plasmid containing: a *Yarrowia* autonomous replication sequence (ARS18); a ColE1 plasmid origin of replication; an ampicillin-resistance gene (Amp$^R$) for selection in *E. coli*; a *Yarrowia* LEU2 gene (E. C. 1.1.1.85, encoding isopropylmalate isomerase) for selection in *Yarrowia*; the translation elongation promoter (TEF) for expression of heterologous genes in *Yarrowia*; and the extracellular protease gene terminator (XPR2) for transcriptional termination of heterologous gene expression in *Yarrowia*.

pY5-13 was constructed as a derivative of pY5 to faciliate subcloning and heterologous gene expression in *Yarrowia lipolytica* (see WO 2004/101757).
Construction of Plasmids pY20 and pLV5
Plasmid pY20 (SEQ ID NO:32; FIG. 3B) is a derivative of pY5. It was constructed by inserting a Not I fragment containing a chimeric hygromycin resistance gene into the Not I site of pY5. Specifically, the *E. coli* hygromycin resistance gene (SEQ ID NO:33; "HPT"; Kaster, K. R. et al., *Nucleic Acids Res.* 11:6895-6911 (1983)) was PCR amplified for expression. The chimeric gene had the hygromycin resistance ORF under the control of the *Y. lipolytica* TEF promoter.

Plasmid pLV5 is a derivative of pY20. It was constructed by replacing the hygromycin resistant gene with the *Yarrowia* Ura3 gene. A 1.7 kB DNA fragment (SEQ ID NO:35) containing the *Yarrowia* Ura3 gene was PCR amplified using oligonucleotides KU5 and KU3 (SEQ ID NOs:37 and 38) as primers and *Yarrowia* genomic DNA as template.

Example 5

Cloning of a Partial *Yarrowia lipolytica* Acyl-CoA:Diacylglycerol Acyltransferase (DGAT2) Gene and Disruption of the Endogenous DGAT2 Gene The present Example describes the use of degenerate PCR primers to isolate a partial coding sequence of the *Yarrowia lipolytica* DGAT2 and the use of the partial sequence to disrupt the native gene in *Y. lipolytica*.
Cloning of a Partial Putative DGAT2 Sequence from *Yarrowia lipolytica* by PCR using Degenerate PCR Primers and Chromosome Walking Genomic DNA was isolated from *Y. lipolytica* (ATCC #76982) using a DNeasy Tissue Kit (Qiagen, Catalog #69504) and resuspended in kit buffer AE at a DNA concentration of 0.5 μg/μl. PCR amplifications were performed using the genomic DNA as template and several sets of degenerate primers designed to encode conserved amino acid sequences among different known DGAT2s (i.e., GenBank Accession Nos. NC_001147 [*Saccharomyces cerevisiae*] and AF391089 and AF391090 *[Mortierella ramanniana]*). The best results were obtained with degenerate primers P7 and P8, as shown in the Table below.

TABLE 8

Degenerate Primers Used For Amplification Of A Partial Putative DGAT2

| Primer Set | Description | Degenerate Nucleotide Sequence | Corresponding Amino Acid Sequence |
|---|---|---|---|
| P7 | (32) 29-mers | 5'-AACTACATCTTCGGCTA YCAYCCNCAYGG-3' (SEQ ID NO:39) | NYIFGYHPHG (SEQ ID NO:40) |
| P8 | (48) 29-mers | 5'-AGGGACTCGGAGGCGC CGCCNCANACDAT-3' (SEQ ID NO:41) | complementary to IVVGGASESL (SEQ ID NO:42) |

[Note:
Abbreviations are standard for nucleotides and proteins. The nucleic acid degeneracy code used is as follows: Y = C/T; D = A/G/T; and N = A/C/G/T.]

The PCR was carried out in a RoboCycler Gradient 40 PCR machine (Stratagene) using the manufacturer's recommendations and Accuprime Taq polymerase (Invitrogen). Amplification was carried out as described in the General Methods.

The expected PCR product (ca. 264 bp) was detected by 4% NuSieve (FMC) agarose gel electrophoresis, isolated, purified, cloned into the TOPO® cloning vector (Invitrogen) and sequenced. The resultant sequence (contained within SEQ ID NO:43) had homology to known DGAT2s, based on BLAST program analysis (Basic Local Alignment Search Tool; Altschul, S. F. et al., *J. Mol. Biol.* 215:403-410 (1993)).

Using the 264 bp fragment as an initiation point, a 673 bp fragment was obtained by chromosome walking using the TOPO® Walker Kit (Invitrogen, Catalog #K8000-01). The chromosome walking was carried out in 6 steps, as described briefly below:

1.) Genomic DNA (5 µg) was digested with restriction enzymes Pst I or Sac I, leaving a 3' overhang;
2.) Digested DNA was treated with 0.1 U calf intestinal alkaline phosphatase to dephosphorylate DNA;
3.) Primer extension was performed, using the DGAT2 specific primer P80 (SEQ ID NO:45) and Taq polymerase;
4.) TOPO® Linker (1 µl) was added and the reaction was incubated at 37° C. for 5 min to ligate TOPO® Linker to the DNA;
5.) PCR was performed using the DGAT2 gene specific primer, P81 (SEQ ID NO:46) and LinkAmp primer 1 (SEQ ID NO:47); and
6.) The newly amplified fragment was sequenced with primer P81 and LinkAmp primer 1.

The sequence of the 673 bp fragment obtained by chromosome walking also showed homology to known DGAT2 sequences.

Targeted Disruption of the *Yarrowia lipolytica* DGAT2 Gene

Targeted disruption of the DGAT2 gene in *Y. lipolytica* ATCC #90812 and ATCC #76982 was carried out by homologous recombination-mediated replacement of the endogenous DGAT2 gene with a targeting cassette designated as plasmid pY21 DGAT2. pY21 DGAT2 was derived from plasmid pY20 (Example 4; SEQ ID NO:32). Specifically, pY21 DGAT2 was created by inserting a 570 bp Hind III/Eco RI fragment into similarly linearized pY20. The 570 bp DNA fragment contained (in 5' to 3' orientation): 3' homologous sequence from position +1090 to +1464 (of the coding sequence (ORF) in SEQ ID NO:43), a Bgl II restriction site and 5' homologous sequence from position +906 to +1089 (of the coding sequence (ORF) shown in SEQ ID NO:43). The fragment was prepared by PCR amplification of 3' and 5' sequences from the 673 bp DGAT2 PCR product obtained by chromosome walking using two pairs of PCR primers, P95 and P96 (SEQ ID NOs:48 and 49), and P97 and P98 (SEQ ID NOs:50 and 51), respectively.

pY21 DGAT2 was linearized by Bgl II restriction digestion and transformed into mid-log phase *Y. lipolytica* ATCC #90812 and ATCC #76982 cells, as described in the General Methods. The cells were plated onto YPD hygromycin selection plates and maintained at 30° C. for 2 to 3 days.

Four *Y. lipolytica* ATCC #76982 hygromycin-resistant colonies and fourteen *Y. lipolytica* ATCC #90812 hygromycin-resistant colonies were isolated and screened for targeted disruption by PCR. One set of PCR primers (P115 and P116 [SEQ ID NOs:52 and 53, respectively]) was designed to amplify a specific junction fragment following homologous recombination. Another pair of PCR primers (P115 and P112 [SEQ ID NO:54]) was designed to detect the native gene.

All (4 of 4) of the hygromycin-resistant colonies of ATCC #76982 strains were positive for the junction fragment and negative for the native fragment; and, 2 of the 14 hygromycin-resistant colonies of ATCC #90812 strains were positive for the junction fragment and negative for the native fragment. Thus, targeted integration was confirmed in these 6 strains. Disruption of the gene was further confirmed by GC analysis of total lipids of one of the disrupted strains, designated as "S-D2" (see Example 11).

Example 6

Cloning of a Partial *Yarrowia lipolytica* Phospholipid:Diacylglycerol Acyltransferase (PDAT) Gene and Disruption of the Endogenous PDAT Gene The present Example describes the use of degenerate PCR primers to isolate a partial coding sequence of *Y. lipolytica* PDAT and the use of the partial sequence to disrupt the native gene in *Y. lipolytica*.

Cloning of a Partial Putative PDAT Sequence From *Yarrowia lipolytica* by PCR using Degenerate PCR Primers and Chromosome Walking Genomic DNA was isolated from *Y. lipolytica* (ATCC #76982) using a DNeasy Tissue Kit (Qiagen, Catalog #69504) and resuspended in kit buffer AE at a DNA concentration of 0.5 µg/µl. PCR amplifications were performed using genomic DNA as the template and several pairs of degenerate primers encoding conserved amino acid sequences in different known PDATs (GenBank Accession Nos. NP 190069 and AB006704 [(gi:2351069*Arabidopsis thaliana*], and NP_596330 [*Schizosaccharomyces pombe*]; and the *Saccharomyces cerevisiae* Lro 1 gene [Dahlqvist et al., *Proc. Natl. Acad. Sci. USA* 97:6487 (2000)]). The best results were obtained with degenerate primers P26 and P27, as shown in the Table below.

TABLE 9

Degenerate Primers Used For Amplification Of A Partial Putative PDAT

| Primer Set | Description | Degenerate Nucleotide Sequence | Corresponding Amino Acid Sequence |
|---|---|---|---|
| P26 | (32) 29-mers | 5'-ATGCTGGACAAGGAG ACCGGNCTNGAYCC-3' (SEQ ID NO:55) | MLDKETGLDP (SEQ ID NO:56) |
| P27 | (16) 33-mers | 5'-CCAGATGACGTCGCCG CCCTTGGGNARCATNGA-3' (SEQ ID NO:57) | complementary to SMLPKGGEVIW (SEQ ID NO:58) |

[Note:
Abbreviations are standard for nucleotides and proteins. The nucleic acid degeneracy code used is as follows: R = A/G; Y = C/T; and N = A/C/G/T.]

The PCR was carried out in a RoboCycler Gradient 40 PCR machine (Stratagene), using the amplification conditions described in the General Methods. The expected PCR product (ca. 600 bp) was detected by 4% NuSieve (FMC) agarose gel electrophoresis, isolated, purified, cloned into the TOPO® cloning vector (Invitrogen) and sequenced. The resultant sequence (contained within SEQ ID NO:59) had homology to known PDATs, based on BLAST program analysis (Altschul, S. F. et al., *J. Mol. Biol.* 215:403-410 (1993)).

Targeted Disruption of *Yarrowia lipolytica* PDAT Gene

Following the sequencing of this ca. 600 bp partial coding region for PDAT, a larger DNA fragment encoding this sequence was discovered in the public *Y. lipolytica* protein database of the "Yeast project *Genolevures*" (Center for Bioinformatics, LaBRI, Talence Cedex, France) (see also Dujon, B. et al., *Nature* 430 (6995):35-44 (2004)). This allowed isolation of a 1008 bp genomic DNA fragment comprising a portion of the PDAT gene from *Y. lipolytica* ATCC #90812 using PCR primers P39 and P42 (SEQ ID NOs:61 and 62).

Targeted disruption of the PDAT gene in *Y. lipolytica* ATCC #90812 was carried out by homologous recombination-mediated replacement of the endogenous PDAT gene with a targeting cassette designated as pLV13 (SEQ ID NO:63; FIG. 3C). pLV13 was derived from plasmid pLV5 (Example 4). Specifically, pLV13 was created by inserting a 992 bp Bam HI/Eco RI fragment into similarly linearized pLV5. The 992 bp DNA fragment contained (in 5' to 3' orientation): 3' homologous sequence from position +877 to +1371 (of the coding sequence (ORF) in SEQ ID NO:59), a Bgl II restriction site and 5' homologous sequence from position +390 to +876 (of the coding sequence (ORF) in SEQ ID NO:59). The fragment was prepared by PCR amplification of 3' and 5' sequences from the 1008 bp PCR product described above, using PCR primers P39 and P41 (SEQ ID NOs:61 and 64) and P40 and P42 (SEQ ID NOs:65 and 62), respectively.

pLV13 was linearized by Bgl II restriction digestion and was transformed into mid-log phase *Y. lipolytica* ATCC #90812 cells by the lithium acetate method (General Methods). The cells were plated onto Bio101DOB/CSM-Ura selection plates and maintained at 30° C. for 2 to 3 days.

Ten *Y. lipolytica* ATCC #90812 colonies were isolated and screened for targeted disruption by PCR. One set of PCR primers (P51 and P52 [SEQ ID NOs:66 and 67, respectively]) was designed to amplify the targeting cassette. Another set of PCR primers-(P37 and P38 [SEQ ID NOs:68 and 69, respectively]) was designed to detect the native gene. Ten of the ten strains were positive for the junction fragment and 3 of the 10 strains were negative for the native fragment, thus confirming successful targeted integration in these 3 strains. Disruption of the gene was further confirmed by GC analysis of total lipids in one of the disrupted strains, designated as "S-P" (see Example 11).

Example 7

Construction of a *Yarrowia lipolytica* Double Knockout Strain Containing Disruptions in both PDAT and DGAT2 Genes The present Example describes the creation of a double knockout strain that was disrupted in both PDAT and DGAT2 genes.

Specifically, the *Y. lipolytica* ATCC #90812 hygromycin-resistant "S-D2" mutant (containing the DGAT2 disruption from Example 5) was transformed with plasmid pLV13 (from Example 6) and transformants were screened by PCR, as described in Example 6. Two of twelve transformants were confirmed to be disrupted in both the DGAT2 and PDAT genes. Disruption of the gene was further confirmed by GC analysis of total lipids in one of the disrupted strains, designated as "S-D2-P" (see Example 11).

Example 8

Cloning of Full-Length *Yarrowia lipolytica* DGAT2 and PDAT Genes

The present Example describes the recovery of the genomic sequences flanking the disrupted DGAT2 and PDAT genes by plasmid rescue, using the sequence in the rescued plasmid to PCR the intact ORF of the native gene. The full-length genes and their deduced amino acid sequences are compared to other fungal DGAT2 and PDAT sequences, respectively.

Plasmid Rescue of *Yarrowia lipolytica* DGAT2 And PDAT Genes

Since the acyltransferase genes were disrupted by the insertion of the entire pY21 DGAT2 and pLV13 vectors that each contained an *E. coli* ampicillin-resistant gene and *E. coli* ori, it was possible to rescue the flanking PDAT and DGAT2 sequences in *E. coli*. For this, genomic DNA of *Y. lipolytica* strain "S-D2" (carrying the disrupted DGAT2 gene; Example 5) and *Y. lipolytica* strain "S-P" (carrying the disrupted PDAT gene; Example 6) was isolated using the DNeasy Tissue Kit. Specifically, 10 μg of the genomic DNA was digested with 50 U of the following restriction enzymes in a reaction volume of 200 μl: for DGAT2—Age I and Nhe I; for PDAT—Kpn I, Pac I and Sac I. Digested DNA was extracted with phenol:chloroform and resuspended in 40 μl deionized water. The digested DNA (10 μl) was self-ligated in a 200 μl ligation mixture containing 3 U T4 DNA ligase. Each ligation reaction was carried out at 16° C. for 12 hrs. The ligated DNA was extracted with phenol:chloroform and resuspended in 40 μl deionized water. Finally, 1 μl of the resuspended ligated DNA was used to transform *E. coli* by electroporation and plated on LB containing ampicillin (Ap). Ap-resistant transformants were isolated and analyzed for the presence of plasmids. The following insert sizes were found in the recovered or rescued plasmids (Tables 10 and 11):

TABLE 10

Insert Sizes Of Recovered DGAT2 Plasmids, According To Restriction Enzyme

| Enzyme | plasmid insert size (kB) |
|---|---|
| AgeI | 2.3 |
| NheI | 9.5 |

TABLE 11

Insert Sizes Of Recovered PDAT Plasmids, According To Restriction Enzyme

| Enzyme | plasmid insert size (kB) |
|---|---|
| Kpn I | 6.9 |
| Sac I | 5.4 |
| Sph I | 7.0 |

Sequencing of the DGAT2 rescued plasmids was initiated with sequencing primers P79 (SEQ ID NO:70) and P95 (SEQ ID NO:48). In contrast, sequencing of the PDAT plasmids was initiated with sequencing primers P84 (SEQ ID NO:71) and P85 (SEQ ID NO:72).

Based on the sequencing results, a full-length gene encoding the *Y. lipolytica* DGAT2 gene was assembled (2119 bp; SEQ ID NO:43). Specifically, the sequence encoded an open reading frame (ORF) of 1545 bases (nucleotides +291 to +1835 of SEQ ID NO:43), while the deduced amino acid sequence was 514 residues in length (SEQ ID NO:44). Since this ORF has an initiation codon ('ATG') at position 1, as well as at positions 56 and 160, it contains at least two additional nested (smaller) ORFs. Specifically, one ORF is 1380 bases long (nucleotides +456 to +1835 of SEQ ID NO:43, corresponding to SEQ ID NO:73), with a deduced amino acid sequence of 459 residues (SEQ ID NO:74); another ORF is 1068 bases long (nucleotides +768 to +1835 of SEQ ID NO:43, corresponding to SEQ ID NO:75) with a deduced amino acid sequence of 355 residues (SEQ ID NO:76).

The ORF encoded by SEQ ID NO:75 has a high degree of similarity to other known DGAT2 enzymes and because disruption in SEQ ID NO:75 eliminated DAG AT function of the native gene (see Example 11), the polypeptide of SEQ ID NO:76 has been identified as clearly having DGAT2 functionality.

Following sequencing and analysis of the DGAT2 protein described above, a *Yarrowia lipolytica* DGAT2 protein sequence was published within the public *Y. lipolytica* protein database of the "Yeast project *Genolevures*" (sponsored by the Center for Bioinformatics, LaBRI, bâtiment A30, Université Bordeaux 1, 351, cours de la Libération, 33405 Talence Cedex, France) (see also Dujon, B. et al., *Nature* 430 (6995): 35-44 (2004)). Specifically, the sequence disclosed therein was identified as ORF YALI-CDS2240.1, encoding 514 amino acids, and the protein was reported to share some similarities with tr|Q08650 *Saccharomyces cerevisiae* YOR245C DGA1 acyl-CoA:diacylglycerol acyltransferase.

In a manner similar to that used to deduce the full-length sequence of DGAT2, a full-length gene encoding the *Y. lipolytica* PDAT gene was assembled (2326 bp; SEQ ID NO:59) based on sequencing results. Specifically, the sequence encoded an open reading frame of 1944 bases (nucleotides +274 to +2217 of SEQ ID NO:59), while the deduced amino acid sequence was 648 residues in length (SEQ ID NO:60).

Following sequencing and analysis of the PDAT protein described above, the *Yarrowia lipolytica* PDAT protein sequence was published as part of the public *Y. lipolytica* protein database of the "Yeast project *Genolevures*" (supra). The PDAT sequence disclosed therein was identified as ORF YALI-CDS1359.1, encoding 648 amino acids, and the protein was reported to share some similarities to sp|P40345 *Saccharomyces cerevisiae* YNR008w LRO1, a lecithin cholesterol acyltransferase-like gene which mediates diacylglycerol esterification.

Example 9

Identification of Additional Putative *Yarrowia lipolytica* DAG ATs

In order to identify additional DAG ATs in *Yarrowia*, the public *Y. lipolytica* protein database of the "Yeast project *Genolevures*" (supra) was searched using the *Saccharomyces cerevisiae* ARE1 (Sc ARE1; GenBank Accession No. CAA42296) and ARE2 (Sc ARE2; GenBank Accession No. P53629) protein sequences (Yang, H. et al., *Science*. 272 (5266):1353-1356 (1996)). Both searches identified the following *Y. lipolytica* ORFs as the first and second hits, respectively:

(1) YALI-CDS2011.1: annotated as "similar to sp|P53629 *Saccharomyces cerevisiae* YNR019w ARE2 acyl-CoA sterol acyltransferase, hypothetical start"; 543 amino acids in length (SEQ ID NOs:77 and 78); and (2) YALI-CDS2141.1: annotated as "unnamed protein product; weakly similar to tr|Q9FUL6 *Perilla frutescens* Diacylglycerol acyltransferase (Pf DGAT1), hypothetical start"; 526 amino acids in length (SEQ ID NOs:79 and 80).

The percent identities between these proteins were determined by the Megalign program of DNASTAR using Clustal W according to the parameters described in the General Methods. The percent (%) identities are shown below, wherein the % identity is defined as percentage of amino acids that are identical between the two proteins:

TABLE 12

Percent Identities Between Known Acyltransferases And *Yarrowia lipolytica* ORFs

|  | Sc ARE1 | Sc ARE2 | Pf DGAT1 |
|---|---|---|---|
| YALI-CDS2141.1 | 16.6 | 14.5 | 29.5 |
| YALI-CDS2011.1 | 32.6 | 33.8 | 18.4 |

Based on this comparison, YALI-CDS2141.1 and YALI-CDS2011.1 (designated herein as "Yl DGAT1" and "Yl ARE2", respectively) were candidates ORFs that were likely to encode proteins having DAG AT functionality in *Yarrowia*.

Following the analysis of the proteins described above, the *Yarrowia lipolytica* strain CLIB99 complete genome was published in GenBank as part of the *Genolevures* project. Thus, the ORF identified as YALI-CDS2011.1 corresponds to GenBank Accession No. NC_006072, locus_tag="YALI0F06578g" and the ORF identified as YALI-CDS2141.1 corresponds to GenBank Accession No. CR382130, locus_tag="YALI0D07986g".

Example 10

Cloning of a *Yarrowia lipolytica* Acyl-CoA:Diacylglycerol Acyltransferase (DGAT1) Gene and Disruption of the Endogenous DGAT1 Gene The present Example describes the use of degenerate PCR primers to isolate the full-length coding sequence of the *Yarrowia lipolytica* DGAT1 (encoded by ORF YALI-CDS2011.1 (Example 9)) and the use of the sequence to disrupt the native gene in *Y. lipolytica*.

Cloning of a Putative DGAT1 Sequence from *Yarrowia lipolytica* by PCR using Degenerate PCR Primers The full-length Yl DGAT1 ORF was cloned by PCR using degenerate PCR primers P201 and P203 (SEQ ID NOs:81 and 82, respectively) and *Y. lipolytica* ATCC #76982 (from Example 5) genomic DNA as template. The degenerate primers were required, since the nucleotide sequence encoding Yl DGAT1 was not known.

The PCR was carried out in a RoboCycler Gradient 40 PCR machine, using the components and thermocycler conditions described in the General Methods. The expected PCR product (ca. 1.6 kB) was detected by agarose gel electrophoresis, isolated, purified, cloned into the TOPO® cloning vector (Invitrogen), and partially sequenced to confirm its identity.

Targeted Disruption of the *Yarrowia lipolytica* DGAT1 Gene

Targeted disruption of the putative DGAT1 gene in *Y. lipolytica* ATCC #90812 was carried out by homologous recombination-mediated replacement of the endogenous DGAT1 gene with a targeting cassette (using the methodology described in Example 5). Specifically, the 1.6 kB isolated Yl DGAT1 ORF (SEQ ID NO:83) was used as a PCR template molecule to construct a Yl DGAT1 targeting cassette consisting of: 5' homologous Yl DGAT1 sequence, the *Yar-*

*rowia* Leucine 2 (Leu2) gene, and 3' homologous YI DGAT1 sequence. For this, each portion of the targeting cassette was first individually amplified, using the primers set forth below:

Upper primer P214 and lower primer P215 (SEQ ID NOs: 85 and 86, respectively), for amplification of the 5' homologous DGAT1 sequence;

Upper primer P216 and lower primer P217 (SEQ ID NOs: 87 and 88, respectively), for amplification of the 3' homologous DGAT1 sequence; and, Upper primer P218 and lower primer P219 (SEQ ID NOs: 89 and 90, respectively), for amplification of the Leu2 gene (GenBank Accession No. AAA35244).

The PCRs were performed using Pfu Ultra polymerase (Stratagene, Catalog #600630), as described in the General Methods, and purified. The three correct-sized, purified fragments were mixed together as template molecules for a second PCR reaction using PCR primers P214 and P219 (SEQ ID NOs:85 and 90) to obtain the YI DGAT1 disruption cassette.

The targeting cassette was gel purified and used to transform mid-log phase wildtype *Y. lipolytica* (ATCC #90812). Transformation was performed as described in the General Methods.

Transformants were plated onto Bio101 DOB/CSM-Leu selection plates and maintained at 30° C. for 2 to 3 days. Several leucine prototrophs were screened by PCR to confirm the targeted DGAT1 disruption. Specifically, one set of PCR primers (P226 and P227 [SEQ ID NOs:91 and 92, respectively]) was designed to amplify a junction between the disruption cassette and native target gene. Another set of PCR primers (P214 and P217 [SEQ ID NOs:85 and 88, respectively]) was designed to detect the native gene.

All of the leucine prototroph colonies were positive for the junction fragment and negative for the native fragment. Thus, targeted integration was confirmed in these strains. Disruption of the gene was further confirmed by GC analysis of total lipids of one of the disrupted strains, designated as "S-D1" (see Example 11).

In a similar manner, the DGAT1 targeting cassette was used to disrupt the DGAT1 gene in strains containing single disruptions in either PDAT ("S-P" from Example 6), DGAT2 ("S-D2" from Example 5), or double disruptions in PDAT and DGAT2 ("S-D2-P" from Example 7). This resulted in the creation of strains with double knockouts in DGAT1 and PDAT ("S-D1-P"), in DGAT2 and DGAT1 ("S-D2-D1") and triple knockouts in DGAT2, DGAT1 and PDAT ("S-D2-D1-P").

Example 11

Determination of TAG Content in Mutant and Wildtype *Yarrowia lipolytica* Strains (ATCC #90812)

The present Example describes a comparison of TAG content in wildtype and mutant *Y. lipolytica* ATCC #90812 containing: (1) single disruptions in PDAT, DGAT2 and DGAT1; (2) double disruptions in PDAT and DGAT2, DGAT1 and PDAT, and DGAT1 and DGAT2; and (3) triple disruptions in PDAT, DGAT2 and DGAT1. In general, results demonstrated that TAG content was decreased in *Y. lipolytica* with acyltransferase disruptions.

Specifically, single colonies of wildtype and mutant *Y. lipolytica* containing single disruptions in PDAT ("S-P", from Example 6), DGAT2 ("S-D2", from Example 5), DGAT1 ("S-D1", from Example 10), double disruptions in PDAT and DGAT2 ("S-D2-P", from Example 7), DGAT1 and PDAT ("S-D1-P", from Example 10), DGAT1 and DGAT2 ("S-D1-D2", from Example 10), and triple disruptions ("S-D1-D2-P", from Example 10) were separately grown using conditions that induce oleaginy. One loopful of cells from each culture was each individually inoculated into 3 mL YPD medium and grown overnight on a shaker (300 rpm) at 30° C. The cells were harvested and washed once in 0.9% NaCl and resuspended in 50 mL of HGM. Cells were then grown on a shaker for 48 hrs. Cells were washed in water and the cell pellet was lyophilized. Twenty (20) mg of dry cell weight was used for total fatty acid by GC analysis and the oil fraction following TLC (infra) and GC analysis.

Thin Layer Chromatography (TLC)

The methodology used for TLC is described below in the following five steps: (1) The internal standard of 15:0 fatty acid (10 μl of 10 mg/mL) was added to 2 to 3 mg dry cell mass, followed by extraction of the total lipid using a methanol/chloroform method. (2) Extracted lipid (50 μl) was blotted across a light pencil line drawn approximately 1 inch from the bottom of a 5×20 cm silica gel 60 plate, using 25-50 μl micropipettes. (3) The TLC plate was then dried under $N_2$ and was inserted into a tank containing about ~100 mL 80:20:1 hexane:ethyl ether:acetic acid solvent. (4) After separation of bands, a vapor of iodine was blown over one side of the plate to identify the bands. This permitted samples on the other side of the plate to be scraped using a razor blade for further analysis. (5) Basic transesterification of the scraped samples and GC analysis was performed, as described in the General Methods.

Results from GC Analysis

GC results are shown below in Table 13. Cultures are described as the "S" strain (wildtype), "S-P" (PDAT knockout), "S-D1" (DGAT1 knockout), "S-D2" (DGAT2 knockout), "S-D1-D2" (DGAT1 and DGAT2 knockout), "S-P-D1" (PDAT and DGAT1 knockout), "S-P-D2" (PDAT and DGAT2 knockout) and "S-P-D1-D2" (PDAT, DGAT1 and DGAT2 knockout). Abbreviations utilized are: "WT"=wildtype; "FAs"=fatty acids; "dcw"=dry cell weight; and, "FAs % dcw, % WT"=FAs % dcw relative to the % in wildtype, wherein the "S" strain is wildtype.

TABLE 13

Lipid Content In *Yarrowia* ATCC #90812 Strains With Single, Double Or Triple Disruptions In PDAT, DGAT2 And DGAT1

| | | | Total Fatty Acids | | | TAG Fraction | | |
| --- | --- | --- | --- | --- | --- | --- | --- | --- |
| Strain | Residual DAG AT | dcw, mg | FAs, μg | FAs % dcw | FAs % dcw, % WT | FAs, μg | FAs % dcw | FAs % dcw, % WT |
| S | D1, D2, P | 32.0 | 797 | 15.9 | 100 | 697 | 13.9 | 100 |
| S-D1 | D2, P | 78.8 | 723 | 13.6 | 86 | 617 | 11.6 | 83 |
| S-D2 | D1, P | 37.5 | 329 | 6.4 | 40 | 227 | 4.4 | 32 |
| S-P | D1, D2 | 28.8 | 318 | 6.0 | 38 | 212 | 4.0 | 29 |
| S-D1-D2 | P | 64.6 | 219 | 4.1 | 26 | 113 | 2.1 | 15 |
| S-D1-P | D2 | 76.2 | 778 | 13.4 | 84 | 662 | 11.4 | 82 |
| S-D2-P | D1 | 31.2 | 228 | 4.3 | 27 | 122 | 2.3 | 17 |
| S-D1-D2-P | None | 52.2 | 139 | 2.4 | 15 | 25 | 0.4 | 3 |

The results in Table 13 indicate the relative contribution of the three DAG ATs to oil biosynthesis. DGAT2 contributes the most, while PDAT and DGAT1 contribute equally but less than DGAT2. The residual oil content ca. 3% in the triple knockout strain may be the contribution of the acyl-CoA: sterol-acyltransferase (ARE2), encoded by ORF YALI-CDS2141.1 (Example 9)).

Example 12

Generation of EPA-Producing *Yarrowia lipolytica* ATCC #20362 Strains EU and MU

The present Example describes the construction of strains EU and MU, derived from *Yarrowia lipolytica* ATCC #20362, capable of producing significant concentrations of EPA relative to the total lipids (FIG. 4A). The affect of various acyltransferase knockouts was examined in these EPA-producing strains based on analysis of TAG content and/or fatty acid composition, as described in Examples 13 and 14 (infra).

The development of strain MU herein required the construction of strain M4 (producing 8% DGLA), strain Y2034 (producing 10% ARA), strain E (producing 10% EPA), strain EU (producing 10% EPA) and strain M26 (producing 14%).

Construction of Strain M4 Producing 8% DGLA

Construct pKUNF12T6E (FIG. 4B; SEQ ID NO:93) was generated to integrate four chimeric genes (comprising a Δ12 desaturase, a Δ6 desaturase and 2 elongases) into the Ura3 loci of wild type *Yarrowia* strain 5 ATCC #20362, to thereby enable production of DGLA. The pKUNF12T6E plasmid contained the following components:

TABLE 14

Description of Plasmid pKUNF12T6E (SEQ ID NO: 93)

| RE Sites And Nucleotides Within SEQ ID NO: 93 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S:Pex20, comprising: FBAIN: FBAIN promoter (SEQ ID NO: 94; see also U.S. patent application Ser. No. 10/987548) EL1S: codon-optimized elongase 1 gene (SEQ ID NO: 95), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 97), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: FBA promoter (SEQ ID NO: 99; see also U.S. patent application Ser. No. 10/987548) F.Δ12: *Fusarium moniliforme* Δ12 desaturase gene (SEQ ID NO: 100) Lip2: Lip2 terminator sequence from *Yarrowia* Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 102), derived from *Thraustochytrium aureum* (U.S. Pat. No. 6,677,145) |

TABLE 14-continued

Description of Plasmid pKUNF12T6E (SEQ ID NO: 93)

| RE Sites And Nucleotides Within SEQ ID NO: 93 | Description Of Fragment And Chimeric Gene Components |
|---|---|
| | XPR: XPR terminator sequence of *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura- strains. Single colonies of Ura- strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E (FIG. 4B), but not in the wild type *Yarrowia* control strain. Most of the selected 32 Ura⁻ strains produced about 6% DGLA of total lipids. There were 2 strains (i.e., strains M4 and 13-8) that produced about 8% DGLA of total lipids.

Construction of Strain Y2034 Producing about 10% ARA

Constructs pDMW232 (FIG. 4C; SEQ ID NO:104) was generated to integrate two Δ5 chimeric genes into the Leu2 gene of *Yarrowia* strain M4. The plasmid pDMW232 contained the following components:

TABLE 15

Description of Plasmid pDMW232 (SEQ ID NO: 104)

| RE Sites And Nucleotides Within SEQ ID NO: 104 | Description Of Fragment And Chimeric Gene Components |
|---|---|
| AscI/BsiWI (5550-4755) | 788 bp 5' part of *Yarrowia* Leu2 gene (GenBank Accession No. AF260230) |
| SphI/PacI (8258-8967) | 703 bp 3' part of *Yarrowia* Leu2 gene (GenBank Accession No. AF260230) |
| SwaI/BsiWI (2114-4755) | FBAIN::MAΔ5::Pex20, comprising: FBAIN: FBAIN Promoter (SEQ ID NO: 94; see also U.S. patent application Ser. No. 10/987548) MAΔ5: *Mortierella alpina* Δ5 desaturase gene (SEQ ID NO: 105) (GenBank Accession No. AF067654) Pex20: Pex20 terminator sequence of *Yarrowia* Pex20 gene (GenBank Accession No. AF054613) |
| SwaI/ClaI (2114-17) | TEF::MAΔ5::Lip1, comprising: TEF: TEF promoter (GenBank Accession No. AF054508) MAΔ5: as described for FBAIN::MAΔ5::Pex20 (supra) Lip1: Lip1 terminator sequence of *Yarrowia* Lip1 gene (GenBank Accession No. Z50020) |
| PmeI/ClaI (5550-4755) | *Yarrowia* Ura3 gene (GenBank Accession No. AJ306421) |

Plasmid pDMW232 was digested with AscI/SphI, and then used to transform strain M4 according to the General Methods. Following transformation, the cells were plated onto MMLe plates and maintained at 30° C. for 2 to 3 days. The individual colonies grown on MMLe plates from each transformation were picked and streaked onto MM and MMLe plates. Those colonies that could grow on MMLe plates but not on MM plates were selected as Leu2⁻ strains. Single colonies of Leu2⁻ strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW232 transformants, but not in the parental M4 strain. Specifically, among the 48 selected Leu2⁻ transformants with pDMW232, there were 34 strains that produced less than 5% ARA, 11 strains that produced 6-8% ARA, and 3 strains that produced about 10% ARA of total lipids in the engineered *Yarrowia*. One of the strains that produced 10% ARA was named "Y2034".

Construction of Strain E, Producing about 10% EPA

Construct pZP3L37 (FIG. 5A; SEQ ID NO:107) was created to integrate three synthetic Δ17 desaturase chimeric genes into the acyl-CoA oxidase 3 (i.e., POX3) gene of the Y2034 strain. The plasmid pZP3L37 contained the following components:

TABLE 16

Description of Plasmid pZP3L37 (SEQ ID NO: 107)

| RE Sites And Nucleotides Within SEQ ID NO: 107 | Description Of Fragment And Chimeric Gene Components |
|---|---|
| AscI/BsiWI (6813-6043) | 763 bp 5' part of *Yarrowia* Pox3 gene (GenBank Accession No. AJ001301) |
| SphI/PacI (9521-10345) | 818 bp 3' part of *Yarrowia* Pox3 gene (GenBank Accession No. AJ001301) |
| ClaI/BsiWI (4233-6043) | TEF::Δ17S::Pex20, comprising:<br>TEF: TEF promoter (GenBank Accession No. AF054508)<br>Δ17S: codon-optimized Δ17 desaturase gene (SEQ ID NO: 108), derived from *S. diclina* (U.S. 2003/0196217 A1)<br>Pex20: Pex20 terminator sequence of *Yarrowia* Pex20 gene (GenBank Accession No. AF054613) |
| ClaI/PmeI (4233-1811) | FBAIN::Δ17S::Lip2, comprising:<br>FBAIN: FBAIN promoter (SEQ ID NO: 94; see also U.S. patent application Ser. No. 10/987548)<br>Δ17S: SEQ ID NO: 108 (supra)<br>Lip2: Lip2 terminator sequence of *Yarrowia* Lip2 gene (GenBank Accession No. AJ012632) |
| PmeI/SwaI (1811-1) | *Yarrowia* Leu2 gene (GenBank Accession No. AF260230) |
| PacI/SwaI (10345-1) | FBAINm::Δ17S::Pex16, comprising:<br>FBAINm: FBAINm promoter (SEQ ID NO: 110; see also U.S. patent application Ser. No. 10/987548)<br>Δ17S: SEQ ID NO: 108 (supra)<br>Pex16: Pex16 terminator sequence of *Yarrowia* Pex16 gene (GenBank Accession No. U75433) |

Plasmid pZP3L37 was digested with AscI/SphI, and then used to transform strain Y2034 according to the General Methods. Following transformation, the cells were plated onto MM plates and maintained at 30° C. for 2 to 3 days. A total of 48 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in most of the transformants with pZP3L37, but not in the parental strain (i.e., Y2034). Among the 48 selected transformants with pZP3L37, there were 18 strains that produced less than 2% EPA, 14 strains that produced 2-3% EPA, and 1 strain that produced about 7% EPA of total lipids in the engineered *Yarrowia*.

The strain that produced 7% EPA was further analyzed after culturing the strain as follows ("two-stage growth conditions"). First, cells were grown in triplicate in liquid MM at 30° C. with shaking at 250 rpm/min for 48 hrs. The cells were collected by centrifugation and the liquid supernatant was extracted. The pelleted cells were resuspended in HGM and grown for 72 hrs at 30° C. with shaking at 250 rpm/min. The cells were again collected by centrifugation and the liquid supernatant was extracted.

GC analyses showed that the engineered strain produced about 10% EPA of total lipids after the two-stage growth. The strain was designated as the "E" strain.

Construction of Strain EU Producing about 10% EPA

Strain EU (Ura⁻) was created by identifying mutant cells of strain E that were 5-FOA resistant. Specifically, one loop of *Yarrowia* E strain cells were inoculated into 3 mL YPD medium and grown at 30° C. with shaking at 250 rpm for 24 hrs. The culture with diluted with YPD to an $OD_{600}$ of 0.4 and then incubated for an additional 4 hrs. The culture was plated (100 μl/plate) onto FOA selection plates and maintained at 30° C. for 2 to 3 days. A total of 16 FOA resistant colonies were picked and streaked onto MM and FOA selection plates. From these, 10 colonies grew on FOA selection plates but not on MM plates and were selected as potential Ura⁻ strains.

One of these strains was used as host for transformation with pY37/F15, comprising a chimeric GPD::*Fusarium moniliforme* Δ15::XPR2 gene and a Ura3 gene as a selection marker (FIG. 5B; SEQ ID NO:111). After three days of selection on MM plates, hundreds of colonies had grown on the plates and there was no colony growth of the transformation control that carried no plasmid. This 5-FOA resistant strain was designated as strain "EU".

Single colonies of the EU strain were then inoculated into liquid MMU additionally containing 0.1 g/L uridine and cultured for 2 days at 30° C. with shaking at 250 rpm/min. The cells were collected by centrifugation, lipids were extracted, and fatty acid methyl esters were prepared by trans-esterification and subsequently analyzed with a Hewlett-Packard 6890 GC. GC analyses showed that the EU strain produced about 10% EPA of total lipids.

Construction of Strain M26, Producing 14% EPA

Construct pKO2UM26E (FIG. 5C, SEQ ID NO:112) was used to integrate a cluster of three chimeric genes (comprising an elongase, a Δ6 desaturase and a Δ12 desaturase) and a Ura3 gene into the *Yarrowia* Δ12 desaturase gene site of strain EU. Plasmid pKO2UM26E contained the following components:

TABLE 17

Description of Plasmid pKO2UM26E (SEQ ID NO: 112)

| RE Sites And Nucleotides Within SEQ ID NO: 112 | Description Of Fragment And Chimeric Gene Components |
|---|---|
| HindIII/AscI (1-728) | 728 bp 5' part of *Yarrowia* Δ12 desaturase gene (SEQ ID NO: 113) |
| SphI/EcoRI 3436-3992) | 556 bp 3' part of *Yarrowia* Δ12 desaturase gene (SEQ ID NO: 113) |
| BsiWI/HindIII (11095-1) | GPAT::EL1S::XPR, comprising:<br>GPAT: GPAT promoter (SEQ ID NO: 115; see also U.S. patent application Ser. No. 60/610060)<br>EL1S: codon-optimized elongase 1 gene (SEQ ID NO: 95), derived from *Mortierella alpina* (GenBank Accession No. AX464731) |

TABLE 17-continued

Description of Plasmid pKO2UM26E (SEQ ID NO: 112)

| RE Sites And Nucleotides Within SEQ ID NO: 112 | Description Of Fragment And Chimeric Gene Components |
|---|---|
| | XPR: terminator sequence of *Yarrowia* Xpr2 gene (GenBank Accession No. M17741) |
| BglII/BsiWI (8578-11095) | FBAIN::M.Δ12.Pex20, comprising: FBAIN: FBAIN promoter (SEQ ID NO: 94; see also U.S. patent application Ser. No. 10/987548) M.Δ12: *Mortieralla isabellina* Δ12 desaturase gene (GenBank Accession No. AF417245; SEQ ID NO: 116) Pex20: Pex20 terminator sequence of *Yarrowia* Pex20 gene (GenBank Accession No. AF054613) |
| SalI/PacI (6704-8202) | *Yarrowia* Ura3 gene (GenBank Accession No. AJ306421) |
| EcoRI/SalI (3992-6704) | FBAIN::M.Δ6B::Pex20, comprising: FBAIN: FBAIN promoter (SEQ ID NO: 94; see also U.S. patent application Ser. No. 10/987548) M.Δ6B: *Mortieralla alpina* Δ6 desaturase gene "B" (GenBank Accession No. AB070555; SEQ ID NO: 118) Pex20: Pex20 terminator sequence of *Yarrowia* Pex20 gene (GenBank Accession No. AF054613) |

The plasmid pKO2UM26E was digested with SphI/AscI, and then used to transform EU strain according to the General Methods. Following transformation, cells were plated onto MM plates and maintained at 30° C. for 2 to 3days.

A total of 48 transformants grown on MM plates were picked and re-streaked onto fresh MM plates. Once grown, these strains were individually inoculated into liquid MM at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC.

GC analyses showed that EPA was produced in almost all transformants with pKO2UM26E after one-day growth in MM media. Among the 48 selected transformants, 5 strains produced less than 4% EPA, 23 strains produced 4-5.9% EPA, 9 strains produced 6-6.9% EPA and 11 strains produced 7-8.2% EPA of total lipids in the engineered *Yarrowia*. The strain that produced 8.2% EPA was selected for further analysis using a two-stage growth procedure (i.e., 48 hrs MM+96 hrs in HGM). GC analyses showed that the engineered strain produced about 14% EPA of total lipids. The strain was designated as strain "M26". The final genotype of the M26 strain with respect to wildtype *Yarrowia lipolytica* ATCC #20362 was as follows: Pox3-, Y.Δ12-, FBA::F.Δ12::Lip2, FBAIN::MΔ12::Pex20, TEF.:Δ6S::Lip1, FBAIN::Δ6B::Pex20, FBAIN::E1S::Pex20; GPAT::EIS:: Xpr, TEF::E2S::Xpr,; FBAIN::MAΔ5::Pex20, TEF::MAΔ5::Lip 1, FBAIN::Δ17S::Lip2, FBAINm::Δ17S::Pex16 and TEF::Δ17S::Pex20.

Construction of Strain MU, Producing about 9-12% EPA

Strain MU was a Ura auxotroph of strain M26. This strain was made by transforming strain M26 with 5 μg of plasmid PZKUM (FIG. 5D; SEQ ID NO:120) that had been digested with PacI and HincII. Transformation was performed using the Frozen-EZ Yeast Transformation kit (Zymo Research Corporation, Orange, Calif.) and transformants were selected by plating 100 μl of the transformed cell mix on an agar plate with the following medium: 6.7 g/L yeast Nitrogen Base (DIFCO Laboratories, Detroit, Mich.), 20 g/L dextrose, 50 mg/L uracil and 800 mg/L FOA. After 7 days, small colonies appeared that were plated on MM and MMU agar plates. All were Ura auxotrophs. One of the strains was designated "MU". GC analyses showed that the engineered strain produced about 912% EPA of total lipids (supra, Example 13).

Example 13

Determination of TAG Content in Mutant and Wildtype *Yarrowia lipolytica* Strain EU Engineered for EPA Biosynthesis After examining the effect of various acyltransferase knockouts in wildtype *Y. lipolytica* ATCC #90812 (Example 11), TAG content and fatty acid composition was then studied in DGAT2 knockout strains of the EU strain (i.e., engineered to produce 10% EPA; see Example 12). Lipid content and composition is compared in each of these strains in various lipid fractions following growth in 2 different growth conditions. In general, results demonstrated that TAG content is decreased and EPA content is increased in *Yarrowia lipolytica* strain EU with a disrupted DGAT2 gene.

Specifically, the DGAT2 gene in strain EU was disrupted as described for the S strain (ATCC #90812) in Example 5. The DGAT2-disrupted strain was designated EU-D2. EU and EU-D2 strains were harvested and analyzed following growth according to two different conditions. In the condition referred to in the Table below as "3 mL", cells were grown for 1 day in 3 mL MM medium, washed and then grown for 3 days in 3 mL HGM. Alternatively, in the condition referred to in the Table below as "51 mL", cells were grown for 1 day in 51 mL MM medium, washed and then grown for 3 days in 51 mL HGM. The fatty acid compositions of phosphatidylcholine (PC), phosphatidyletanolamine (PE), and triacylglycerol (TAG or oil) were determined in the extracts of 51 mL cultures following TLC separation ("Fraction").

GC results are shown below in Table 18. Cultures are described as the "EU" strain (wildtype) and the "EU-D2" strain (DGAT2 knockout). Fatty acids are identified as 16:0, 16:1, 18:0, 18:1 (oleic acid), 18:2 (LA), GLA, DGLA, ARA, ETA and EPA; and the composition of each is presented as a % of the total fatty acids.

TABLE 18

Lipid and EPA Content In *Yarrowia* Strain E With Disruption In DGAT2

| Strain & Growth | Fraction | TFAs % dcw | % 16:0 | % 16:1 | % 18:0 | % 18:1 | % 18:2 | % GLA | % DGLA | % ARA | % ETA | % EPA |
|---|---|---|---|---|---|---|---|---|---|---|---|---|
| EU, 3 mL | Total | — | 19 | 10 | 2 | 16 | 12 | 19 | 6 | 0 | 3 | 10 |
| EU-D2, 3 mL | Total | — | 17 | 10 | 1 | 6 | 7 | 24 | 5 | 0 | 6 | 19 |
| EU, 51 mL | Total | 37 | 18 | 11 | 3 | 19 | 31 | 5 | 1 | — | 1 | 4 |
| | PC | 2 | 12 | 9 | 1 | 8 | 43 | 7 | 3 | — | 5 | 4 |
| | PE | 1 | 24 | 14 | 0 | 14 | 37 | 5 | 0 | — | 0 | 1 |
| | TAG | 34 | 18 | 12 | 3 | 21 | 29 | 5 | 1 | — | 1 | 4 |
| EU-D2, 51 mL | Total | 18 | 18 | 8 | 1 | 5 | 7 | 25 | 5 | — | 5 | 20 |
| | PC | 1 | 18 | 6 | 1 | 2 | 4 | 26 | 5 | — | 11 | 22 |

TABLE 18-continued

Lipid and EPA Content In *Yarrowia* Strain E With Disruption In DGAT2

| Strain & Growth | Fraction | TFAs % dcw | % 16:0 | % 16:1 | % 18:0 | % 18:1 | % 18:2 | % GLA | % DGLA | % ARA | % ETA | % EPA |
|---|---|---|---|---|---|---|---|---|---|---|---|---|
| | PE | 1 | 25 | 7 | 0 | 2 | 5 | 14 | 2 | — | 3 | 8 |
| | TAG | 15 | 16 | 9 | 1 | 6 | 5 | 26 | 6 | — | 5 | 21 |

The results show that the DGAT2 knockout resulted in doubling of the % EPA (of total FAs) and halving of the lipid content (as % dcw). Furthermore, almost all of the changes observed in the lipid content are due to changes in the TAG fraction. The lower than expected % EPA in the 51 mL culture of strain EU is likely due to instability.

Example 14

Determination of TAG Content in Mutant and Wildtype *Yarrowia lipolytica* Strain MU Engineered For EPA Biosynthesis Based on the increased EPA content and reduced lipid content resulting from a single DGAT2 knockout in strain EU-D2 (Example 13), TAG content and fatty acid composition was then studied in various acyltransferase knockout strains of *Yarrowia lipolytica* strain MU (Example 12; capable of producing about 9-12% EPA, supra). More specifically, single disruptions in PDAT, DGAT2 and DGAT1 and double disruptions in PDAT and DGAT2 were created in strain MU. Lipid content and composition is compared in each of these strains, following growth in 4 different growth conditions. In general, the results demonstrated that TAG content is decreased and EPA content is increased in *Yarrowia lipolytica* strain MU with disrupted acyltransferase genes.

More specifically, single disruptions in PDAT, DGAT2, DGAT1 were created in strain MU (supra, Example 12), using the methodology described in Examples 5, 6, and 10 (with the exception that selection for the DGAT1 disruption relied on the URA3 gene). This resulted in single knockout strains identified as "MU-D1" (disrupted in DGAT1), "MU-D2" (disrupted in DGAT2) and "MU-P" (disrupted in PDAT). Individual knockout strains were confirmed by PCR. Additionally, the MU-D2 strain was disrupted for the PDAT gene and the disruption confirmed by PCR. The resulting double knockout strain was designated "MU-D2-P".

The MU-D1, MU-D2, MU-P and M-D2-P knockout strains were analyzed to determine each knockout's effect on lipid content and composition, as described below. Furthermore, the growth conditions promoting oleaginy were also explored to determine their effect on total lipid content. Thus, in total, four different experiments were conducted, identified as "Experiment A", "Experiment B", "Experiment C" and "Experiment E". Specifically, three loops of cells from plates containing each strain above were inoculated into MMU [3 mL for Experiments B and C; and 50 mL for Experiments A and E] and grown in a shaker at 30° C. for 24 hrs (for Experiments A, B and C) or 48 hrs (for Experiment E). Cells were harvested, washed once in HGM, resuspended in either HGM (50 mL for Experiments A and E; and 3 mL for Experiment B) or HGM with uracil ("HGMU") (3 mL for Experiment C) and cultured as above for 4 days. One aliquot (1 mL) was used for lipid analysis by GC as described according to the General Methods, while a second aliquot was used for determining the culture OD at 600 nm. The remaining culture in Experiments A and E was harvested, washed once in water and lyophilized for dry cell weight (dcw) determination. In contrast, the dcw in Experiments B and C were determined from their $OD_{600}$ using the equation showing their relationship. The fatty acid compositions of each of the different strains in Experiments A, B, C and E were also determined.

The results are shown in Table 19 below. Cultures are described as the "MU" strain (the parent EPA producing strain), "MU-P" (PDAT knockout), "MU-D1" (DGAT1 knockout), "MU-D2" (DGAT2 knockout) and "MU-D2-P" (DGAT2 and PDAT knockouts). Abbreviations utilized are: "WT"=wildtype (i.e., MU); "OD"=optical density; "dcw"=dry cell weight; "TFAs"=total fatty acids; and, "TFAs % dcw, % WT"=TFAs % dcw relative to the wild type ("MU") strain. Fatty acids are identified as 16:0, 16:1, 18:0, 18:1 (oleic acid), 18:2 (LA), GLA, DGLA, ARA, ETA and EPA; and the composition of each is presented as a % of the total fatty acids.

TABLE 19

Lipid And EPA Content In *Yarrowia* Strain MU With Various Acyltransferase Disruptions

| Expt | Strain | Residual DAG AT | 1st Phase Growth Condition | 2nd Phase Growth Condition | OD | dcw (mg) | TFAs (µg) | TFAs % dcw |
|---|---|---|---|---|---|---|---|---|
| A | MU | D1, D2, P | 1 day, | 4 days, | 4.0 | 91 | 374 | 20.1 |
| A | MU-D2 | D1, P | 50 mL | 50 mL | 3.1 | 75 | 160 | 10.4 |
| A | MU-D1 | D2, P | MMU | HGM | 4.3 | 104 | 217 | 10.2 |
| A | MU-P | D1, D2 | | | 4.4 | 100 | 238 | 11.7 |
| B | MU | D1, D2, P | 1 day, | 4 days, | 5.9 | 118 | 581 | 24.1 |
| B | MU-D2 | D1, P | 3 mL | 3 mL | 4.6 | 102 | 248 | 11.9 |
| B | MU-D1 | D2, P | MMU | HGM | 6.1 | 120 | 369 | 15.0 |
| B | MU-P | D1, D2 | | | 6.4 | 124 | 443 | 17.5 |
| C | MU | D1, D2, P | 1 day, | 4 days, | 6.8 | 129 | 522 | 19.9 |
| C | MU-D2 | D1, P | 3 mL | 3 mL | 5.6 | 115 | 239 | 10.2 |
| C | MU-D1 | D2, P | MMU | HGMU | 6.9 | 129 | 395 | 15.0 |
| C | MU-P | D1, D2 | | | 7.1 | 131 | 448 | 16.8 |
| E | MU | D1, D2, P | 2 days, | 4 days, | 4.6 | 89 | 314 | 17.3 |
| E | MU-D2 | D1, P | 50 mL | 50 mL | 2.8 | 62 | 109 | 8.5 |

TABLE 19-continued

Lipid And EPA Content In *Yarrowia* Strain MU With Various Acyltransferase Disruptions

| E | MU-P    | D2, P |    | MM |    |    | HGM |    | 5.0 | 99 | 232 | 11.5 |
|---|---------|-------|----|----|----|----|-----|----|-----|----|-----|------|
| E | MU-D2-P | D1    |    |    |    |    |     |    | 4.2 | 98 | 98  | 4.9  |

| Expt | Strain  | TFAs % dcw, % WT | % 16:0 | % 16:1 | % 18:0 | % 18:1 | % 18:2 | % GLA | % DGLA | % ARA | % ETA | % EPA |
|------|---------|------------------|--------|--------|--------|--------|--------|-------|--------|-------|-------|-------|
| A    | MU      | 100              | 17     | 10     | 2      | 18     | 10     | 22    | 7      | 1     | 3     | 9.7   |
| A    | MU-D2   | 52               | 16     | 12     | 0      | 8      | 9      | 23    | 7      | 0     | 8     | 17.4  |
| A    | MU-D1   | 51               | 15     | 10     | 2      | 11     | 10     | 22    | 7      | 0     | 7     | 17.4  |
| A    | MU-P    | 58               | 16     | 9      | 2      | 11     | 7      | 24    | 7      | 1     | 6     | 17.5  |
| B    | MU      | 100              | 17     | 9      | 3      | 18     | 10     | 22    | 8      | 1     | 3     | 9.1   |
| B    | MU-D2   | 50               | 16     | 10     | 0      | 7      | 10     | 24    | 7      | 1     | 7     | 17.8  |
| B    | MU-D1   | 62               | 18     | 9      | 3      | 14     | 11     | 20    | 7      | 1     | 5     | 12.0  |
| B    | MU-P    | 72               | 15     | 8      | 3      | 16     | 10     | 25    | 6      | 1     | 4     | 11.9  |
| C    | MU      | 100              | 16     | 10     | 2      | 13     | 11     | 21    | 10     | 1     | 4     | 12.6  |
| C    | MU-D2   | 51               | 17     | 9      | 1      | 6      | 11     | 21    | 8      | 1     | 7     | 18.9  |
| C    | MU-D1   | 75               | 15     | 9      | 2      | 12     | 12     | 20    | 10     | 1     | 5     | 13.5  |
| C    | MU-P    | 84               | 17     | 8      | 3      | 14     | 11     | 20    | 10     | 1     | 4     | 11.3  |
| E    | MU      | 100              | 16     | 12     | 2      | 18     | 9      | 22    | 7      | 1     | 4     | 11.2  |
| E    | MU-D2   | 49               | 14     | 12     | 1      | 6      | 8      | 25    | 6      | 0     | 7     | 20.0  |
| E    | MU-P    | 66               | 16     | 10     | 2      | 14     | 7      | 24    | 7      | 1     | 5     | 15.8  |
| E    | MU-D2-P | 28               | 18     | 10     | 0      | 7      | 12     | 20    | 5      | 0     | 6     | 22.5  |

The data showed that the lipid content within the transformed cells varied according to the growth conditions. Furthermore, the contribution of each acyltransferase on lipid content also varied. Specifically, in Experiments B, C and E, DGAT2 contributed more to oil biosynthesis than either PDAT or DGAT1. In contrast, as demonstrated in Experiment A, a single knockout in DGAT2, DGAT1 and PDAT resulted in approximately equivalent losses in lipid content (i.e., 48%, 49% and 42% loss, respectively [see "TFAs % dcw, % WT"]).

With respect to fatty acid composition, the data shows that knockout of each individual DAG AT gene resulted in lowered oil content and increased EPA content. For example, the DGAT2 knockout resulted in about half the lipid content and ca. double the % EPA in total fatty acids (similar to the results observed in strain EU-D2, supra). Knockout of both DAGAT2 and PDAT resulted in the least oil and the most % EPA.

The results reported herein, suggest that disruption of the native DGAT2 and/or DGAT1 and/or PDAT may be a useful means to substantially increase the total EPA content in a strain of *Yarrowia lipolytica* engineered to produce high concentrations of this particular PUFA.

Example 15

Sequencing of *Yarrowia lipolytica* DGAT1

The present Example describes the sequencing of YI DGAT1.

First, the ORF of *Y. lipolytica* DGAT1 was PCR-amplified using degenerate primers P201 and P203 (SEQ ID NOs:81 and 82) and genomic DNA of *Y. lipolytica* ATCC #90812 as template (from Example 5). The PCR was performed using the Expand High Fidelity PCR System of Roche Applied Sciences (Indianapolis, Ind.), as described in the General Methods.

The expected 1.6 kB fragment was isolated by standard agarose gel electrophoresis, purified, and cloned into pCR4-TOPO vector from Invitrogen (Carlsbad, Calif.) to yield plasmid pYAP42-23. Plasmid pYAP42-23 was transformed into *E. coli* XL2; and, transformants comprising pYAP42-23 were confirmed by plasmid miniprep analysis and restriction enzyme digestions with either NotI or NcoI. The DNA insert in plasmid pYAP42-23 was sequenced according to the methodology described in the General Methods using sequencing primers T7, T3, P239 (SEQ ID NO:121) and P240 (SEQ ID NO:122), to obtain the complete nucleotide sequence of the YI DGAT1 ORF.

The nucleotide sequence of the YI DGAT1 ORF is provided as SEQ ID NO:83; the translated product has the amino acid sequence provided in SEQ ID NO:84. The resultant sequence was compared to other known proteins, based on BLAST program analysis (Basic Local Alignment Search Tool; Altschul, S. F. et al., *J. Mol. Biol.* 215:403-410 (1993)). In particular, SEQ ID NO:83 was identical to the YI DGAT1 partial sequence that was obtained in Example 10, except for the presence of 6 silent mutations in the region of the degenerate PCR primers. These mutations included: an A-to-G mutation at position 6; an A-to-G mutation at position 21; an A-to-G mutation at position 24; a T-to-C mutation at position 1548; a C-to-T mutation at position 1552; and a T-to-C mutation at position 1557. Since these mutations resulted from the use of degenerate PCR primers, the deduced amino acid sequence of SEQ ID NO:83, i.e., SEQ ID NO:84 is identical to ORF YALI-CDS2141.1 (SEQ ID NO:80, corresponding to GenBank Accession No. NC_006072, locus_tag="YALI0F06578g").

Example 16

Construction and Sequencing of a *Mortierella alpina* cDNA Library

The present Example describes the construction of a cDNA library of *Mortierella alpina* and subsequent sequencing of the library.

Synthesis of *M. alpina* cDNA

*M. alpina* cDNA was synthesized using the BD-Clontech Creator Smart® cDNA library kit (Mississauga, ON, Canada) as described in Example 1, with the exception that upon PCR amplification using the $1^{st}$ strand cDNA synthesis mixture as template, the following thermocycler conditions were used: 95° C. for 20 sec, followed by 14 cycles of 95° C. for 5 sec and 68° C. for 6 min. PCR product was quantitated by agarose gel electrophoresis and ethidium bromide staining.

Seventy-five µl of the above PCR products (cDNA) were mixed with 3 µl of 20 µg/l proteinase K supplied with the kit. The mixture was incubated at 45° C. for 20 min, then 75 µl of water was added and the mixture was extracted with 150 µl phenol:chloroform:isoamyl alcohol mixture (25:24:1). The aqueous phase was further extracted with 150 µl chloroform: isoamyl alcohol (25:1). The aqueous phase was then mixed with 15 µl of 3 M sodium acetate, 2 µl of 20 µg/µl glycogen and 400 µl of 100% ethanol. The mixture was immediately centrifuged at room temperature for 20 min at 14000 rpm in a microfuge. The pellet was washed once with 150 µl of 80% ethanol, air dried and dissolved in 79 µl of water.

Dissolved CDNA was subsequently digested with Sfil (79 µl of the CDNA was mixed with 10 µl of 10×Sfil buffer, 10 µl of Sfil enzyme and 1 µl of 100×BSA and the mixture was incubated at 50° C. for 2 hrs). Xylene cyanol dye (2 µl of 1%) was added. The mixture was then fractionated on the Chroma Spin400 column provided with the kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 µl of water, and ligated into kit-supplied pDNR-LIB.

Library Sequencing

The ligation products were used to transform E. coli XL-1 Blue electroporation competent cells (Stratagene). An estimated total of 2×10$^6$ colonies was obtained. Sequencing of the cDNA library was carried out by Agencourt Bioscience Corporation (Beverly, Mass.), using an M13 forward primer (SEQ ID NO:123).

Example 17

Identification and Cloning of a *Mortierella alpina* Diacylglycerol Acyltransferase (DGAT1) Gene The present Example describes the identification of a putative *M. alpina* DGAT1 within one of 9,984 cDNA sequences. Specifically, the *Y. lipolytica* DGAT1 protein sequence (Example 10, SEQ ID NO:84) was used as a query sequence against each of the *M. alpina* cDNA sequences using BLAST program analysis (Basic Local Alignment Search Tool; Altschul, S. F. et al., *J. Mol. Biol.* 215:403-410 (1993)). One cDNA fragment bore significant homology to the *Y. lipolytica* DGAT1 and thus was tentatively identified as the *M. alpina* DGAT1 (SEQ ID NO:124). Subsequent BLAST analyses with SEQ ID NO:124 as the query against publically available sequence databases confirmed the cDNA's significant degree of similarity with the DGAT1 s from several other species. Rapid amplification of cDNA ends (RACE) technology and genome walking were then used to isolate the entire *Mortierella alpina* coding sequence thereof.

Cloning of the 5'-End Region of the Putative DGAT1 Gene

A Clontech Universal GenomeWalker™ kit (Palo Alto, Calif.) was utilized to obtain a piece of genomic DNA corresponding to the 5'-end region of the *M. alpina* DGAT1. Based on the partial DGAT1 gene sequence available (SEQ ID NO:124), the following primers were synthesized for use in the cloning: MARE2-N1 and MARE2-N2 (SEQ ID NOs:125 and 126). Methodology was described in Example 3, but is briefly summarized below. *M. alpina* genomic DNA was digested with DraI, EcoRV, PvuII or StuI individually, purified and ligated with Genome Walker adaptors (SEQ ID NOs: 20 and 21). First PCR reactions were carried out using each of the ligation products as templates, although the PCR reaction mixture contained 1 µl of 20 µM MARE2-N1 (SEQ ID NO:125) instead of MDGAT-3-1 (SEQ ID NO:15). Similarly, second PCR reactions were conducted using 1 µl of 20 µM MARE2-N2 (SEQ ID NO:126) instead of MDGAT-3-2 (SEQ ID NO:17).

A ~1.6 kb PCR product was observed when the DraI-digested and adaptor-ligated genomic DNA was used as template. This fragment was purified using a Qiagen PCR purification kit, ligated into pCR2.1-TOPO, and sequenced. Analysis of the sequence (SEQ ID NO:127) showed that this DNA fragment was the 5'-end extension of the DGAT1 cDNA fragment.

Cloning of the 3'-End Region of the Putative DGAT1 Gene

To clone the 3'-region of the putative DGAT1 gene by RACE, the following primers were synthesized: ARE-N3-1 and ARE-N3-2 (SEQ ID NOs:128 and 129, respectively). 3'-end RACE was carried out using InVitrogen's 3'-end RACE kit, using the procedure described in Example 3 unless noted below. Specifically, the first PCR reaction mixture contained 1 µl of 20 µM ARE-N3-1 (SEQ ID NO:128) instead of MDGAT-3-1 (SEQ ID NO:15), while the second round of PCR was conducted with primer ARE-N3-2 (SEQ ID NO:129) replacing primer MDGAT-3-2 (SEQ ID NO:17).

A ca. 300 bp fragment was obtained from the PCR. After purification with Qiagen's QiaQuick PCR purification kit, the fragment was cloned into pCR2.1-TOPO and sequenced. Sequence analysis verified that the sequence encoded the 3'-end of the DGAT1 cDNA, including the polyA tail (SEQ ID NO:130).

Complete Assembly of the Nucleotide Sequence Encoding *M. alpina's* DGAT1

Assembly of the sequence of the 5'-region (SEQ ID NO:127), the original CDNA fragment (SEQ ID NO:124) and the 3'-region (SEQ ID NO:130) yielded the entire *M. alpina* DGAT1 coding sequence (SEQ ID NO:131). The 5'-region genomic sequence included an intron (nucleotide bases 449 to 845 within SEQ ID NO:131).

Example 18

Identification of DGAT1 Fungal Homologs

The present Example describes the use of the *Yarrowia lipolytica* and *Mortierella alpina* DGAT1 sequences (SEQ ID NOs:83 and 131, respectively) to identify orthologous proteins in other fungi.

Orthologous DGAT1 fungal proteins were identified by conducting BLAST searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The *Yarrowia lipolytica* and *Mortierella alpina* DGAT1 sequences (SEQ ID NOs:83 and 131) were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database, using the BLASTX algorithm (Gish, W. and States, D. *J. Nature Genetics* 3:266-272 (1993)) provided by the NCBI. These searches resulted in the identification of 4 orthologous proteins (as shown below in Table 20). Table 20 additionally shows the results of sequence comparisons between the *Yarrowia lipolytica* DGAT1 sequence (SEQ ID NO:83) with each of the DGAT1 proteins disclosed herein, in terms of the observed "% Ident." (defined as the percentage of amino acids that are identical between the two proteins).

TABLE 20

Comparison Of *Yarrowia lipolytica* DGAT1 To Orthologous DGAT1s From Fungi

| Organism | Abbreviation | % Ident | GenBank Accession No., Reference and Annotation | SEQ ID NO |
|---|---|---|---|---|
| *Mortierella alpina* | Ma DGAT1 | 32.4 | — | 132 |
| *Neurospora crassa* strain OR74A | Nc DAGAT1 | 37.0 | XP_322121; gi\|32403016\|ref\| XP_322121.1\| hypothetical protein; gi\|28918105\|gb\| EAA27786.1\| hypothetical protein | 133 |
| *Gibberella zeae* PH-1 | Fm DAGAT1 | 38.1 | EAA77624; gi\|42554781\| gb\| EAA77624.1\| hypothetical protein FG06688.1 | 134 |
| *Magnaporthe grisea* 70-15 | Mg DAGAT1 | 36.2 | EAA52634; gi\|38106308\| gb\|EAA52634.1\| hypothetical protein MG05326.4 | 135 |
| *Aspergillus nidulans* FGSC A4 | An DAGAT1 | 41.7 | EAA57945; gi\|40738755\|gb\|EAA57945.1\| hypothetical protein AN6159.2 | 136 |

Example 19

Identification of Universal and Fungal DGAT1 Motifs

The present Example describes the use of the *M. alpina, N. crassa, G. zeae, M. grisea, A. nidulans* and *Y. lipolytica* DGAT1 sequences, in conjunction with other known DGAT1 sequences, to identify fungal and universal DGAT1 motifs.

To identify motifs (i.e., a set of amino acids conserved at specific positions along an aligned sequence of evolutionarily related proteins) that are indicative of a DGAT1 protein, it was first necessary to generate an alignment of DGAT1 sequences. For this, the following fungal sequences were used: SEQ ID NOs:84, 132, 133, 134, 135 and 136. Additionally, DGAT1 orthologs from 6 non-fungal sources were also included in the comparative alignment: mouse (Mm DGAT1; GenBank Accession No. AF384160, corresponding to SEQ ID NO:137 herein); soy (Gm DGAT1; SEQ ID NO:16 of US20040088759A1, corresponding to SEQ ID NO:138 herein); Arabidopsis (At DGAT1; SEQ ID NO:2 of US20040088759A1, corresponding to SEQ ID NO:139 herein); rice (Os DGAT1; SEQ ID NO:14 of US20040088759A1, corresponding to SEQ ID NO:140 herein); wheat (Ta DGAT1; SEQ ID NO:22 of US20040088759A1, corresponding to SEQ ID NO:142 herein); and *Perilla frutescens* (Pf; GenBank Accession No. AF298815, corresponding to SEQ ID NO:141 herein).

Alignment was done using the Megalign program of DNASTAR using Clustal W with the following parameters: gap penalty=10, gap length penalty=0.2, delay divergent seqs (%)=30, DNA transition weight=0.5 and protein weight matrix by Gonnet series. The results of this alignment are shown in FIG. 6a, 6b, 6c, 6d, 6e, 6f, 6g and 6h. Based on analysis of the alignment, 8 motifs were identified as unique to fungal DGAT1 sequences. Additionally, 7 motifs that were universally present in DGAT1 sequences from plants, animals and fungi were also deduced.

TABLE 21

Fungal and Universal DGAT1 Motifs

| Motif | Alignment Position* | Fungal Motif Sequence and SEQ ID NO | Universal Motif Sequence and SEQ ID NO |
|---|---|---|---|
| #1 | 97-104 | (F/Y)xGFxN(L/I)(M/G) (SEQ ID NO: 143) | xxGxxNxx (SEQ ID NO: 151) |
| #2 | 278-284 | (P/Q)YPxN(I/V)T (SEQ ID NO: 144) | n/a |
| #3 | 334-340 | QYAxPx(L/M) (SEQ ID NO: 145) | Q(Y/W)xxPxx (SEQ ID NO: 152) |
| #4 | 364-374 | KL(A/S)(T/S)x$_1$SXX(I/V)WL (wherein x$_1$ can not be P) (SEQ ID NO: 146) | KL(A/S)xxxxxxWL (SEQ ID NO: 153) |
| #5 | 418-424 | PV(Y/N)(Q/T/I)(Y/F)(F/M) (K/R) (SEQ ID NO: 147) | PVxxxxx (SEQ ID NO: 154) |
| #6 | 415-424 | WN(K/R/S)PV(Y/N)x$_1$(Y/F) (F/M)(K/R) (wherein x$_1$ can not be K) (SEQ ID NO: 148) | WNxPVxxxxx (SEQ ID NO: 155) |
| #7 | 456-466 | LxGxPTHxx(I/Y)G (SEQ ID NO: 149) | xxxxPxxxxxx (SEQ ID NO: 156) |
| #8 | 513-519 | A(L/F)(L/M)Y(F/Y)X(A/H) (SEQ ID NO: 150) | x(L/F)(L/M)Yxxx (SEQ ID NO: 157) |

*[Note:
Alignment positions are with respect to that of the *Yarrowia lipolytica* DGAT1, herein identified as SEQ ID NO: 84. Those residues shown in bold-type face and underlined are conserved only in fungal DGAT1 sequences.]

These motifs, located at positions 97-104, 278-284, 334-340, 364-374, 418-424, 415-424, 456-466 and 513-519 (wherein the alignment positions are with respect to SEQ ID NO:84) in a sequence alignment of a family of protein homologues, have a high degree of conservation among DGAT1 proteins; as such, it is expected that the amino acids residues located therein are essential in the structure, the stability, or the activity of the protein. Based on the sequence conservation observed, one skilled in the art will know how to use the motifs provided as SEQ ID NOs:143-157 as an identifier, or "signature", to determine if a protein with a newly determined sequence belongs to the DGAT1 protein family described herein.

Example 20

Transformation of Somatic Soybean Embryo Cultures with a Chimeric Gene Comprising a Down-Regulated DAG AT This Example describes methods that will be used for the cultivation of soybean, following their transformation with a chimeric gene that will result in down-regulation of a native DAG AT coding region.

Transformation of Somatic Soybean Embryo Cultures

Soybean embryogenic suspension cultures (cv. Jack) will be maintained in 35 mL liquid medium SB196 (infra) on a rotary shaker at 150 rpm and 26° C. with cool white fluorescent lights on a 16:8 hr day/night photoperiod with a light intensity of 60-85 µE/m$^2$/s.

SB 196—FN Lite Liquid Proliferation Medium (Per Liter)

| MS FeEDTA 100x Stock | 10 mL |
|---|---|
| MS Sulfate 100x Stock | 10 mL |
| FN Lite Halides 100x Stock | 10 mL |
| FN Lite P, B, Mo 100x Stock | 10 mL |
| B5 vitamins (1 mL/L) | 1.0 mL |
| 2,4-D (10 mg/L final concentration) | 1.0 mL |
| KNO$_3$ | 2.83 g |

| | | |
|---|---|---|
| (NH$_4$)$_2$SO$_4$ | 0.463 g | |
| Asparagine | 1.0 g | |
| Sucrose (1%) | 10 g | |
| pH 5.8 | | |

| FN Lite Stock Solutions | 1000 mL | 500 mL |
|---|---|---|
| 1 MS Fe EDTA 100x Stock | | |
| Na$_2$ EDTA* | 3.724 g | 1.862 g |
| FeSO$_4$—7H$_2$O | 2.784 g | 1.392 g |
| 2 MS Sulfate 100x stock | | |
| MgSO$_4$—7H$_2$O | 37.0 g | 18.5 g |
| MnSO$_4$—H$_2$O | 1.69 g | 0.845 g |
| ZnSO$_4$—7H$_2$O | 0.86 g | 0.43 g |
| CuSO$_4$—5H$_2$O | 0.0025 g | 0.00125 g |
| 3 FN Lite Halides 100x Stock | | |
| CaCl$_2$—2H$_2$O | 30.0 g | 15.0 g |
| KI | 0.083 g | 0.0715 g |
| CoCl$_2$—6H$_2$O | 0.0025 g | 0.00125 g |
| 4 FN Lite P, B, Mo 100x Stock | | |
| KH$_2$PO$_4$ | 18.5 g | 9.25 g |
| H$_3$BO$_3$ | 0.62 g | 0.31 g |
| Na$_2$MoO$_4$—2H$_2$O | 0.025 g | 0.0125 g |

*Add first, dissolve in dark bottle while stirring

Cultures will be subcultured every 7-14 days by inoculating approximately 35 mg of tissue into 35 mL of fresh liquid SB196 (the preferred subculture interval is every 7 days).

Soybean embryogenic suspension cultures will be transformed by the method of particle gun bombardment (Klein et al., Nature, 327:70 (1987)). A DuPont Biolistic PDS1000/HE instrument (helium retrofit) will be used for all transformations (E.I. duPont de Nemours and Co., Inc., Wilmington, Del.).

Soybean Embryogenic Suspension Culture Initiation

Soybean cultures will be initiated twice each month with 5-7 days between each initiation.

Between 45-55 days after planting, pods with immature seeds from available soybean plants will be picked and the seeds will be removed from their shells and placed into a sterilized magenta box. The soybean seeds will be sterilized by shaking for 15 min in the following solution: 95 mL of autoclaved distilled water plus 5 mL Clorox and 1 drop of soap. Seeds will be rinsed using two 1 L bottles of sterile distilled water and those less than 4 mm will be placed on individual microscope slides. The small end of the seed will be cut and the cotyledons pressed out of the seed coat. Cotyledons (25-30 per plate) will be transferred to plates containing SB1 medium.

SB1 Solid Medium (per L) comprises: 1 package MS salts (Gibco/BRL, Catalog #11117-066), 1 mL B5 Vitamins Stock (infra), 31.5 g sucrose, 2 mL 2,4-D (20 mg/L final concentration; 2,4-D stock is obtained premade from Phytotech, Catalog #D 295 as 1 mg/mL), pH to 5.7, 8 g TC agar. B5 Vitamins Stock (per L) comprises: 10 g myo-inositol, 100 mg nicotinic acid, 100 mg pyridoxine HCl and 1 g thiamine. Aliquots are stored at −20° C.; and, if the solution does not dissolve quickly enough, a low level of heat can be applied via a hot stir plate.

Plates containing the cotyledons will be wrapped with fiber tape and stored for 8 wks. After this time, secondary embryos will be cut and placed into SB196 liquid media for 7 days.

Preparation of DNA for Bombardment

Either an intact plasmid or a DNA plasmid fragment containing the chimeric gene of interest and the selectable marker gene will be used for bombardment. Fragments are obtained by gel isolation of double digested plasmids. In each case, 100 µg of plasmid DNA is digested in 0.5 mL of the appropriate enzyme mix. The resulting DNA fragments are separated by gel electrophoresis on 1% Sea Plaque GTG agarose (Bio-Whittaker Molecular Applications, Rockland, Me.) and the DNA fragments containing chimeric genes are cut from the agarose gel. DNA is purified from the agarose using the GELase digesting enzyme following the manufacturer's protocol (EpiCentre, Madison, Wis.).

A 50 µl aliquot of sterile distilled water containing 3 mg of gold particles (3 mg gold) will be added to 5 µl of a 1 µg/µl DNA solution (either intact plasmid or DNA fragment prepared as described above), 50 µl 2.5 M CaCl$_2$ and 20 µl of 0.1 M spermidine. The mixture will be shaken 3 min on level 3 of a vortex shaker and spun for 10 sec in a bench microfuge. After a wash with 400 µl 100% ethanol, the pellet will be suspended by sonication in 40 µl of 100% ethanol. Five µl of DNA suspension will be dispensed to each flying disk of the Biolistic PDS1000/HE instrument disk. Each 5 µl aliquot will contain approximately 0.375 mg gold per bombardment (i.e., per disk).

Tissue Preparation and Bombardment with DNA

Approximately 150-200 mg of 7 day old embryonic suspension cultures will be placed in an empty, sterile 60×15 mm petri dish and the dish will be covered with plastic mesh. Tissue will be bombarded 1 or 2 shots per plate with the membrane rupture pressure set at 1100 PSI and the chamber evacuated to a vacuum of 27-28 inches of mercury. Tissue will be placed approximately 3.5 inches from the retaining/stopping screen.

Selection of Transformed Embryos

Transformed embryos will be selected using hygromycin (when the hygromycin phosphotransferase, HPT, gene is used as the selectable marker) or chlorsulfuron (when the acetolactate synthase, ALS, gene is used as the selectable marker). In either case, the tissue will be placed into fresh SB196 media and cultured as described above following bombardment. Six days post-bombardment, the SB196 will be exchanged with fresh SB196 containing a selection agent of either 30 mg/L hygromycin or 100 ng/mL chlorsulfuron (chlorsulfuron stock: 1 mg/mL in 0.01 N ammonium hydroxide). The selection media will be refreshed weekly. Four to six weeks post-selection, green, transformed tissue may be observed growing from untransformed, necrotic embryogenic clusters. Isolated, green tissue will be removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated. For embryo maturation, embryos will be cultured for 4-6 wks at 26° C. in SB196 under cool white fluorescent (Phillips Cool White Econowatt F40/CWIRS/EW) and Agro (Phillips F40 Agro; 40 watt) bulbs on a 16:8 hr photoperiod with a light intensity of 90120 µE/m$^2$/s. After this time, embryo clusters will be removed to SB166 solid agar media for 1-2 weeks. SB 166 Solid Medium (per L) comprises: 1 package MS salts (Gibco/BRL, Cat# 11117-066), 1 mL B5 vitamins 1000×stock, 60 g maltose, 750 mg MgCl$_2$ hexahydrate, 5 g activated charcoal, pH 5.7 and 2 g gelrite.

Clusters are then subcultured to medium SB103 (media prepared the same as for SB 166, except no activated charcoal is included) for 3 weeks. During this period, individual embryos can be removed from the clusters and screened for alterations in their fatty acid compositions. It should be noted that any detectable phenotype, resulting from the expression of the genes of interest, could be screened at this stage. This would include, but not be limited to: alterations in fatty acid profile, protein profile and content, carbohydrate content, growth rate, viability or the ability to develop normally into a soybean plant.

Matured individual embryos will be desiccated by placing them into an empty, small petri dish (35×10 mm) for approximately 4-7 days. The plates are sealed with fiber tape (creating a small humidity chamber). Desiccated embryos are planted into SB 71-4 medium where they are left to germinate under the same culture conditions described above. SB 71-4 Solid Medium comprises (per L): 1 bottle Gamborg's B5 salts w/ sucrose (Gibco/BRL, Catalog #21153-036), pH 5.7 and 5 g TC agar.

Germinated plantlets will be removed from germination medium and rinsed thoroughly with water and then planted in Redi-Earth in 24-cell pack trays, covered with clear plastic domes. After 2 weeks, the domes will be removed and plants hardened off for a further week. If plantlets look hardy, they are transplanted to 10" pots of Redi-Earth with up to 3 plantlets per pot. After 10-16 weeks, mature seeds will be harvested, chipped and analyzed for fatty acids.

Example 21

Analysis of Somatic Soy Embryos Comprising a Down-Regulated DAG AT

This Example describes methods that will be useful to analyze fatty acid content in transformant soybean comprising a down-regulated DAG AT.

Theory

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, TAG becomes the most abundant lipid class; and, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is therefore a good and rapid model system for analyzing the phenotypic effects of modifying the expression of genes in the fatty acid biosynthetic pathway. Most importantly, the model system is also predictive of the fatty acid composition of seeds from plants derived from transgenic embryos.

Fatty Acid Analysis

Transgenic somatic soybean embryos will be analyzed. For this, fatty acid methyl esters will be prepared from single, matured, somatic soy embryos by transesterification. Embryos will be placed in a vial containing 50 μL of trimethylsulfonium hydroxide (TMSH) and 0.5 mL of hexane and incubated for 30 min at room temperature while shaking. Fatty acid methyl esters (5 μL injected from hexane layer) will be separated and quantified using a Hewlett-Packard 6890 Gas Chromatograph fitted with an Omegawax 320 fused silica capillary column (Supelco Inc., Bellefonte, Pa.; Catalog #24152).

Mature plants will be regenerated from transformed embryos, and the fatty acid analyses will be performed on the seeds that are produced by the regenerated plants. These plants will then be crossed with other transgenic plants expressing ω—3 fatty acid biosynthetic pathway genes (wherein the combined levels of EPA and DPA are frequently greater than 15%, and are as high as 23.5% of the total; see, e.g., U.S. Patent Application No, 2004/0172682). Representative genes preferred for making PUFAs (e.g., EPA) include one or more of the following:

TABLE 22

EPA Biosynthetic Pathway Genes

| Gene | Organism | Plasmid Name | Reference |
|---|---|---|---|
| Δ6 desaturase | S. diclina | pRSP1 | WO 02/081668 |
| Δ6 desaturase | M. alpina | pCGR5 | U.S. Pat. No. 5,968,809 |
| Elongase | M. alpina | pRPB2 | WO 00/12720 |
| Elongase | T. aureum | pRAT-4-A7 | WO 02/08401 |
| Δ5 desaturase | M. alpina | pCGR4 | U.S. Pat. No. 6,075,183 |
| Δ5 desaturase | S. diclina | pRSP3 | WO 02/081668 |
| Δ4 desaturase | S. aggregatum | pRSA1 | WO 02/090493 |

What is claimed is:

1. A method for increasing the percent of polyunsaturated fatty acids in the total lipid or oil of an oleaginous *Yarrowia* sp., comprising:
   a) providing an oleaginous *Yarrowia* sp. which produces at least 25% of its dry cell weight as oil, comprising
      (i) at least one native gene encoding a phospholipid:diacylglycerol acyltransferase;
      (ii) at least one native gene encoding an acyltransferase selected from the group consisting of: a diacylglycerol acyltransferase 1, a diacylglycerol acyltransferase 2 and a combination of these; and (iii) at least one gene encoding a protein of a functional polyunsaturated fatty acid biosynthetic pathway;
   b) reducing the activity of the native acyltransferase of step a) (i) and the activity of at least one of the native acyltransferases in step a) (ii), wherein the overall rate of oil biosynthesis is reduced and the percent of polyunsaturated fatty acids in the total lipid or oil is increased in the *Yarrowia* sp. as compared with the *Yarrowia* sp. where the activity of at least one native acyltransferase enzyme is not reduced.

2. The method according to claim 1, wherein the activity of the at least one native acyltransferase is reduced by a means selected from the group consisting of:
   a) gene disruption;
   b) antisense or iRNA technology;
   c) use of a mutant host having diminished diacylglycerol acyltransferase activity;
   d) over-expression of a mutagenized heterosubunit; and, e) manipulation of the regulatory sequences controlling expression of the protein.

3. The method according to claim 1, wherein the oleaginous fungus is *Yarrowia lipolytica*.

4. The method according to claim 1, wherein the protein of the functional polyunsaturated fatty acid biosynthetic pathway is selected from the group consisting of: desaturases and elongases.

5. The method according to claim 4, wherein the desaturase is selected from the group consisting of: Δ9 desaturase, Δ12 desaturase, Δ6 desaturase, Δ5 desaturase, Δ17 desaturase, Δ8 desaturas, Δ15 desaturase and Δ4 desaturase.

6. The method according to claim 4, wherein the functional polyunsaturated fatty acid biosynthetic pathway is either native to the oleaginous *Yarrowia* sp. or genetically engineered.

7. The method according to claim 1, wherein the polyunsaturated fatty acid produced in step (b) is eicosapentaenoic acid.

8. The method according to claim 3 wherein the oleaginous *Yarrowia lipolytica* is a strain selected from the group consisting of *Yarrowia lipolytica* ATCC #20362, *Yarrowia lipolytica* ATCC #76982, *Yarrowia lipolytica* ATCC #90812, and *Yarrowia lipolytica* ATCC #18944.

\* \* \* \* \*